United States Patent
Ginns et al.

(10) Patent No.: US 7,939,310 B2
(45) Date of Patent: May 10, 2011

(54) SYSTEMS AND METHODS FOR ANALYZING NUCLEIC ACID SEQUENCES

(75) Inventors: Edward I. Ginns, Shrewsbury, MA (US); Marzena Galdzicka, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 343 days.

(21) Appl. No.: 10/913,280

(22) Filed: Aug. 6, 2004

(65) Prior Publication Data

US 2005/0089894 A1 Apr. 28, 2005

Related U.S. Application Data

(60) Provisional application No. 60/493,238, filed on Aug. 6, 2003, provisional application No. 60/568,958, filed on May 7, 2004.

(51) Int. Cl.
*C12M 1/00* (2006.01)
(52) U.S. Cl. .................................................. 435/283.1
(58) Field of Classification Search .................. None
See application file for complete search history.

(56) References Cited

U.S. PATENT DOCUMENTS

| | | | |
|---|---|---|---|
| 6,274,321 B1 * | 8/2001 | Blumberg | 435/6 |
| 6,326,147 B1 | 12/2001 | Oldham et al. | |
| 2002/0009394 A1 * | 1/2002 | Koster et al. | 422/65 |
| 2002/0059030 A1 * | 5/2002 | Otworth et al. | 702/19 |
| 2002/0091664 A1 | 7/2002 | Larder et al. | |
| 2002/0110904 A1 | 8/2002 | Nelson et al. | |
| 2002/0150450 A1 * | 10/2002 | Bevirt et al. | 414/225.01 |
| 2003/0129760 A1 | 7/2003 | Aguilera et al. | |

OTHER PUBLICATIONS

Ross et al. ("Analysis of DNA fragments from conventional and microfabricated PCR devices using delayed extraction MALDI-TOF mass spectrometry" Anal Chem. May 15, 1998;70(10):2067-73).*
Voyager Biospectrometry Workstation User's Guide ("Chapter 1: Introducing the Voyager Biospectrometry Workstations" Applied Biosystems. 2000; pp. 1-1-1-46).*
Printout from: http://www.gwu.edu/~clade/faculty/allard/sequencinglab.html (Feb. 18, 2005).*

* cited by examiner

*Primary Examiner* — Christopher M. Babic
(74) *Attorney, Agent, or Firm* — Fish & Richardson P.C.

(57) ABSTRACT

The invention relates to systems and methods for analyzing clinically relevant nucleic acid sequences.

1 Claim, 53 Drawing Sheets

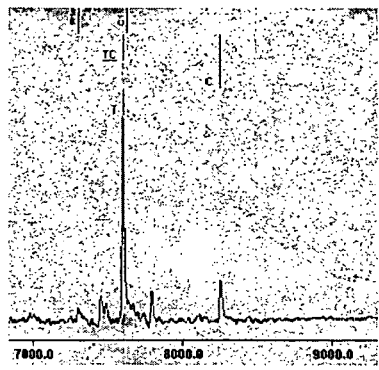 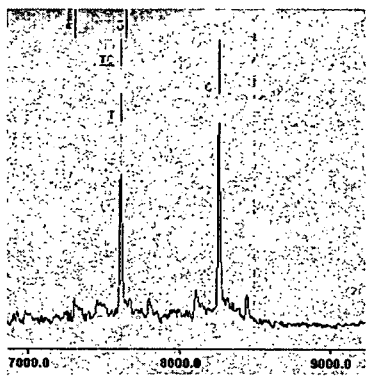 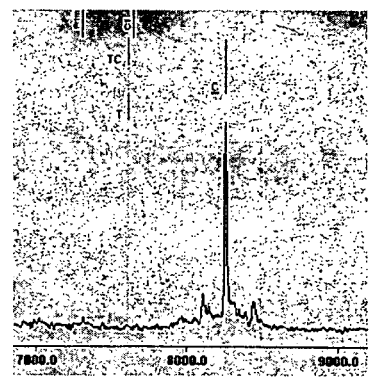
IS11/400 copies/ml    IS12/400 copies/ml    IS13/400 copies/ml
FIG. 13A1    FIG. 13A2    FIG. 13A3

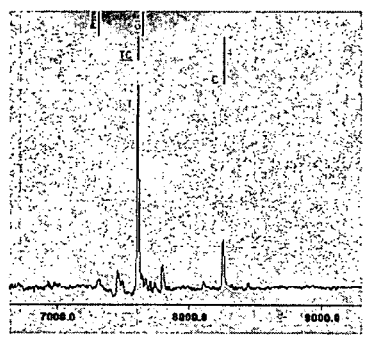 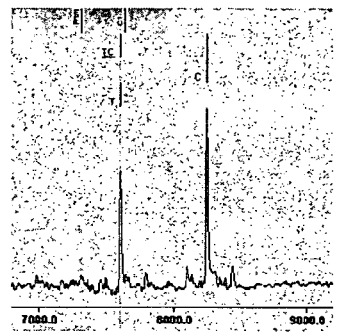 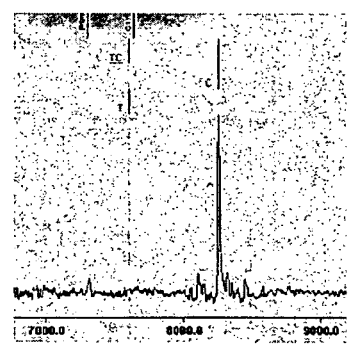
IS10/4000 copies/ml    IS11/4000 copies/ml    IS12/4000 copies/ml
FIG. 13B1          FIG. 13B2          FIG. 13B3

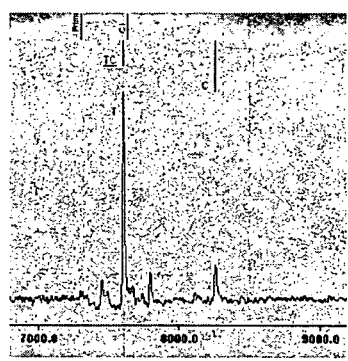
IS9/40,000 copies/ml
FIG. 13C1
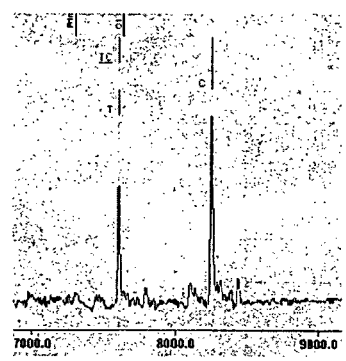
IS10/40,000 copies/ml
FIG. 13C2
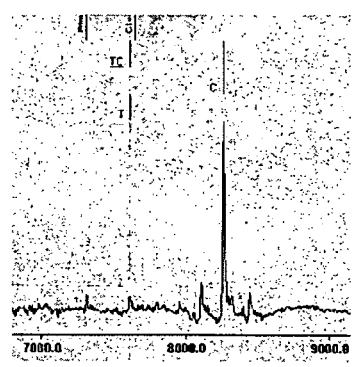
IS11/40,000 copies/ml
FIG. 13C3

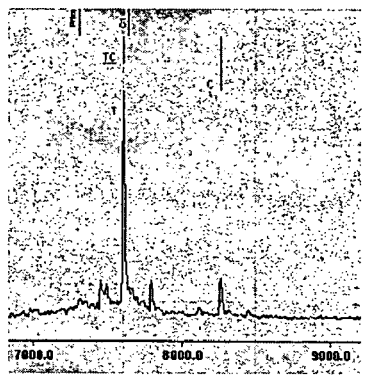 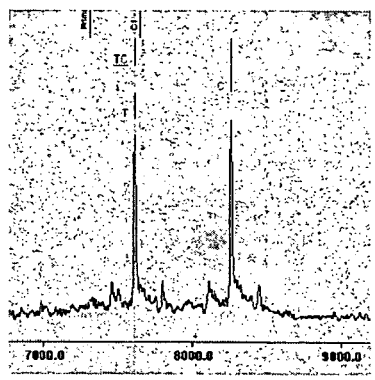 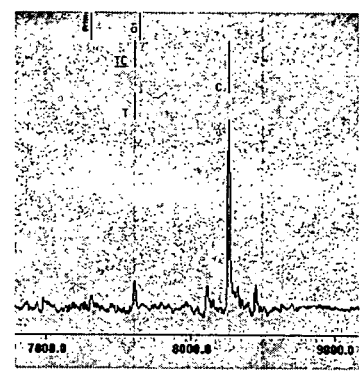
IS8/400,000 copies/ml     IS9/400,000 copies/ml     IS10/400,000 copies/ml
FIG. 13D1     FIG. 13D2     FIG. 13D3

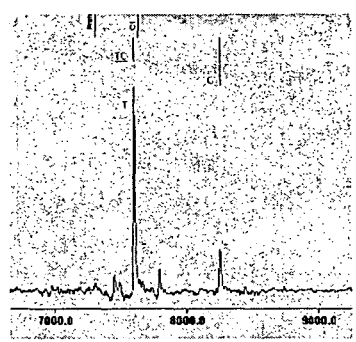
IS7/4,000,000 copies/ml
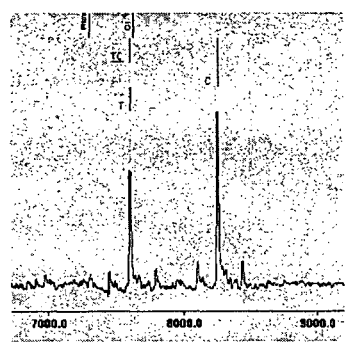
IS8/4,000,000 copies/ml
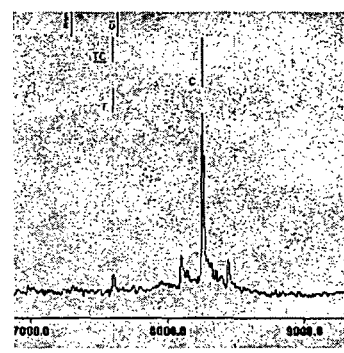
IS9/4,000,000 copies/ml
FIG. 13E1  FIG. 13E2  FIG. 13E3

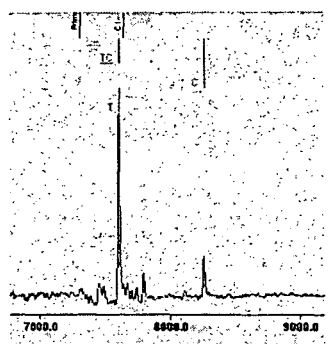 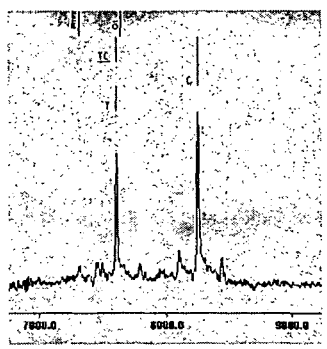 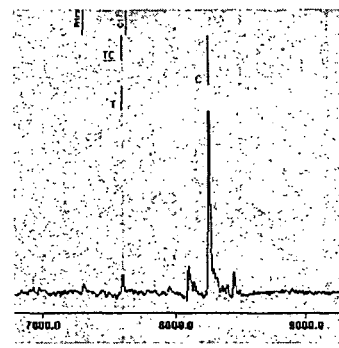
IS6/40,000,000 copies/mlIS7/40,000,000 copies/mlMTIS/40,000,000 copies/ml
FIG. 13F1FIG. 13F2FIG. 13F3

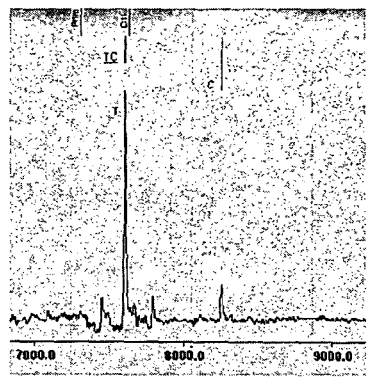 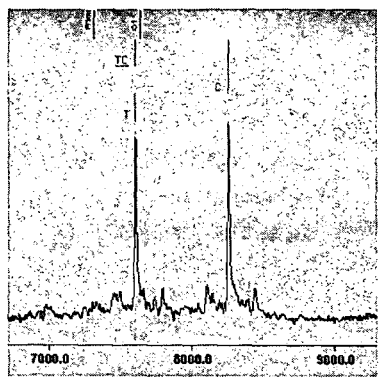 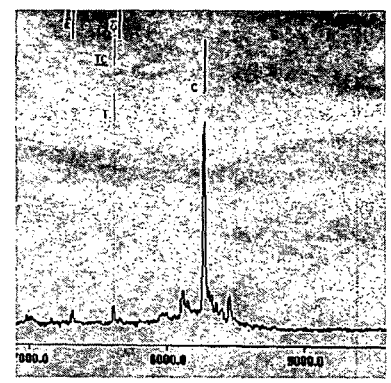
MT5/400,000,000 copies/ml     MT6/400,000,000 copies/ml     MT7/400,000,000 copies/ml
FIG. 13G1           FIG. 13G2           FIG. 13G3

Clinical Mutations

| Disorder | Achondroplasia | | Canavan | Canavan | Canavan |
|---|---|---|---|---|---|
| MIM # | 100800 | | 271900 | 271900 | 271900 |
| Gene Symbol | FGFR3 | | ASPA | ASPA | ASPA |
| Gene Name | fibroblast growth factor receptor 3 | | aspartoacylase | aspartoacylase | aspartoacylase |
| Terminator Mix | ACT | | ACG | CGT | ACT |
| Mutation | G1138C & G1138A | | 433-2A->G | Glu285Ala | Ala305Glu |
| SEQ ID NO: | 61 | | 64 | 67 | 70 |
| Forward PCR primer | ACGTTGGATGCCAGGATGAACAGGAAGAAG | | ACGTTGGATGTAAACGTAGCAGGGTAGTGG | ACGTTGGATGTACCGTGTACCCCGTGTTTG | ACGTTGGATGCCGTGTAAGATGTAAGCTGG |
| SEQ ID NO: | 62 | | 65 | 68 | 71 |
| Reverse PCR primer | ACGTTGGATGACGAGGCGGGCAGTGTGTAT | | ACGTTGGATGCTCTGTTGAAGCAAAAGAGAAC | ACGTTGGATGTGAGCGTAGTTTAGTTGTC | ACGTTGGATGGAAGCTTTTGCAAAGACAAC |
| SEQ ID NO: | 63 | | 66 | 69 | 72 |
| Extend primer | CAGGAAGAAGCCCACCC | | GTGGAGCCAGAGAAGTC | CCCCGTGTTTGTGAATG | CAGCAGCGGAATA |
| Analyte 1 | G | | G | C | A |
| SEQ ID NO: | 505 | | 508 | 510 | 514 |
| Ext 1 | CAGGAAGAAGCCCACCCC | | GTGGAGCCAGAGAAGTCC | CCCCGTGTTTGTGAATGC | CAGCAGCGGAATACTTTTT |
| Analyte 2 | A | | A | A | C |
| SEQ ID NO: | 506 | | 509 | 511 | 515 |
| Ext 2 | CAGGAAGAAGCCCACCCCT | | GTGGAGCCAGAGAAGTCTG | CCCCGTGTTTGTGAATGAG | CAGCAGCGGAATACTTTTTGC |
| Analyte 3 | C | | | | |
| SEQ ID NO: | 507 | | | | |
| Ext 3 | CAGGAAGAAGCCCACCCCGT | | | | |

FIG. 15A

| Gaucher | Gaucher | Gaucher | Gaucher | | Canavan |
|---|---|---|---|---|---|
| 230800 | 230800 | 230800 | 230800 | | 271900 |
| GBA | GBA | GBA | GBA | | ASPA |
| Glucocerebrosidase | Glucocerebrosidase | Glucocerebrosidase | Glucocerebrosidase | | aspartoacylase |
| ACG | ACG | ACT | ACT | | CGT |
| IVS2+1G>A | Arg463Cys | Arg496His | G84GG | | Tyr231X (X=stop codon) |
| 85 ACGTTGGATGT TCTACTTCAGG CAGTGTCG | 82 ACGTTGGATGA ACGTGTCTC AGCCCACT | 79 ACGTTGGATGA GTGCCTCCTTG AGTATCTG | 76 ACGTTGGATGA GCCTTTGAGTA GGGTAAGC | | 73 ACGTTGGATGA TTTCCTCCCTGC GCCATTG |
| 86 ACGTTGGATGC CCAAGGCAACAG AGTAAGAC | 83 ACGTTGGATGT TGGGTGCGTAA CTTTGTCG | 80 ACGTTGGATGT TGGGTGCGTAA CTTTGTCG | 77 ACGTTGGATGC CCAGGCAACAG AGTAAGAC | | 74 ACGTTGGATGT TAGGATGGATG ATAGCAGC |
| 87 CACTGCCTTGA CTCACTCA G | 84 GTTGTGGTCGT GCTAAAC C | 81 CACCTACCTGT GGCGTC A | 78 GGCAGCCTCAC AGGATTG C | | 75 AAAATTATAGA GAAAGTTGATT C A |
| 524 CACTGCCTTGA CTCACTCAC A | 522 GTTGTGGTCGT GCTAAACC T | 520 CACCTACCTGT GGCGTCA G | 518 GGCAGCCTCAC AGGATTGC G | | 516 AAAATTATAGA GAAAGTTGATT AC A |
| 525 CACTGCCT TGACTCAC TCATC | 523 GTTGTGGT CGTGCTAAA ACTG | 521 CACCTACC TGTGGCGT CGC | 519 GGCAGCCT CACAGGAT TGGC | | 517 AAAATTATA GAGAAAGT TGATTAAC |

FIG. 15B

| Factor V Deficiency | Factor V Deficiency | Gaucher | Gaucher | Gaucher | Gaucher |
|---|---|---|---|---|---|
| 227400 | 227400 | 230800 | 230800 | 230800 | 230800 |
| FV, F5 | FV, F5 | GBA | GBA | GBA | GBA |
| Coagulation Factor V | Coagulation Factor V | Glucocerebrosidase | Glucocerebrosidase | Glucocerebrosidase | Glucocerebrosidase |
| ACT | ACT | ACT | ACG | CGT | ACG |
| G1691A | C1690T | Asp409His | Asn370Ser | Val394Leu | Leu444Pro |
| 103 ACGTTGGATGCTCTGGGCTAATAGGACTAC | 100 ACGTTGGATGCTGAAAGGTTACTTCAAGGAC | 97 ACGTTGGATGCGTAACTTTGTCGACAGTCC | 94 ACGTTGGATGTCGGGGTCAGGGCAAGG | 91 ACGTTGGATGCTACAATGATGGGACTGTCG | 88 ACGTTGGATGGCTGGTTGCCAGTCAGAAGA |
| 104 ACGTTGGATGCTGAAAGGTTACTTCAAGGAC | 101 ACGTTGGATGCTCTGGGCTAATAGGACTAC | 98 ACGTTGGATGCCCCTCCACTCACCTGAAG | 95 ACGTTGGATGGTTGAGCCTTTGTCTCTTTG | 92 ACGTTGGATGACTGGAACCTTGCCCTGAAC | 89 ACGTTGGATGTTTAGCACGACCACAACAGC |
| 105 CAGATCCCTGGACAGGC | 102 GGACAAAATACCTGTATTCCTCT | 99 CATCATTGTAGACATCACCAAGC | 96 CCACATGGTACAGGAGGG | 93 CTGTCGACAAAGGTTACGCAG | 90 CCAGTCAGAAAGAACGACCC |
| 536 CAGATCCCTGGACAGGCAG | 534 GGACAAAATACCTGTATTCCTCAC | 532 CATCATTGTAGACATCACCAAGGC | 530 CCACATGGTACAGGAGGCA | 528 CTGTCGACAAAGGTTACGCACT | 526 CCAGTCAGAAAGAACGACCT |
| 537 CAGATCCCCGA | 535 TACCTGTATTCCTCGC | 533 GGACAAAATCCAAGGA | 531 TACAGGAGGTTC | 529 AAAGGTTACGCAAC | 527 AAGAACGACCTG |

| | | Fanconi Anemia, Complementati | Fanconi Anemia, Complementati | Factor VII Deficiency | Factor VII Deficiency | Factor VII Deficiency |
|---|---|---|---|---|---|---|
| | | 227645 | 227645 | 227500 | 227500 | 227500 |
| | | FANCC | FANCC | FVII, F7 | FVII, F7 | FVII, F7 |
| | | FANCC | FANCC | | | |
| | | | | Coagulation Factor VII | Coagulation Factor VII | Coagulation Factor VII |
| | | CGT | CGT | ACG | ACT | ACT |
| | | IVS4+4A>T | IVS4+4A>T | Arg353Gln | ins/del decamer | F VII -122 C>T |
| | | 118 ACGTTGGATGC CACAGAATTCT GGACAATC | 115 ACGTTGGATGT CAAAGAAGTGC AGAGCAAG | 112 ACGTTGGATGT GACGATGCCCG TCAGGTAC | 109 ACGTTGGATGG CACCAACACTT CAAATACG | 106 ACGTTGGATGA AAGTTCTCTGC CTCCAAGG |
| | | 119 ACGTTGGATGA ATTCAAAGAAG TGCAGAGC | 116 ACGTTGGATGA GAACCACAGAA TTCTGGAC | 113 ACGTTGGATGT ACTCGGATGGC AGCAAGGA | 110 ACGTTGGATGT GGGACAAGTTT TCATCTGC | 107 ACGTTGGATGG GCCAGGTGCAG CTCTCAG |
| | | 120 CTTAACTCCTG GATACAGGTA T | 117 TGCAGAGCAAG ATTACTCTC A | 114 TCAGGTACCAC GTGCCC G | 111 GATCTAGAATT CCAAACCCCTA T | 108 ACACAGGGCGTC CTCTGA T |
| | | 546 CTTAACTCCTG GATACAGGTAT A | 544 TGCAGAGCAAG ATTACTCTCT T | 542 TCAGGTACCAC GTGCCCC A | 540 CCAAACCCCTA A C | 538 CTCTGAA C |
| | | 547 CTTAACTCC TGGATACA GGTAAG | 545 TGCAGAGC AAGATTTA CTCTCAT | 543 TCAGGTAC CACGTGCC CTG | 541 GATCTAGA ATTCCAAA CCCCTAGT | 539 ACACAGGC GTCCTCTG AGC |

| Nieman-Pick Type A | Nieman-Pick Type A | | Familial Dysautonomia | Familial Dysautonomia | Familial Dysautonomia |
|---|---|---|---|---|---|
| 257200 | 257200 | | 223900 | 223900 | 223900 |
| ASM | ASM | | IKBKAP | IKBKAP | IKBKAP |
| acid sphingomyelinase | acid sphingomyelinase | | inhibitor of kappa light polypeptide gene enhancer in b cells, kinase complex-associated protein | | |
| ACT | ACT | | ACT | ACT | ACT |
| Arg496Leu | Leu305Pro (T905C) | | Arg696Pro | IVS2+6T->C | Arg696Pro |
| 133 ACGTTGGATGA GTACCCTTGCT CCTTGCC | 130 ACGTTGGATGT TACCCACAGCA GGGTACAC | | 127 ACGTTGGATGT GAGCAGCAATC ATGTGTCC | 124 ACGTTGGATGT CAAGGGTCATA CCCACATG | 121 ACGTTGGATGT ACAAGCTTTGT GTCCTGGG |
| 134 ACGTTGGATGC TCCCGGAGTAG TTTCCATC | 131 ACGTTGGATGA GACTCGTCAGG ACCAACTG | | 128 ACGTTGGATGT ACAAGCTTTGT GTCCTGGG | 125 ACGTTGGATGT CTGATAGAAGT AGACCCTG | 122 ACGTTGGATGT GAGCAGCAATC ATGTGTCC |
| 135 CCCCACACATCCT TGCAGGTTACC | 132 CCCAGGAACTT CCTCACA | | 129 AGTGGAGAGG GTTCAC | 126 TGCTGGCATTC TACATCAGTA | 123 GGCACAACAGT GACAATC |
| T | T | | C | T | G |
| 556 CCCCACACATCCTT GCAGGTTACCT | 554 CCCAGGAACTT CCTCACAA | | 552 AGTGGAGAGGG GTTCACC | 550 TGCTGGCATTC TACATCAGTAA | 548 GGCACAACAGT GACAATCC |
| G | C | | G | C | C |
| 557 CCCCACAT CCTTGCAG GTTACCGT | 555 CCCAGGAA CTTCCTCAC AGGT | | 553 AGTGGAGA CGGGGTTCA CGGA | 551 TGCTGGCA TTCTACATC AGTAGC | 549 GGCACAAC TCGGT |
| | | | | | |
| | | | | | |
| | | | | | |

FIG. 15E

| TaySachs | TaySachs | TaySachs | Nieman-Pick Type A | Nieman-Pick Type A | Nieman-Pick Type A |
|---|---|---|---|---|---|
| 272800 | 272800 | 272800 | 257200 | 257200 | 257200 |
| HEXA | HEXA | HEXA | ASM | ASM | ASM |
| hexosaminidase | hexosaminidase | hexosaminidase | acid sphingomyelinase | acid sphingomyelinase | acid sphingomyelinase |
| ACT | ACG | ACT | CGT | ACG | ACG |
| IVS12+1G>C | IVS9+1G>A | IVS9+1G>A | Arg496Leu | frameshift Pro330 | L305P (T905C) |
| 151 ACGTTGGATGTGTGGACAAACAAAACCTGG | 148 ACGTTGGATGACAGGAGGACCCCCAAGGGA | 145 ACGTTGGATGATGAGGAAGAAGGCTTCGG | 142 ACGTTGGATGCTCCCGGAGTAGTTCCATC | 139 ACGTTGGATGCTGTGGGTAACCATGAAAGC | 136 ACGTTGGATGAGACTCGTCAGGACCAACTG |
| 152 ACGTTGGATGTCTCTAAGGGAGAACTCCTG | 149 ACGTTGGATGTCAAGCAGCTGGAGTCCTTC | 146 ACGTTGGATGCCACCCACCCTCCTTCCTT | 143 ACGTTGGATGAGTACCCTTGCTCCTTGCC | 140 ACGTTGGATGTTGGCCATCGCTTCATAGAG | 137 ACGTTGGATGTTACCCACAGCAGGGTACAC |
| 153 CTGGTCCCCAGC | 150 ACCCTCCTTCCTCA G | 147 GGAGTCCTTCTACATCCAGAC A | 144 GTTCCATCTATTTGGTACACA G | 141 CAATAGCTTCCCTCCCCCC C | 138 GACCACCGTCACAGCAC C |
| 568 CTGGTCCCCAGGCTCTGC | 566 ACCCTCCTTCCTTCCTCAC | 564 GGAGTCCTTCTACATCCAGACA | 562 GTTCCATCTATTGGTACACAC T | 560 CAATAGCTTCCCTCCCCCC T | 558 GACCACCGTCACAGCAC T |
| 569 CTGGTCCCCAGGCTCTGCGGT | 567 ACCCTCCTTCCTTCCTCTCATG | 565 GGAGTCCTTCTACATCCAGACAGCT | 563 GTTCCATCTATTTGGTACACACAAG | 561 CAATAGCTTCCCTCCCCCCCCTTC | 559 GACCACCGTCACAGCACTTG |
| | | | | | |
| | | | | | |
| | | | | | |

FIG. 15F

| Disease | OMIM | Gene | Protein | Codon | Mutation | SeqID/Seq 1 | SeqID/Seq 2 | SeqID/Seq 3 | SeqID/Seq 4 | SeqID/Seq 5 |
|---|---|---|---|---|---|---|---|---|---|---|
| TaySachs | 272800 | HEXA | hexosaminidase | ACG | TATC1278 | 175 ACGTTGGATGTATGAAGGAGCTGGAACTGG | 176 ACGTTGGATGGGCCATAGGATATACGGTTC | 177 CCGGGCCCCTTCC | 584 CCGGGCCCCTTCT | 585 CCGGGCCTTCTCTGTA |
| TaySachs | 272800 | HEXA | hexosaminidase | ACT | Arg247Trp | 172 ACGTTGGATGGGAGTGTCAAACTCTGCAAG | 173 ACGTTGGATGACACAGCACAGGATGTGAAG | 174 ACGGATACCCCGGAGCC | 582 ACGGATACCCCGGAGCCA | 583 ACGGATACCCCGGAGCCGT |
| TaySachs | 272800 | HEXA | hexosaminidase | ACG | Arg247Trp | 169 ACGTTGGATGACACAGCACAGGATGTGAAG | 170 ACGTTGGATGAGAGTGTCAAACTCTGCAAG | 171 GAAGGAGGTCATTGAATACGCAC | 580 TTGAATACGCAC | 581 TCATTGAATACGCATG |
| TaySachs | 272800 | HEXA | hexosaminidase | ACT | Arg249Trp | 166 ACGTTGGATGGGAGTGTCAAACTCTGCAAG | 167 ACGTTGGATGACACAGCACAGGATGTGAAG | 168 CAAGCACACGGATACCCCT | 578 CAAGCACACGGATACCCCA C | 579 CAAGCACACCCGGA |
| TaySachs | 272800 | HEXA | hexosaminidase | ACG | Arg249Trp | 163 ACGTTGGATGACACAGCACAGGAGTGTGAAG | 164 ACGTTGGATGAGAGTGTCAAACTCTGCAAG | 165 GTCATTGAATACGCACGGCTC C | 576 GTCATTGAATACGCACGGCTCC T | 577 GTCATTGAATACGGCAGGCTCTG |
| TaySachs | 272800 | HEXA | hexosaminidase | ACG | Gly269Ser | 160 ATAACAAGCAGAGTCCCTC | 161 TTGCAGAGTTTGACACTCC | 162 CTGGTCCCAGACATCATTCTTACG | 574 CTGGTCCCAGACATCATTCTTAC A | 575 CTGGTCCCAGACATCATTCTTACTT G |
| TaySachs | 272800 | HEXA | hexosaminidase | ACT | Gly269Ser | 157 TTGCAGAGTTTGACACTCC | 158 ATAACAAGCAGAGTCCCTC | 159 CTTTGTCCTGGGACCA A | 572 CTTTGTCCTGGGACCAA G | 573 CTTTGTCCTGGGGACCAGGT |
| TaySachs | 272800 | HEXA | hexosaminidase | ACT | IVS12+1G>C | 154 ACGTTGGATGTCTCTAAGGGAGAACTCCTG | 155 ACGTTGGATGTGTGGACAACACAAACCTGG | 156 CCCCCCCGAAAAGCCCTTA G | 570 CCCCCCCGAAAAG CCCTTAC C | 571 CCCCCCGAAACCCTTAGC |

FIG. 15G

| | | | | | All Other | TaySachs |
|---|---|---|---|---|---|---|
| 107741 | 107680 | 603302 | 603302 | 106180 | | 272800 |
| APOE | APOA1 | APOA1 | ADCY9 | ACE | | HEXA |
| apolipoprotein E | apolipoprotein A-1 | apolipoprotein A-1 | adenylate cyclase 9 | angiotensin I-converting enzyme | | hexosaminidase |
| ACG | ACG | ACT | ACG | ACG | | ACT |
| Cys112Arg | 93C->T in 5' UTR | 121G->A in 5'UTR | rs731471 | rs4341 | | TATC1278 |
| 193 ACGTTGGATGAGGAAGTCCAAGGAGCTGCA | 190 ACGTTGGATGCTGAAATCAGGTAAGACATAG | 187 ACGTTGGATGTTTTTCTCCCACAATGTAG | 184 ACGTTGGATGATAGATGTGACCTCCCTCC | 181 ACGTTGGATGATTCGTCAGATCTGGTAGGG | | 178 ACGTTGGATGGCCATAGGATATACGGTTC |
| 194 ACGTTGGATGTCGCCGCGGGTACTGCACCA | 191 ACGTTGGATGGCACATAAAGCCATGGCATA | 188 ACGTTGGATGAACTGGGAATTTCATGAATC | 185 ACGTTGGATGTGGGCGACGCAATGAAAACAG | 182 ACGTTGGATGATTCTCTGAGCTCCCCTTAC | | 179 ACGTTGGATGTATGAAGGAGCTGGAACTGG |
| 195 CGGACATGGAGGACGTG | 192 ATATAAGAATCTATTTTTCTCC | 189 ATGTAGTAAAAATACATATGCCAT | 186 CACTTGATTTTTTTCTCCT | 183 TGGTAGGGGGTTGAATG | | 180 GTTCAGGTACCAGGGGG |
| 596 CGGACATGGAGGACGTGC | 594 ATTATAAGAATTATTTTTCTCCC | 592 ATGTAGTAAAAATACATATGCCATA | 590 CACTTGATTTTTTTCTCCTC | 588 TGGTAGGGGGTTGAATGC | | 586 GTTCAGGTACCAGGGGGC |
| 597 CGGACATGGAGGACGTG | 595 AATTATATTTTCTCCTA | 593 AAAATACATATGCCATGC | 591 CACTTGATTCTTG | 589 TGGTAGGGGTTTGAATGTC | | 587 GTTCAGGTACCACCAGGGGGGA |

FIG. 15H

| | | | | |
|---|---|---|---|---|
| 134830 | 146790 | 131210 | 131210 | 131210 |
| FGB | FCGR2A | E-Selectin, ELAM1 | E-Selectin, ELAM1 | E-Selectin, ELAM1 |
| fibrinogen beta chain | fc fragment of IGG, low affinity IIa, receptor | endothelial leukocyte adhesion molecule 1 | endothelial leukocyte adhesion molecule 1 | endothelial leukocyte adhesion molecule 1 |
| ACT | ACG | CGT | ACT | ACG |
| C(-148)T promoter | His131Arg | Ser128Arg | Leu554Phe | G98T in UTR ex2 |
| 208 ACGTTGGATGC ACTTGTTGGCT GAACCATT | 205 ACGTTGGATGT GTGGTTTGCTT GTGGGATG | 202 ACGTTGGATGG TCCTCCTCATCA TGCTTG | 199 ACGTTGGATGT CCGTAAGCATT TCCGAAGC | 196 ACGTTGGATGG AGAGCTGAGAG AAACTGTG |
| 209 ACGTTGGATGT CTAAACTAGAC CAACAAAG | 206 ACGTTGGATGG GTCAAGGTCAC ATTCTCC | 203 ACGTTGGATGG ATGGTCTCTAC ACATTCAC | 200 ACGTTGGATGC TTGGTAGCTGG ACTTTCTG | 197 ACGTTGGATGC CCAGGAAAGTA TTTCAAGC |
| 210 AACATCTTCCC AGCAAA | 207 GAGAAGGTGG GATCCAAA | 204 CCTGTACCAAT ACATCCTGC | 201 TTTCCGAAGCC AGAGGA | 198 TCATGACTTCA AGAGTTCTTT |
| T | G | C | T | G |
| 606 AACATCTTCCCA GCAAAA | 604 GAGAAGGTGGG ATCCAAAC | 602 CCTGTACCAAT ACATCCTGCC | 600 TTTCCGAAGCC AGAGGAA | 598 TCATGACTTCAA GAGTTCTTTTC |
| C | A | A | C | A |
| 607 AACATCTTC CCAGCAAA GC | 605 GAGAAGGT GGGATCCA AATG | 603 CCTGTACC AATACATC CTGCAG | 601 TTTCCGAA GCCAGAGG AGA | 599 TCATGACTT CAAGAGTT CTTTTA |
| | | | | |
| | | | | |
| | | | | |

FIG 15I

| 227400 | 176930 | 176930 | 134830 | 134830 | 134830 | 134830 | 134830 |
|---|---|---|---|---|---|---|---|
| FV, F5 | FII | FII | FGB | FGB | FGB | FGB | FGB |
| coagulation factor V | coagulation factor II, prothrombin | coagulation factor II, prothrombin | fibrinogen beta chain | fibrinogen beta chain | fibrinogen beta chain | fibrinogen beta chain | fibrinogen beta chain |
| ACT | ACT | ACT | CGT | ACT | ACG | ACG | ACT |
| Arg506Gln | G20210A | G20210A | IVS2-490T>A | IVS2-177T>A | G(-455)A promoter | G(-455)A promoter | C(-148)T promoter |
| 232 ACGTTGGATGC TCTGGGCTAAT AGGACTAC | 229 ACGTTGGATGT GGAACCAATCC CGTGAAAG | 226 ACGTTGGATGT GGAACCAATCC CGTGAAAG | 223 ACGTTGGATGT TAAAGGTTGAT TCTACTTG | 220 ACGTTGGATGG CTTTATCCTAAG GCCTCTC | 217 ACGTTGGATGG CTTATGTTTTCT GACAATG | 214 ACGTTGGATGG CTTATGTTTTCT GACAATG | 211 ACGTTGGATGC ACTTGTTGGCT GAACCATT |
| 233 ACGTTGGATGC TGAAAGGTTAC TTCAAGGAC | 230 ACGTTGGATGT GAATAGCACTG GGAGCATT | 227 ACGTTGGATGT GAATAGCACTG GGAGCATT | 224 ACGTTGGATGA AGACCTACAAG TAGCCGAG | 221 ACGTTGGATGC TGTAGGTTGCT TACTGTTC | 218 ACGTTGGATGG TCTAAAACAAAA GATAAACAC | 215 ACGTTGGATGG TCTAAAACAAAA GATAAACAC | 212 ACGTTGGATGT CTAAACTAGAC CAACAAAG |
| 234 CAGATCCCTGG A | 231 GTGACTCTCAG C | 228 CCCAATAAAAG TGACTCTCAGC | 225 GGTTGATTCTA CTTGGAATTT A | 222 TGTGCAGTTGG TCTTTCT | 219 AATTCTATTTCA AAAGGGGC | 216 ATTCTATTTCAA AAGGGGCC | 213 GCAACATCTTC CCAGCAAA |
| A | C | A | A | A | G | G | T |
| 622 CAGATCCCTGG ACAGGCA | 620 GTGACTCTCAG CA | 618 TCCCAATAAAA A | 616 GGTTGATTCTA CTTGGAATTT | 614 TGTGCAGTTGG TCTTTCTA | 612 AATTCTATTTCA AAAGGGGCC | 610 ATTCTATTTCAA AAGGGGCC | 608 GCAACATCTTC CCAGCAAAA |
| G | G | G | T | G | A | A | C |
| 623 CAGATCCC TGGACAGG CGA | 621 TCCCAATA AAAGTGAC TCTCAGCG A | 619 CCCAATA AAGTGACT CTCAGGGA | 617 CTACTTGG AATTTAT | 615 TGGTCTTTC TGC | 613 TCAAAAGG GGCTA | 611 CAAAAGGG GCTA | 609 TTCCCAGC AAAGC |

FIG 15J

| | | | | | |
|---|---|---|---|---|---|
| 139130 | 139130 | 134570 | 227500 | 227400 | 227400 |
| | | | FVII, F7 | FV, F5 | FV, F5 |
| GNB3 | GNB3 | FXIII | | | |
| guanine nucleotide-binding protein, beta-3 | guanine nucleotide-binding protein, beta-3 | factor XIII | coagulation factor VII | coagulation factor V | coagulation factor V |
| ACT | ACT | ACT | ACG | ACG | ACG |
| Trp339Leu | Cyt285Thr | Val34Leu | Arg353Gln | Arg485Leu | Arg506Gln |
| 250 ACGTTGGATGA CAGGTTCCTGG GACAGCTT | 247 ACGTTGGATGT CGTAGCCAGCG AATAGTAG | 244 ACGTTGGATGC GACGATGCAGCGG AAGATGAC | 241 ACGTTGGATGT GACGATGCCCG TCAGGTAC | 238 ACGTTGGATGG TCCAGGGATCT GCTCCTAC | 235 ACGTTGGATGC TGAAAGGTTAC TTCAAGGAC |
| 251 ACGTTGGATGT GTTCACTGCCTT CCACTTC | 248 ACGTTGGATGT CTCCCACGAGA GCATCATC | 245 ACGTTGGATGT CATACCTTGCA GGTTGACG | 242 ACGTTGGATGT ACTCGGATGGC AGCAAGGA | 239 ACGTTGGATGC ATACTACAGTG ACGTGGAC | 236 ACGTTGGATGC TCTGGCTAAT AGGACTAC |
| 252 GGGACAGCTTC CTCAAAATCT T | 249 CCACTGAGGGA GAAGGCCAC T | 246 CCACAGTGGGAG CTTCAGGGC T | 243 TCAGGTACCAC GTGCCC G | 240 GCCCAGAGGGC GATGTCT G | 237 AGGACAAAATA CCTGTATTCCT G |
| 634 GGGACAGCTTC CTCAAAATCTT G | 632 CCACTGAGGGA GAAGGCCACA C | 630 CCACAGTGGGAG CTTCAGGGCT G | 628 TCAGGTACCAC GTGCCCC A | 626 GCCCAGAGGGCG ATGTCTC A | 624 AGGACAAAATA CCTGTATTCCTC A |
| 635 TTCCTCAAA ATCTGGA | 633 CCACTGAG GGAGAAGG CCACGGA | 631 CCACAGTG GGAGCTTCA GGGCGT | 629 CCACAGTG CACGTGCC CTG | 627 GCCCAGAG GCGGATGTC TTTC | 625 AGGACAAA ATACCTGT ATTCCTTG |
| | | | | | |
| | | | | | |
| | | | | | |

FIG. 15K

| 192974 | 147840 | 606672 | 606672 | 192974 |
|---|---|---|---|---|
| ITGA2 | ICAM1 | GPIba | GpIba | GpIa; ITGA2 |
| glycoprotein Ia/IIa (a2);integrin, alpha-2; | intercellular adhesion molecule 1 | glycoprotein Ib, platelet, alpha polypeptide | glycoprotein Ib, platelet, alpha polypeptide; | integrin, alpha-2; glycoprotein Ia/IIa |
| ACT | ACT | ACT | ACG | ACT |
| C807T (Phe224) | Gly241Arg | Thr161Met | C5T Kozak | G873A (Thr246) |
| 265 ACGTTGGATGT GGCCTATTAGC ACCAAAAC | 262 ACGTTGGATGA CTGTGGGGTTC AACCTCTG | 259 ACGTTGGATGT GTTAGCCAGAC TGAGCTTC | 256 ACGTTGGATGA TCCACTCAAGG CTCCCTTGC | 253 ACGTTGGATGT ATTCAGCAGCT TCTGGTGG |
| 266 ACGTTGGATGT CCAGAGACATCC CAATATGG | 263 ACGTTGGATGA GGGGACCGTGG TCTGTTC | 260 ACGTTGGATGA CCTGAAAGGCA ATGAGCTG | 257 ACGTTGGATGA TGGCAGCAGGA GCAGCAAG | 254 ACGTTGGATGC CATCATGTGATT CACCGTC |
| 267 TTGCATATATTGA ATTGCTCC | 264 CGAGACTGGGG AACAGCC | 261 TCTCCAGCTTG GGTGTGGGC | 258 GCTCCCCTTGCC CACAGG | 255 GGGGCGACGAA GTGCTAC |
| T | G | T | C | A |
| 644 TTGCATATATTGAA TTGCTCCA | 642 CGAGACTGGGGA ACAGCCC | 640 TCTCCAGCTTG GGTGTGGGGCA | 638 GCTCCCCTTGCC CACAGGC | 636 GGGGCGACGAAG TGCTACA |
| C | C | C | T | G |
| 645 TTGCATATT GAATTGCT CCGA | 643 CGAGACTG GGAACAGC CGGT | 641 TCTCCAGC TTGGGTGT GGGCGT | 639 GCTCCCCTT GCCCACAG GTC | 637 GGGCGACG AAGTGCTA CGA |

FIG. 15L

| 607759 | 607759 | 607759 | 192974 |
|---|---|---|---|
| GpIIb; ITGA2B | GpIIb; ITGA2B | GpIIb; ITGA2B | ITGA2 |
| platelet glycoprotein IIb; integrin, alpha-2b | platelet glycoprotein IIb; integrin, alpha-2b | platelet glycoprotein IIb; integrin, alpha-2b | glycoprotein Ia/IIa (a2);integrin, alpha-2; |
| ACT | ACT | ACT | ACG |
| rs5912 (Pro605) | rs5915 Thr40Ile | rs5910 (Val1021) | C807T (Phe224) |
| 277 ACGTTGGATGTTGTGCTCAGCCTCAATGTG | 274 ACGTTGGATGATCCAAACTGGCTGCCATTG | 271 ACGTTGGATGTCCCCCTCTTCATCATCTTC | 268 ACGTTGGATGTCCAGACATCCCAATATGG |
| 278 ACGTTGGATGACATGGGTGTCTCCATGCAG | 275 ACGTTGGATGAGCTCTTGGGACCTTGTGCT | 272 ACGTTGGATGTCTGTATACCTGACCTTGG | 269 ACGTTGGATGTGGCCTATTAGCACCAAAAC |
| 279 CCTCAATGTGTCCCTACC A | 276 TGGGGCCTGCAT TAGAAG | 273 TTCCGCTTGAA GAAGCC | 270 GGGACCTCACAAACACATT C |
| 652 CCTCAATGTGTCCCTACCA G | 650 TGGGGCCTGCATAGAAGA C | 648 TTCCGCTTGAAGAAGCCA C | 646 GGGACCTCACAAACACATTC T |
| 653 CCTCAATGTGTCCCTACCGC | 651 TGGGGCCTGCATAGAAGGT | 649 TTCCGCTTGAAGAAGCCGA | 647 GGGACCTCACAAACACATTTG |

FIG. 15M

| | | | |
|---|---|---|---|
| 173470 | 607759 | 607759 | 607759 |
| ITGB3; GpIIIa | GpIIb; ITGA2B | GpIIb; ITGA2B | GpIIb; ITGA2B |
| glycoprotein IIb/IIIa; integrin, beta-3; | platelet glycoprotein IIb; integrin, alpha-2b | platelet glycoprotein IIb; integrin, alpha-2b | platelet glycoprotein IIb; integrin, alpha-2b |
| ACT | CGT | ACT | ACT |
| Leu33Pro (T196C) | Y968N | rs5913 (Pro972) | rs5916 (Leu855) |
| 289 ACGTTGGATGC AGATTCTCCTTC AGGTCAC | 286 ACGTTGGATGC ACGCATGGTTC AACGTGTC | 283 ACGTTGGATGC ACGCATGGTTC AACGTGTC | 280 ACGTTGGATGC TCTTACCTTGAG AGGGTTG |
| 290 ACGTTGGATGT TGCTGGACTTC TCTTTGGG | 287 ACGTTGGATGA CACTCACCTGA GCTTCCCC | 284 ACGTTGGATGA CACTCACCTGA GCTTCCCC | 281 ACGTTGGATGA CATCCTGGATA TACAGCCC |
| 291 GGTCACAGCGGA GGTGAGCCC | 288 TTCAACGTGTC CTCCCTTCCCC | 285 TCCCCTATGCG GTGCCCCC | 282 GGCTGTGGGA AGCACTG |
| T | T | A | T |
| 660 GGTCACAGCGGA GGTGAGCCCA | 658 TTCAACGTGTC CTCCCTTCCCCT | 656 TCCCCTATGCG GTGCCCCA | 654 GGCTGTGGGAA GCACTGA |
| C | A | G | C |
| 661 GGTCACAG CGAGGTGA GCCCGGA | 659 TTCAACGT GTCCTTCC TCCCAAT | 657 TCCCCTAT GCGGGTGCC CCGC | 655 GGCTGTGG GAAGCACT GGA |
| | | | |
| | | | |
| | | | |

FIG. 15N

| | | | |
|---|---|---|---|
| 173470 | 173470 | 173470 | 173470 |
| ITGB3; GpIIIa | ITGB3; GpIIIa | ITGB3; GpIIIa | ITGB3; GpIIIa |
| glycoprotein IIb/IIIa; integrin, beta-3; | glycoprotein IIb/IIIa; integrin, beta-3; | glycoprotein IIb/IIIa; integrin, beta-3; | glycoprotein IIb/IIIa; integrin, beta-3; |
| ACG | ACT | ACT | ACG |
| Arg169Glu | rs5919 (Pro294) | rs4642 (Glu511) | Leu33Pro (T196C) |
| 301 ACGTTGGATGG AAGCCAATCCG CAGGTTAC | 298 ACGTTGGATGA CTACCAACATG ACACTGCC | 295 ACGTTGGATGT GCTCAGAGGAG GACTATCG | 292 ACGTTGGATGT TGCTGGACTTC TCTTTGGG |
| 302 ACGTTGGATGA TCTGTGGGAGCA TCCAGAAC | 299 ACGTTGGATGT ACCACTGATGC CAAGACTC | 296 ACGTTGGATGA TTGACCACAGA GGCACTCG | 293 ACGTTGGATGA GCAGATTCTCC TTCAGGTC |
| 303 GGTTACTGGTG AGCTTT | 300 ACATGACACTG CCCGTCATT | 297 CCTTCCCAGCA GGACGA | 294 GCCCTGCCTCT GGGCTCACC |
| G | T | A | C |
| 668 GGTTACTGGTG AGCTTTC | 666 ACATGACACTG CCCGTCATTA | 664 CCTTCCCAGCA GGACGAA | 662 GCCCTGCCTCT GGGCTCACCC |
| A | C | G | T |
| 669 GGTTACTG GTGAGCTT TTG | 667 ACATGACA CTGCCCGT CATTGGGC | 665 CCTTCCCA GCAGGACG AGT | 663 GCCCTGCC TCTGGGCT CACCTC |
| | | | |
| | | | |
| | | | |

FIG. 150

| | | | |
|---|---|---|---|
| 607093 | 153240 | 153240 | 142910 |
| MTHFR | L-Selectin | L-Selectin | HMGCR |
| methylene tetrahydrofolate reductase | lymphocyte adhesion molecule 1 | lymphocyte adhesion molecule 1 | 3-hydroxy-3-methylglutaryl-coa reductase |
| ACT | ACT | ACT | ACT |
| A1298C | Thr49Ser | Phe206Leu | SNP29 |
| 313 ACGTTGGATGT CTCCCGAGAGG TAAAGAAC | 310 ACGTTGGATGT TCTAGCCCTTG CCAGTC | 307 ACGTTGGATGG AAGCAAAGAAA GGAAAGAG | 304 ACGTTGGATGG AGACTATGTAT CACTCACC |
| 314 ACGTTGGATGA GGAGCTGCTGA AGATGTGG | 311 ACGTTGGATGT GCAGATTCCT GGCACATC | 308 ACGTTGGATGT TACACCTGCAA CTGTGATG | 305 ACGTTGGATGG GACACAATGGA TTAGGCTG |
| 315 GAACAAAGACT TCAAAGACACT A | 312 GGTAAGTCCAG CAGTCG | 309 GAAAGGAAAGA GACTTACCAA T | 306 GGTCTTTTCCA AACTCTTT T |
| 676 GAACAAAGACT TCAAAGACACT TT | 674 GGTAAGTCCAG CAGTCGC | 672 GAAAGGAAAGA GACTTACCAAA C | 670 GGTCTTTTCCAA ACTCTTTT G |
| 677 GAACAAAG ACTTCAAA GACACTTG | 675 GGTAAGTC CAGCAGTC GGT | 673 GAAAGGAA AGAGACTT ACCAAGC | 671 GGTCTTTTC CAAACTCTT TGGT |
| | | | |
| | | | |

FIG. 15P

| | | | |
|---|---|---|---|
| 173360 | 173360 | 607093 | 607093 |
| PAI-1 | PAI-1 | MTHFR | MTHFR |
| plasminogen activator inhibitor 1 | plasminogen activator inhibitor 1 | methylene tetrahydrofolate reductase | methylene tetrahydrofolate reductase |
| CGT | ACT | ACG | ACT |
| 1-BP del/ins, 4G/5G | 1-BP del/ins, 4G/5G | C677T | C677T |
| 325 ACGTTGGATGCTCCGATGATACACGGCTGA | 322 ACGTTGGATGCACAGAGAGAGTCTGGACAC | 319 ACGTTGGATGCTTGAAGGAGAAGGTGTCTG | 316 ACGTTGGATGCTTCACAAAGCGGAAGAATG |
| 326 ACGTTGGATGGTTGTTGACACAAGAGAGCC | 323 ACGTTGGATGCTCTTGGTCTTTCCCTCATC | 320 ACGTTGGATGCTTCACAAAGCGGAAGAATG | 317 ACGTTGGATGCTTGAAGGAGAAGGTGTCTG |
| 327 TACACGGGCTGA | 324 GAGTCTGGACACGTGGGG | 321 GAAGGTGTCTGCGGGAG | 318 GCGTGATGATGAAATCG |
| G | A | C | T |
| 684 TACACGGCTGA | 682 GAGTCTGGACACGTGGGGA | 680 GAAGGTGTCTGCGGGAGC | 678 GCGTGATGATGAAATCGA |
| T | G | T | C |
| 685 TACACGGCCAC | 683 GAGTCTGGACACGTGGGGGA | 681 GAAGGTGTCTGCGGGAGTC | 679 GCGTGATGATGAAATCGGC |
| | | | |
| | | | |
| | | | |

FIG. 15Q

| | | | | |
|---|---|---|---|---|
| 191160 | 188040 | 188040 | 600742 | 173610 |
| TNF alpha | THBD | THBD | TGFBR3 | P-Selectin, GMP-140, CD62 |
| tumor necrosis factor | thrombomodulin | thrombomodulin | transforming growth factor-beta receptor, type III | platelet alpha-granule membrane protein |
| ACG | ACT | ACT | ACG | ACT |
| G(-308)A promoter | Ala25Thr (G127A) | Ala455Val (C1418T) | rs284157 | Thr715Pro |
| 340 ACGTTGGATGGATTGTGTGTAGGACCCTG | 337 ACGTTGGATGACGACTGCTTCGCGCTCTAC | 334 ACGTTGGATGAGTCACAGTCGGTGCCAATG | 331 ACGTTGGATGAGTTACAGAACCCCCACATC | 328 ACGTTGGATGATTGTACCTTGGCAGGTTGG |
| 341 ACGTTGGATGGTCCCCAAAAGAAATGGAGG | 338 ACGTTGGATGAGCGCACTGTCATTAGGTGG | 335 ACGTTGGATGTACCTTCGAGTGCATCTGCG | 332 ACGTTGGATGCAGCAAATGCATCTGTTCCC | 329 ACGTTGGATGAATGGCTCTGCACAAACAGC |
| 342 GAGGCTGAACCCCGTCC G | 339 CGCTCTACCCGGGCCCC A | 336 CGGTGCCAATG TGGCGG T | 333 TCCAAAACTCG ACAGAA G | 330 TGGCAGGTTGG CACGGTAG A |
| 694 GAGGCTGAACCCCGTCCC A | 692 CGCTCTACCCG GGCCCCA G | 690 CGGTGCCAATG TGGCGGA C | 688 TCCAAAACTCG ACAGAAC A | 686 TGGCAGGTTGG CACGGTAGT C |
| 695 GAGGCTGA CCCCGTC CTC | 693 CGCTCTAC CCGGGCCCC CGC | 691 CGGTGCCA ATGTGGCCG GGC | 689 TCCAAAAC TCGACAGA ATG | 687 TGGCAGGT TGGCACGG TAGGT |
| | | | | |
| | | | | |
| | | | | |

FIG. 15R

| | | | | |
|---|---|---|---|---|
| 601167 | 605546 | 187930 | 187930 | 192225 |
| P2RY1 | GP6 | F2R | F2R | VCAM1 |
| purinergic receptor P2Y, g protein-coupled, 1 | glycoprotein VI, platelet | coagulation factor II receptor | coagulation factor II receptor | vascular cell adhesion molecule |
| ACT | ACG | CGT | ACG | ACT |
| rs1065776 | S219P;rs1613662 | Tyr187Asn | Ser166Gly | Gly413Ala (G1238C) |
| 355 ACGTTGGATGTGTTCCCCAGGAGAAACC | 352 ACGTTGGATGTCTGATTTCCCAGGAACCTC | 349 ACGTTGGATGGAAACCGGTCAATGCTTATG | 346 ACGTTGGATGCAATTCAGACCCAAACTGCC | 343 ACGTTGGATGCTAGGAACCTTGCAGCTTAC |
| 356 ACGTTGGATGAAGTCGAGGAGGAGAGAATG | 353 ACGTTGGATGATGGACCCTGCAGAACCTAC | 350 ACGTTGGATGATTGTGTCGCTTCGTCACTG | 347 ACGTTGGATGTGCTGTTTGTGTCTGTGCTC | 344 ACGTTGGATGCCCTAGAGATCCAGAAATCG |
| 357 CCCAGGACGAAACCCGGACC | 354 TACCAACAGAACCACCTTCC | 351 GAGCAAGAGATAGAGGCGT | 348 CCCAAACTGCCAATCAC | 345 CTCCCCATTCACGAGGCCA |
| T | C | A | G | G |
| 704 CCCAGGACGAAACCCGGACCA | 702 TACCAACAGAACCACCTTCCC | 700 GAGCAAGAGATAGAGGCGTT | 698 CCCAAACTGCCAATCACC | 696 CTCCCCATTCACGAGGCCAC |
| C | T | T | A | C |
| 705 CCCAGGACACCGGC | 703 TACCAACAGAACCACCTTCCTC | 701 GAGCAAGAGATAGAGGCGTAC | 699 CCCAAACTGCCAATCACTG | 697 CTCCCCATTCACGAGGCCAGC |
| | | | | |
| | | | | |
| | | | | |

FIG. 15S

| | | | |
|---|---|---|---|
| 176805 | 600515 | 600515 | 600515 |
| PTGS1 | P2YR12 | P2YR12 | P2YR12 |
| prostaglandin-endoperoxide synthase 1 | purinergic receptor P2Y, G protein-coupled, 12; | purinergic receptor P2Y, G protein-coupled, 12; | purinergic receptor P2Y, G protein-coupled, 12; |
| ACT | ACG | ACG | ACT |
| G1497A (Ala499) | C18T(Asn6) | IVS2+742 | G36T (Gly12) |
| 367 ACGTTGGATGC AGCAGAGTTGG AGGAATTG | 364 ACGTTGGATGC CAACAAGAAAT GCAAGCCG | 361 ACGTTGGATGT CAATTCACTTA TCTCTGG | 358 ACGTTGGATGA AATGCAAGCCG TCGACAAC |
| 368 ACGTTGGATGG GATGGCACTTT TCAAGAAG | 365 ACGTTGGATGA GAGGACCTGGG TGATTTG | 362 ACGTTGGATGT ATGGCATCTAC ATCTTGGG | 359 ACGTTGGATGA GAGGACCTGGG TGATTTTG |
| 369 TGTATGGAGAC ATTGATGC A | 366 ATGCAAGCCGT CGACAA C | 363 TGGTGAAATAA AAAGATTACAA A C | 360 AACCTCACCTC TGCGCCTGG T |
| 712 TGTATGGAGAC ATTGATGCA G | 710 ATGCAAGCCGT CGACAAC T | 708 TGGTGAAATAA AAAGATTACAA AC T | 706 AACCTCACCTCT GCGCCTGGT G |
| 713 TGTATGGA GACATTGA TGCGT | 711 ATGCAAGC CGTCGACA ATC | 709 TGGTGAAA TAAAAAGA TTACAAAT G | 707 AACCTCAC CTCTGCGC CTGGGA |
| | | | |
| | | | |

FIG. 15T

| | | |
|---|---|---|
| 176805 | 176805 | 176805 |
| PTGS1 | PTGS1 | PTGS1 |
| prostaglandin-endoperoxide synthase 1 | prostaglandin-endoperoxide synthase 1 | prostaglandin-endoperoxide synthase 1 |
| ACT | ACG | ACT |
| Gly213 (C>A) | Gly230Ser | Cys68 C>T |
| 376 ACGTTGGATGTCCTAGGTACTCACCCCATG | 373 ACGTTGGATGTCCTTAAAGAGCCGCAGTTG | 370 ACGTTGGATGGAAGGAGTGAGGGCTGAAGG |
| 377 ACGTTGGATGACTTCACCCACCAGTTCTTC | 374 ACGTTGGATGAACCCCTCTCTGTCCACAGG | 371 ACGTTGGATGTACCAGTGTGACTGCACCCG |
| 378 AAGCCAGGACCCATCTT A | 375 GTCTCCATAAAG | 372 AGGCCCAGCTCTACGGATGGT T |
| 718 AAGCCAGGACCCATCTTT C | 716 GTCTCCATAAATGTGGCC A | 714 AGGCCCAGCTCACGGATGGTA C |
| 719 AAGCCAGGACCATCTTGC | 717 GTCTCCATAAATGTGGCTG | 715 AGGCCCAGCTCACGGATGGTGC |
| | | |
| | | |
| | | |

FIG. 15U

| | | |
|---|---|---|
| 176805 | 176805 | 176805 |
| PTGS1 | PTGS1 | PTGS1 |
| prostaglandin-endoperoxide synthase 1 | prostaglandin-endoperoxide synthase 1 | prostaglandin-endoperoxide synthase 1 |
| ACT | ACT | ACG |
| IVS3+206 | VS2+842 | IVS10-29T>C |
| 385 ACGTTGGATGA CCCTCACTCCT GCTTCTG | 382 ACGTTGGATGG ATCTGAACTCA GGTCTGTC | 379 ACGTTGGATGG AAAAAGGTGGA CCTGGAAG |
| 386 ACGTTGGATGA CATGACAGAGA CAGAACCG | 383 ACGTTGGATGT CCATTGTGGGT AGAAGCAG | 380 ACGTTGGATGC TCCTACAAGGA GATAAGGG |
| 387 CCCTGCTTCTG AGTTCCATG | 384 CGTCCACACAC TTCGCA | 381 AATGGCATCAT GGATCTGA |
| A | A | C |
| 724 CCCTGCTTCTG AGTTCCATGA | 722 CGTCCACACAC TTCGCAA | 720 AATGGCATCAT GGATCTGAC |
| G | G | T |
| 725 CCCTGCTT CTGAGTTC CATGGT | 723 CGTCCACA CACTTCGC AGGGT | 721 AATGGCAT CATGGATC TGATG |
| | | |
| | | |
| | | |

FIG. 15V

| | | |
|---|---|---|
| 176805 | 176805 | 176805 |
| PTGS1 | PTGS1 | PTGS1 |
| prostaglandin-endoperoxide synthase 1 | prostaglandin-endoperoxide synthase 1 | prostaglandin-endoperoxide synthase 1 |
| ACT | ACT | ACT |
| IVS7+14delA | IVS6+51 | IVS3+32 |
| 394 ACGTTGGATGAGTCTTGCCAGGGAAGACC | 391 ACGTTGGATGACTGCTCTGGACCTAATTTG | 388 ACGTTGGATGATCCGTGAGCTGGGCCTTCA |
| 395 ACGTTGGATGTGGGAAACTCAAGTACCAGG | 392 ACGTTGGATGTCTACCTGTGGACAGAGAGG | 389 ACGTTGGATGTTAGGGTCTAGGAGAAAGGG |
| 396 CCCTCTGCCCTA | 393 GGACCTAATTTA | 390 CAGCCCTCACTA |
| 730 CCCTCTGCCCTACCCCC | 728 GGACCTAATTTGGCACGCA | 726 CAGCCCTCACTCCTTCCA |
| C | G | G |
| 731 CCCTCTGCCTACCCCCGGC | 729 GGACCTAATTTGGCACGCGT | 727 CAGCCCTCACTCCTTCCGT |
| | | |
| | | |
| | | |

FIG. 15W

| | | |
|---|---|---|
| 176805 | 176805 | 176805 |
| PTGS1 | PTGS1 | PTGS1 |
| prostaglandin-endoperoxide synthase 1 | prostaglandin-endoperoxide synthase 1 | prostaglandin-endoperoxide synthase 1 |
| ACT | ACG | ACT |
| Leu237Met | Lys341Arg | Lys185Thr |
| 403 ACGTTGGATGTTCCATCCTTAAAGAGCCG | 400 ACGTTGGATGTGCAGGAAATAGCCACTCAG | 397 ACGTTGGATGAACATGAGGTTGGTGCCTTG |
| 404 ACGTTGGATGTCTGTCCACAGGTAGACCTC | 401 ACGTTGGATGCTATTTCCAATCCTGCCCTG | 398 ACGTTGGATGAGTTGCCAGATGCCCAGCTC |
| 405 TTGATACTGACGCTCCA | 402 CGTACTCCTCGATGACAATCG | 399 GGGGGTCAGGTATGAACA |
| 736 TTGATACTGACGCTCCAT | 734 CGTACTCCTCGATGACAATCC | 732 GGGGGTCAGGTATGAACTC |
| 737 TTGATACTGACGCTCCAGA | 735 CGTACTCCTCGATGACAATCTTG | 733 GGGGGTCAGGTATGAACGT |
| | | |
| | | |
| | | |

FIG. 15X

| | | |
|---|---|---|
| 176805 | 176805 | 176805 |
| PTGS1 | PTGS1 | PTGS1 |
| prostaglandin-endoperoxide synthase 1 | prostaglandin-endoperoxide synthase 1 | prostaglandin-endoperoxide synthase 1 |
| ACT | ACT | ACG |
| Gln41G>A | Pro504 T>C | Pro17Leu |
| 412 ACGTTGGATGTTCTCACCACAGTGAATCC | 409 ACGTTGGATGGGATGGCACTTTCAAGAAG | 406 ACGTTGGATGTCATCTCTCTCCTCTGCAGG |
| 413 ACGTTGGATGGGGTGCAGTCACACTGGTAG | 410 ACGTTGGATGCAGCAGAGTTGGAGGAATTG | 407 ACGTTGGATGCTGGGTCCGCGAGCAGGA |
| 414 TTGTTACTATCCATGCCA | 411 CACTTTTCAAGAAGCAGTCC | 408 GTTCCTGCTCCTGCTCC |
| A | T | C |
| 742 TTGTTACTATCCATGCCAA | 740 CACTTTTCAAGAAGCAGTCCA | 738 GTTCCTGCTCCTGCTCCC |
| G | C | T |
| 743 TTGTTACTAGCCATGCCAGC | 741 CACTTTTCAAGAAGCAGTCCGGGGT | 739 GTTCCTGCTCCTG |
| | | |
| | | |
| | | |

FIG. 15Y

| | | |
|---|---|---|
| 176805 | 176805 | 176805 |
| PTGS1 | PTGS1 | PTGS1 |
| prostaglandin-endoperoxide synthase 1 | prostaglandin-endoperoxide synthase 1 | prostaglandin-endoperoxide synthase 1 |
| ACT | ACT | ACT |
| rs1330344 promoter | Arg8Tyr | Arg53His |
| 421 ACGTTGGATGCACCCATCTGCACTCAAAAC | 418 ACGTTGGATGGAGCAGGAGCAGGAACAGCA | 415 ACGTTGGATGCTGTTGTTACTATCCATGCC |
| 422 ACGTTGGATGTCTGATTCTGAGGTGAAGGC | 419 ACGTTGGATGTCATCTCTCCTCTGCAGG | 416 ACGTTGGATGAATAGCCCGTGCGGGTGCAG |
| 423 TGTGTGGCCCTT | 420 CAGGAACAGCAAGAACC | 417 CCGCTTCGGCCTTGACC A |
| 748 TGTGTGGCCCTGGGCACTA C | 746 CAGGAACAGCAAGAACCA C | 744 CCGCTTCGGCCTTGACCA G |
| 749 TGTGTGGGCCTGGCACTGA | 747 CAGGAACAGCAAGAACCGGA | 745 CCGCTTCGGCCCTGACCGC |
| | | |
| | | |
| | | |

FIG. 15Z

| | | |
|---|---|---|
| 600262 | 600262 | 176805 |
| PTGS2 | PTGS2 | PTGS1 |
| prostaglandin-endoperoxide synthase 2; | prostaglandin-endoperoxide synthase 2; | prostaglandin-endoperoxide synthase 1 |
| CGT | ACT | ACG |
| Gly537Gly | 2242T>C | Ser476 |
| 430 ACGTTGGATGGAGACTGAATTGAGGCAGTG | 427 ACGTTGGATGTGCACTGATACCTGTTTTG | 424 ACGTTGGATGCCTTCAATGAGTACCGCAAG |
| 431 ACGTTGGATGATATGTTCTCCTGCCTACTG | 428 ACGTTGGATGGCATCTTCCATGATGCATTAG | 425 ACGTTGGATGGAAACAGCTGCTCACCTAC |
| 432 TGAAAACCCACTTCTCCG | 429 TTTTGTTTTGATGACAGAAAAAT T | 426 GGCATGAAACCCTACACCTC C |
| 754 TGAAAACCCACTTCTCCT | 752 TTTTGTTTTGATGACAGAAAATAC | 750 GGCATGAAACCCTACACCTCCT |
| 755 TGAAAACCCACTTCTCCAC | 753 TTTTGTTTTGATGACAGAAAAATGA | 751 GGCATGAAACCCTACACCTCTTTC |
| | | |
| | | |
| | | |

FIG. 15AA

| | | |
|---|---|---|
| 600262 | 600262 | 600262 |
| PTGS2 | PTGS2 | PTGS2 |
| prostaglandin-endoperoxide synthase 2; | prostaglandin-endoperoxide synthase 2; | prostaglandin-endoperoxide synthase 2; |
| ACT | ACT | ACG |
| (-162) promoter | (-1195) promoter | IVS6+38 |
| 439 ACGTTGGATGTTCCTGGGTTTCCGATTTTC | 436 ACGTTGGATGAGCACTACCCATGATAGATG | 433 ACGTTGGATGTAAGGAACACATTTTAGGG |
| 440 ACGTTGGATGAAAATTGCGTAAGCCCGGTG | 437 ACGTTGGATGTGGAACATAGTTGGATGAGG | 434 ACGTTGGATGTCAGGTATGCTTCCTTTGAC |
| 441 TGGGTTTCCGATTTTCTCATTTC | 438 CAAAAGCAAAGATGAAATTCCAA | 435 GGGATTTTAAAATATGGGTATAG |
| 760 TGGGTTTCCGATTTTCTCATTTCG | 758 CAAAAGCAAAGATGAAATTCCAAG | 756 GGGATTTTAAAATATGGGTATAAGC |
| 761 TGGGTTTCCGATTTTCTCATTTGC | 759 CAAAAGCAAAGATGAAATTCCAGC | 757 GGGATTTTAAAATATGGGTATAAGTG |
| | | |
| | | |
| | | |

FIG. 15 BB

| | | |
|---|---|---|
| 600262 | 600262 | 600262 |
| PTGS2 | PTGS2 | PTGS2 |
| prostaglandin-endoperoxide synthase 2; | prostaglandin-endoperoxide synthase 2; | prostaglandin-endoperoxide synthase 2; |
| ACT | ACT | ACG |
| (-765) promoter | (-90) promoter | (-199T) promoter |
| 442 ACGTTGGATGA GGGATCAGACA GGAGAGTG | 445 ACGTTGGATGT AACCTTACTCG CCCCAGTC | 448 ACGTTGGATGA CAGGGTAACTG CTTAGGAC |
| 443 ACGTTGGATGG AGAAAATCGGA AACCCAGG | 446 ACGTTGGATGC CGTGTCTGGTC TGTACGTC | 449 ACGTTGGATGA CTGTTCTCCGTA CCTTCAC |
| 444 CCCCCTCTGCT CCCAAA | 447 CCGACGTGACT CCTCGACC | 450 TGAGGAGAATT TACCTTTCCC |
| C | C | C |
| 762 CCCCCTCTGCT CCCAAAC | 764 CCGACGTGACT CCTCGACCC | 766 TGAGGAGAATT TACCTTTCCCC |
| T | G | G |
| 763 CCCCCTCT GCTCCCAA ATTG | 765 CCGACGTG ACTTCCTC GACCGT | 767 TGAGGAGA ATTTACCTT TCCCGC |
| | | |
| | | |
| | | |

FIG. 15CC

| | | |
|---|---|---|
| 600262 | 600262 | 600262 |
| PTGS2 | PTGS2 | PTGS2 |
| prostaglandin-endoperoxide synthase 2; | prostaglandin-endoperoxide synthase 2; | prostaglandin-endoperoxide synthase 2; |
| ACT | ACT | ACT |
| C306G (Val102) | 10G/T | Arg288His |
| 457 ACGTTGGATGA TTCCCTTCCTTC GAAATGC | 454 ACGTTGGATGA GGAAGGTTCTC TCGGTTAG | 451 ACGTTGGATGA TTTACGGTGAA ACTCTGGC |
| 458 ACGTTGGATGC TTTGAGAAGGC TAAAAACC | 455 ACGTTGGATGT GCTGAGGAGTT CCTGGACG | 452 ACGTTGGATGA GTCAAAGGAAG CATACCTG |
| 459 GAAATGCAATT ATGAGTTATGT C | 456 GGTTAGCCGACC AATTGTCA T | 453 TGAAACTCTGG CTAGACAGC A |
| 772 GAAATGCAATT ATGAGTTATGT G | 770 GGTTAGCGACC AATTGTCAT G | 768 TGAAACTCTGG CTAGACAGCA G |
| 773 GAAATGCA ATGAGTTATGT TTATGTGT | 771 GGTTAGCG ACCAATTG TCAGA | 769 TGAAACTC TGGCTAGA CAGCGT |
| | | |
| | | |
| | | |

FIG. 15 DD

| | | | | |
|---|---|---|---|---|
| 188070 | 188070 | 188070 | 188070 | 600262 |
| TBXA2R | TBXA2R | TBXA2R | TBXA2R | PTGS2 |
| thromboxane A2 receptor, platelet; | thromboxane A2 receptor, platelet; | thromboxane A2 receptor, platelet; | thromboxane A2 receptor, platelet; | prostaglandin-endoperoxide synthase 2; |
| CGT | CGT | ACT | ACT | ACG |
| rs5746 | rs5743 | rs5742 | rs4523 | Val511Ala |
| 472 ACGTTGGATGTACCATCGTGGTGTCCCAGC | 469 ACGTTGGATGCTGGGACACCACGATGGTAC | 466 ACGTTGGATGGGTGGTGCATACCTGTAATC | 463 ACGTTGGATGTGCTGAGGCGAGGCTGGAGA | 460 ACGTTGGATGCTTCTGGTAGAAAAGCCTCG |
| 473 ACGTTGGATGAAGAAGATCATGACGACGCC | 470 ACGTTGGATGACGCGCTCCTCCTTCCTCAC | 467 ACGTTGGATGAAACATCACTTCCCCTGTCG | 464 ACGTTGGATGACCTGGAACCAGATCCTGGAC | 461 ACGTTGGATGCCATAAGTCCTTTCAAGGAG |
| 474 CAGCACGCCGCGCTCTTCG A | 471 CGGTGAGGACGAGGCCGC T | 468 TACCTGTAATCCCAGCT A | 465 GCGCGGGCGGAACAGGAT A | 462 TTGGTGAAACCATGGTAGAAG C |
| 782 CAGCACGCCGCTCTCTTCGT | 780 CGGTGAGGACGAGGCCGCT A | 778 TACCTGTAATCCCAGCTA G | 776 GCGCGGGCGGAACAGGATA G | 774 TTGGTGAAACCATGGTAGAAGC T |
| 783 CAGCACGCCGCGCTCTCGAG | 781 CGGTGAGGACGAGGCCGCAG | 779 TACCTGTAATCCCAGCTGC | 777 GCGCGGGCGGAACAGGATGT | 775 TTGGTGAAACCATGGTAGAAGTTG |
| | | | | |
| | | | | |
| | | | | |

FIG. 15EE

| | | | | |
|---|---|---|---|---|
| 188070 | 188070 | 188070 | 188070 | 188070 |
| TBXA2R | TBXA2R | TBXA2R | TBXA2R | TBXA2R |
| thromboxane A2 receptor, platelet; | thromboxane A2 receptor, platelet; | thromboxane A2 receptor, platelet; | thromboxane A2 receptor, platelet; | thromboxane A2 receptor, platelet; |
| ACT | CGT | ACG | ACT | CGT |
| rs5751 | rs5750 | rs5749 | rs5748 | rs5747 |
| 487 ACGTTGGATGT TCGGGCTGCTC TTCTCCAT | 484 ACGTTGGATGA GCGTCAGGAAG CACCAGGA | 481 ACGTTGGATGA CCAGGACCCCG GGTATTGC | 478 ACGTTGGATGA GAGCGCTACCT GGGTATCA | 475 ACGTTGGATGA AGAAGATCATG ACGACGCC |
| 488 ACGTTGGATGT GGTAGACGTGG CACAGGGT | 485 ACGTTGGATGT GGGCCTGCTGC CCCTGCT | 482 ACGTTGGATGC ACCGTGGGGCT GGTGTGG | 479 ACGTTGGATGA CACCAGCCCCA CGGTGGC | 476 ACGTTGGATGT ACCATCGTGGT GTCCCAGC |
| 489 CTGTCCTTCCT GCTGAACACG | 486 AGGACCCCGG GTATTGC | 483 CAGGCCCAGC GCCAGCG | 480 CGCCCCGGCGG TCGCCTC | 477 CGACAGAGACG GCAGCC |
| T | T | C | T | T |
| 792 CTGTCCTTCCTG CTGAACACGA | 790 AGGACCCCGGG TATTGCT | 788 CAGGCCCAGCG CCAGCGC | 786 CGCCCCGGCGGT CGCCTCA | 784 CGACAGAGACG GCAGCCT |
| C | A | T | C | A |
| 793 CTGTCCTTC CTGCTGAA CACGGT | 791 AGGACCCC GGGTATTG CAC | 789 CAGGCCCA CCAGCGC GTG | 787 CGCCCCGGC GGTCGCCT CGC | 785 CGACAGAG ACGGCAGC CAG |
| | | | | |
| | | | | |
| | | | | |

| | validated assays | | | | | |
|---|---|---|---|---|---|---|
| | | | 188060 | 188060 | 188070 | 188070 |
| | | | THBS1 | THBS1 | TBXA2R | TBXA2R |
| | | | thrombospondin I | thrombospondin I | thromboxane A2 receptor, platelet; | thromboxane A2 receptor, platelet; |
| | | ACT | CGT | ACG | ACG | ACT |
| | | rs1866389 | rs8089 | rs2228262 | rs5753 | rs5752 |
| | | 502 ACGTTGGATGT TTCTGCACTAG GTCTGCAC | 499 ACGTTGGATGA ACTGGTTCCTC TAGTGGG | 496 ACGTTGGATGG CAGTGGTAAGT CGCATTGG | 493 ACGTTGGATGG TCAACCCAAAA CCCTGCTG | 490 ACGTTGGATGA GAGCCCCTACT CACCAGAA |
| | | 503 ACGTTGGATGT TAACGCAGATC GAGTTGGG | 500 ACGTTGGATGA AACCCAAGTGC CTTCAGAG | 497 ACGTTGGATGA GGCAATGGCAT CATCTGCG | 494 ACGTTGGATGT CTGCCTGTTCT GAGGATTC | 491 ACGTTGGATGA GGTGGGAGATGA TGGCTCAG |
| | | 504 ATGAGTGTCGA AATGGA | 501 GGGTTAGATGT TCATCTCTG | 498 GCCACGGCACAC CAGGTTCTCA | 495 GCTGCTGATGC CCACTG | 492 GGGCAGCCAA CACACGCT |
| | | G | G | G | C | T |
| | | 802 ATGAGTGTCGA AATGGAC | 800 GGGTTAGATGT TCATCTCTGC | 798 GCCACGCACAC CAGGTTCTCAC | 796 GCTGCTGATGC CCACTGC | 794 GGGCAGCCAAC ACACGCTT |
| | | C | T | A | T | G |
| | | 803 ATGAGTGT CGAAATGG AGC | 801 GGGTTAGA TGTTCATCT CTGAG | 799 GCCACGCA CCAGGT TCTCATTG | 797 TGCCCACT GTC | 795 GGGCAGCC AACACACG CTGGC |

SYSTEMS AND METHODS FOR ANALYZING NUCLEIC ACID SEQUENCES

CROSS-REFERENCE TO RELATED APPLICATIONS

This application claims priority to U.S. Provisional Application Nos. 60/493,238, filed on Aug. 6, 2003, and 60/568,958, filed on May 7, 2004. The contents of both of those provisional applications is incorporated herein by reference in its entirety.

TECHNICAL FIELD

This invention relates to systems and methods for analyzing clinically relevant nucleic acid sequences.

BACKGROUND

The healthcare delivery system has changed remarkably over the past several decades. Clinical laboratories are under increasing pressure to deliver low cost and highly accurate analytical services with the rapid turn-around time required by physicians and patients. Laboratory testing has changed and improved in recent years to meet the challenge. Robotics has been introduced to the laboratory to increase efficiency and reduce the need for human participation, and laboratory instruments have been designed to decrease the biological sample volumes needed to perform various assays. However, more improvement in the clinical laboratory area is required to meet the demands of the ever-changing healthcare system.

SUMMARY

The present invention provides novel automated systems and methods to perform assays on nucleic acid sequences (e.g., clinically relevant nucleic acid sequences). The system can provide assay results quickly, accurately, and in a format easily accessible by health care providers and/or third party payors (e.g., insurance companies). The invention also provides novel and highly accurate assays using mass spectrometry (e.g., matrix-assisted laser desorption/ionization (MALDI)).

In one aspect, the invention provides a system for performing a diagnostic assay on a biological sample. The system includes, as its main components (a) a central controller programmed to: (i) exchange information about the biological sample with an outside system or database; and (ii) exchange information about the biological sample with one or more modules of the system; (b) a sample transfer module for transferring a portion of the sample to a first container; (c) a nucleic acid extraction module for extracting nucleic acids from cells within the portion and for transferring the portion from the first container to a second container; (d) a nucleic acid measurement module for measuring the concentration of nucleic acids in the portion; (e) a PCR preparation module for adding polymerase chain reaction (PCR) reaction materials (e.g., individual nucleotides, primers, polymerase enzymes, and reagents) to the portion; (f) a thermocyling module for amplifying a target sequence and extending a primer in the portion; (g) a primer extension preparation module for adding primer extension reaction materials to the portion; (h) a mass spectrometry preparation module for removing a sample of the portion from the second container to a support (e.g., chip or microwell) for analysis by mass spectrometry; and (i) a mass spectrometry module for analyzing the sample.

The central controller can be a computer system, e.g., a commercially available personal computer system, and can include linking software that enables the central controller to communicate with at least one other module in the system. The system can also include a plate editor module that provides sample information to the PCR preparation module, a transport module comprising one or more robotic arms or tracks to transport a biological sample, or portion thereof, between at least two modules of (a) to (i), and arranged to receive information from and transmit information to the central controller. The system can also include a detection module for detecting the presence of a sample and monitoring the progress of the sample through the system, and arranged to receive information from and transmit information to the central controller. The nucleic acids measurement system can include an ultraviolet light spectrophotometer or a fluorometer. The PCR preparation module can include a pipetting robot, and the thermocycling system can include a thermocyler. The system can further include a computer-readable medium comprising one or more programs for instructing a given module.

The PCR preparation module can include PCR materials, e.g., at least one primer set described herein, e.g., a primer set selected from among SEQ ID NOS:1 to 504, each primer set including two amplification primers and one detection extension primer. The sample transfer system can include a pipetting robot.

In another aspect, the invention provides a method of performing a diagnostic assay on a biological sample. The method includes (a) performing on a biological sample an assay using a clinical assay system; wherein the assay comprises mass spectrometry analysis of a target nucleic acid; and (b) automatically reporting information about the assay from a central controller of the clinical assay system to an outside system or database accessible by at least one health care provider (e.g., at least 2, 10, or more than 10) or at least one third party payor (e.g., at least 2, 10, or more than 10). The clinical assay system can include at least one component selected from the group consisting of: a central controller, a sample transfer module, a nucleic acid extraction module, a nucleic acid measurement module, a PCR preparation module, a thermocyling module, a primer extension preparation module, a mass spectrometry preparation module, and a mass spectrometry module.

In another aspect, the invention provides a method of performing a diagnostic assay on a biological sample. The method includes (a) receiving a biological sample, generating information about the biological sample, and transmitting the information to a central controller; (b) transferring a portion of the biological sample to a first container; (c) extracting nucleic acids from cells within the portion and transferring the portion to a second container; (d) measuring the concentration of extracted nucleic acids in the portion; (e) adding polymerase chain reaction (PCR) materials to the portion; (f) amplifying target nucleic acids in the portion; (g) adding primer extension reaction materials to the portion; (h) extending a detection extension primer in the portion; (i) transferring a sample of the portion from the second container to a support; (j) analyzing the sample and exporting data to the central controller using a mass spectrometry system; and (k) transmitting the data from the central controller to an output device, external system, or database. In certain embodiments, steps (a) to (k) can be performed automatically by an automated system. The automated system can include at least one component selected from the group consisting of: a central controller, a sample transfer module, a nucleic acid extraction module, a nucleic acid measurement module, a PCR preparation module, a thermocyling module, a primer extension preparation module, a mass spectrometry preparation module, and a mass spectrometry module.

In certain embodiments, the diagnostic assay can be an assay for detecting mutations in a gene. The gene can be a gene selected from the group consisting of: 5,10-Methylenetetrahydrofolate Reductase (MTFR); Coagulation Factor II; Coagulation Factor V; hemochromatosis (IFE); and a glucocerebrosidase (GC). fibroblast growth factor receptor 3; aspartoacylase; Glucocerebrosidase; Coagulation Factor VII; Fanconi Anemia, Complementation Group C (FANCC); inhibitor of kappa light polypeptide gene enhancer in b cells, kinase complex-associated protein; acid sphingomyelinase; hexosaminidase; angiotensin i-converting enzyme; adenylate cyclase 9; apolipoprotein A-1; apolipoprotein E; endothelial leukocyte adhesion molecule 1; fc fragment of IGG, low affinity IIIa, receptor; fibrinogen beta chain; coagulation factor II, factor XIII; guanine nucleotide-binding protein beta-3; integrin, alpha-2, glycoprotein Ia/IIa; glycoprotein Ib, platelet, alpha polypeptide; intercellular adhesion molecule 1; glycoprotein Ia/IIa (a2), integrin, alpha-2; platelet glycoprotein Iib, integrin, alpha-2b; glycoprotein IIb/IIIa, integrin, beta-3; 3-hydroxy-3-methylglutaryl-coa reductase; lymphocyte adhesion molecule 1; methylene tetrahydrofolate reductase; plasminogen activator inhibitor 1; platelet alpha-granule membrane protein; transforming growth factor-beta receptor, type III; thrombomodulin; tumor necrosis factor; vascular cell adhesion molecule; coagulation factor II receptor; glycoprotein VI, platelet; purinergic receptor P2Y, g protein-coupled, 1; purinergic receptor P2Y, G protein-coupled, 12; prostaglandin-endoperoxide synthase 1; prostaglandin-endoperoxide synthase 2; thromboxane A2 receptor, platelet; and thrombospondin I.

In other embodiments, the diagnostic assay is an assay for detecting a pathogen in the sample, e.g., a virus, bacterium, or fungus. The virus can be a virus of the family Herpesviridae, e.g., cytomegalovirus (CMV).

In another aspect, the invention provides an method, e.g., an automated method, for detecting mutations in a target gene. The method includes a) amplifying a target sequence using PCR and performing, e.g., automatically, a primer extension reaction using a set of three primers, each set of primers including two amplification primers and one detection extension primer; b) transferring, e.g., automatically, detection extension primers to a mass spectrometry device; and c) determining, e.g., automatically, the molecular weights of the detection extension primers by mass spectrometry following the primer extension reaction, wherein a change in the molecular weight of the extended primer, as compared to a control, indicates the presence of a mutation in the gene. The method can include automatically transmitting information related to the presence of the mutation to a central controller.

In certain embodiments, the gene is a 5,10-Methylenetetrahydrofolate Reductase (MTFR) gene, and the set of three primers is selected from the group consisting of: SEQ ID NOS: 1, 2, and 3; SEQ ID NOS: 4, 5 and 6; SEQ ID NOS: 7, 8, and 9; and SEQ ID NOS: 10, 11, and 12; each set of primers including two amplification primers and one detection extension primer.

In other embodiments, the gene is a Coagulation Factor II gene, and the set of three primers is selected from the group consisting of: SEQ ID NOS: 13, 14, and 15 and SEQ ID NOS: 16, 17 and 18; each primer set including two amplification primers and one detection extension primer.

In still other embodiments, the gene is a Coagulation Factor V gene, and the set of three primers is selected from the group consisting of: SEQ ID NOS: 19, 20, and 21 or SEQ ID NOS: 22, 23 and 24; each primer set including two amplification primers and one detection extension primer.

In yet other embodiments, the gene is a hemochromatosis (HFE) gene, and the set of three primers is selected from the group consisting of: SEQ ID NOS: 40, 41, and 42, SEQ ID NOS: 43, 44 and 45; SEQ ID NOS: 46, 47 and 48; SEQ ID NOS: 49, 50 and 51; SEQ ID NOS: 52, 53 and 54; or SEQ ID NOS: 55, 56 and 57; each set of primers including two amplification primers and one detection extension primer.

In another aspect, the invention includes a method, e.g., an automated method, for detecting a pathogen in a biological sample. The method includes a) amplifying a target sequence using PCR and performing, e.g., automatically, a primer extension reaction using a set of three primers, each set of primers including two amplification primers and one detection extension primer; b) transferring, e.g., automatically, detection extension primers to a mass spectrometry device; and c) determining, e.g., automatically, the molecular weights of the detection extension primers by mass spectrometry following the primer extension reaction, wherein a change in the molecular weight of the extended primer, as compared to controls, indicates the presence of a pathogen in the sample. The controls can include an internal control for determining the amount of the pathogen in the sample.

In some embodiments, the pathogen is cytomegalovirus (CMV), and the three primers are selected from the group consisting of: SEQ ID NOS: 25, 26, and 27; SEQ ID NOS: 28, 29 and 30; SEQ ID NOS: 31, 32, and 33; SEQ ID NOS: 34, 35, and 36; SEQ ID NOS: 37, 38, and 39; and SEQ ID NOS: 58, 59, and 60; each primer set including two amplification primers and one detection extension primer.

In another aspect, the invention includes an isolated DNA selected from the group consisting of SEQ ID NOS.:1 to 504.

In still another aspect, the invention includes a kit that includes at least one primer set described herein, e.g., a primer set selected from among SEQ ID NOS: 1 to 504, each primer set including two amplification primers and one detection extension primer, and instructions for using the primer set to detect or analyze a target nucleic acid sequence in a biological sample. For example, instructions can be provided to describe how to use the primers to detect the presence of, or identify mutations in, a particular nucleic acid sequence or gene. As another example, the instructions can describe how to use the primers to detect the presence of a pathogen (e.g., a virus, bacterium, and/or fungus), the quantity of the pathogen, and/or the genotype of the pathogen.

In yet another aspect, the invention includes a computer readable medium that includes a program for instructing a central controller in an automated system for performing an assay on a biological sample to: (a) receive a biological sample, generate information about the biological sample, and transmit the information into a central controller; (b) transfer a portion of the biological sample to a first container; (c) extract nucleic acids from cells within the portion and transfer the portion to a second container; (d) measure the concentration of extracted nucleic acids in the portion; (e) add polymerase chain reaction (PCR) materials to the portion; (f) amplify target nucleic acids in the portion; (g) add primer extension reaction materials to the portion; (h) extend a detection extension primer in the portion; (i) transfer a sample of the portion from the second container to a support; (j) analyze the sample and exporting data to the central controller using a mass spectrometry system; and (k) transmit the data from the central controller to an output device, external system, or database.

Unless otherwise defined, all technical and scientific terms used herein have the same meaning as commonly understood by one of ordinary skill in the art to which this invention belongs. Although methods and equipment or software similar or equivalent to those described herein can be used in the practice of the present invention, suitable methods, equipment, and software are described below. All publications and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features and advantages of the invention will be apparent from the description and drawings, and from the claims.

DESCRIPTION OF DRAWINGS

FIGS. 13A1-13A3 is a set of mass spectra in a CMV quantitative assay on samples containing 400 CMV copies/ml.

FIGS. 13B1-13B3 is a set of mass spectra in a CMV quantitative assay on samples containing 4000 CMV copies/ml.

FIGS. 13C1-13C3 is a set of mass spectra in a CMV quantitative assay on samples containing 40,000 CMV copies/ml.

FIGS. 13D-13D3 is a set of mass spectra in a CMV quantitative assay on samples containing 400,000 CMV copies/ml.

FIGS. 13E1-13E3 is a set of mass spectra in a CMV quantitative assay on samples containing 4,000,000 CMV copies/ml.

FIGS. 13F1-13F3 is a set of mass spectra in a CMV quantitative assay on samples containing 40,000,000 CMV copies/ml.

FIGS. 13G1-13G3 is a set of mass spectra in a CMV quantitative assay on samples containing 400,000,000 CMV copies/ml.

FIGS. 15A-15GG is a table that lists a number of genetic targets for the assays of the invention, along with exemplary primers for those targets.

DETAILED DESCRIPTION

The invention provides a new highly automated system for performing clinical assays, optionally with automatic billing to third party providers such as insurance companies. The invention also provides novel assays using mass spectrometry (e.g., matrix-assisted laser desorption/ionization (MALDI). The assays are highly accurate and can detect, for example, sequence variations (e.g., mutations and/or polymorphisms) and foreign sequences (e.g., viral sequences) incorporated into a target gene. The assays are also useful for infectious disease/pathogen testing.

The entire process, or portions thereof, can be automated, i.e., performed by machine(s). Accordingly, the present invention also includes a high-throughput process for performing the assays described herein. Thus, the new system can perform dozens (e.g., 96, 128, 384) of different assays on dozens of different biological samples at the same time.

Clinical Assay System

Overview of System

Figure 1:
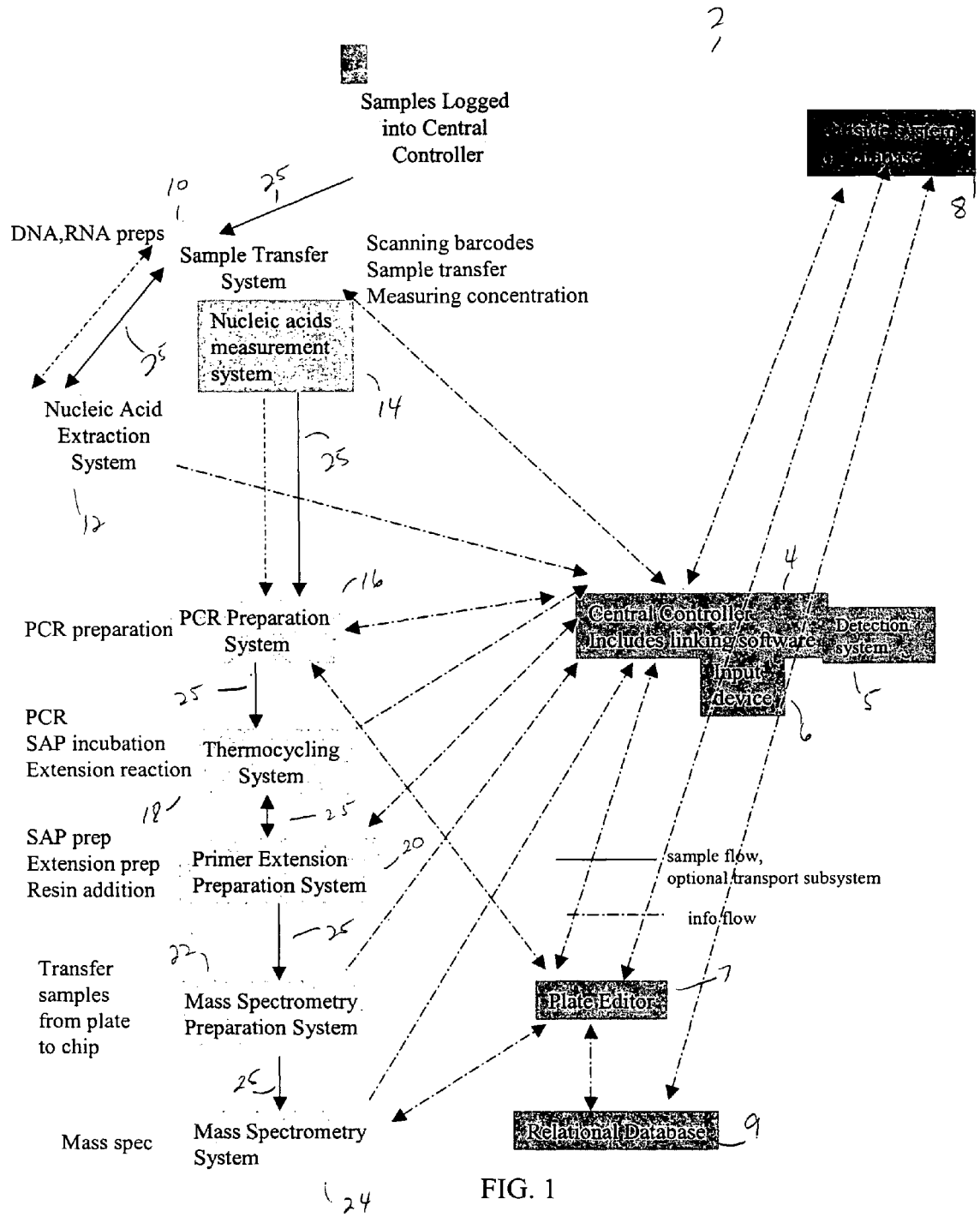
FIG. 1 is a diagram illustrating the main components of a clinical assay system and the flow of biological samples and information through the system.

FIG. 1 provides an overview of the clinical assay system 2 of the present invention. The clinical assay system includes, as its main components, the following modules. A central controller 4 for exchanging information about the biological sample with an outside system or database 8 and with one or more modules or systems within clinical assay system, and an input device 6; a sample transfer system 10 for transferring a portion of the sample to a first container; a nucleic acid extraction system 12 for extracting nucleic acids from the portion and for transferring the portion from the first container to a second container; a nucleic acid measurement system 14 for measuring the concentration of nucleic acids in the portion; a PCR preparation system 16 for adding polymerase chain reaction (PCR) reaction materials to the portion; a thermocycling system 18 for amplifying a target sequence and extending a primer in the portion; a primer extension preparation system 20 for adding primer extension reaction materials to the portion; a mass spectrometry preparation system 22 for removing a sample of the portion from the second container to a platform for analysis by mass spectrometry; and a mass spectrometry system 24 for analyzing the sample.

The central controller is capable of controlling one or more system modules, collecting and organizing data obtained from one or more of the system modules and an outside system or database, and of sending data to one or more of the system modules and an outside database (e.g., a database accessible by healthcare providers or third parties) or system (e.g., an outside computer through which health care providers or third parties can access the data). The input device 6 associated with the central controller can be a bar code reader. The system can optionally include a detection system 5 for detecting and tracking a sample as it progresses through the system. The system can also include a transport subsystem 25, e.g., a system of one or more robotic arms and/or tracks, for transporting samples between two or more modules within the system.

Central Controller

Typically, the central controller 4 is a computer system. The computer systems that can be used are commonly available personal computers having read-write memory, or industrial counterparts thereof. The central controller is provided with a suitable input device 6 such as a keyboard, touch screen, card reader, bar code scanner, or another computer (e.g., for inputting biological sample processing instructions and patient identification information).

The central controller 4 is run by linking software, which directs the central controller to receive information from, and/or transmit information to, each of the modules in the overall system. For example, the central controller can be configured to exchange information with one or more modules within the clinical assay system, and to relay that information to one or more other modules. Such information may include information about a biological sample, e.g., sample identification, information as to which assay(s) is to be/has been performed on a sample, and the location of a sample within the clinical assay system and within a given batch of samples being processed.

The central controller 4 is also configured to exchange information with outside systems and/or databases 8 (i.e., systems or databases not part of the clinical assay system). This configuration allows the central controller to report, e.g., the results of the clinical assays described herein, along with other data, e.g., billing amounts, patient identification, and other data to health-care providers (e.g., technicians, nurses, physicians) and/or third parties (e.g., insurance providers) at other sites. Reporting can occur automatically. Exemplary of outside systems are systems capable of interfacing directly with the central controller, or with a database accessible by both the outside system and the central controller. For example, Meditech™ provides a laboratory application that allows multisite and/or multifacility specimen tracking, through which the central controller can exchange information with outside systems.

Sample Transfer Module

The sample transfer system 10 can be any system capable of receiving a biological sample, e.g., a blood sample, removing an aliquot of the sample, and placing the aliquot into one or more receptacles. Exemplary systems are pipetting robots, such as the Genesis® Freedom™ Automated Workstation. The system is capable of scanning sample tube barcodes and multiwell (e.g., 96-well) plates, and creating a file that indicates where on the multiwell plate a sample is located following the transfer. The file can include information such as the barcodes of scanned sample tubes, the location of these samples on the multiwell plate, the volume transferred from the sample tube to the plate, and overall identifying information (e.g., a barcode) for of the multiwell plate (called DNA plate).

Nucleic Acid Extraction Module

The nucleic acid extraction system 12 can be any system capable of carrying out techniques, such as those described herein, for purifying nucleic acids (i.e., DNA and/or RNA) from one or more biological samples. An example of such a system is the BioRobot® MDx produced by Qiagen.

Nucleic Acids Measurement Module

The nucleic acids measurement system 14 can be any system capable of measuring the concentration of nucleic acids in a sample. For example, the system can be a commercially available ultraviolet (UV) light spectrophotometer, which is capable of determining the concentration of nucleic acids using optical density measurements. As another example, the system can be capable of measuring the UV-induced fluorescence of dye (e.g., ethidium bromide or Pico Green) intercalated into the nucleic acid, such as a fluorometer. The Genesis® Freedom™ Automated Workstation produced by Tecan can include such a fluorometer. The nucleic acid measurement system can be associated with (e.g., a part of) the sample transfer system, or it can be a stand-alone module.

PCR Preparation Module

The PCR preparation system 16 can be any system capable of adding appropriate materials, e.g., enzymes (e.g., Taq polymerase), nucleic acid primers, individual nucleotides, and reagents, to an aliquot in preparation for amplifying a target sequence in the aliquot. The PCR preparation also prepares appropriate control reaction mixes. Examples of such systems are the Genesis® Automated Workstation and the Tecan TeMO™ multi-pipetting module.

Overall, the PCR preparation system is capable of performing at least two steps. The first is to dispense appropriate assay mixes. Assay mixes can be prepared by an individual, e.g., a technician, or by a robot, according to typical laboratory procedures, and placed into holders. These PCR preparation system dispenses the mixes from the holders to a position on a second multiwell (e.g., 384) plate, according to instructions (e.g., sample identification and assays to be performed) it receives from a plate editor 7 (described in detail below). The second is to add samples to the appropriate assay mix. Using the file received by the PCR preparation system 16 from the sample transfer system 10, the PCR preparation system transfers samples from the first multiwell (e.g., 96 well) plate to the second multiwell (e.g., 384 well) plate. In this way, the PCR preparation system is able to transfer samples from a first plate to a second plate, while keeping track of the location of the samples, and to ensure that the appropriate assays are performed on each sample.

Thermocycling Module

The thermocycling system 18 can be any system capable of performing PCR reactions, e.g., PCR amplification and/or primer extension reactions, and is typically a commercially available thermocycler. Exemplary systems include the GeneAmp PCR System 9700 manufactured by Applied Biosystems, the Perkin Elmer 2000 PCR thermocycler, and the PTC-200 thermocycler manufactured by MJ Research.

Primer Extension Preparation Module

The primer extension preparation system 20 can be any system capable of adding appropriate materials, e.g., Shrimp Alkaline Phosphatase (SAP; to dephosphorylate unincorporated dNTPs), extension primers (e.g., the extension primers described herein), and appropriate mixtures of dNTPs and ddNTPs, to an aliquot in preparation for performing primer extension reactions. An exemplary system is the Multimek™ manufactured by Beckman-Coulter Mass Spectrometry Preparation Module The mass spectrometry preparation system 22 can be any system capable of removing a sample of an aliquot and placing the sample on a support, e.g., a chip, for analysis by mass spectroscopy. The support can be composed of any material known to those skilled in the art to be usable in mass spectrometry, e.g., silicon, plastic, glass, and/or ceramic. A wide variety of chips are commercially available. Exemplary of chips is the Sequenom® SpectroCHIP™, which is supplied in 384 well format and are pre-spotted with a specially formulated matrix assisted laser desorption ionization (MALDI) matrix. The matrix can be of any composition known in the art of mass spectrometry, e.g., α-cyano-4-hydroxy cinnamic acid (CHCA), 2,4,6-trihydroxy acetophenone (THAP), or 3-dydroxypicolinic acid (3-HPA) in ammonium citrate, the choice of which will depend, e.g., on the mass spectrometry system used and the assay to be performed. Exemplary of the mass spectrometry preparation systems is the Sequenom® SpectroPOINT™, a nanoliter sample dispensing instrument.

Mass Spectrometry Module

The mass spectrometry system 24 can be any commercially available mass spectrometer. The clinical assay system of the present invention can be configured to utilize mass spectrometer formats including matrix assisted laser desorption ionization (MALDI), electrospray (ES), ion cyclotron resonance (ICR) and Fourier Transform. In one embodiment, maMALDI is utilized in the clinical assay system of the present invention. An exemplary mass spectrometry system is the Sequenom® Autoflex™ Mass Spectrometer.

With MALDI mass spectrometry, various mass analyzers can be used, e.g., magnetic sector/magnetic deflection instruments in single or triple quadrupole mode (MS/MS), Fourier transform and time-of-flight (TOF) configurations as is known in the art of mass spectrometry. For the desorption/ionization process, numerous matrix/laser combinations can be used. Ion-trap and reflectron configurations can also be employed. In one embodiment of the present invention, MALDI-TOF is employed to analyze the biological samples.

Transport Subsystem

Optionally, the clinical assay system includes a transport system 25. The transport system can be capable of (i) transporting containers, e.g., containing biological samples, from a source (e.g., a separate site in which biological samples are obtained from a patient) to the clinical assay system; (ii) transporting containers between at least two modules within the clinical assay system; and/or (iii) transporting containers away from the clinical assay system to a predefined destination after completion of the assay. The transport system is capable of communicating with the central controller so the central controller can direct the transport system and/or receive information as to the location of sample within the clinical assay system. The transport system can comprise one or more robotic arms or tracks, or a combination of robotic arms and tracks.

Detection System

Optionally, the clinical assay system includes a detection system 5 for detecting the presence of a biological sample and monitoring the progress of the sample through the system. The detection system is capable of receiving information from and transmitting information to the central controller. The detection system can include a network of sensors, e.g., barcode readers, reed switches, weight systems (where the detector detects the presence of a sample by its weight); or optical interrupters, or combinations thereof, arranged throughout the clinical assay system, each of which are capable of transmitting information, directly or indirectly, to the central controller.

Software

The clinical assay system includes novel software for adapting one or more modules to be used in the system. For example, the central controller includes a novel software program to provide an interface between itself and an outside system or database (e.g., Meditech). In addition to causing the central controller to receive data from an outside source, the software causes the central controller to send information (e.g., automatically) about the clinical assays (e.g., the results and/or billing information) to at least one outside system (e.g., a computer not associated with the clinical assay system) or at least one outside database (e.g., a Meditech database). This configuration allows the clinical assay system to directly report results and billing information to at least one healthcare provider, at least one third party payor (e.g., an insurance company), or to both.

Optionally, the software can be written such that the central controller performs a final check of assay results before sending to the outside system or database, halting transmission of the data and/or alerting a technician of potential problems with the results. For example, where two samples from the same patient are submitted for duplicate analyses by the clinical assay system, the interface program can include a checking scheme to ensure that the results of the duplicate analyses agree with each other. If the duplicates do not agree (e.g., where both a positive and a negative result are reported to the central controller by the clinical assay system), the interface program can halt transmission of the results so that the mass spectroscopy data can be reanalyzed or to allow the assays to be performed again.

The central controller also includes a software program for linking at least one other module of the system to the central controller ("linking software"). The module(s) also include linking software allowing the module(s) to communicate with the central controller. For example, the linking software can allow the central controller to control the module (e.g., to instruct the module as to when and whether to execute a function), and to provide to the module(s) information about the biological sample (e.g., the tests to be performed on the sample). The linking software also allows the central controller to receive information from the module(s), e.g., assay results, information about the location of the sample, and the like.

Also included within the clinical assay system is plate editor software 7. The plate editor software can be loaded on the central controller and/or on a separate computer, e.g., a second computer system. The plate editor software can receive information from an outside system or database, such as patient information, tests to be performed, billing information, etc., and create a file that maps on a hypothetical 384-well plate where each assay for each sample will be located, and links this location to all data and information associated with each assay (one sample can have several assays, e.g., 1, 2, 3, or 4 assays). In this way, the plate editor software "maps out," in advance of processing a batch of samples through the clinical assay system, an arrangement of assays on a 384-well plate. This file can be used by other modules in the system, e.g., the sample PCR preparation system and the mass spectrometry system, to track the samples and their associated assay results as they move through the system.

Also included is a relational database 9, e.g., Oracle software. Like the plate editor software, the relational database can be loaded on the central controller and/or a separate controller, e.g., a second computer system. The relational database stores information from the plate editor and from an outside database or system (e.g., Meditech), and can be accessed by the outside system or database.

The sample transfer system 10 can include software causing it to receive at least one biological sample (e.g., a batch of samples), to obtain information about each sample (e.g., from a bar code associated with the sample), and to place an aliquot of the sample into a multiwell plate while keeping track of the location of the aliquot within the multiwell (e.g., a 96 well) plate. The software can instruct the sample transfer system to compile the information (e.g., identity of the sample and the location of the sample in the multiwell plate) into a file, which can then be transmitted to the central controller and/or other modules, e.g., the PCR preparation system.

An example of software that can be used, for example, with sample transfer system 10 is attached hereto as Appendix 1 and is described in detail below.

OutFileGenerator.exe

Laboratory software, e.g., Gemini™ (Tecan) software, allows users to control robotic and liquid handling functions and to write specific application scripts based on the user's needs. OutFileGenerator.exe is part of the Gemini program that performs specimen transfer from original bar-coded tubes into a 96-well destination plate, prior to extraction. First, all racks, test tubes, and destination plates are scanned by the barcode scanner. The positions of all racks, tubes, and destination plates, are loaded to the file C:\Program Files\Gemini\Output\" created by Gemini the function. OutFileGenerator.exe creates another file, called "outputdestID.csv" (destID=barcode of the destination plate), by rewriting the original "Output" file such that it contains the following information in a consistent order: DNA ID, DestWellID (well number in the destination plate), Dest ID (ID of destination plate (as determined by the barcode of the plate), SourceWell ID (position of the tube in the rack), and Source ID (barcode of the rack).

Because samples are often transferred from one plate to another during the extraction process, both plates can be assigned the same barcode number. Alternatively, a script similar to "output file generator" can be used to rename the file and destination plate ID after extraction is complete.

The PCR preparation system can include software causing it to obtain information (e.g., sample identification and assays to be performed on each sample) about each sample from the sample transfer system and the plate editor, and causing it to add specific PCR materials (e.g., specific primers, nucleotides, etc.) to each sample. In this way, the PCR preparation system is instructed as to which test(s) is to be performed on a given sample, and the PCR preparation system adds the materials appropriate for performing that test(s).

In particular and as discussed above, the software can cause the PCR preparation system to (a) dispense appropriate assay mixes; and (b) to add samples to the appropriate assay mix. Examples of programs instructing functions (a) and (b) are attached hereto as Appendix 2 and 3, respectively, and are described in further detail below.

(a) Assay Transfer.gem

Assay Transfer.gem is an exemplary Gemini program (Appendix 2) for dispensing an aliquot 3 µl, e.g., of assay mixes to PCR plates, e.g., 384-well plates, (i.e., performing function (a) as discussed above). It uses a file called "input file," which is exported from Plate Editor MassARRAY (Sequenom). This file contains all information about the PCR plate, e.g., the location on a plate a particular assay will be run and into which a particular DNA sample should be placed, as well as the barcode of the plate. The following fields are exported from the Plate Editor and are contained in "input file": Plate ID—PCR plate barcode number; Group ID—name of the MassARRAY file; Assay ID—name of the assay; Sample ID—specimen's barcode; and Well Position—position in the plate. Hence, each position in the plate(s) is described by the fields described above, i.e., plate ID, Assay ID, and Sample ID. This file is used in both Assay Transfergem and DNA Transfergem, which is described in further detail below.

In this Gemini program are imbedded three executable scripts written in Visual Basic (VB): PCRMix Transfer.exe, Move File Assays.exe, and MoveFileProcessed.exe. Generally, in this program, Module 1 changes the name of a letter/number well (e.g., A1, A2) description, into a well number for a 96 well plate; Module 2 performs the same function as Module 1, but for a 384 well plate; Module 3 includes comments for module 4 execution; and Module 4 generates a worklist for making the transfer of assay mixes into a 384 well plate.

Specifically, the events as dictated by the program are as follows:

1) the barcode of the PCR plate is read by barcode reader (Gemini script);
2) the major part of the program is run by PCRMix Transfer.exe, VB script:
   a) the input file is opened and the column "Well Position" containing alphanumeric characters is divided into two columns: one contains alpha-characters and the second contains numerical characters;
   b) the file is sorted by column containing numerical characters, meaning that assay mixes will be dispensed later by columns. Hence, all 8 tips will be used at the same time in most cases, speeding up the process of dispensing PCR mixes;
   c) module 2 PCR Mix takes a combination letter/number well description and converts it to a well number for a plate (e.g., A1=1);
   d) the Gemini program loads "worklist," and Module 3 contains directions to read the .ini file which describes the location and names of: Input File=C: Gemini\Data\Assays\Input File; Worklist file=C:\ Gemini\Data\Assays\assays.gwl; Source Type=Trough 1 column; Dest Plate=384 well Marsh; Volume=3 (volume of assay mix dispensed); and WashWorklist; and
   e) module 4: (1) opens the sorted Input file and parses it to determine the well into which a particular PCR mix goes into; (2) gives information about where to find the PCR Mix—the ID of the PCR Mix (assay) is written in Gemini file by naming the Trough with the PCR Mix ID; (3) directs when, where and how washes are performed. Each wash is carried out as follows: (i) aspiration of 290-400 µl of bleach; (ii) tips are immersed in the bleach for 10 seconds; (iii) bleach is dispensed into wash station; followed by (iv) three washes with water, for example: 10 ml, 5 ml, 5 ml each. Bleach washes of the tips are performed if the Mix ID is different. A full wash (both bleach and water) is always performed at the end of worklist.
3) the data from the run is exported into an output file by the "Export Data" command in the Gemini program;
4) the worklist is copied and saved under a barcode.txt file name (i.e., barcode of 384-well PCR plate) by Move File Assays.exe. Hence, the worklist file is emptied and ready for the next run; and
5) the above file is moved from the original directory into an Output Processed Directory by MoveFileProcessed.exe script.

In short, the following commands are contained in the Gemini program: number of plates to be run (in Gemini); reading of barcodes (instructions in Gemini); Execute: C:\programFiles\PCRMixTransfer\PCRMix Transfer.exe; Load Worklist;
C;Gemini\Data\Assays\assays.gwl; Execute loaded worklist; Export Data; Execute:
C:\ProgramFiles\\Project\Move File Assays.exe; and Execute:
C:\ProgramFiles\MoveFileProcessed\MoveFileProcessed.exe.

(b) DNA Transfer.gem

The DNA Transfer.gem program (Appendix 3) is an exemplary Gemini program for obtaining an aliquot, e.g., 2 μl, of DNA aspirated from DNA plate, e.g., a 96-well plate, and dispensing it to PCR plate, e.g., a 384 well plate, which contains a particular PCR mix. There are four executable scripts written in VB in this program: DNATransfer.exe; MoveFile.exe; FinalOutputConverter.exe; and CompareFiles.exe.

Generally, the program uses two files. The first, "InputFile," is exported from the Plate Editor of MassARRAY software saved in csv format (which is the same file used in AssayTranfer.gem for dispensing the PCR mixes). This file dictates where the DNA will be dispensed in the PCR plate (e.g., 384-well plate) by giving for each specimen ID an exact destination, i.e., a specific plate and well. The second, "Output barcode#.csv," (made on Freedom™ (Tecan) by OutFileGenerator.exe) specifies the location of DNA samples in a particular 96-well DNA plate. Based on these two files, a worklist is prepared, which dictates where the DNA samples are dispensed to the PCR plate (destination plate).

In short, the following commands are contained in this Gemini program: How many DNA plates will be run (in Gemini)?; How many PCR plates will be run (in Gemini)?; Reading the plates barcodes (instructions in Gemini); Execute: C:\programFiles\DNATransfer\DNATransfer.exe; Loading worklist C:\Gemini\Data\DNAtransfer\DNA list gwl; Execute loaded worklist; Export Data; Execute: C:\programFiles\MoveExistFiles\MoveFile.exe; Execute: C:\programFiles\FinalOutputConverter\FinalOutputConverter.exe; and Execute: C:\programFiles\CompareFiles\CompareFiles.exe The details of the program are provided below.

1) At the start of the program, there are instructions written in Gemini which ask: how many DNA plates will be run? How many PCR plates will be run? Instructions for reading the barcodes of each DNA plate and PCR plate are provided.

2) The major part of the DNA Transfer.gem is run by DNA Transfer.exe inVB script:

Module 1: instructs that the 'input file' is opened and the column "Well Position" containing alphanumeric characters is divided into two columns: one contain alpha-characters characters and second containing numerical characters; the file is sorted by column containing numerical characters first and then by column with alpha-characters.

Module 2: instructs conversion of combination letter/number well descriptions to a well number for a 384 well plate. (for example A1=1).

Module 3: contains instructions to read the .ini file which describes the location and names of: DataFile-=Input File; Worklist;Source Type=96 well plate Sarstedt; Destination Plate=384-well Marsh; and Volume=2 (volume of dispensed DNA).

Module 4: (a) contains a loop that takes each DNA ID from the 'inputfile' and goes through all files in the Output directory (containing Output'barcode#.csv" files) looking for the match of the ID to determine which well of the source plate from which a sample should be taken; and (b) creates a workfile containing all information needed for each DNA transfer, such as DNA ID, source well number, source plate type, source plate ID (that is a barcode of the 96-well DNA plate), volume to transfer, destination plate type, destination plate ID (barcode of 384-well PCR plate), destination well and tip number to be used; (c) CreatesTextFile("C:\ Gemini\Logfiles\ DNAIdLog.txt"); (d) instructs when, where and how the washes are performed. Each wash is carried out as follows: (i) aspiration of 290-400 μl of bleach; (ii) tips are immersed in the bleach for 10 seconds; (iii) bleach is dispensed into wash station; followed by (iv) three washes with water, for example: 10 ml, 5 ml, 5 ml each. Bleach washes of the tips are performed if the Mix ID is different. A full wash (both bleach and water) is always performed at the end of worklist; and e) instructs termination of the run if it cannot file DNA in the outputbarcode file .csv plate, giving the message: "DNA Ids missing! See DNAIdLog, fix files, and rerun"; (f) when all DNAs are found, the worklist is made and the files Output'barcode#.csv are moved from :\Gemini\Output directory to C:\Gemini\OutputProcessed.

3) Worklist is loaded to Gemini and executed by Gemini command.

4) Worklist is copied and saved under 'outbarcode.txt' file name (barcode of 384-well PCR plate) by MoveFile.exe. Hence, the worklist file is emptied (cleaned out) and ready for the next run.

5) FinalOutputConverter.exe module 1 converts the original output file and puts it in a readable format containing: "DNA ID," "Destination Well ID," "Destination plate ID," "Source Well ID," and "Source Plate Id." Module 2 converts well number from integer (1) back to alphanumeric well number (A1). Module 3 scans the directory and looks for files and converts them by adding the date to the files.

6) In addition to checking DNA IDs between two files: 'InputFile' and 'BarcodeOutput file(s)' before the transfer starts (DNATransfer.exe module 4) CompareFiles.exe compares the "InputFile" with LogFile for correctness in transfer from source 96-well plate(s) to destination 384-well plate(s). It gives an error message if DNA is found to be missing.

The primer extenstion preparation system can include similar software, i.e., software that causes it to receive information about each sample and the assays to be performed, so that the primer extension preparation system adds the specific primer extension reaction materials (e.g., specific detection extension primers, termination mixes, etc.) appropriate for performing that test(s) on the sample.

Implementation

The methods and systems described herein can use a communications network to transmit information from the system (e.g., from the central controller) to healthcare providers and/or insurance companies. These communications networks can use either wired or wireless interfaces. For example, a communications network can be the internet, or a wire or optical cable.

The new methods can be carried out using various means of data storage. For example, the information or data relating to each sample can be stored on a computer-readable medium or in a computer memory. The information can be transferred physically on diskettes or electronically, e.g., on a dedicated intranet, or on the Internet. The data can be encrypted using standard encryption software from such companies as RSA Security (Bedford, Mass.) and Baltimore®. The data can be stored in various formats, e.g., spreadsheets or databases.

The invention can be implemented in hardware or software, or a combination of both. The invention can be implemented in computer programs using standard programming techniques following the method steps and figures disclosed herein. The programs (or scripts) should be designed to execute on the various modules or in the central controller. The output information is transmitted to one or more output devices such as a printer, or a CRT or other monitor, or a web page on a computer monitor with access to a website.

Each program used in the new methods can be implemented in a procedural or object oriented programming language to communicate with a computer system. However, the programs can be implemented in assembly or machine language, if desired. In any case, the language can be a compiled or interpreted language.

Each computer program can be stored on a storage medium or device (e.g., ROM or magnetic diskette) readable by a general or special purpose programmable computer, for configuring and operating the central controller when the storage media or device is read by the controller (or a given module) to perform the steps or procedures described herein. The system can also be considered to be implemented as a computer-readable medium, configured or encoded with a computer program, where the storage medium so configured causes a computer to operate in a specific and predefined manner to perform the functions described herein.

Although any communications network can be used, the Internet provides a useful choice to transmit data. In this method, files of data are transmitted from the system to a user in encrypted form, with each party privy to the decryption technique necessary to process the particular data, ending with the completely processed data being sent to the health care provider over the Internet in a similarly encrypted manner. In this method, the entire process can be performed in minutes once the biological sample has been obtained and processed.

Electronic Data Storage and Processing

The data is typically provided in digital form that can be transmitted and read electronically, e.g., via the Internet, on diskette, or any other mode of electronic or non-electronic communication.

As used herein, "sequence information" refers to any nucleotide and/or amino acid sequence information, including but not limited to full-length nucleotide and/or amino acid sequences, partial nucleotide and/or amino acid sequences, or mutated sequences. Moreover, information "related to" the sequence information includes detection of the presence or absence of a sequence (e.g., detection of a mutation or deletion), determination of the concentration of a sequence in the sample, and the like. These sequences can be read by electronic apparatus and can be stored on any suitable medium for storing, holding, or containing data or information that can be read and accessed by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon sequence information.

As used herein, the term "electronic apparatus" is intended to include any suitable computing or processing apparatus or other device configured or adapted for storing data or information. Examples of electronic apparatus suitable for use with the present invention include stand-alone computing apparatus; communications networks, including local area networks (LAN), wide area networks (WAN), Internet, Intranet, and Extranet; and local and distributed processing systems.

As used herein, "stored" refers to a process for encoding information on the electronic apparatus readable medium. Those skilled in the art can readily adopt any of the presently known methods for recording information on known media to generate manufactures comprising the sequence information.

A variety of software programs and formats can be used to store the sequence information on the electronic apparatus readable medium. Any number of data processor structuring formats (e.g., text file or database) can be employed to obtain or create a medium having recorded thereon the sequence information.

By providing sequence information in computer-readable form, one can routinely access the sequence information for a variety of purposes. For example, one skilled in the art can use the sequence information in readable form to compare a specific sequence with the sequence information stored within a database. Search means are used to identify fragments or regions of the sequences that match a particular sequence.

The present invention therefore provides a medium for holding instructions for performing a method for determining whether an individual has a specific disease or disorder or a pre-disposition, for a specific disease or disorder based on genetic information.

Methods of Using the Clinical Assay System

The new methods make use of the new clinical assay systems described herein. One method 26 of using an exemplary configuration of the clinical assay system is described below and illustrated in FIG. 2.

Figure 2:
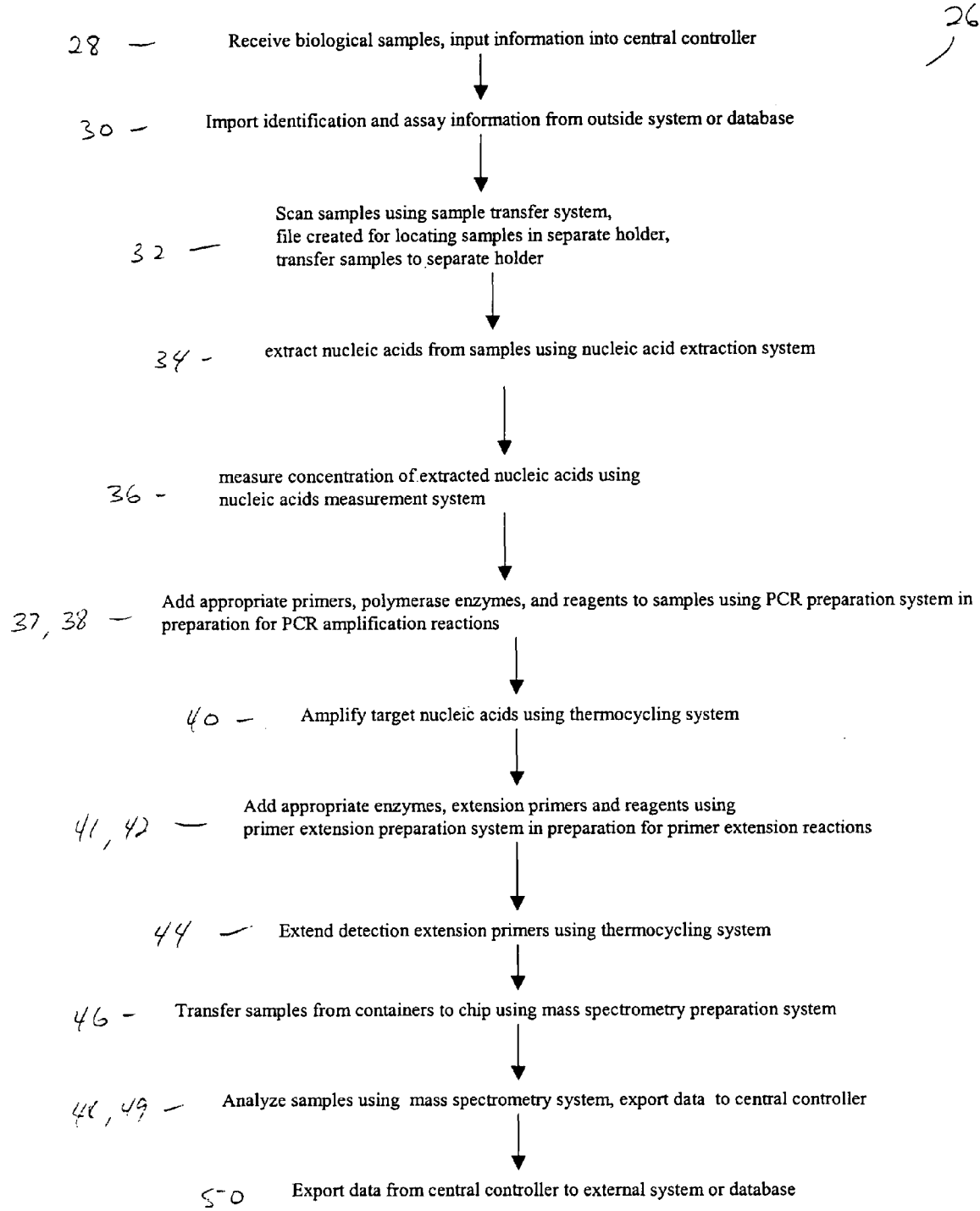
FIG. 2 is a flow diagram illustrating the steps of the clinical assay system.

Biological samples to be processed (e.g., blood samples) typically arrive at the clinical assay system in multiple containers such as test tubes. Information about the samples (e.g., patient identification, tests to be performed, expected turnaround time) can accompany the sample and/or can be encoded within a barcode associated with the sample. Referring to FIG. 2, the information is first entered into the central controller (step 28) and/or the plate editor, e.g., using a keyboard or bar code scanner, and optionally coordinated (e.g., matched) with information about the sample received by the central controller from an outside system or database (step 30) (e.g., via a Meditech interface). Information obtained by the central controller can be transmitted to one or more modules of the clinical assay system immediately and/or at appropriate intervals during operation of the system.

The biological samples are deposited in holders in the sample transfer system. Aliquots of the biological samples are removed from the biological sample containers and deposited into multiwell plates by the sample transfer system (step 32). The sample transfer system can include a subsystem, e.g., a barcode scanner and appropriate software, capable of tracking where each aliquot of a biological sample is deposited within the multiwell plate. The information generated via the subsystem can be transmitted to the subsequent modules in the system and/or to the central controller.

The plate containing the aliquots is then transferred to the nucleic acid extraction system for DNA or total nucleic acids extraction (step 34). Following execution of the extraction process, the aliquots are transferred by the nucleic acid extraction system to a different multiwell plate.

The plate containing extracted nucleic acid samples is then transferred to the nucleic acid measurement system wherein the concentration of extracted nucleic acids in each aliquot is measured (step 36). The nucleic acid measurement system can include a subsystem, e.g., appropriate software, for assigning the data generated during the measurement process to each individual aliquot and transmitting this data to the central controller.

The plate is then transferred to the PCR preparation system. The PCR preparation system performs at least related two steps: (1) dispensing appropriate assay mixes, which include all components required for carrying out PCR reactions (e.g., buffers, dNTPs, primers, and polymerase enzyme(s)) (step 37); and (2) dispensing nucleic acid samples, e.g., control and patient DNA samples (step 38). The PCR preparation system can also include a subsystem, e.g., appropriate software, which allows the PCR preparation system to receive from the central controller information specifying which assay(s) is to be performed on a given aliquot, to locate the aliquot on the plate, and to dispense appropriate primers and nucleic acid samples based on those specifications into the aliquot.

The plate is then transferred to the theromcycling system for amplification of the target nucleic acid sequence (step 40). The PCR reactions can be performed using any appropriate thermocycling protocol, e.g., a protocol as described in the Examples section of the present application.

Following execution of the PCR reaction, the plate is transferred from the thermocycling system to the primer extension preparation system. The primer extension preparation system adds a dephosphorylating enzyme, e.g., Shrimp Alkaline Phosphatase (SAP), to each aliquot to dephosphorylate unincorporated dNTPs leftover from the PCR reaction (step 41). The plate is then optionally incubated. An extension mix, which includes the extension primer, appropriate enzymes, and a mixture of dNTPs and ddNTPs, is added to each aliquot by the primer extension preparation system (step 42). The primer extension preparation system can also include a subsystem, e.g., appropriate software, which allows the primer extension preparation system to receive from the plate editor information specifying which assay(s) is to be performed on a given aliquot, to locate the aliquot on the plate, and to dispense into each aliquot appropriate extension primers and mixtures of dNTPs and ddNTPs based to those specifications.

The plates are then transferred back to the thermocycling system, or to a second thermocycling system (e.g., a second thermocycling system contained within the primer extension preparation system), to allow the primer extension reaction to occur (step 44). After the primer extension reaction is complete, the plates are optionally transferred back to the primer extension preparation system, where resin is added by the system to the plates to remove salts, which could potentially interfere with MALDI-TOF analysis.

The plates are then transferred to the mass spectrometry preparation system. The system transfers a sample (e.g., nanoliter volume samples) of each aliquot on the plate to a chip (e.g., a silicon chip) for MALDI-TOF analysis (step 46).

Chips containing the samples are transferred from the the mass spectrometry preparation system to the mass spectrometry system. The mass spectrometry system analyzes the samples using MALDI-TOF mass spectrometry (step 48). Specifically, the mass spectrometry system analyzes extended detection extension primers on the basis of molecular weight. Software associated with the mass spectrometry system receives the raw mass spectrometry data, performs digital signal processing (e.g., de-noise, baseline determination, and data compression), analyzes the data, and calls the genotype according to the resulting data (e.g., mass data). The software associated with the mass spectrometry system optionally receives information from the central controller and matches the data with information about the sample (e.g., patient identification and the assay performed). The data is exported from the mass spectrometry system to the relational database and/or central controller (step 49).

The finalized data, e.g., patient name, assays performed, and genotype, are exported from the relational database and/or the central controller to an outside system or database (e.g., a Meditech database) (step 50), e.g., via an interface program, e.g., automatically. The outside system or database is accessible by healthcare providers and/or third party payors. Optionally, the information exported from the central controller to the outside system or database can include billing information, e.g., billing codes for the test or tests performed, allowing direct billing of a third party payor for services rendered.

Optionally, the central controller can be programmed to include with the test results diagnosis information. Such information can be used to facilitate, or give a definitive, diagnosis. For example, with regard to infectious diseases, the diagnostic information can include an indication that a patient has been infected with a particular pathogen, the severity of the infection, the genotype of the organism (e.g., to facilitate the tailoring of a treatment, e.g., to treat a drug resistant organism with a drug to which it is sensitive), and a recommended regimen of treatment. As another example, with respect to genetic mutations that predispose an individual to genetic disease, the information can indicate whether the patient is hetero- or homozygous for the mutation, the likelihood that the patient will develop a disease or condition because of the mutation, and recommend a course of action such as a regimen of treatment or prevention. Such information can be associated with the patient data as necessary and exported from the central controller to the outside database or system.

Clinical Assays

In addition to the new system, the present invention provides novel diagnostic assays. The assays employ novel primer sequences and mass spectrometry (e.g., MALDI) to detect the presence of target nucleic acid sequences and/or sequence variations (e.g., insertions, mutations and/or polymorphisms) in biological samples. The assays can be categorized into two groups: genetic tests (e.g., to detect mutations) and infectious disease/pathogen testing (e.g., to detect the presence and/or amount of foreign, e.g., viral and/or bacterial, nucleic acids, and/or to genotype the pathogen). A general description of the assays is provided below, and several exemplary assays are described in the Examples.

Design of Primers and Specific Considerations

In one embodiment, the novel genetic assays of the present invention require primers for PCR amplification of a target sequence and detection extension primers for carrying out primer extension reactions.

A target sequence can be, e.g., a sequence that is part of a gene, or a mutation (e.g., insertions, deletions, transitions, or transversions), which is known, or suspected, to be associated with (e.g., cause, increase, or decrease the risk of) a genetic disease or disorder. A target sequence can also be a sequence that is part of a pathogen's (e.g., a virus, bacterium, or fungus) genome, which optionally is known or suspected to include variations (e.g., insertions, deletions, transitions, transversions, etc.) conferring special characteristics, e.g., possession of virulence factors and/or drug resistance, and/or which serve to differentiate among strains of the organism.

Generally, to generate amplification primers, a 100 bp stretch of nucleotides is first selected from either or both sides of a target sequence. A set of primers is then created manually and/or by using commercially available primer-generating software. An example of such a program is the Sequenom®

Spectro Designer™ program. This results in a first generation of amplification primers and appropriate detection extension primers.

The first generation of extension and/or amplification primers is analyzed using a second program, such as OLIGO® Primer Analysis Software (Macintosh, Molecular Biology Insights, Inc.), which evaluates each primer with regard to melting temperature of the primer (Tm), potential hairpins in each primer (judged by free energy ($\Delta$G), number of nucleotides in the loop, and Tm of the hairpin), and potential for primer dimerization. This analysis results in a second generation of primers.

The second generation of amplification and/or extension primers is then compared to other known sequences, e.g., using a BLAST program (see, e.g., the National Institutes of Health's National Center for Biotechnology Information (NCBI) website on the World Wide Web at address ncbi.nlm.nih (top level domain ".gov")). Primers that match with a sequence other than the target sequence are disregarded. Primers that match with only the target sequence are considered a third generation of amplification primers and are retained for further analysis.

All possible combinations of the third generation of amplification primers and the detection extension primers are run through the diagnostic genetic assay with positive and negative controls to identify sets of primers that are accurate in 100% of genotype calls. Amplification primers so identified are considered a fourth generation of amplification primers, and are suitable for use in the assays of the present invention.

The procedures discussed above can be modified for designing primers for a target gene when a homologous pseudogene(s) is known to be present, e.g., the glucocerebrosidase (GC) gene, which is involved in Gaucher Disease. Many commercially available software packages are not able to design specific primers when a homologous sequence to the target gene is present in the genome. Many design primers that amplify short stretches of DNA sequence (60 bp to 150 bp) because PCR is more efficient when short fragments of DNA are amplified. Where pseudogenes are present, however, the amplified fragments of DNA often must be as large as 1000 bp or more. In such cases, at least one of the amplification primer sequences directed against the functional gene must not be present in the pseudogene sequence. For example, based on a comparison of the target gene and pseudogene sequences, a primer can be designed, manually or using software, e.g., software other than SpectroDESIGNER™, that will prime the target gene, but not the pseudogene (homologous) sequence. The extension primer can then be designed using software, e.g., SpectroDESIGNER™. Each amplification and extend primer can then be analyzed using a program like BLAST for specificity (i.e. absence of repetitive or homologous sequences) of the sequence. At least one of the amplification primers should be specific.

In certain embodiments of the invention, duplicative confirming assays are used. In such cases, an assay is designed around a target using both the sense and antisense strand sequences, designing both forward and reverse detection extension primers. The results from both assays can be compared. Duplicative confirming assays can be beneficial, for example, if the region surrounding the target includes polymorphisms that prevent the PCR amplification and/or extension primers from working, which would cause erroneous results. They can also reduce the occurrence of mistaken calls, e.g., the calling of a heterozygote as a homozygote in an instance when one primer on one allele does not work because of a polymorphic sequence. Generally, when designing these types of confirming assays, two sets of amplification primers are prepared, each extend primer having its own pair of amplification primers. The second pair of amplification primers are designed either manually or using a program, e.g., a program other than SpectroDESIGNER™.

In certain other embodiments, primers for targets can be designed using more than one type of software, e.g., using SpectroDESIGNER with the input of another sequence aligning software, for additional security when manipulating sequences. For example, in one assay design protocol, the sequence having the deletion/insertion is duplicated. One of the sequences is used to design a forward extension primer, while the other sequence is used to design a reverse extension primer. SpectroDESIGNER™ is used to design extension primers in the forward or reverse direction. To force SpectroDESIGNER™ to design extend primers in the forward or reverse direction, the letter "N" can be introduced into the sequence at a position 3' to the deletion/insertion site when designing the forward extend primer, or 5' to the deletion/insertion site when designing a reverse extension primer.

The targets for SpectroDESIGNER™ when designing primers for a deletion/insertion site is the first base in the deletion or insertion and the first base after the deletion or insertion. Often, these two nucleotide targets differ for the forward and reverse extension primers. The sequence following the target nucleotides for a forward extend primer can omit the first nucleotide after the deletion/insertion; and, similarly for the reverse extend primer, the nucleotide prior to the deletion/insertion can be omitted. For the purpose of designing the assay with a forward extension primer, in certain instances the sequence following a target should be the sequence that actually follows the deletion/insertion site in genomic DNA. In other cases, the target should be followed by the deleted/inserted sequence. Similar considerations are applicable to designing reverse primers. The choices of how to design the primers in view of these considerations can be dictated to SpectroDESIGNER™ by a second type of software, e.g., software other than SpectroDESIGNER™. The validity of the extension primer designed by SpectroDESIGNER™ is checked by aligning the extended primer sequences (Ext1 and Ex2) with the template sequence, with and without the insertion/deletion in order to check the validity of assay design.

Novel Primers

A number of novel primers were isolated for use in the assays of the present invention. Accordingly, the present invention includes the following nucleic acid sequences, in which the MTHFR primers are used to detect mutations in the 5,10-Methylenetetrahydrofolate Reductase gene, the FaII primers are used to detect mutations in the Coagulation Factor II (FII) gene, the FaV primers are used to detect mutations in the Coagulation Factor V (FaV) gene, and the HFE and FM primers are used to detect mutations in the HFE gene. All others are used to detect the presence and amount of cytomegalovirus (CMV) in a biological sample.

```
MTHFR-F1                                (SEQ ID NO: 1)
5'-ACGTTGGATGATGCCTTCACAAAGCGGAAG-3'

MTHFR-R2                                (SEQ ID NO: 2)
5'-ACGTTGGATGCTTGAAGGAGAAGGTGTCTG-3'

MTHFR-E3                                (SEQ ID NO: 3)
5'-TGCGTGATGATGAAATCG-3'

MTHFR-F17                               (SEQ ID NO: 4)
5'-ACGTTGGATGAGTGATGCCCATGTCGGTG-3'
```

-continued

```
MTHFR-R18                              (SEQ ID NO: 5)
5'-ACGTTGGATGCTGACCTGAAGCACTTGAAG-3'

MTHFR-E6                               (SEQ ID NO: 6)
5'-GGAGAAGGTGTCTGCGGGAG-3'

MTHFR-F4                               (SEQ ID NO: 7)
5'-ACGTTGGATGTCTACCTGAAGAGCAAGTCC-3'

MTHFR-R5                               (SEQ ID NO: 8)
5'-ACGTTGGATGTCTCCCGAGAGGTAAAGAAC-3'

MTHFR-E11                              (SEQ ID NO: 9)
5'-AACAAAGACTTCAAAGACACTT-3'

MTHFR-F7                              (SEQ ID NO: 10)
5'-ACGTTGGATGACTACTACCTCTTCTACCTG-3'

MTHFR-R8                              (SEQ ID NO: 11)
5'-ACGTTGGATGCTCCAGCATCACTCACTTTG-3'

MTHFR-E14                             (SEQ ID NO: 12)
5'-GAGGAGCTGACCAGTGAAG-3'

FaII-F18                              (SEQ ID NO: 13)
5'-ACGTTGGATGACTCATATTCTGGGCTCCTG-3'

FaII-R19                              (SEQ ID NO: 14)
5'-ACGTTGGATGAGAGAGCTGCCCATGAATAG-3'

FaII-E16                              (SEQ ID NO: 15)
5'-CACTGGGAGCATTGAGGCT-3'

FaII-F10                              (SEQ ID NO: 16)
5'-ACGTTGGATGTGGAACCAATCCCGTGAAAG-3'

FaII-R11                              (SEQ ID NO: 17)
5'-ACGTTGGATGAGAGAGCTGCCCATGAATAG-3'

FaII-E15                              (SEQ ID NO: 18)
5'-CAATAAAAGTGACTCTCAGC-3'

FaV-F16:                              (SEQ ID NO: 19)
5'-ACGTTGGATGAAGACCATACTACAGTGACG-3'

FaV-R17:                              (SEQ ID NO: 20)
5'-ACGTTGGATGCATTATTTAGCCAGGAGACC-3'

FaV-E10:                              (SEQ ID NO: 21)
5'-GACAAAATACCTGTATTCCT-3'

FaV-F18:                              (SEQ ID NO: 22)
5'-ACGTTGGATGCTCTGGGCTAATAGGACTAC-3'

FaV-R19:                              (SEQ ID NO: 23)
5'-ACGTTGGATGCTGAAAGGTTACTTCAAGGAC-3'

FaV-E9:                               (SEQ ID NO: 24)
5'-GCAGATCCCTGGACAGGC-3'

460 F1                                (SEQ ID NO: 25)
5'-ACGTTGGATGGTCGTGTATGCCACTTTGAC-3'

460 R2                                (SEQ ID NO: 26)
5'-ACGTTGGATGTGAGGCTGTAATCGCACAGC-3'

460 E3                                (SEQ ID NO: 27)
5'-CCACTTTGACATTACACCC-3'

520 F8                                (SEQ ID NO: 28)
5'-ACGTTGGATGTCTTTCAGGAGACGGGTACG-3'

520 R9                                (SEQ ID NO: 29)
5'-ACGTTGGATGAGATGAGCAGCTTCTGCAGC-3'

520 E10:                              (SEQ ID NO: 30)
5'-TCTGCGCGAATGTTACCA-3'

591 F12                               (SEQ ID NO: 31)
5'-ACGTTGGATGAGGCGTTGCTCTTTAAGCAC-3'

591 R13                               (SEQ ID NO: 32)
5'-ACGTTGGATGAGTGCGTGAGCTTACCGTTC-3'

591 E14                               (SEQ ID NO: 33)
5'-TTAAGCACGCCGGCGCGG-3'

607 F28                               (SEQ ID NO: 34)
5'-ACGTTGGATGTCATTTGCGCCGCCAGAATG-3'

607 R29                               (SEQ ID NO: 35)
5'-ACGTTGGATGTTGCTCTTTAAGCACGCCGG-3'

607 E30                               (SEQ ID NO: 36)
5'-GCCGCCAGAATGAGCAGA-3'

CV-F31                                (SEQ ID NO: 37)
5'-ACGTTGGATGGGAGACGACGTGGACGGCAC-3'

CV-R32                                (SEQ ID NO: 38)
5'-ACGTTGGATGCGTGCTTGGACACGCGACTT-3'

CV33 E                                (SEQ ID NO: 39)
5'-CTCCTTGTCCGAAGCCGC-3'

HFE-F1                                (SEQ ID NO: 40)
5'-ACGTTGGATGATGACCAGCTGTTCGTGTTC-3'

HFE-R2                                (SEQ ID NO: 41)
5'-ACGTTGGATGTCTACTGGAAACCCATGGAG-3'

FM3-E                                 (SEQ ID NO: 42)
5' CTCCACACGGCGACTCTCAT-3'

HFE-F7                                (SEQ ID NO: 43)
5'-ACGTTGGATGTTCATGGGTGCCTCAGAGC-3'

HFE-R8                                (SEQ ID NO: 44)
5'-ACGTTGGATGCCACATCTGGCTTGAAATTC-3'

HFE-E3                                (SEQ ID NO: 45)
5' CAGCTGTTCGTGTTCTATGAT 3'

HFE-F4                                (SEQ ID NO: 46)
5'-ACGTTGGATGTGGATAACCTTGGCTGTACC-3'

HFE-R5                                (SEQ ID NO: 47)
5'-ACGTTGGATGTATCACAATGAGGGGCTGATC-3'

FM6-E                                 (SEQ ID NO: 48)
5' GCCTGGGTGCTCCACCTGG 3'

HFE-F9                                (SEQ ID NO: 49)
5'-ACGTTGGATGTAATGGGATGGGACCTACC-3'

HFE-R10                               (SEQ ID NO: 50)
5'-ACGTTGGATGTGCTCTCATCAGTCACATACC-3'

HFE-E6                                (SEQ ID NO: 51)
5' GGGAAGAGCAGAGATATACGT 3'

HFE-F1                                (SEQ ID NO: 52)
5'-ACGTTGGATGATGACCAGCTGTTCGTGTTC-3'

HFE-R2                                (SEQ ID NO: 53)
5'-ACGTTGGATGTCTACTGGAAACCCATGGAG-3'

HFE S65C_E1                           (SEQ ID NO: 54)
5' GGGCTCCACACGGCGAC 3'

HFE-F7                                (SEQ ID NO: 55)
5'-ACGTTGGATGTTCATGGGTGCCTCAGAGC-3'

HFE-R8                                (SEQ ID NO: 56)
5'-ACGTTGGATGCCACATCTGGCTTGAAATTC-3'

HFE S65C_E5                           (SEQ ID NO: 57)
5' TTCGTGTTCTATGATCATGAG 3'
```

```
CMV560-S:                                    (SEQ ID NO: 58)
5'-ACGTTGGATGCGCTTCTACCACGAATGCTC-3'

CMV560-L:                                    (SEQ ID NO: 59)
5'-ACGTTGGATGATAAATACAGCCCGTCGCTC-3'

CMV560-E:                                    (SEQ ID NO: 60)
5'-CTTTCTGACGTATTCGTGCAGCAT-3'
```

Additional primers are set forth in FIGS. 15A-15GG, which includes a listing of the target gene, amplification primers and extension primers for that target, and the analytes.

Assays

In general, an assay of the present invention can be performed as follows. A biological sample is obtained. As used herein, a "biological sample" is material obtained from any living source (e.g. human, animal, plant, bacteria, fungi, protist, virus) that can be solid material (e.g. tissue, cell pellets, biopsies, fecal matter, nucleic acid samples) and/or fluids (e.g., urine, blood, saliva, sputum, amniotic fluid, mouth wash).

If necessary (i.e., when the starting material is an intact biological sample and not previously-extracted nucleic acids), nucleic acids are extracted from the biological sample. Extractions can be performed using any art-known method, the choice of which will depend, e.g., on the biological sample from which the nucleic acids are to be isolated. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (see, e.g., Rolff, A et al. PCR: Clinical Diagnostics and Research, Springer (1994)). There are numerous kits available for extracting nucleic acids from samples, e.g., the MagneSil® ONE, the Fixed Yield Blood Genomic System (Promega), and kits manufactured by Qiagen.

The target gene is then amplified via polymerase chain reaction (PCR) using fourth generation primers designed as described herein. Procedures for performing PCR are well known in the art, and are described in, e.g., Sambrook et al., Molecular Cloning: A Laboratory Manual, Cold Spring Harbor Laboratory Press, 1989. Where the nucleic acids to be analyzed are RNA (e.g., viral RNA), the assays of the present invention can be adapted to include reverse transcriptase PCR (RT-PCR) reactions, if necessary.

In certain embodiments of the invention, an oligo base extension method is then used to detect mutations in, or the presence of, a target nucleic acid. The method is based on the extension of a detection primer (i.e., a detection extension primer designed as described above) that anneals adjacent to a variable nucleotide position on the amplified target DNA, using a DNA polymerase, a mixture of dNTPs (e.g., 3 dNTPs), and the missing dideoxy nucleotides (e.g., one missing dideoxy nucleotide). Any art known primer extension method can be utilized.

The sample is then analyzed using mass spectrometry. Any mass spectrometer format can be used to analyze the samples, e.g., matrix assisted laser desorption ionization (MALDI), electrospray (ES), ion cyclotron resonance (ICR) and Fourier Transform. Various mass analyzers can be used, e.g., magnetic sector/magnetic deflection instruments in single or triple quadrupole mode (MS/MS), Fourier transform, and time-of-flight (TOF) configurations as is known in the art of mass spectrometry. In an embodiment of the present invention, samples are analyzed using MALDI-TOF mass spectrometry.

The molecular weight of extended primers is determined by mass spectrometry, and a change in the molecular weight of the extended primer, as compared to a control, indicates the presence of the target sequence and/or whether a mutation (e.g., insertion or deletion), is present in the target sequence. The results are analyzed using methods described in the Examples section below, and an analysis report is generated.

In other embodiments of the present invention, the assay described above is modified to include, e.g., homogenous MassCLEAVAGE™ (hMC) reactions (Sequenom GmbH, Hamburg, Germany). During PCR amplification of the target region, a T7 promoter for in vitro transcription is introduced to the 5' end of one strand of the amplicon. One PCR is performed with a T7 promotor in the forward primer to mediate transcription of the forward DNA strand, and a second PCR is performed with the T7 promotor incorporated in the reverse primer to mediate transcription of the reverse DNA strand. Following the PCR reaction, SAP is added to each reaction to degrade any unincorporated nucleotides from the PCR reactions. For in vitro transcription production, each PCR reaction is split into two transcription reactions and performed. Next, base-specific cleavage using RNase A is conducted, yielding fragmented RNA molecules.

The final steps in the hMC reaction are sample conditioning and MALDI-TOF MS followed by spectra pattern analysis. The hMC reaction is a high throughput tool for sequence variation identification by comparative sequence analysis. The principle behind it is to generate signal patterns that are specific to a reference sequence in which changes, when compared to a sample sequence, can be tracked as a sequence variation in the form of SNPs or insertion/deletions.

Uses of Assays and the Clinical Assay System

The assays described above can be used to diagnose genetic diseases (or a patient's or subjects increased risk therefore), to identify foreign sequences (e.g., viral sequences) incorporated into a target gene, and for infectious disease/pathogen testing. The term "subject" as used herein, refers to an animal, or a human, and includes, but is not limited to, mammals, e.g., primates, pigs, rodents such as mice and rats, rabbits, guinea pigs, hamsters, cows, horses, cats, dogs, sheep, and goats. Agricultural analyses, e.g., analysis of biological samples from plants can also be made with the new systems and methods.

For example, the assays can be adapted to diagnose any of the more than 3000 genetic diseases or disorders currently known (e.g. hemophilias, Gaucher's disease, thalassemias, Duchenne Muscular Dystrophy (DMD), Huntington's Disease (HD), Alzheimer's Disease and Cystic Fibrosis (CF)). and lysosomal and metabolic diseases.

The assays can also be used to diagnose chromosomal abnormalities such as Trisomy 21 (Down's syndrome), Trisomy 13 (Platau Syndrome), Trisomy 18 (Edward's Syndrome), Monosomy X (Turner's Syndrome) and other sex chromosome aneuploidies such as Klienfelter's Syndrome (XXY), which result in birth defects, and to determine whether an individual has a genetic mutation(s) that predispose the individual to any of a number of disorders such as diabetes, arteriosclerosis, obesity, various autoimmune diseases, stroke, and cancer (e.g. colorectal, breast, ovarian, lung); chromosomal abnormality (either prenatally or postnatally); or a predisposition to a disease or condition (e.g. obesity, atherosclerosis, cancer, venous thromboembolism (VTE), neural tube defects (NTD), and the like) and lysosomal and metabolic The assays can also be used in the detection of "DNA fingerprints," e.g., polymorphisms, such as "microsatellite sequences," which are useful for determining identity or heredity (e.g. paternity or maternity).

Further, the assays can be used to detect or quantify in a biological sample nucleic acid sequences that are specific to infectious organisms. Such assays are useful for diagnosing or monitoring infection. Examples of disease-causing viruses that infect humans and animals and that may be detected by the disclosed processes include: Retroviridae (e.g., human immunodeficiency viruses, such as HIV-1 (also referred to as HTLV-III, LAV or HTLV-III/LAV, see Ratner, L. et al., Nature, 313: 227-284 (1985); and Wain Hobson, S. et al., Cell, 40: 9-17 (1985)); HIV-2 (see Guyader et al., Nature, 328: 662-669 (1987); European Patent Publication No. 0 269 520; Chakraborti et al., Nature 328: 543-547 (1987); and European Patent Application No. 0 655 501); and other isolates, such as HIV-LP (International Publication No. WO 94/00562 entitled "A Novel Human Immunodeficiency Virus"; Picornaviridae (e.g., polio viruses, hepatitis A virus, (Gust, I. D., et al., Intervirology, Vol. 20, pp. 1-7 (1983); entero viruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbivirses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses), and Epstein-Barr virus (EBV).

Examples of infectious bacteria include: *Helicobacter pyloris, Borelia burgdorferi, Legionella pneumophilia, Mycobacteria* sps (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus influenzae, Bacillus anthracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleatum, Streptobacillus moniliformis, Treponema pallidium, Treponema pertenue, Leptospira*, and *Actinomyces israelii*.

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium falciparum* and *Toxoplasma gondii*.

FIGS. 15A-15GG describes a number of specific genetic targets that can be assayed according to the invention, as well as exemplary primers that can be used in those assays. For example, exemplary primers are provided for the following genetic targets: 5,10-Methylenetetrahydrofolate Reductase (MTFR); Coagulation Factor II; Coagulation Factor V; hemochromatosis (HFE); and a glucocerebrosidase (GC). fibroblast growth factor receptor 3; aspartoacylase; Glucocerebrosidase; Coagulation Factor VII; Fanconi Anemia, Complementation Group C (FANCC); inhibitor of kappa light polypeptide gene enhancer in b cells, kinase complex-associated protein; acid sphingomyelinase; hexosaminidase; angiotensin i-converting enzyme; adenylate cyclase 9; apolipoprotein A-1; apolipoprotein E; endothelial leukocyte adhesion molecule 1; fc fragment of IGG, low affinity Ia, receptor; fibrinogen beta chain; coagulation factor II, factor XIII; guanine nucleotide-binding protein beta-3; integrin, alpha-2, glycoprotein Ia/Iia; glycoprotein Ib, platelet, alpha polypeptide; intercellular adhesion molecule 1; glycoprotein Ia/IIa (a2), integrin, alpha-2; platelet glycoprotein Iib, integrin, alpha-2b; glycoprotein IIb/IIIa, integrin, beta-3;3-hydroxy-3-methylglutaryl-coa reductase; lymphocyte adhesion molecule 1; methylene tetrahydrofolate reductase; plasminogen activator inhibitor 1; platelet alpha-granule membrane protein; transforming growth factor-beta receptor, type III; thrombomodulin; tumor necrosis factor; vascular cell adhesion molecule; coagulation factor II receptor; glycoprotein VI, platelet; purinergic receptor P2Y, g protein-coupled, 1; purinergic receptor P2Y, G protein-coupled, 12; prostaglandin-endoperoxide synthase 1; prostaglandin-endoperoxide synthase 2; thromboxane A2 receptor, platelet; and thrombospondin I. The figure lists the disorder associated with the mutation; the gene information (e.g., gene number, symbol, and name), the target mutation, the termination mix that can be used in and assay, the amplification primers, the extension primers, the analytes, and the extended primers (Ext 1, 2, and 3, i.e., the extension primer as it would appear after extension).

The invention will be further described in the following examples, which do not limit the scope of the invention defined by the claims.

EXAMPLES

Example 1

Screen for 5,10-Methylenetetrahydrofolate Reductase (MTHFR) Mutations

Introduction

In one exemplary assay, a biological sample (e.g., a blood sample) is tested for the presence or absence of mutations in the MTHFR gene. MTHFR catalyzes the conversion of 5,10-methylenetetrahydrofolate to 5-methyltetrahydrofolate, a cosubstrate for homocysteine remethylation to methionine. MTHFR plays a key role in folate metabolism by channeling one-carbon units between nucleotide synthesis and methylation reactions. Severe enzyme deficiency leads to hyperhomocysteinemia and homocystinuria, with altered folate distribution and a phenotype that is characterized by damage to the nervous and vascular systems.

Two common mutations that can occur in MTHFR include MTHFR C677T (or Ala222Val) and MTHFR A1298C (or Glu429Ala). Assays to detect these mutations are described below. The C677T mutation is common in the general population, with a variable frequency depending on the subpopulation studied. In Caucasians of European descent, the frequency of homozygotes for this mutation ranges from approximately 5% (in Dutch and Finnish populations) to 12-15% (in French Canadian and other European populations). African Americans have a low frequency of 1.4% The A1298C mutation is also common in the general population with an allele frequency estimated at 0.33.

Individuals homozygous for the C677T mutation have significantly elevated plasma homocysteine levels. It has been suggested that the 677T variant of the MTHFR gene is a genetic risk factor for preeclampsia. From studies of the C677T mutation in cardiovascular patients and controls, investigators have concluded that homozygosity for this frequent mutation in the MTHFR gene is associated with a 3-fold increase in risk for premature cardiovascular disease. The association was stronger in homozygotes than in heterozygotes. Therefore, the C677T polymorphism may be a risk factor for coronary artery disease.

Currently, at least 22 other mutations in MTHFR gene are known and assays similar to those described herein can be designed to detect those mutations as well.

Gene Information
  Gene Locus: 1p36.3.
  Gene Symbol: MTHFR.
  Gene Product: 5,10-METHYLENETETRAHYDROFOLATE REDUCTASE.
  Mutations: MTHFR C677T, Ala222Val, FR A1298C, Glu429Ala.
  Gene OMIM number: 607093
  mRNA NCBI Acc Nos.: XM_030156 5,10-methylenetetrahydrofolate reductase mRNA; AJ237672 Homo sapiens mRNA for 5,10-methylenetetrahydrofolate reductase mRNA; NM_005957 Homo sapiens 5,10-methylenetetrahydrofolate reductase (NADPH) (MTHFR) mRNA; U09806 Synthetic construct methylenetetrahydrofolate reductase (MTIFR) mRNA, complete cds. (Goyette, 1994 Frosst 1995)
  Genomic Acc No.: GA_x5L2HTU1V1E CELERA Data-Base Clinical Significance The test can be used to screen for the MTHFR gene mutation before surgery, which may identify patients at an increased risk of graft thrombosis. The MTHFR mutation assay is also useful for patients with early-onset arteriosclerotic vascular disease or thrombosis, particularly those with hyperhomocysteinemia or significant family histories. The clinical scenario should be considered carefully, since additional genetic and non-genetic factors are important in the development of cardiovascular disease. MTHFR mutation analysis is also useful for patients with variable or ambiguous homocysteine levels, since plasma levels are dependent on nutritional status or sample handling before testing. MTHFR mutational analysis can also be offered for patients with a neural tube defect (NTD). The MTHFR mutation assay is also useful in the elderly and in patients with idiopathic venous thromboembolism (VTE) disease and arterial disease.

MTHFR-C677T E3 Assay

This section describes the amplification and detection extension primers for the MTHFR-C677T E3 Assay and provides the sequences of the primers. The sequences of the resulting extended primers are provided in Table 1, below.

Wild type target: AAAGCTGCGTGATGATGAAATCCGCTCCCGCAGACACCTTCTCCTTCA
(SEQ ID NO.: 804)
Mutated target: AAAGCTGCGTGATGATGAAATCGACTCCCGCAGACACCTTCTCCTTCA
(SEQ ID NO.: 805)
Extension primer ⎯⎯⎯⎯⎯⎯⎯▶
MTHFR-E3

Amplification Primers*:

```
MTHFR-F1                          (SEQ ID NO: 1)
5'-acgttggatgATGCCTTCACAAAGCGGAAG-3'

MTHFR-R2                          (SEQ ID NO: 2)
5'-acgttggatgCTTGAAGGAGAAGGTGTCTG-3'
```

Resulting Amplicon length: 89 bp

* amplification primers have the 10-mer tag specific for the homogeneous MassEXTEND™ assay (hME) method: acgttggatg.

Detection Extension Primer:

```
MTHFR-E3                          (SEQ ID NO: 3)
5'-TGCGTGATGATGAAATCG-3'
```

Termination mix: ddA/ddC/ddT

TABLE 1

Sequence, length and mass of extension primer, extended primer (G and A) and pause product for MTHFR-C677T

| Allele | Sequence | Length | Mass |
|---|---|---|---|
| MTHFR-E3 | TGCGTGATGATGAAATCG | 18 bp | 5578.6 |
| T mutant allele (ext A) | TGCGTGATGATGAAATCGA | 19 bp | 5875.9 |
| C wild type allele (ext G) | TGCGTGATGATGAAATCGGC | 20 bp | 6181 |
| Contaminant (pausing peak) | | | 5907.9 |

SEQ ID NOS.: 806, 807, and 808)

MTHFR C677T E6 Assay

This section describes the amplification and detection extension primers for the MTHFR C677T E6 Assay and provides the sequences of the primers. The sequences of the resulting extended primers are provided in Table 2, below.

Wild type target: AAAGCTGCGTGATGATGAAATCCGCTCCCGCAGACACCTTCTCCTTCA (SEQ ID NO: 809)

Mutated target: AAAGCTGCGTGATGATGAAATCGACTCCCGCAGACACCTTCTCCTTCA (SEQ ID NO: 810)

Extension primer MTHFR-E6

Amplification Primers*

```
MTHFR-F17                             (SEQ ID NO: 4)
5'-acgttggatgAGTGATGCCCATGTCGGTG-3'

MTHFR-R18                             (SEQ ID NO: 5)
5'-acgttggatgCTGACCTGAAGCACTTGAAG-3'
```

Amplicon length: 122 bp
* amplification primers have the 10-mer tag specific for the hME method:acgttggatg.
Detection Extension Primer:

```
MTHFR-E6                              (SEQ ID NO: 6)
5'-GGAGAAGGTGTCTGCGGGAG-3'
```

Termination mix: ddA/ddC/ddG

TABLE 2

Sequence, length and mass of extension primer, extended primer (G and A) and pause product for MTHFR-C677T

| Allele | Sequence | Length | Mass |
|---|---|---|---|
| MTHFR-E6 | GGAGAAGGTGTCTGCGGGAG | 20 bp | 6303.1 |
| T mutant allele (ext A) | GGAGAAGGTGTCTGCGGGAGTC | 22 bp | 6880.5 |
| C wild type allele (ext G) | GGAGAAGGTGTCTGCGGGAGC | 21 bp | 6576.3 |
| Contaminant (pausing peak) | | | 5907.9 |

[SEQ ID NOS: 811, 812, and 813]

MTHFR-A1298C Assay

This section describes the amplification and detection extension primers for the MTHFR-A1298C assay and provides the sequences of the primers. The sequences of the resulting extended primers are provided in Table 3, below.

Amplification Primers*

```
MTHFR-F4                              (SEQ ID NO: 7)
5'-acgttggatgTCTACCTGAAGAGCAAGTCC-3'

MTHFR-R5                              (SEQ ID NO: 8)
5'-acgttggatgTCTCCCGAGAGGTAAAGAAC-3'
```

Amplicon length: 109 bp
* amplification primers have the 10-mer tag specific for the hME method:acgttggatg (SEQ ID No.816)
Detection Extension Primer:

```
MTHFR-E11                             (SEQ ID NO: 9)
5'-AACAAAGACTTCAAAGACACTT-3'
```

Termination mix: ddA/ddC/ddT

TABLE 3

Sequence, length and mass of extension primer, extended primers and pause product for MTHFR-A1298C E11:

| Allele | Sequence | Length | Mass |
|---|---|---|---|
| MTHFR-E11 | AACAAAGACTTCAAAGACACTT | 22 bp | 6704.4 |
| A mutant allele | AACAAAGACTTCAAAGACACTTT | 23 bp | 6992.60 |
| C wild type allele | AACAAAGACTTCAAAGACACTTGC | 24 bp | 7306.80 |
| Contaminant (pausing peak) | | | 7033.60 |

(SEQ ID NOS: 817, 818, and 819)

MTHFR A1298C E14 Assay

This section describes the amplification and detection extension primers for the MTHFR A1298C E14 Assay and provides the sequences of the primers. The sequences of the resulting extended primers are provided in Table 4, below.

Wild type target: GGGAGGAGCTGACCAGTGAAGAAAGTGTCTTTGAAGTCTTTGTTCTTT (SEQ ID NO: 814)

Mutated target: GGGAGGAGCTGACCAGTGAAGCAAGTGTCTTTGAAGTCTTTGTTCTTT (SEQ ID NO: 815)

Extension primer MTHFR-E11 (reverse sequence)

Wild type target: GGGAGGAGCTGACCAGTGAAGAAAGTGTCTTTGAAGTCTTTGTTCTTT
(SEQ ID NO: 820)

Mutated target: GGGAGGAGCTGACCAGTGAAGAACGTGTCTTTGAAGTCTTTGTTCTTT
(SEQ ID NO: 821)

Extension primer ⟶
MTHFR-E14

Amplification Primers*

```
MTHFR-F7                              (SEQ ID NO: 10)
5'-acgttggatgACTACTACCTCTTCTACCTG-3'

MTHFR-R8                              (SEQ ID NO: 11)
5'-acgttggatgCTCCAGCATCACTCACTTTG-3'
```

Amplicon length: 159 bp
* amplification primers have the 10-mer tag specific for the hME method: acgttggatg.

Detection Extension Primer

```
MTHFR-E14                             (SEQ ID NO: 12)
5'-GAGGAGCTGACCAGTGAAG-3'
```

Termination mix: ddC/ddG/ddT

TABLE 4

Sequence, length and mass of extension primer, extended primers and pause product for MTHFR-A1298C E14

| Allele | Sequence | Length | Mass |
|---|---|---|---|
| MTHFR-E14 | GAGGAGCTGACCAGTGAAG | 19 bp | 5926.90 |
| A mutant allele | GAGGAGCTGACCAGTGAAGAAG | 23 bp | 7179.70 |
| C wild type allele | GAGGAGCTGACCAGTGAAGC | 20 bp | 6200.10 |
| Contaminant (pausing peak) | | | 6240.10 |

(SEQ ID NOS: 822, 823, and 824)

Testing Procedure

This section generally describes procedures useful in the MTHFR assays.

Specimens: Whole blood samples were collected in the same manner routinely used for any laboratory test. Exemplary test results, with specific numbers of samples, are provided below in Tables 12, 13, 14, and 15.

Specimen Storage and Stability
1. After arrival, blood was extracted on the same or next day. Specimen was not allowed to remain at +15° C. to +30° C. longer than 8 hours. If assays were not completed within 8 hours, specimen was stored at +2° C. to +8° C.
2. Tubes of blood should were kept closed at all times in a vertical, stopper-up position.
3. Blood specimen were not frozen.

Sample Volume
The minimum volume was 1.0 mL of sample.
Criteria for Unacceptable Specimens
Unlabeled specimens.
Insufficient quantity.
Clotted specimen.

Specimen Handling
Blood samples were received with the lab barcode identification numbers. Sample identification is ensured thought out the process by the tracking system on Freedom, BioRobot MDx, Genesis, and MassARRAY systems.

Procedures Involved in Assays:
Nucleic acids extraction, nucleic acid concentration measurement, Uniplex and Multiplex PCR Procedure on Genesis™ in conjunction with Freedom™ and MassARRAY™ software, Homogeneous MassEXTEND™ Reaction using the MassARRAY™ System.

Quality Control
PCR primers were analyzed ensure specificity for the prothrombin gene in the BLAST search and that the PCR product did not show allelic dropout. Validation of each assay was accomplished.

Four types of control material were analyzed with each PCR plate: (A) blank control (water), (B) DNA negative control (wild type), (C) heterozygous positive controls and (D) positive homozygous mutant. In each run at least two samples of each control were used if available. More frequent use of controls or the use of additional controls was left to the discretion of the user based on work load and work flow. Tables 5 and 6, below, provide a list of control DNAs used in the presently described assays.

TABLE 5

Controls used in MTHFR- C677T assay

| 39354 | T | MTHFR | homozygous |
|---|---|---|---|
| GM881 | T | MTHFR | homozygous |
| GM1278 | C | MTHFR | negative- wild |
| NA1464 | C | MTHFR | negative- wild |
| GM779 | C | MTHFR | negative- wild |
| NA1465 | C | MTHFR | negative- wild |
| GM972 | CT | MTHFR | heterozygo |
| NA0375 | CT | MTHFR | heterozygo |
| NA1359 | CT | MTHFR | heterozygo |
| NA1464 | CT | MTHFR | heterozygo |
| NA1470 | CT | MTHFR | heterozygo |
| NA1600 | CT | MTHFR | heterozygo |
| NA1602 | CT | MTHFR | heterozygo |

TABLE 6

Controls used in MTHFR-A1298C assay

| GM7798 | C | MTHFRA1298C | homozygous mutant |
|---|---|---|---|
| GM8810 | A | MTHFRA1298C | negative- wild type |
| NA16028 | A | MTHFRA1298C | negative- wild type |
| GM12783 | AC | MTHFRA1298C | heterozygous |
| NA14641 | AC | MTHFRA1298C | heterozygous |
| NA16000 | AC | MTHFRA1298C | heterozygous |

PCR Procedure
The master PCR mix was made, biannually or as necessary, in 11.954 ml total volume and aliquoted into 47 Sarstedt tubes, 250 ll each. The composition of the PCR master mix is provided in Table 7, below.

TABLE 7

Composition of master PCR mix

| Reagent | Stock Concentration | Final Concentration | Volumes used to make master PCR mix |
|---|---|---|---|
| Water | N/A | N/A | 8,514 µl |
| Buffer/MgCl$_2$ | 15 mM (10×) | 1.5 mM | 2,150 µl |
| MgCl$_2$ | 25 mM (10×) | 2.5 mM | 860 µl |
| dNTPs | 10 mM (50×) | 200 µM | 430 µl |
| Total volume | | | 11,954 µl |

The 5 µM primer mix was made by diluting 10 times 50 µM stock primers. The volumes used to make 2000 µl of 5 µM primer mix is shown in Table 8, below. The primer mix was aliquoted to 10 Sarstedt tubes, 200 µl each.

TABLE 8

Composition of 5 µM Primer Mix

| Reagent | Stock Concentration | Concentration in the mix | Volumes used to make 5 µM mix |
|---|---|---|---|
| Water | N/A | N/A | 1,200 µl |
| Forward primer | 50 µM | 5 µM | 200 µl |
| Reverse primer | 50 µM | 5 µM | 200 µl |
| Total Volume | | | 2000 µl |

The composition of the PCR reaction is shown in Table 9. To calculate the volumes per run, the volumes per reaction of PCR mix, Primer Mix, and HotStarTaq™ need to be multiplied by number of reactions and then by 1.5. Table 9 shows an example of the calculations per 384 reactions. Increasing the final volume by 50% is to account for pipetting losses and 'dead' volume when using the robotics.

TABLE 9

Composition of single PCR reaction and PCR reaction for 384-well plate

| Reagent | Stock Concentration | Final Concentration | Reaction Volume | Volume per 384 reactions and ×1.5 |
|---|---|---|---|---|
| PCR mix per reaction | 10× | 1× | 2.78 µl | 1601.28 µl |
| Primer Mix (F + R) | 5 µM (40×) | 200 nM | 0.2 µl | 115.2 µl |
| HotStarTaq | 5 units/µl (50×) | 0.1 unit per reaction | 0.02 µl | 11.52 µl |
| TOTAL volume | | | 3.00 µl | 1728 µl |

3 µl of PCR mix were dispensed into each well of the 384-well plate. The protocol "PCR Procedure" (MD008) was utilized. 2 µl of DNA (2.5 ng/µl) were added to each well. The standard PCR program on the PCR machine was run:

| | | |
|---|---|---|
| 95° C. | 15 minutes | |
| 95° C. | 20 seconds | |
| 56° C. | 30 seconds | } 45 cycles |
| 72° C. | 1 minute | |
| 72° C. | 3 minutes | |
| 4° C. | forever (hold) | |

Dephosphorylation Procedure

SAP (Shrimp Alkaline Phosphatase) was diluted according to Table 10, multiplying the volumes by the number of the samples and then by 1.5.

TABLE 10

Composition of SAP mix

| Reagent | Stock Concentration | Final Concentration | Reaction Volume | Volume per 384-well plate |
|---|---|---|---|---|
| Nanopure Water | N/A | N/A | 1.53 µl | 881.3 µl |
| hME buffer | 10× | 1× * | 0.17 µl | 97.9 µl |
| SAP | 1 unit/µl | 0.15 units/µl | 0.30 µl | 172.8 µl |
| TOTALS: | | | 2.00 µl | 1152.00 µl |

2 µl of the diluted Shrimp Alkaline Phosphatase were dispensed to each well (Refer to MassARRAY procedure MD 009). The SAP PCR program was run on the PCR machine:

| | |
|---|---|
| 37° C. | 20 minutes |
| 85° C. | 5 minutes. |
| 4° C. | forever (hold) |

Homogeneous Massextend (hME) Reaction Procedure

The hME cocktail was prepared according to Table 11. Multiply one reaction volume by the number of samples and then by 1.38.

TABLE 11

Components of hME cocktail

| Reagent | Stock Concentration | Final Concentration | Reaction Volume | Volume per 384-well plate* |
|---|---|---|---|---|
| Nanopure Water | N/A | N/A | 1.674 µl | 887.09 µl |
| hME Mix (10× buffer w/2.25 mM d/ddNTPs) | 10× | 1× | 0.2 µl | 105.98 µl |
| Extension primer | 50 µM | 2.7 µM | 0.108 µl | 57.23 µl |
| Thermo Sequenase$^\&$ | 32 units/µl | 0.063 unit/µl | 0.018 µl | 9.54 µl |
| TOTALS: | | | 2.0 µl | 1059.84 µl |

*Volumes are for a 384- well microplate and include a 38% overage to account for possible pipetting loss and dead volume in the 96-well microtiter plate used on the Multimek.
$^\&$ThermoSequenase is stored at (−20)° C. until it is added to the reaction cocktail.

2 µl of the hME cocktail mix were dispensed to the appropriate wells containing 7 µl dephosphorylated PCR product. Refer to MassARRAY procedure MD008. The Extension Reaction program was run on the PCR machine:

| | | |
|---|---|---|
| 94° C. | 2 minutes | |
| 94° C. | 5 seconds | |
| 52° C. | 5 seconds | } 45 cycles |
| 72° C. | 5 seconds | |
| 4° C. | forever (hold) | |

Spectroclean Resin Clean Up Procedure

Using the SpectroClean plate, transfer resin into the 96-well Marsh plate. Run the hME cation Cleanup method on the Multimeck. Refer for details to MassARRAY protocol MD008.

Results Analysis

The Genotyper® Analyzer software reads the spectrum generated for each sample by the mass spectrometer, and uses a 3-parameter model to calculate the significance of each putative genotype:

1. Conservative: The most conservative set makes no error in reading the data.
2. Aggressive: The most aggressive set makes the most errors (still less than 1 percent).
3. Moderate: The moderate set is a compromise between the two extremes.

The interpretation of the results is as follows: If the results of two assays for the same mutation are called (i.e., interpreted) identically by conservative or moderate calls or conservative and aggressive calls, the result is acceptable. If the assays are called identically by moderate and aggressive calls, the test needs to be looked at by the director or the designee. If the assays are called only by aggressive calls, the test needs to be repeated. If there is a call on one but not the other assay, the "non call" assay needs to be repeated.

The non-calls can be further categorized into the following groups: (a) Low Probability: Implies that the spectrum in question contains peaks that fail any criteria of significance even for the aggressive parameter set; (b) Conflict: Implies that there is more that one read or spectrum corresponding to one sample, and these reads give rise to different and conflicting genotypes; (c) Bad spectrum: The spectrum for the sample doesn't exist above noise level; and (d) Bad Assay: results of analyst or operator input errors in defining the assays. The most common errors are mass values of analytes or contaminants that are out of range of the spectrum, or contaminants and analytes having the same mass; and (e) user call: The analyst or operator select a genotype in the table and performs a manual call.

In the presently described examples, each sample will have at least two different assays that together will confirm, e.g., the presence of a mutation. However, in many instances, accurate results can be obtained using one assay per sample and, therefore, performing two different assays is optional.

Figure 3:
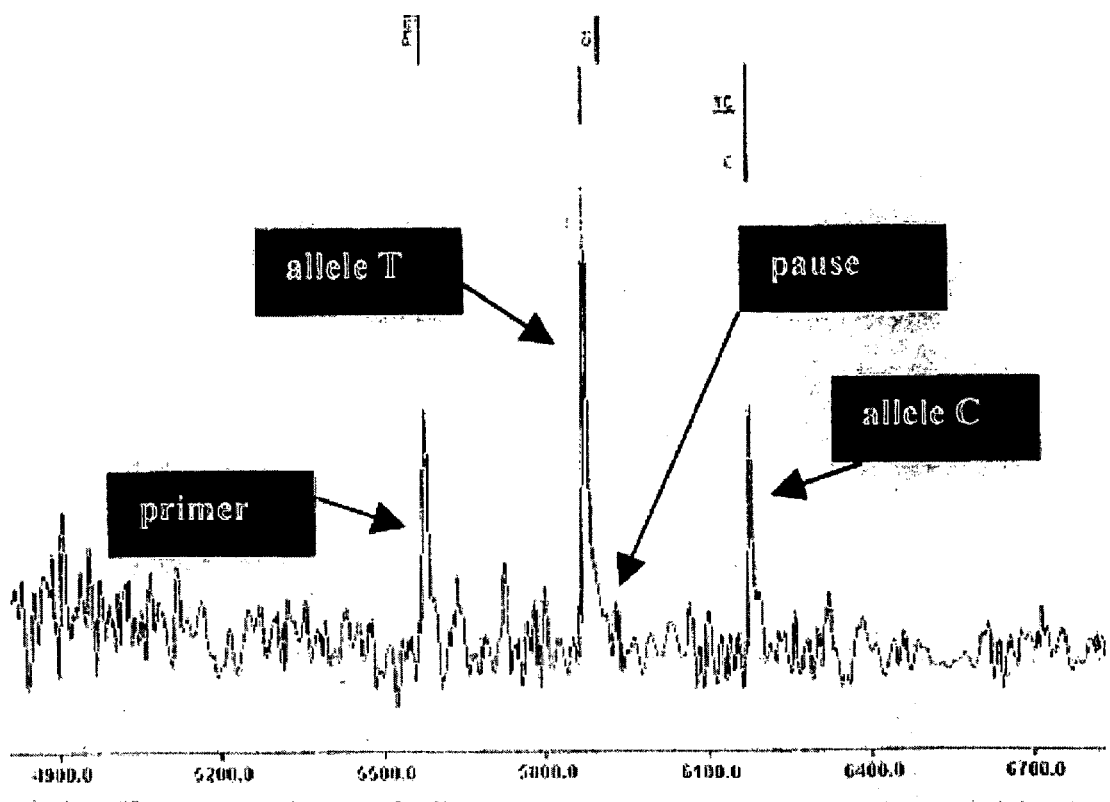
FIG. 3 is a mass spectrum of a heterozygous "TC" allele (heterozygous positive) generated using a screen for a C677T mutation in the 5,10-Methylenetetrahydrofolate Reductase (MTFR) gene.

FIG. 3 is a mass spectrum of a heterozygous "TC" allele (heterozygous positive) generated using a screen for a C677T mutation in the 5,10-Methylenetetrahydrofolate Reductase (MTFR) gene. Exemplary test results are provided in Tables 12, 13, 14, and 15, below.

TABLE 12

MTHFR C677T E3

| Source of DNA | Conservative | Moderate | Aggressive | Low Probability |
|---|---|---|---|---|
| Associated Regional and University Pathologists (ARUP) DNAs + Coriel Institute DNAs | 147 | 3 | 0 | |

TABLE 13

MTHFR C677T E6

| Source of DNA | Conservative | Moderate | Aggressive | Low Probability |
|---|---|---|---|---|
| ARUP DNAs + Coriel DNAs | 150 | 2 | 0 | |

TABLE 14

MTHFR A1298C E11

| Source of DNA | Conservative | Moderate | Aggressive | Low Probability |
|---|---|---|---|---|
| ARUP DNAs + Coriel DNAs | 125 | 26 | 1 | |

TABLE 15

MTHFR A1298C E14

| Source of DNA | Conservative | Moderate | Aggressive | Low Probability |
|---|---|---|---|---|
| ARUP DNAs + Coriel DNAs | 89 | 53 | 6 | |

The results of the assays were 100% in agreement with results from Associated Regional and University Pathologists (ARUP). In both (E3 and E6) MTHFR-C677T assays, negative controls (homozygous wild type) GM12783, GM7798, NA14641 (Coriell) were homozygous CC, positive heterozygous controls NA13591, NA14646, NA14702, and NA16000 (Coriell) were TC, and, positive homozygous control NA8810 (Coriell) was TT. In both MTHFR-A1298C assays, negative control (homozygous wild type) GM7798 (Coriell) was homozygous CC, positive heterozygous controls NA14641 and NA 16000 (Coriell) were both AC, and positive homozygous control NA 16028 (Coriell) was AA. As indicated in Tables 12, 13, 14, and 15, above, the majority of geneotype calls (i.e., the genotype called by the software for each sample) for each assay were conservative calls, indicating a high level accuracy.

Example 2

Screen for Coagulation Factor II (FII) G20210A Mutations

Mutation G20210A in the prothrombin gene is associated with hyperprothrombinemia and increased risk of venous thromboembolism (VTE). It has been established that the FII G20210A mutation increases the risk of VTE 2-5 fold. The 20210A prothrombin allele also represents an inherited risk factor for acute coronary syndrome among patients who have limited extent of coronary disease at angiography or who lack major metabolic and acquired risk factors.

Mutation G20210A involves the last nucleotide of the transcribed prothrombin RNA. The mechanism by which prothrombin levels are altered is unknown. One explanation is that increased adenylation and increased mRNA stability are involved.

In southern Europe, the prevalence of the G20210A mutation is 3.0 percent (CI95 2.3 to 3.7%), nearly twice as high as the prevalence in northern Europe 1.7% (CI95 1.3 to 2.2%), the highest of 7.8% reported in a Greek-Cypriot population. In the United States, the overall prevalence estimates are between 1% and 2%, although this is highly dependent on race. The mutation is fairly uncommon in African Americans (~0.2%), and is also rarely seen in Asians and Native Americans.

At least 28 missense mutations, one insertion, one deletion, and one substitution (in the regulatory region) are known to occur in the prothrombin gene. Accordingly, assays similar to those described herein can be designed to detect those mutations as well.

Gene Information

Gene Locus: 11p11-q12

Gene Symbol: F2, PRT

Gene Product: COAGULATION FACTOR II, prothrombin

Mutations: G20210A

Mutation Frequency: The 20210G-A variation in the prothrombin gene is predominant only in the Caucasian population, among whom the prevalence of heterozygous carriers varies between 1% to 8%, and depends on the geographical location and ethnic background.

OMIM number: 176930 mRNA NCBI Acc No.: NM_000506 coagulation factor II mRNA; M17262. Human prothrombin mRNA Genomic Acc No.: AF478696 H.coagulation factor II (thrombin) (F2) gene.

Clinical Significance

Prothrombin (G20210A) testing can be recommended, for example, in the following cases: when inherited thrombophilia is suspected; when the testing for factor V Leiden muatation is recommended; in patients with a history of recurrent VTE; in patients with a first episode of VTE before the age of 50 years; in patients with a history of an unprovoked VTE at any age; where thrombosis occurs in unusual anatomic sites, such as cerebral, mesenteric, portal, or hepatic veins; where there is a first-degree relative with VTE; in patients with a first VTE related to pregnancy, the puerperium, or oral contraceptive use; where there is a history of VTE related to pregnancy loss during the second or third trimesters; in young women smokers (age <50 years) with an MI; in older patients (age >50 years) with a first provoked VTE event in the absence of a cancer or an intravascular device; where there is a first VTE related to serum estrogen receptor modifier or tamoifen; in selected cases of women with unexplained severe preeclampsia, placental abruption, or intrauterine growth restriction; in asympthomatic adult family members of probands with known prothrombin G20210A mutations, especially those with a strong family history of thrombosis at young age; and asymptomatic female family members who are pregnant or are considering oral contraceptives or pregnancy.

This section describes the amplification and detection extension primers for the FaII-E16 Assay and provides the sequences of the primers. The sequences of the resulting extended primers are provided in Table 16, below.

| Wild type target | CCAATAAAAGTGACTCTCAGCGAGCCTCAATGCTCCCA |
| Mutated target | CCAATAAAAGTGACTCTCAGCAAGCCTCAATGCTCCCA |
| Extension primer FaII-E16 | ← |

Amplification Primers*:

```
    FaII-F18                              (SEQ ID NO: 13)
    5'-ACGTTGGATGACTCATATTCTGGGCTCCTG-3'

FaII-R19                              (SEQ ID NO: 14)
    5'-ACGTTGGATGAGAGAGCTGCCCATGAATAG-3'
```

Detection Extension Primer:

```
    FaII-E16                              (SEQ ID NO: 15)
    5'-CACTGGGAGCATTGAGGCT-3'
```

Termination mix: ddA/ddC/ddG

* amplification primers have the 10-mer tag specific for the hME method: acgttggatg.

TABLE 16

Sequence, length and mass of extension primer, extended primer (G and A) and pause product)

| Allele | Sequence | Length | Mass |
|---|---|---|---|
| FaII-E16 (G20210A) | CACTGGGAGCATTGAGGCT | 19 bp | 5868.8 |
| Negative (wild type) | CACTGGGAGCATTGAGGCTC | 20 bp | 6142 |
| Homozygouse (mutant) | CACTGGGAGCATTGAGGCTTG | 21 bp | 6486.2 |
| Contaminant (pausing peak) | | | 6173 |

(SEQ ID NOS: 825 826, and 827)

FaII-E15 ASSAY

This section describes the amplification and detection extension primers for the FaII-E15 Assay and provides the sequences of the primers. The sequences of the resulting extended primers are provided in Table 17, below:

Wild type target    CCAATAAAAGTGACTCTCAGCGAGCCTCAATGCTCCCA
(SEQ ID NO: 828)
Mutated target    CCAATAAAAGTGACTCTCAGCAAGCCTCAATGCTCCCA
(SEQ ID NO: 829)
Extension primer FaII-E15    →

Amplification Primers*:

```
FaII-F10                                    (SEQ ID NO: 16)
5'-ACGTTGGATGTGGAACCAATCCCGTGAAAG-3'

FaII-R11                                    (SEQ ID NO: 17)
5'-ACGTTGGATGAGAGAGCTGCCCATGAATAG-3'
```

Amplicon length: 112 bp
* amplification primers have the 10-mer tag specific for the hME method: acgttggatg.

Detection Extension Primer:

```
FaII-E15                              (SEQ ID NO: 18)
5'-CAATAAAAGTGACTCTCAGC-3'
```

Termination mix: ddA/ddC/ddT

TABLE 17

Sequence, length and mass of extension primer, extended primer (G and A) and pause product)

| Allele | Sequence | Length | Mass |
|---|---|---|---|
| FaII-E15 (G2020A) | CAATAAAAGTGACTCTCAGC | 20 bp | 6094.00 |
| Negative (wild type) | CAATAAAAGTGACTCTCAGCGA | 22 bp | 6720.4 |
| Homozygouse (mutant) | CAATAAAAGTGACTCTCAGCA | 21 bp | 6391.2 |
| Contaminant (pausing peak) | | | 6423.20 |

(SEQ ID NOS: 830, 831, and 832)

Testing Procedure

Blood specimens and quality control procedures were performed according to protocols described in Example 1. Table 18, below, provides a list of controls used in the presently described assay.

TABLE 18

Controls used in Coagulation Factor II assay

| | | |
|---|---|---|
| 64FaII030106 | A | Factor II G20210A homozygous mutant |
| NA16000 | A | Factor II G20210A homozygous mutant |
| 7740 | G | Factor II G20210A negative- wild type |
| 7776 | G | Factor II G20210A negative- wild type |
| GM14899 | G | Factor II G20210A negative- wild type |
| GM7776 | G | Factor II G20210A negative- wild type |
| GM7798 | G | Factor II G20210A negative- wild type |
| GM8810 | G | Factor II G20210A negative- wild type |
| GM9729 | G | Factor II G20210A negative- wild type |
| NA14646 | G | Factor II G20210A negative- wild type |
| NA14650 | G | Factor II G20210A negative- wild type |
| NA14899 | G | Factor II G20210A negative- wild type |
| NA16028 | AG | Factor II G20210A heterozygous |

PCR, dephosphorylation, homogenous MASSEXTEND (HE, and spectroclean resin clean up procedures were carried out as described in Example 1, above.

Results Analysis

Figure 4:
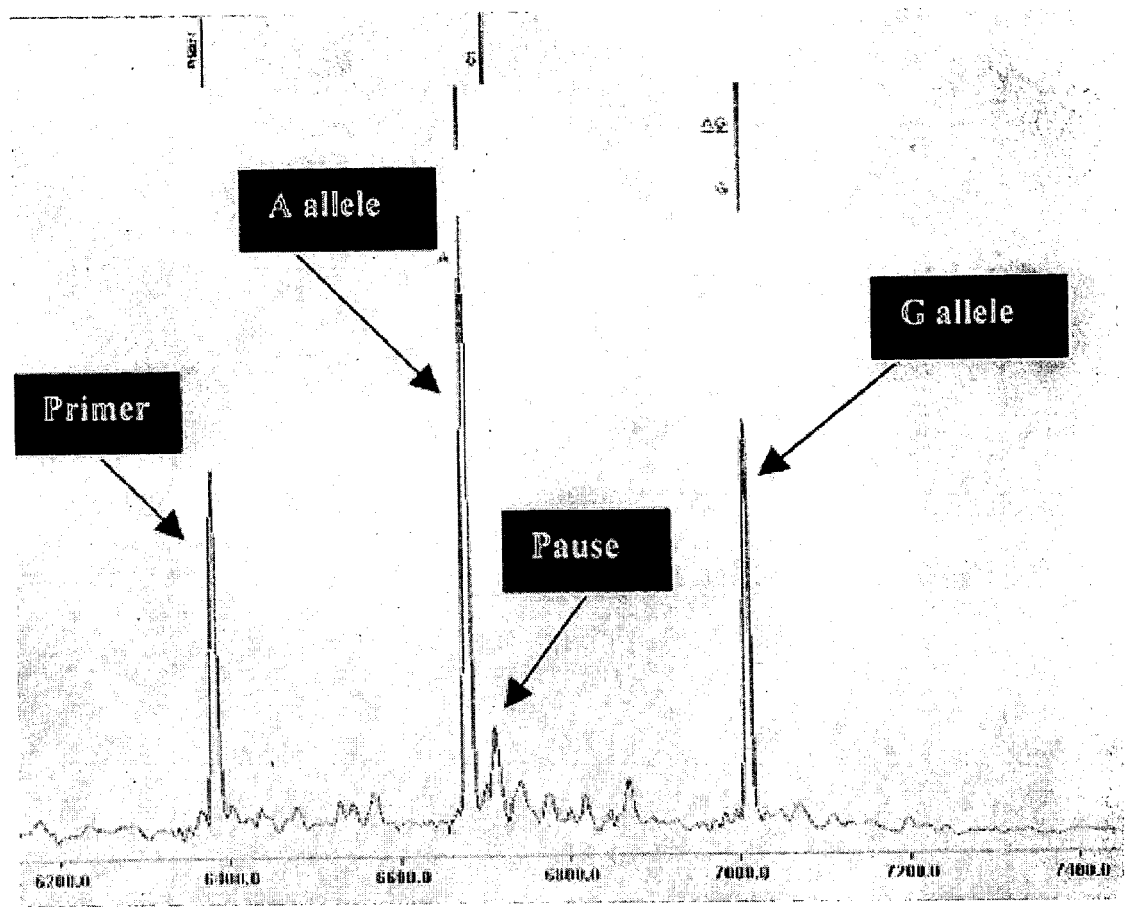
FIG. 4 is a mass spectrum of a heterozygous "GA" allele (heterozygous positive) generated using a screen for a G20210A mutation in the Coagulation Factor II (FII) gene.

Results were analyzed as described in Example 1, above. FIG. 4 is a mass spectrum of a heterozygous "GA" allele (heterozygous positive) generated using a screen for a G20210A mutation in the Coagulation Factor II (FII) gene. Exemplary test results are provided in Tables 19 and 20, below.

TABLE 19

| | FaII-E15 | | | |
|---|---|---|---|---|
| Source of DNA | Conservative | Moderate | Aggressive | Low Probability (No results) |
| ARUP DNAs | 126 | 4 | 0 | 2 |
| Coriell control DNAs | 8 | 0 | 0 | 0 |

Results of this assay were in 100% in agreement with results from ARUP. Negative controls (homozygous wild type) GM7798, GM8810, GM9729, GM14899, NA14646, NA14650 (Coriell Institute) were homozygous GG, and positive heterozygous control NA 16028 (Coriell) was AG, and positive homozygous mutant control NA16000 (Coriell Institute) was AA. Due to blood clogging the DNA was not extracted and could not be re-extracted because of the too small volume of blood obtained (<0.5 ml). Two samples that had no DNA gave no signal. As indicated in Table 19, out of 140 samples tested, the majority of geneotype calls for this assay were conservative calls, indicating a high level of accuracy.

TABLE 20

| | FaII-E16 | | | |
|---|---|---|---|---|
| Source of DNA | Conservative | Moderate | Aggressive | Low Probability (No results) |
| ARUP DNAs | 128 | 0 | 1 | 3 |
| Coriell control DNAs | 8 | 0 | 0 | 0 |

Results of this assay were in 100% in agreement with results from ARUP. Negative controls (homozygous wild type) GM7798, GM8810, GM9729, GM14899, NA14646, NA14650 (Coriell Institute) were homozygous GG, and positive heterozygous control NA16028 (Coriell) was AG, and positive homozygous mutant control NA16000 (Coriell Institute) was AA. Due to blood clogging the DNA was not extracted and could not be re-extracted because of the too small volume of blood obtained (<0.5 ml). Two samples that had no DNA gave no signal. As indicated in Table 20, out of 140 samples tested, the majority of geneotype calls for this assay were conservative calls, indicating a high level of accuracy.

Example 3

Screen for Coagulation Factor V R506Q Mutations

The Factor V mutation (Factor V Leiden) is the most common genetic cause of venous thrombosis. It is involved in 20-40% of cases and is present in 3% of the general population. In a population study of 180 individuals from Germany, the heterozygosity rate was 7.8% with a confidence interval 4 to 11%. The mutation causes resistance to activated protein C (APC) and induces a defect in the natural anticoagulation system. The other major genetic causes of venous thrombosis (deficiencies of protein C, protein S and antithrombin III) together account for only 5-10% of cases.

Presence of the factor V mutation increases the risk for venous thrombosis 7-fold in heterozygotes and 80-fold in homozygotes. This risk is increased still further when the factor V mutation is present along with situations such as pregnancy, oral contraceptive use, estrogen therapy, malignancy, diabetes mellitus, immobilization or surgery. Ten percent of heterozygotes and almost all homozygotes experience venous thrombosis in their lifetime. The discovery of the factor V mutation has revolutionized the diagnostic work-up of patients with hypercoagulability, and the ability to detect this mutation in asymptomatic relatives offers the opportunity to prevent venous thrombosis through special management of those at risk.

Gene Information
  Gene Locus: 1q23
  Gene Symbol: F5 (FV)
  Gene Product: Coagulation Factor V
  Mutations: 1691 G-A; R506Q; Factor V Leiden
  Mutation Frequency: 2-8% in most populations
  OMIM number: 227400
  mRNA NCBI Acc No.: XM 171908, XM 118651, XM 069970
  Genomic Acc No.: NM_000130

Clinical Significance

Testing can be recommended, for example, in patients: having venous thrombosis or pulmonary embolism, transient ischemic attacks or premature stroke, peripheral vascular disease, particularly lower extremity occlusive disease, a history of a thrombotic event, family history of thrombosis or known factor V mutation in a relative; prior to major surgery, pregnancy, postpartum, oral contraceptive use or estrogen therapy if there is a personal or family history of thrombosis; or where there has been a previous finding of activated protein C resistance by laboratory analysis.

FaV-E10 Assay

This section describes the amplification and detection extension primers for the FaV-E10 Assay and provides the sequences of the primers. The sequences of the resulting extended primers are provided in Table 21, below.

Amplification Primers*:

FaV-F16: (SEQ ID NO: 19)

5'-acgttggatgAAGACCATACTACAGTGACG-3'

FaV-R17: (SEQ ID NO: 20)

5'-acgttggatgCATTATTTAGCCAGGAGACC-3'

Extension Primer:

FaV-E10: (SEQ ID NO: 21)

5'-GACAAAATACCTGTATTCCT-3'

* amplification primers have the 10-mer tag specific for hME method: acgttggatg.

Amplicon length: 189 bp

Termination mix: ddA/ddC/ddG

TABLE 21

Sequence, length and mass of extension primer, extended primer (C and T) and pause product

| Allele | Sequence | Length | Mass |
|---|---|---|---|
| FaV-E10 R506Q | GACAAAATACCTGTATTCCT | 20 bp | 6060 |
| C (R) wild type | GACAAAATACCTGTATTCCTC | 21 bp | 6333.2 |
| T (Q) mutant | GACAAAATACCTGTATTCCTTG | 22 bp | 6677.4 |
| Contaminant (pausing peak) | | | 6364.2 |

(SEQ ID NOS: 835, 836, and 837)

FaV-E9 Assay

This section describes the amplification and detection extension primers for the FaV-E9 Assay and provides the sequences of the primers. The sequences of the resulting extended primers are provided in Table 22, below.

Wild type target CTTCAAGGACAAAATACCTGTATTCCTCGCCTGTCCAGGGATCTGCT (SEQ ID NO: 833)

Mutated target CTTCAAGGACAAAATACCTGTATTCCTTGCCTGTCCAGGGATCTGCT (SEQ ID NO: 834)

Extension primer FaV-E10 ———————→

Wild type target CTTCAAGGACAAAATACCTGTATTCCTCGCCTGTCCAGGGATCTGCT (SEQ ID NO: 838)
Mutated target CTTCAAGGACAAAATACCTGTATTCCTTGCCTGTCCAGGGATCTGCT (SEQ ID NO: 839)
Extension primer FaV-E9

Amplification Primers*:

```
FaV-F18:                              (SEQ ID NO: 22)
5'-acgttggatgCTCTGGGCTAATAGGACTAC-3'

FaV-R19:                              (SEQ ID NO: 23)
5'-acgttggatgCTGAAAGGTTACTTCAAGGAC-3'
```

Detection Extension Primers:

```
    FaV-E9:                           (SEQ ID NO: 24)
    5'-GCAGATCCCTGGACAGGC-3'
```

* amplification primers have the 10-mer tag specific for hME method: acgttggatg.
Amplicon length: 92 bp
Termination mix: ddA/ddC/ddT

TABLE 22

Sequence, length and mass of extension primer, extended primer (C and T) and pause product

| Allele | Sequence | Length | Mass |
|---|---|---|---|
| FaV-E9 R506Q | GCAGATCCCTGGACAGGC | 18 bp | 5509.6 |
| C (R) wild type | GCAGATCCCTGGACAGGCGA | 20 bp | 6136 |
| T (Q) mutant | GCAGATCCCTGGACAGGCA | 19 bp | 5806.8 |
| Contaminant (pausing peak) | | | 5838.8 |

(SEQ ID NOS: 840, 841, and 842)

Testing Procedure

Blood specimens and quality control procedures were performed according to protocols described in Example 1. Table 23, below, provides a list of controls used in the presently described assay.

TABLE 23

Controls used in Coagulation Factor V assay

| | | | |
|---|---|---|---|
| 11313817 | T | Factor V R506Q | homozygous mutant |
| 3109017 | T | Factor V R506Q | homozygous mutant |
| GM10701 | C | Factor V R506Q | negative- wild type |
| GM11053 | C | Factor V R506Q | negative- wild type |
| GM12784 | C | Factor V R506Q | negative- wild type |
| GM14646 | C | Factor V R506Q | negative- wild type |
| NA14646 | C | Factor V R506Q | negative- wild type |
| GM9730 | C | Factor V R506Q | negative- wild type |
| GM8811 | C | Factor V R506Q | negative- wild type |
| GM8914 | CT | Factor V R506Q | heterozygous |
| GM8915 | CT | Factor V R506Q | heterozygous |
| NA14641 | CT | Factor V R506Q | heterozygous |
| NA14650 | CT | Factor V R506Q | heterozygous |
| NA16028 | CT | Factor V R506Q | heterozygous |

PCR, dephosphorylation, homogenous MASSEXTEND (HME), and spectroclean resin clean up procedures were carried out as described in Example 1, above.

Results Analysis

Figure 5:
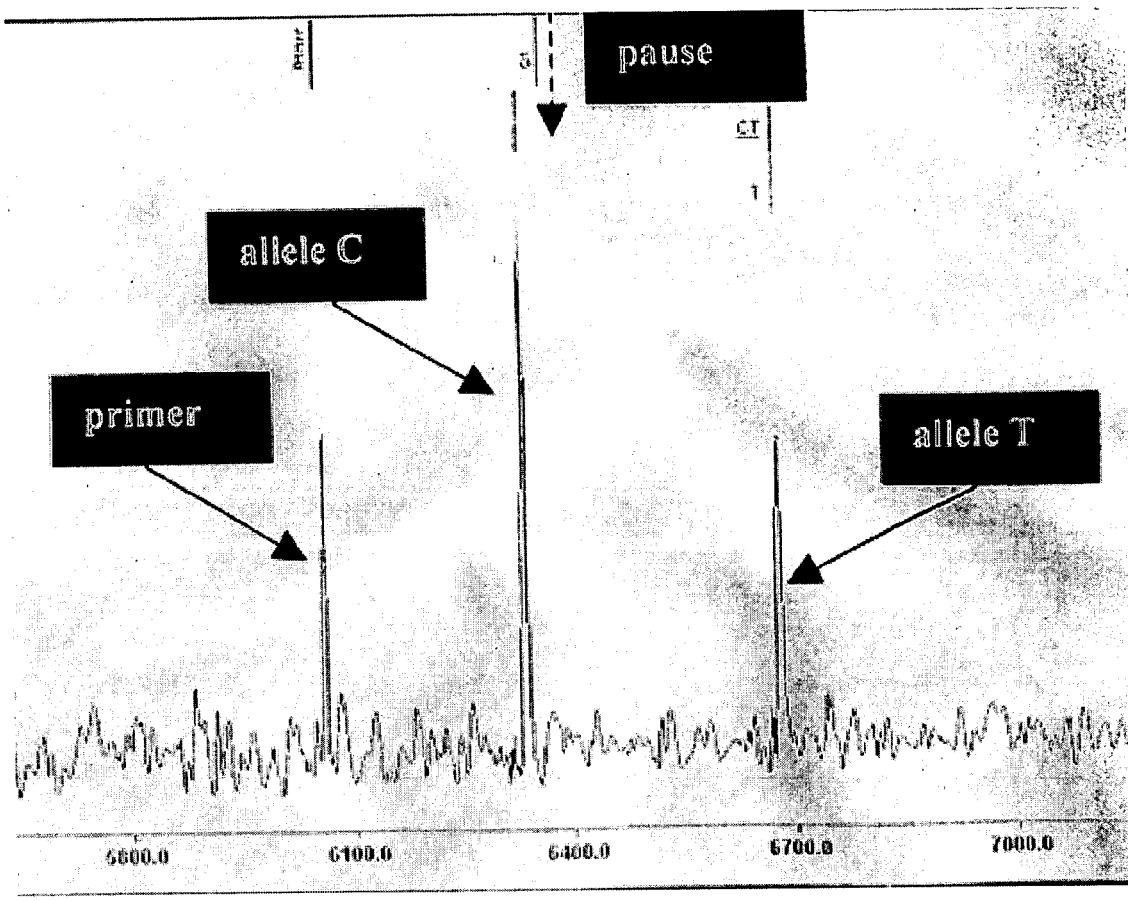
FIG. 5 is a mass spectrum of a heterozygous "GA" allele (heterozygous positive) generated using a screen for a R506Q mutation in the Coagulation Factor V gene.
Figure 6:
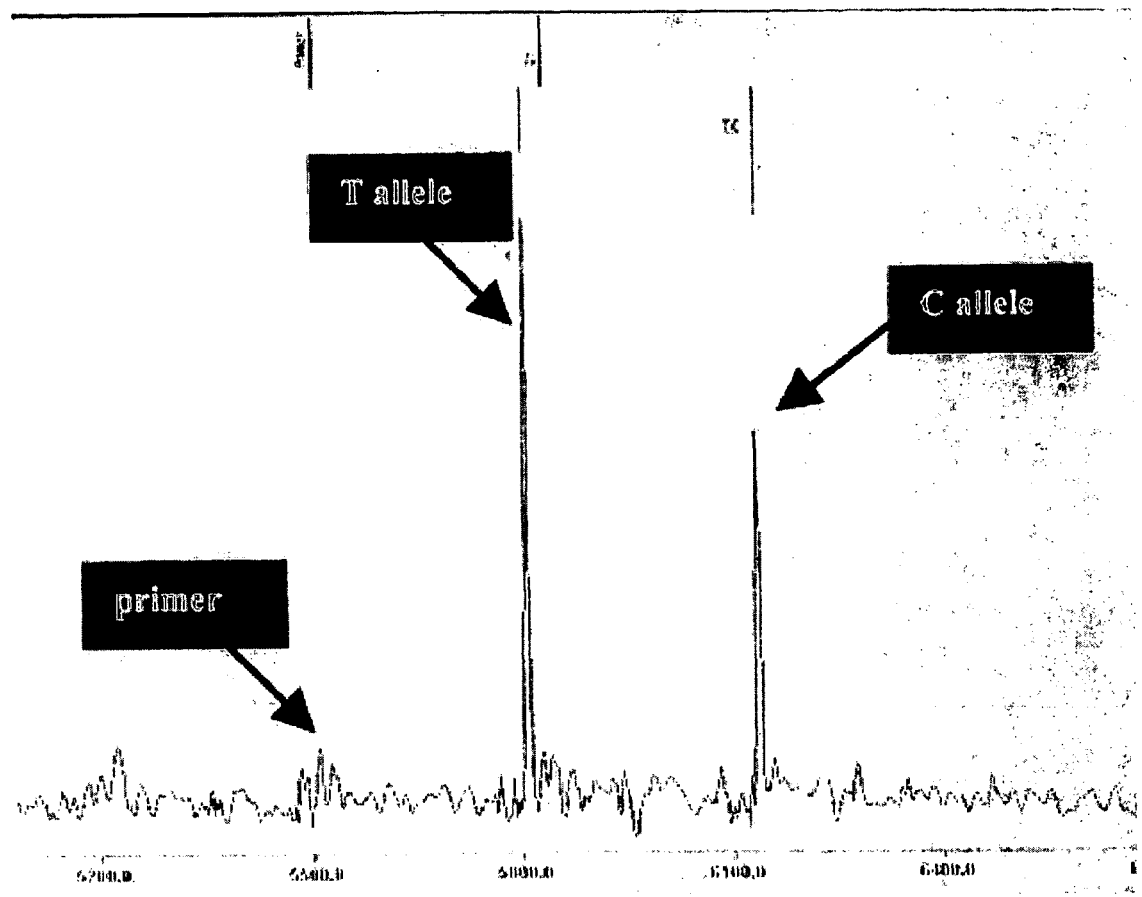
FIG. 6 is a mass spectrum of a heterozygous "GA" allele (heterozygous positive) generated using a screen for a R506Q mutation in the Coagulation Factor V gene.

Results were analyzed as described in Example 1, above. FIG. 5 is a mass spectrum of a heterozygous "GA" allele (heterozygous positive) generated using the FaV-E10 screen for a mutation in the Coagulation Factor V gene. FIG. 6 is a mass spectrum of a heterozygous "GA" allele (heterozygous positive) generated using the FaV-E9 screen for a mutation in the Coagulation Factor V gene. Exemplary test results are provided in Tables 24 and 25, below.

TABLE 24

FaV-E9

| Source of DNA | Conservative | Moderate | Aggressive | Low Probability No Results |
|---|---|---|---|---|
| 68 ARUP DNAs | 65 | 2 | 0 | 1 |
| 71 ARUP DNAs | 66 | 2 | 0 | 3 |
| 8 Coriell DNAs | 8 | 0 | 0 | 0 |
| 2 UMMHC | 2 | 0 | 0 | 0 |
| Total # of DNAs 149 | 140 | 5 | 0 | 4 |

TABLE 25

FaV-E10

| Source of DNA | Conservative | Moderate | Aggressive | Low Probability No Results |
|---|---|---|---|---|
| 68 ARUP DNAs | 65 | 2 | 0 | 1 |
| 71 ARUP DNAs | 66 | 2 | 0 | 3 |
| 8 Coriell DNAs | 8 | 0 | 0 | 0 |
| 2 UMMHC | 2 | 0 | 0 | 0 |
| Total # of DNAs 149 | 140 | 5 | 0 | 4 |

Due to blood clogging the DNA was not extracted and could not be re-extracted because of the too small volume of blood obtained (<0.5 ml). As indicated in Tables 24 and 25, above, the majority of genotype calls for each assay were conservative calls, indicating a high level of accuracy.

Example 4

Cytomegalovirus (CMV) Testing

Clinical Significance

CMV is an opportunistic infection found throughout all geographic locations and socioeconomic groups, infecting about 50% of the general population of the United States by 40 years of age and 90% of people with HIV. CMV is transmitted from person to person by close personal contact. Infectious CMV may be shed in the bodily fluids of any previously infected person, and thus may be found in urine, saliva, blood, tears, semen, and breast milk. CMV can be sexually transmitted and can also be transmitted via breast milk, transplanted organs, and rarely from blood transfusions. In most healthy people, CMV remains in the body indefinitely without causing any harm. Therefore, CMV infection may not be a serious problem for the vast majority of infected individuals.

However, for those with a weakened immune system, including those infected with HIV, or who have undergone bone marrow transplantation or chemotherapy related to cancer, a CMV infection can cause serious and possibly fatal complications. Furthermore, generalized infection and infections of the central nervous system may occur and can be fatal. CMV is also frequently transmitted to a developing child before birth. CMV infection is widespread in developing countries and in areas of lower socioeconomic conditions. For most healthy individuals who acquire CMV after birth, there are few symptoms and no long-term health consequences. Some individuals with symptoms experience a mononucleosis-like syndrome with prolonged fever and a mild hepatitis. Once an individual becomes infected, the virus remains within that individual's body for life, often in a dormant state. Recurrent disease rarely occurs unless the individual's immune system is suppressed, e.g., due to therapeutic drugs or disease.

Infection with CMV is a major cause of disease and death in immunocompromised patients, including organ transplant recipients, patients undergoing hemodialysis, patients with cancer, patients receiving immunosuppressive drugs, and HIV-infected patients. Pneumonia, retinitis (an infection of the eyes), and gastrointestinal disease are the common manifestations of disease.

Because of this risk, exposing immunosuppressed patients to outside sources of CMV should be minimized. Whenever possible, patients without CMV infection should be given organs and/or blood products that are free of the virus.

The risk of developing CMV disease in patients is directly related to the presence and quantity of CMV DNA in blood. The ability to measure CMV viral load is a valuable tool in the management of HIV-1 infected patients. The infection is treatable with drugs. Optimum treatment depends on early and accurate detection.

Overview of Assay

A quantitative CMV assay combines competitive PCR with MassEXTEND™ procedures and matrix assisted laser desorption/ionization time-of-flight mass spectrometry (MALDI-TOF MS). Following isolation of DNA from plasma, PCR amplification is performed on CMV DNA mixed with a known amount of internal standard (oligo—synthetic DNA molecule), which resembles the sequence of the targeted CMV DNA region in all positions except a single base which serves as an assay target. MassARRAY Typer Gene Expression Analysis™ software allows calculating the ratio of internal standard and patient CMV on each spot and the viral concentration in the extracted sample, which is further recalculated into viral particles per ml of patient sample. The method can be used for sensitive and accurate detection of viral nucleic acid with a broad dynamic range (e.g., from 100 to $4 \times 10^8$ viral copies/ml).

The CMV560 quantitative assay quantifies CMV DNA extracted from plasma of CMV infected individuals using PCR and mass spectrometry. The test can quantify CMV DNA over the range of 100-400,000,000 CMV copies/ml.

The assay can be used in conjunction with clinical presentation and other laboratory markers of disease status as an aid to management of individuals infected with CMV. CMV quantitative results from the assay can be used to assess prognosis of disease progression and to monitor the efficacy of antiretroviral therapy by measuring changes in CMV levels during the course of therapy.

This example generally describes amplification and detection extension primers for detecting the presence and amount of CMV in a biological sample. The sequences of the primers are provided below. The procedures described in Example 1, above, can be modified as necessary for handling and analyzing biological samples containing viruses.

460 E3 Assay

Wild type target TGTATGCCACTTTGACATTACACCCATGAACGTGCTCATCGACGTGAACCCG (SEQ ID NO: 843)
Mutated target TGTATGCCACTTTGACATTACACCCGTGAACGTGCTCATCGACGTGAACCCG (SEQ ID NO: 844)

Amplification Primers*:

```
460 F1                                    (SEQ ID NO: 25)
5'-ACGTTGGATGGTCGTGTATGCCACTTTGAC-3'

460 R2                                    (SEQ ID NO: 26)
5'-ACGTTGGATGTGAGGCTGTAATCGCACAGC-3'
```

Detection Extension Primer:

```
460 E3                                    (SEQ ID NO: 27)
5'-CCACTTTGACATTACACCC-3'
```

* amplification primers have the 10-mer tag specific for hME method: acgttggatg.

Termination mix: ddA/ddC/ddT

The sequences of the detection extension primers as they would exist after the extension reaction are provided in Table 26, below.

TABLE 26

| Sequence, length and mass of extension primer | | |
|---|---|---|
| Allele | Sequence | Mass |
| 460 E3 | CCACTTTGACATTACACCC | 5667.7 Da |
| variant A | CCACTTTGACATTACACCCA | 5964.9 Da |
| variant G | CCACTTTGACATTACACCCGT | 6285.1 Da |

(SEQ ID NOS: 845, 846, and 847)

520 E10 Assay

Wild type target CTCGCACCGTCTGCGCGAATGTTACCACCCTGCTTTCCGACCCA (SEQ ID NO.: 848)
Mutated target CTCGCACCGTCTGCGCGAATGTTACCAGCCTGCTTTCCGACCCA (SEQ ID NO.: 849)

Amplification Primers*:

```
520 F8                                      (SEQ ID NO: 28)
5'-ACGTTGGATGTCTTTCAGGAGACGGGTACG-3'

520 R9                                      (SEQ ID NO: 29)
5'-ACGTTGGATGAGATGAGCAGCTTCTGCAGC-3'
```

Detection Extension Primer:

```
520 E10:                                    (SEQ ID NO: 30)
5'-TCTGCGCGAATGTTACCA-3'
```

* amplification primers have the 10-mer tag specific for hME method: acgttggatg.

Termination mix: ddA/ddC/ddT

The sequences of the detection extension primers as they would exist after the extension reaction are provided in Table 27, below.

TABLE 27

| Sequence, length and mass of extension primer | | |
|---|---|---|
| Allele | Sequence | Mass |
| 520 E10: | TCTGCGCGAATGTTACCA | 5474.6 Da |
| Variant C: | TCTGCGCGAATGTTACCAC | 5747.8 Da |
| Variant G: | TCTGCGCGAATGTTACCAGC | 6077 Da |

(SEQ ID NOS: 850, 851, and 852)

591 E14 Assay

Wild type target  CGTTGCTCTTTAAGCACGCCGGCGCGGCXTGCCGCGCGTTGGCGAACGGTAA (SEQ ID NO: 853)

Mutated target   CGTTGCTCTTTAAGCACGCCGGCGCGGCXTGCCGCGCGTTGGCGAACGGTAA (SEQ ID NO: 854)

Amplification Primers*:

```
591 F12                                     (SEQ ID NO: 31)
5'-ACGTTGGATGAGGCGTTGCTCTTTAAGCAC-3'

591 R13                                     (SEQ ID NO: 32)
5'-ACGTTGGATGAGTGCGTGAGCTTACCGTTC-3'
```

Detection Extension Primer:

```
591 E14                                     (SEQ ID NO: 33)
5'-TTAAGCACGCCGGCGCGG-3'
```

* amplification primers have the 10-mer tag specific for hME method: acgttggatg.

Termination mix: ddA/ddC/ddG

The sequences of the detection extension primers as they would exist after the extension reaction are provided in Table 28, below.

TABLE 28

| Sequence, length and mass of extension primer | | |
|---|---|---|
| Allele | Sequence | Mass |
| 591 E14 | TTAAGCACGCCGGCGCGG | 5525.6 Da |
| Variant C: | TTAAGCACGCCGGCGCGGC | 5798.8 Da |
| Variant T: | TTAAGCACGCCGGCGCGGTC | 6103 Da |

(SEQ ID NOS: 855, 856, and 857)

607 E30 Assay

| | | |
|---|---|---|
| Wild type target | AAGCTCACGCACTGCTCCGACGCCTAT☒TGCTCATTCTGGCGGCGCAAATGA | (SEQ ID NO: 858) |
| Mutated target | AAGCTCACGCACTGCTCCGACGCCTAT☒TGCTCATTCTGGCGGCGCAAATGA | (SEQ ID NO: 859) |

Amplification Primers*:

```
607 F28                              (SEQ ID NO: 34)
5'-ACGTTGGATGTCATTTGCGCCGCCAGAATG-3'

607 R29                              (SEQ ID NO: 35)
5'-ACGTTGGATGTTGCTCTTTAAGCACGCCGG-3'
```

Detection Extension Primer:

```
    607 E30                          (SEQ ID NO: 36)
    5'-GCCGCCAGAATGAGCAGA-3'
```

* amplification primers have the 10-mer tag specific for hME method: acgttggatg.

Termination mix: ddA/ddC/ddG

The sequences of the detection extension primers as they would exist after the extension reaction are provided in Table 29, below.

TABLE 29

Sequence, length and mass of extension primer

| Allele | Sequence | Mass |
|---|---|---|
| 607 E30 | GCCGCCAGAATGAGCAGA | 5542.6 Da |
| Variant A: | GCCGCCAGAATGAGCAGATA | 6144 Da |
| Variant G: | GCCGCCAGAATGAGCAGAC | 5815.8 Da |

(SEQ ID NOS: 860, 861, and 862)

CV33-E Assay

Termination mix: ddA/ddC/ddT

The sequences of the detection extension primers as they would exist after the extension reaction are provided in Table 30, below.

TABLE 30

Sequence, length and mass of extension primer

| Allele | Sequence | Mass |
|---|---|---|
| CV33 E | CTCCTTGTCCGAAGCCGC | 5411.5 Da |
| Variant C: | CTCCTTGTCCGAAGCCGCGT | 6028.9 Da |
| Variant T: | CTCCTTGTCCGAAGCCGCA | 5708.7 Da |

(SEQ ID NOS: 865, 866, and 867)

CMV 560 Assay

For quantitative PCR the region chosen is situated in the human CMV UL97 region that codes for a viral serine/threonine protein kinase. A standardized quantitation panel was prepared with CMV strain AD169. The CMV stock of $4 \times 10^{10}$ was diluted with human negative plasma (Accrometrix) to concentrations of 40 copies/ml to $4 \times 10^8$ CMV copies per mililiter.

FIGS. 13A1-13G3 illustrate typical results of the CMV assay. FIGS. 13A1-13A3 are a set of mass spectra in a CMV quantitative assay on samples containing 400 CMV copies/

| | | |
|---|---|---|
| Wild type target | CGTGATGCGTGACGGAGAAAAAGAGGA☒GCGGCTTCGGACAAGGAGAACCT | (SEQ ID NO: 863) |
| Mutated target | CGTGATGCGTGACGGAGAAAAAGAGGA☒GCGGCTTCGGACAAGGAGAACCT | (SEQ ID NO: 864) |

Amplification Primers*:

```
CV-F31                               (SEQ ID NO: 37)
5'-ACGTTGGATGGAGACGACGTGGACGGCAC-3'

CV-R32                               (SEQ ID NO: 38)
5'-ACGTTGGATGCGTGCTTGGACACGCGACTT-3'
```

Detection Extension Primer:

```
    CV33 E                           (SEQ ID NO: 39)
    5'-CTCCTTGTCCGAAGCCGC-3'
```

* amplification primers have the 10-mer tag specific for hME method: acgttggatg.

ml compared to internal controls. FIGS. 13B1-13B3 are a set of mass spectra in a CMV quantitative assay on samples containing 4000 CMV copies/ml compared to internal controls. FIGS. 13C1-13C3 is a set of mass spectra in a CMV quantitative assay on samples containing 40,000 CMV copies/ml compared to internal controls. FIGS. 13D-13D3 is a set of mass spectra in a CMV quantitative assay on samples containing 400,000 CMV copies/ml compared to internal controls. FIGS. 13E1-13E3 are a set of mass spectra in a CMV quantitative assay on samples containing 4,000,000 CMV copies/ml compared to internal controls. FIGS. 13F1-13F3 is a set of mass spectra in a CMV quantitative assay on samples containing 40,000,000 CMV copies/ml compared to internal controls. FIGS. 13G1-13G3 is a set of mass spectra in a CMV quantitative assay on samples containing 400,000,000 CMV copies/ml compared to internal controls.

| | |
|---|---|
| Wild type CMV template | 5'-CCACGAATGCTCGCAGACATGCTGCACGAATACGTCAGAA-3' (SEQ ID NO: 868) |
| Mutated oligo template | 5'-CCACGAATGCTCGCAGACATGCTGCACGAATACGTCAGAA-3' (SEQ ID No: 869) |
| Extension primer CMV560 | ← |

Amplification Primers*:

```
CMV560-S:                                (SEQ ID NO: 58)
5'-ACGTTGGATGCGCTTCTACCACGAATGCTC-3'

CMV560-L:                                (SEQ ID NO: 59)
5'-ACGTTGGATGATAAATACAGCCCGTCGCTC-3'
```

Detection Extension Primer:

```
CMV560-E                                 (SEQ. ID NO: 60)
5'-CTTTCTGACGTATTCGTGCAGCAT-3'
```

* amplification primers have the 10-mer tag specific for hME method: acgttggatg.
Amplicon length: 94 bp
Termination mix: ddA/ddC/ddT
The sequences of the detection extension primers as they would exist after the extension reaction are provided in Table 31, below.

TABLE 31

Sequence, length and mass of extension primer

| Allele | Sequence | Length | Mass |
|---|---|---|---|
| CMV560Quant | CTTTCTGACGTATTCGTGCAGCAT | 24 bp | 7309.8 |
| C wild type | CTTTCTGACGTATTCGTGCAGCATG GT | 27 bp | 8256.4 |
| T mutant | CTTTCTGACGTATTCGTGCAGCATA | 25 bp | 7607 |
| Contaminant (1st pause) | | | 7639 |

(SEQ ID NOS: 870, 871, and 872)

Testing Procedure
This section generally describes exemplary procedures used in CMV assays.
Type of Specimen
Blood was collected observing universal precautions for venipuncture.
For plasma samples, blood was collected in sterile tubes containing EDTA (K2) or ACD, and stored at room temperature. Plasma was removed from cells within 4 hours of collection. The samples were separated by centrifugation at 1000×g for 10 to 15 minutes and standard laboratory procedures were used to remove the plasma. Specimens were not clarified by filtration or further centrifugation.
Specimen Storage and Stability
Specimens were stored at −60° to −80° C. in sterile, screw-capped tubes. Specimens may also be stored at 2° to 8° C. for up to 48 hours or at −20° C. in a non-frost free freezer for up to 72 hours prior to freezing at −60° to −80° C. Repeated freeze/thaw of samples was avoided. Specimens were shipped frozen on dry ice and packaged and labeled in compliance with federal and international regulations covering the transport of clinical samples and etiologicalagents.

Sample Volume
This assay was performed with 500 µl of sample for a single determination. At least 1 ml of plasma was used in the tube.
Processing Whole Blood
Specimens were centrifuged at 1000×g for 10-15 minutes within 4 hours of blood collection. Plasma was aseptically removed and aliquoted (without disturbing the white cell layer or clot) into sterile unbreakable tubes (duplicate aliquots of at least 1 mL plasma are advised to avoid freeze-thaw of specimen in case of repeat testing). Plasma was immediately frozen at −60° C. to −80° C. within 30 minutes of separation. Specimens can be stored at −20° C. in a non-frost-free freezer for up to 72 hours.
Criteria for Unacceptable Specimens
Volume of plasma was below 1 ml.
Barcode of the tube was missing or not readable.
Inappropriate specimens, e.g., blood instead of plasma.
Specimen as received was already defrosted.
Specimen Handling
Blood samples were received with the lab barcode identification numbers. The sample identification was ensured throught out the process by the tracking system on Freedom™, BioRobot MDx™, Genesis™, and MasARRAY™ systems. Specimens were handled as if capable of transmitting infection. Specimen was stored immediately after receipt in the −80 C freezer were not processed immediately.
Materials and Equipment
I. Reagents used for PCR amplification: 10 mM dNTPs (Invitrogen), 10 µM primer mix (forward and reverse) (IDT), internal control—oligo (IDT), PCR kit (Qiagen), sterile water, 10% bleach. Each kit (Qiagen) contains the following reagents: 10×PCR/MgCl$_2$ buffer; 25 mM MgCl$_2$; and HotStar Taq DNA Polymerase.
Volumes that were used for the PCR reactions are provided in Table 32, below.

TABLE 32

Composition of PCR reaction

| Reagent | Stock Concentration | Final Concentration | Reaction Volume |
|---|---|---|---|
| Water | N/A | N/A | 0.28 µl |
| Buffer/MgCl$_2$ | 15 mM (10×) | 1.5 mM | 2.0 µl |
| MgCl$_2$ | 25 mM (10×) | 2.5 mM | 0.8 µl |
| dNTPs | 10 mM (50×) | 200 µM | 0.16 µl |
| Primer Mix | 10 µM (×) | 200 nM | 0.4 µl |
| Internal std CMV560 C_T | Variable (see below) | Variable (see below) | 0.2 µl |
| HotStarTaq | 5 units/µl (50×) | 0.1 unit per reaction | 0.16 µl |
| TOTAL volume | | | 4.00 µl |

Reagent Preparation
Oligo-standard (internal control or internal standard) stock solutions were made. The oligo-standard comes in dry-form. The 20 µM solution was made using the following equation for calculating the volume of water needed: µl water=nmol of oligo×1000 µl/20 nmol. The 20 µM solution of the oligo-standard oligo-standard was thawed and vortexed before use if frozen. A 1 µM stock of oligo-standard was made by diluting 20 µl of 20 µM oligo-standard solution in 380 µl of a 1 ng/µl carrier DNA. A series of working solutions was made in 10E-10M to 10E-20M in 10-fold increments by diluting the Oligo Standard (internal control) 1 µM stock solution using the Tecan Gemini program Diluting oligos10x.gem on C:\Gemini\Data\CMV. 10× dilutions were made in 1 ng/µl carrier DNA.

Master mix was prepared with primers as follows: the 10×PCR Buffer, dNTP mix, 25 MM $MgCl_2$, and stock primers were thawed and vortexed before use. The solutions were mixed completely before use to avoid localized salt concentrations. The PCR mixes w/primers were made according to Table 32, above, multiplying the reagent volumes by number of samples and factor which depends on number of samples run.

II. Reagents used for MassARRAY™: SpectroCHiP, 384-well microplates for PCR (Marsh #SP0401Sequen); 96-well polypropylene skirted microplates for resin addition (Marsh # AB-0800); 96-well polystyrene v-bottom microplates for use with liquid handler (Sarstedt #82.1583); Adhesive PCR foil seals for freezing plates (Marsh #AB-0626); Adhesive Plate seals for temporary sealing (Marsh #AB-0580); Adhesive PCR seals for use in thermocycling (Marsh #AB-0558 or ABI MicroAmp #4306311); 20 ul tips for the liquid handler (VWR #BK717254); tips for manual pipettors; tubes for mixing reagents III. Other Materials: hME buffer; hME SAP enzyme (Shrimp Alkaline Phosphatase); ACT MassEXTEND™ Mix; ThermoSequenase™ enzyme; SpectroCLEAN™ resin; 3 point calibrant; Autoclaved or sterile water >18.2 MegaOhm/cm resistivity (store in plastic); Deionized >18.2 MegaOhm/cm resistivity water for instrument wash stations; isopropanol for liquid handler cleaning; 50% ethanol for nanodispenser operation (stored in sealed, plastic container); oligonucleotide primers; Desiccant (silica gel with moisture indicator).

IV. Exemplary Hardware/Software

MassARRAY™ Liquid handler (Beckman Multimek) automated 96-channel pipettor with controller PC; MassARRAY™ Nanodispenser (RoboDesign pin tool) micro-arrayer with controller PC; 384-well microplate Thermocycler; MassARRAY™ Genotype Analyzer (Bruker Autoflex MALDI-TOF Mass Spectrometer controlled by SpectroACQUIRE software); MassARRAY™ RT Workstation; MassARRAY™ Assay Design Software; MassARRAY™ Oracle Database; Plate centrifuge; universal plate holders; SpectroCLEAN™ resin plate, spoon and scraper; dessiccator for chip storage; single and multi-channel pipettors; plate rotator for mixing resin after a plate has been stored frozen.

Reagent Preparation

Appropriate buffer, primers and EXTEND™ mix were defrosted and vortexed to ensure suspension before using, except for enzymes which were mixed by inversion or pipetting. Enzymes were kept in the freezer or cooler at all times. As enzymes are in low viscosity buffer, they were pipetted slowly to make sure correct volume was applied. Autoclaved Type II water was used to make up solutions.

Reagent Volumes for Sap and Reactions

Dephosphorylation

Shrimp Alkaline Phosphatase (SAP) was prepared in a tube according to Table 33, multiplying the volumes by the number of the samples and then by 1.5 (volumes were for a 384-well microplate and included a 50% overage to account for possible pipetting loss and dead volume in the 96-well microtiter plate used on the Multimek).

Volumes that can be used for the SAP reactions are provided in Table 33, below.

TABLE 33

Composition of SAP mix

| Reagent | Stock Concentration | Final Concentration (with 5 ul PCR product) | Reaction Volume | Volume per 384-well plate |
|---|---|---|---|---|
| Nanopure Autoclaved Water | N/A | N/A | 1.53 µl | 881.3 µl |
| hME buffer | 10× | 1× | 0.17 µl | 97.9 µl |
| SAP | 1 unit/µl | 0.04 units/µl | 0.30 µl | 172.8 µl |
| Totals: | | | 2.00 µl | 1152.00 µl |

2 µl of the diluted SAP was dispensed to each well (see testing procedure).

Homogeneous MassExtend (hME) Reaction hME cocktail was prepared in a tube according to Table 34, below. One reaction volume was multiplied by the number of samples and then by 1.38 (volumes were for a 384-well microplate and included a 38% overage to account for possible pipetting loss and dead volume in the 96-well microtiter plate used on a Multimek).

Volumes that can be used for the hME reactions are provided in Table 34, below.

TABLE 34

Components of hME cocktail

| Reagent | Stock Conc. | Final Concentration (with 7 ul PCR/SAP volume in well) | Reaction Volume | Volume per 384-well plate* |
|---|---|---|---|---|
| Nanopure Autoclaved Water | N/A | N/A | 1.58 µl | 837.3 µl |
| hME Mix (10 × buffer w/2.25 mM d/ddNTPs) | 10× | 1× buffer (together with PCR buffer) with 50 uM d/ddNTPs each | 0.2 µl | 106.0 µl |
| Extension primer | 50 µM | 600 nM | 0.18 µl | 95.4 µl |
| Thermo Sequenase<sup>&</sup> | 32 units/µl | 0.063 unit/µl | 0.04 µl | 21.2 µl |
| Totals: | | | 2.0 µl | 1059.9 µl |

<sup>&</sup>ThermoSequenase was kept at −20° C. until added to the reaction cocktail.

2 µl of the hME cocktail mix was dispensed to the appropriate wells containing 7 µl dephosphorylated PCR product (see Testing Procedure).

Spectroclean Resin Clean Up

Using the SpectroCLEAN™ plate, resin was transferred into the 96-well Marsh plate. The SpectroCLEAN™ plate controls the volume of resin added.

Acceptable Reagent Performance

The acceptability of a reagent was determined by ensuring that quality control results (negative, high, and low controls) were within acceptance criteria ±0.5 $\log_{10}$ value when received from the manufacturer (Affimetrix).

Reagent Storage and Stability hME buffer, hME Mix (10× buffer w/d/ddNTPs), SAP enzyme and ThermoSequenase™ enzyme, calibrant and oligonucleotide primers were stored at −20° C. (tube of calibrant in use was stored at 4° C.). SpectroCLEAN™ resin, water and alcohols were stored at room temperature. The resin was stored away from direct sunlight. SpectroCHIPS™ were stored dessicated.

Calibration

Calibration of the Multimek and Autoflex was performed as daily maintenance. Calibration of the SpectroPOINT™ was performed as monthly maintenance. Calibration of the ABI Thermocycler was performed as yearly maintenance. The high, low and negative external standards were run with appropriate internal standards with each run to ensure that oligo-standards were at appropriate concentrations. The eight internal standards (mutated oligos) were run with each patient sample (eight wells).

Standards

The high, low and negative external standards 0/500/5,000/ 50,000 copies/ml were made from human CMV purified virus, strain AD169 from Advanced Biotechnologies Inc., diluted in human CMV negative plasma (Acrometrix). Standards were diluted from the stock $4 \times 10^{10}$ c/ml when needed, assayed concurrently with the previous batch before being used for the quantification of patient specimens. Diluted standards were stored in −80° C. Alternatively, CMV DNA 4 member panel: 0/500/5,000/50,000 copies/ml from Acrometrix (catalog number 94-2014) was used. Pre-assigned values for internal standards were: 1 pm, 100 fM, 10 fM, 1 fM, 100 aM, 10 aM, 1 aM. Standards were assayed with each run according to the plate 384 well map.

Interpreting Results

Procedures Involved In Assays

DNA extraction and concentration measurement, Uniplex PCR Procedure on Genesis with internal standard, and Homogeneous MassEXTEND Reaction using the MassARRAY System were performed using standard procedures.

Quality Control

To monitor assay performance, at least three levels of control material were included with every assay. The assay was considered valid if all the following conditions occurred: the values determined for the CMV positive controls were within $\pm 0.5 \log_{10}$ specified range and the CMV negative control did not give a positive result. If any of the above conditions are not met: patient results from the affected run should not be reported, the cause for quality control failure should be determined, and the run should be repeated if needed. If the assay must be repeated, then do the following: review instructions to ensure that the assay is performed according to the procedure; verify that the standards and controls are in the appropriate location specified by the plate map; verify that the materials are not expired; verify that the liquid handling robotics are pipetting correct volumes (should be done before the original run).

Controls

All controls were diluted in HIV/HCV/CMV negative human plasma. Pre-assigned values for controls appeared on the tubes: a) The negative control was non-reactive for CMV; b) the positive controls contained a specific CMV titer determined previously or stated by manufacturer (Acrometrix). All controls were be assayed in every plate run according to the order on the tray map. The performance of each control are discussed in the Results section.

Testing Procedures

I. CMV DNA Extraction

CMV DNA was extracted on MDX, Qiagen according to standard procedures. The external standards (240 µl) were diluted and pipetted to S-block under the biological hood.

II. PCR Procedure

The composition of a typical PCR reaction is shown in Table 35, below.

TABLE 35

Composition of single PCR reaction in 384-well plate

| Reagent | Stock Concentration | Final Concentration | Reaction Volume |
|---|---|---|---|
| PCR mix w/primers & oligo-standard | 10× | 1× | 4.0 µl |
| CMV DNA | N/A | N/A | 16.0 µl |
| TOTAL volume | | | 20.00 µl |

To calculate the volumes per run, the volumes of reagents per reaction in Table 32 were multiplied by the number of reactions and by multiplication factor which depended on the sample number run with each oligo-standard concentration (see Table 36). Increasing the final volume allowed for pipetting losses and 'dead' volume when using robotics. The mix was stored at 4° C. until use.

TABLE 36

Multiplication factor in calculations reagent volumes for PCR reaction using Tecan AssayTransfer.gem program (8 wells of the same assay mix)

| Number of Wells w/the same Oligo-Standard | Multiplication factor |
|---|---|
| 1 | 56 |
| 2 | 28 |
| 3 | 19 |
| 4-6 | 14 |
| 7 | 8 |
| 8-9 | 7 |
| 10-11 | 6 |
| 12-13 | 5 |
| 14-18 | 4 |
| 19-22 | 3 |
| 23-26 | 2.5 |
| 27-37 | 2 |
| >37 | 1.5 |

4 µl of PCR mix were dispensed into each well of the 384-well plate. 16 µl of extracted CMV DNA was added to each well using TEMO (Tecan). The following PCR program was run on the thermocycler:

| | | |
|---|---|---|
| 95° C. | 15 minutes | |
| 95° C. | 20 seconds | |
| 56° C. | 30 seconds | } 65 cycles |
| 72° C. | 1 minute | |
| 72° C. | 3 minutes | |
| 4° C. | forever (hold) | |

III. Dephosphorylation Procedure:

Before running SAP procedure, 5 µl of the sample were transferred from each well of the original 20 µl 384-well plate to a new 384-well plate using Multimek (program: "PCR-5 µl to 1 384 plate"). If needed, 3 sister plates can be made this way using program "PCR-5 µl to 3 384 plate." SAP was diluted according to Table 36, above, multiplying the volumes by the number of the samples and then by 1.5. The composition of a typical SAP mix is provided in Table 37, below.

TABLE 37

Composition of SAP Mix

| Reagent | Stock Concentration | Final Concentration | Reaction Volume | Volume per 384-well plate |
|---|---|---|---|---|
| Nanopure Water | N/A | N/A | 1.53 µl | 881.3 µl |
| hME buffer | 10× | 1× * | 0.17 µl | 97.9 µl |
| SAP | 1 unit/µl | 0.15 units/µl | 0.30 µl | 172.8 µl |
| Total | | | 2.00 µl | 1152.00 µl |

2 µl of the diluted SAP were dispensed to each well. The SAP PCR program was run on the thermocycler as follows:

| | |
|---|---|
| 37° C. | 20 minutes |
| 85° C. | 5 minutes, |
| 4° C. | forever (hold) |

IV. Homogeneous MassExtend (hME) Reaction Procedure:

hME cocktail was prepared according to Table 37, above. One reaction volume was multiplied by the number of samples and then by 1.38. The composition of a typical hME preparation are provided in Table 38, below.

TABLE 38

Components of hME cocktail

| Reagent | Stock Concentration | Final Concentration | Reaction Volume | Volume per 384-well plate* |
|---|---|---|---|---|
| Nanopure Water | N/A | N/A | 1.58 µl | 837.2 µl |
| hME Mix (10 × buffer w/2.25 mM d/ddNTPs) | 10× | 1× | 0.2 µl | 106 µl |
| Extension primer | 50 µM | 2.7 µM | 0.18 µl | 95.4 µl |
| Thermo Sequenase& | 32 units/µl | 0.063 unit/µl | 0.04 µl | 21.2 µl |
| | | | 2.0 µl | 1059.8 µl |
| TOTALS: | | | 2.0 µl | 1059.8 µl |

*Volumes are for a 384- well microplate and include a 38% overage to account for possible pipetting loss and dead volume in the 96-well microtiter plate used on the Multimek.
&ThermoSequenase ™ was kept at −20° C. in a portable cooler or freezer at all times.

2 µl of the hME cocktail mix was dispensed to the appropriate wells containing 7 µl dephosphorylated PCR product. The Extension Reaction program was run on the PCR machine as follows:

| | | |
|---|---|---|
| 94° C. | 2 minutes | |
| 94° C. | 5 seconds | |
| 52° C. | 5 seconds | } 99 cycles |
| 72° C. | 5 seconds | |
| 4° C. | forever (hold) | |

V. SpectroCLEAN Resin Clean Up Procedure:

Using a SpectroClean plate, resin was transferred into the 96-well Marsh plate. The hME cation Cleanup method was run on the Biomek.

VI. Dispensing Extended Product on a Chip Using Nanodispenser

Extended product was dispensed on chips according to the manufacturer's instructions.

VII. Reading the Chip on Autoflex.

Chips were read according to the manufacturer's instructions.

The specific issues in quantitative assays were:

(1) Sample Group in Plate Editor contained in SampleID column: name of the samples (barcodes) and standards, and Description column contained the concentrations of the standards as molar integers for example 1 aM, 10 aM, 1 fM etc.

(2) After the run was finished, "Gene Expression" report was used for calculating the molar concentration (M) of the CMV DNA in extracted sample.

(3) The molar concentrations needed to be recalculated into copies/ml by macro in excel file or written script.

Exemplary Test Results

FIGS. 13A-13G are spectra in CMV quantitative assays for samples containing 400 to $4 \times 10^8$ copies/ml. The CMV target was read as "C" allele, and the internal standard (IS) as "T" allele. The areas under the signal peaks are were used by Sequenom Quantification software for quantitation of CMV concentration in the sample. Internal Standards (IS): IS5=10E-11M; IS6=10E-12M; IS7=10E-13M; IS8=10E-14M; IS9=10E-15M; IS10=16E-13M; IS11=10E-17M; IS12=10E-18M; IS13=10E-19M.

The data from the Quantitative Assay was measured as the area under the curve (spectrum) for standards, controls, and patient specimens. The concentration of the unknown samples was calculated based on known standards concentration automatically by the Sequenom software MassArray Typer™ version 3.1.4. The external CMV controls were included in each run to ensure the quality of the results. The lower limit for the assay was 100 copies/mL. Specimens quantitating below this cut-off value can be reported as <100 copies/ml. Specimens with values greater than 1×10E8 copies/mL were above the upper limit of quantitation and can be reported as >1×10E8 copies/ml.

Quantitation of CMV required individual interpretation because of the lack of well-established standard levels and the different rates of progression of the infection to overt disease from the time of first detection in different illness (rapid in bone marrow transplant patients, less rapid in patients with HIV-AIDS). The most consistent marker of progression is a rising viral load in an individual patient, rather than an absolute value.

Standards

External standards were diluted CMV: High—4×10E6, Medium—4×10E4, Low—4×10E2 copies/ml. The original stock with 4×10E10 titer was purchesed from ABI Tech, Inc. Internal standards were diluted oligos containing one mismatch at the site that was assayed. Concentration of the internal standards: 1 pM, 100 fM, 10 fM, 1 fM, 100 aM, 10 aM, 1 aM, 0 .aM, 0.01 aM.

Negative Controls

1. The area under the curve of the Negative Control should be less than the corresponding value of the cutoff (100 copies/mL).

2. The assay should be flagged as "Invalid" if the above condition is not met.

Positive Controls
1. The Positive Controls should quantitate within the range ±0.5 log of the value on the standard label for home made standards or on the package insert for Acrometrix standard.
2. If the Positive Controls quantitate outside the above range, the assay should be flagged "Invalid".

Reporting or Results

Results are reported in CMV copies/ml. Results can be saved into a Laboratory computer system and released to the Meditech System after run approval by a Director or designee through the Interface System.

Limitations

The following quantitation limits are defined for CMV QUANT assay:
The Limit of Quantitaion (LoQ) is 100 CMV DNA copies/ml.
The Upper Quantitation Limit (UQL) for this assay has been determined to be 400,000,000 CMV copies/ml.
The quantitation range of the assay is from 100 to 400,000,000 CMV copies/ml.

Multiple Freeze/Thaw Cycles

The effect of 1, 2, 3 and 4 freeze-thaw cycles frozen at −60° to −80° C. was tested on 40 CMV negative and 25 CMV-positive serum specimens. Up to 3 freeze-thaw cycles on CMV-negative or CMV-positive specimens had no effect on the CMV Quant assay performance.

SPECIFICITY of the CMV560 ASSAY—Herpes Virus GROUP

CMV (HSV type 5) is a member of the herpes virus group, which includes herpes simplex virus types 1 and 2, varicella-zoster virus, HSV type 4, (which causes chickenpox), and Epstein-Barr virus, HSV type 3, (which causes infectious mononucleosis). Specificity of the CMV560 assay was determined by testing amplification primers and extend probe against each of the four types, above mention, herpes virus reference standards using $10^3$ DNA copies in each reaction. CMV560 assay was specific only for CMV virus. Also, positive specific tests were run for each of the other type viruses to ensure that there was specific DNA target.

Linearity

Figure 14:
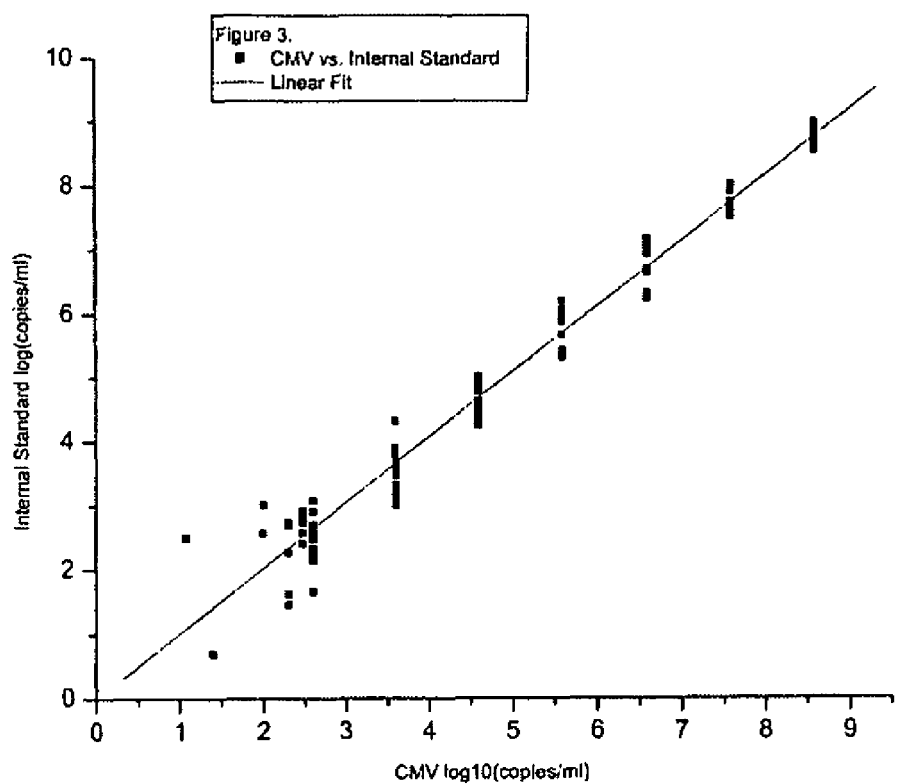
FIG. 14 is a graph that plots CMV plasma samples versus internal standards. A CMV control ($4 \times 10^9$ copies per ml) was diluted down to 40 copies/ml in 10-fold increments, mixed with the Internal Standard of appropriate concentration, extracted (240 µl) on MDX (Qiagen), eluted in 75 µl of buffer and assayed (2 µl) by PCR, followed by SAP treatment, extension reaction and mass spectrometry analysis.

The Linearity of the CMV assay extends over seven logs. An aliquot of quantitated CMV strain AD169 (Advanced Biotechnologies, Columbia, Md.) serially diluted with CMV negative human plasma to concentrations of $4 \times 10^8$ to 40 tcopies/ml was used for assessing the linearity of the assay. Sixteen tests were run for each viral concentration in 10-fold increments from 40 to $4 \times 10^8$ copies/ml (4×4 replicates) and 12 tests for viral concentrations of $4 \times 10^7$ and $4 \times 10^8$ copies/ml (3×4 replicates). The linear range of the CMV assay in this experiment was from 400-40,000,000 copies/ml (FIG. 14). The standard deviation of values in this linear range (over 7 $\log_{10}$) was from 0.001-0.29 log10, and viral load values agreed within 2-fold.

Sensitivity of the Assay

To increase sensitivity of the assay, total volume of the reaction was increased from 5 to 20 μl and the volume of CMV DNA in the reaction was increased 8 folds (from 2 to 16 μl). After this change the MassARRAY™ assay reached a sensitivity of 100% (all samples called) when the input target amount was greater than 100 copies/ml.

Example 5

Screen for Hemachromatosis Mutations

Hereditary hemochromatosis is classically inherited as a recessive trait but is genetically heterogenous. Mutations in the HFE and the TFR2 (transferrin receptor2; Y250X) genes account for about 80% of patients, while a third locus on chromosome 1q is responsible for juvenile hemochromatosis. The nonclassical form of iron overload inherited as an autosomal dominant trait is caused by the mutation N144H in the SLC11A3 protein.

Hematochromatosis is a condition that causes the intestine to absorb too much iron. Over time (often several years) this excess iron is deposited in the cells of the liver, heart, pancreas, joints, and pituitary gland. If untreated, organ damage can result. Iron overload can cause, e.g., liver cancer, diabetes, cirrhosis of the liver, heart disease, arthritis, gray or bronze skin pigmentation, impotence, infertility, and amenorrhea.

The age of onset varies, but symptoms generally begin during middle age. Since hemochromatosis is a hereditary disease, the individuals in the family of a diagnosed individual are at higher risk for having gene mutations. Individuals having a mutation(s) should have iron overload screening since affected individuals are at higher risk for developing iron overload.

There are at least five types of hemochromatosis. Juvenile hemochromatosis or hemochromatosis type 2 (HFE2) is an autosomal recessive disorder. One form, which is designated HFE2A, maps to 1q21. A second form, designated HFE2B, is caused by mutation in the gene encoding hepcidin antimicrobial peptide and maps to 19q13. Hemochromatosis type 3 (HFE3) is an autosomal recessive disorder, caused by mutation in the gene encoding transferrin receptor-2 isoform (TFR2), which maps to 7q22. Hemochromatosis type 4 (HFE4), an autosomal dominant disorder, is caused by mutation N144H in the SLC11A3 gene (604653) that maps to 2q32 and encodes ferroportin 1/IREG1/MTP1—an intestinal iron transporter. Hemochromatosis type 5 is autosomal dominant and caused by mutation in H-ferritin—iron responsive element.

Gene Information
  Gene Locus: 6p21.3
  Gene Symbol: HFE
  Gene Product: HFE protein
  Mutations: H63D; C282Y; S65C
  Mutation Frequency: The prevalence of C282Y homozygosity, H63D homozygosity, and C282Y/H63D compound heterozygosity is estimated to be 0.26%, 1.89% and 1.97%, respectively. The prevalence estimates for C282Y heterozygosity (i.e. C282Y/wild type) are 9.54% among non-Hispanic white population, 2.33% among non-Hispanic blacks, and 2.75% among Mexican-Americans. The prevalence estimates of the C282Y mutation in the US population and of the H63D mutation are 5.4% and 13.5%, respectively.
  OMIM number: 235200
  mRNA NCBI Acc No.: NM_000410: hemochromatosis mRNA (HFE); U60319: haemochromatosis protein (HLA-H); XM_030153: human hemochromatosis mRNA (HFE)

Genomic Acc No.: NG_001335 Homo sapiens genomic large histone family cluster (HFL@) on chromosome 6 (NCBI); NT_007592 Homo sapiens chromosome 6 genomic contig (NCBI); chr 6|GA_x5L2HTUTQ9V (Celera Database)

Clinical Significance

The test can indicate the presence or absence of three mutations that are associated with hereditary hemochromatosis: CYS282TYR (C282Y), HIS63ASP (H63D), and S65C.

CYS282TYR is a missense mutation caused by a G-to-A change at nucleotide position 845 in exon 4 that results in a cysteine to tyrosine transition at position 282 [Cys282Tyr (C282Y)] in the HFE protein. More than 80% of patients with hereditary hemochromatosis are homozygous for this mutation.

HIS63ASP is a mutation caused by a C-to-G change in exon 2 that results in a histidine to asparagine subsitution at position 63 [His63Asp (H63D)] in the HFE protein. Heterozygotes for this mutation are highly prevalent in the general population. This mutation has been found in higher frequency in patients heterozygous for the C282Y substitution than in control individuals. In the homozygous state, His63Asp has been also been observed in a few patients with hereditary hemochromatosis. It is still unclear, however, whether this mutation is a neutral polymorphism or a mutation that in the presence of the C282Y mutation results in a more affected phenotype.

S65C is a mutation, A193T, resulting in a serine to cysteine change at amino acid 65 (S65C) that appears to be associated with milder forms of hereditary hemochromatosis.

The HFE screens described herein can be recommended for a patient, for example, when a member of the patient's family has been diagnosed with HFE and/or when evidence of iron overload exists.

ASSAY For H63D:

This section describes the amplification and detection extension primers for the H63D Assay and provides the sequences of the primers. The sequences of the resulting extended primers are provided in Tables 31 and 32, below.

HFE H63D (C187G) Mutation in Exon 2:

Assay: FM3-E

Overview:

Reverse Reaction:

Amplification by PCR*:

```
HFE-F1                                    (SEQ ID NO: 40)
5'-ACGTTGGATGATGACCAGCTGTTCGTGTTC-3'

HFE-R2                                    (SEQ ID NO: 41)
5'-ACGTTGGATGTCTACTGGAAACCCATGGAG-3'
```

Amplicon length: 74 bp

* amplification primers have the 10-mer tag specific for hME method: acgttggatg.

Extension:

Terminator Bases Mix: ACT

```
Extend Primer (FM3-E):                    (SEQ ID NO: 42)
5' CTCCACACGGCGACTCTCAT-3' (reverse primer)

Analyte C:                                (SEQ ID NO: 876)
5' CTCCACACGGCGACTCTCATGA Analyte G:                                (SEQ ID NO: 877)
5' CTCCACACGGCGACTCTCATC 3'
```

Genotype Calls: C: negative (wild type),
G: homozygous (mutant),
GC: heterozygous.

TABLE 39

Sequence, length and mass of extension primer, extended primers and pause product for HFE FM3-E assay, mutation H63D (C187G)

| Allele | Sequence | Length | Mass |
|---|---|---|---|
| FM3-E | CTCCACACGGCGACTCTCAT | 20 bp | 5997.9 Da |
| C (His) NEGATIVE | CTCCACACGGCGACTCTCATGA | 22 bp | 6624.4 Da |
| G (Asp) HOMOZYGOUS | CTCCACACGGCGACTCTCATC | 21 bp | 6271.2 Da |
| Pause | CTCCACACGGCGACTCTCATG | 21 bp | 6327.2 Da |

(SEQ ID NOS: 878, 879, 880)

Wild type template    TTCGTGTTCTATGAT*ATGAGAGTCGCCGTGTGGAGCCCGA    (SEQ ID NO: 873)

Mutated template    TTCGTGTTCTATGAT*ATGAGAGTCGCCGTGTGGAGCCCGA    (SEQ ID NO: 874)

Extension primer                ATGAGAGTCGCCGTGTGGAG    (SEQ ID NO: 875)

Assay: HFE-E3
Overview:

| | | |
|---|---|---|
| Wild type template | GGATGACCAGCTGTTCGTGTTCTATGATCATGAGAGTCGCCGTGTGGAGCCCCGA | (SEQ ID NO: 881) |
| Mutated template | GGATGACCAGCTGTTCGTGTTCTATGATGATGAGAGTCGCCGTGTGGAGCCCCGA | (SEQ ID NO: 882) |
| Extension primer | CAGCTGTTCGTGTTCTATGAT→ | (SEQ ID NO: 45) |

Amplification by PCR*:

```
HFE-F7                                  (SEQ ID NO: 43)
5'-ACGTTGGATGTTCATGGGTGCCTCAGAGC-3'

HFE-R8                                  (SEQ ID NO: 44)
5'-ACGTTGGATGCCACATCTGGCTTGAAATTC-3'
```

Amplicon length: 153 bp

* amplification primers have the 10-mer tag specific for hME method:acgttggatg.

Extension:
Terminator Bases Mix: ACT

```
Extend Primer (HFE-E3):         (SEQ ID NO: 45)
5' CAGCTGTTCGTGTTCTATGAT 3'

Analyte C:                      (SEQ ID NO: 883)
5' CAGCTGTTCGTGTTCTATGATC 3'

Analyte G:                      (SEQ ID NO: 884)
5' CAGCTGTTCGTGTTCTATGATGA 3'
```

Genotype Calls: C negative (wild type),
G homozygous (mutant),
GC heterozygous.

TABLE 40

Sequence, length and mass of extension primer, extended primers and pause product for HFE-E3 assay, mutation H63D (C187G)

| Allele | Sequence | Length | Mass |
|---|---|---|---|
| HFE-E3 | CAGCTGTTCGTGTTCTATGAT | 21 bp | 6418.2 Da |
| C (His) NEGATIVE | CAGCTGTTCGTGTTCTATGATC | 22 bp | 6691.4 Da |
| G (Asp) HOMO-ZYGOUS | CAGCTGTTCGTGTTCTATGATGA | 23 bp | 7044.6 Da |
| Pause | CAGCTGTTCGTGTTCTATGATG | 22 bp | |

(SEQ ID NOS: 885, 886, and 887)

HFE C282Y (G845A) Mutation in Exon 4:

This section describes the amplification and detection extension primers for the C282Y Assay and provides the sequences of the primers. The sequences of the resulting extended primers are provided in Tables 33 and 34, below.

Assay: FM6-E
Overview:
Reverse Reaction:

| | |
|---|---|
| Wild type template<br>GAGCAGAGATATACGTGCCAGGTGGAGCACCCAGGC | (SEQ ID NO: 888) |
| Mutated template<br>GAGCAGAGATATACGTACCAGGTGGAGCACCCAGGC | (SEQ ID NO: 889) |
| Extension primer<br>←CCAGGTGGAGCACCCAGGC | (SEQ ID NO: 890) |

Amplification by PCR*:

```
HFE-F4                                  (SEQ ID NO: 46)
5'-ACGTTGGATGTGGATAACCTTGGCTGTACC-3'

HFE-R5                                  (SEQ ID NO: 47)
5'-ACGTTGGATGTATCACAATGAGGGGCTGATC-3'
```

Amplicon length: 89 bp

* amplification primers have the 10-mer tag specific for hME method: acgttggatg.

Extension:
Terminator Bases Mix: ACG

```
Extend Primer (FM6-E):          (SEQ ID NO: 48)
5' GCCTGGGTGCTCCACCTGG 3'
(reverse primer)

Analyte G:                      (SEQ ID NO: 891)
5' GCCTGGGTGCTCCACCTGGC 3'

Analyte A:                      (SEQ ID NO: 892)
5' GCCTGGGTGCTCCACCTGGTA 3'
```

Genotype Calls: G negative (wild type),
A homozygous (mutant)
GA heterozygous

TABLE 41

Sequence, length and mass of extension primer, extended primers and pause product for HFE FM6-E assay, mutation C282Y (G845A)

| Allele | Sequence | Length | Mass |
|---|---|---|---|
| FM6-E | GCCTGGGTGCTCCACCTGG | 19 bp | 5796.8 Da |
| G (Cyt) | GCCTGGGTGCTCCACCTGGC | 20 bp | 6070.0 Da |
| A (Tyr) | GCCTGGGTGCTCCACCTGGTA | 21 bp | 6398.2 Da |
| Pause | GCCTGGGTGCTCCACCTGGT | 20 bp | 6101.0 Da |

(SEQ ID NOS: 893, 894, 895, and 896)

Assay: HFE-E6
Overview:

| | | |
|---|---|---|
| Wild type template | TGGGGAAGAGCAGAGATATACGTGCCAGGTGGAGCACCCAGGC | (SEQ ID NO: 897) |
| Mutated template | TGGGGAAGAGCAGAGATATACGTACCAGGTGGAGCACCCAGGC | (SEQ ID NO: 898) |
| Extension primer | GGGAAGAGCAGAGATATACGT  | (SEQ ID NO: 51) |

Amplification by PCR*:

```
    HFE-F9                                  (SEQ ID NO: 49)
    5'-ACGTTGGATGTAATGGGGATGGGACCTACC-3'
```

-continued
```
    HFE-R10                                 (SEQ ID NO: 50)
    5'-ACGTTGGATGTGCTCTCATCAGTCACATACC-3'
```

Amplicon length: 137 bp
* amplification primers have the 10-mer tag specific for hME method: acgttggatg.
Extension:
Terminator Bases Mix: ACT

```
    Extend Primer (HFE-E6):                 (SEQ ID NO: 51)
    5' GGGAAGAGCAGAGATATACGT 3'

Analyte A:                              (SEQ ID NO: 899)
    5' GGGAAGAGCAGAGATATACGTA 3'

Analyte G:                              (SEQ ID NO: 900)
    5' GGGAAGAGCAGAGATATACGTGC 3'
```

Genotype Calls: G negative (wild type)
A homozygous (mutant)
AG heterozygous

TABLE 42

Sequence, length and mass of extension primer, extended primers and pause product for HFE HFE-E6 assay, mutation C282Y (G845A)

| Allele | Sequence | Length | Mass |
|---|---|---|---|
| HFE-E6 | GGGAAGAGCAGAGATATACGT | 21 bp | 6568.3 Da |
| G (Cyt) | GGGAAGAGCAGAGATATACGTGC | 23 bp | 7170.7 Da |
| A (Tyr) | GGGAAGAGCAGAGATATACGTA | 22 bp | 6865.5 Da |
| Pause | GGGAAGAGCAGAGATATACGTG | 22 bp | Da |

(SEQ ID NOS: 901, 902, 903, and 904)

HFE S65C (A193T) Mutation in Exon 2:
This section describes the amplification and detection extension primers for the A193T Assay and provides the sequences of the primers. The sequences of the resulting extended primers are provided in Tables 35 and 36, below.
Assay: HFE S65C_E1
Overview:

| | | |
|---|---|---|
| Wild type template | CAGCTGTTCGTGTTCTATGATCATGAGAGTCGCCGTGTGGAGCCCCGAAC | (SEQ ID NO: 905) |
| Mutated template | CAGCTGTTCGTGTTCTATGATCATGAGTGTCGCCGTGTGGAGCCCCGAAC | (SEQ ID NO: 906) |
| Extension primer | GTCGCCGTGTGGAGCCC  | (SEQ ID NO: 907) |

Amplification by PCR*:

```
    HFE-F1                                  (SEQ ID NO: 52)
    5'-ACGTTGGATGATGACCAGCTGTTCGTGTTC-3'

HFE-R2                                  (SEQ ID NO: 53)
    5'-ACGTTGGATGTCTACTGGAAACCCATGGAG-3'
```

Amplicon length: 74 bp
* amplification primers have the 10-mer tag specific for hME method: acgttggatg.
Extension:
Terminator Bases Mix: CGT

```
    Extend Primer (HFE S65C_E1):            (SEQ ID NO: 54)
    5' GGGCTCCACACGGCGAC 3'
    (reverse primer)

Analyte A:                              (SEQ ID NO: 908)
    5' GGGCTCCACACGGCGACT 3'
    (reverse primer)

Analyte T:                              (SEQ ID NO: 909)
    5' GGGCTCCACACGGCGACAC 3'
    (reverse primer)
```

Genotype Calls: A negative (wild type)
T homozygous (mutant)
AT heterozygous

TABLE 43

Sequence, length and mass of extension primer, extended primers and pause product for HFE S65C-E1 assay, mutation A193T

| Allele | Sequence | Length | Mass |
|---|---|---|---|
| HFE S65C_E1 | GGGCTCCACACGGCGAC | 17 bp | 5181.4 Da |
| A NEGATIVE | GGGCTCCACACGGCGACT | 18 bp | 5469.6 Da |

TABLE 43-continued

Sequence, length and mass of
extension primer, extended primers and pause
product for HFE S65C-E1 assay, mutation A193T

| Allele | Sequence | Length | Mass |
|---|---|---|---|
| T HOMOZYGOUS | GGGCTCCACACGGCGACAC | 19 bp | 5767.8 Da |
| Pause | GGGCTCCACACGGCGACA | 18 bp | Da |

(SEQ ID NOS: 910, 911, 912, and 913)

Assay: HFE S65C_E5
  Overview:

Wild type template    CAGCTGTTCGTGTTCTATGATCATGAGGTCGCCGTGTGGAGCCCCGAAC  (SEQ ID NO: 914)

Mutated template    CAGCTGTTCGTGTTCTATGATCATGAGGTCGCCGTGTGGAGCCCCGAAC  (SEQ ID NO: 915)

Extension primer    TTCGTGTTCTATGATCATGAG    (SEQ ID NO: 57)

Amplification by PCR*:

```
HFE-F7                                  (SEQ ID NO: 55)
5'-ACGTTGGATGTTCATGGGTGCCTCAGAGC-3'

HFE-R8                                  (SEQ ID NO: 56)
5'-ACGTTGGATGCCACATCTGGCTTGAAATTC-3'
```

Amplicon length: 153 bp
* amplification primers have the 10-mer tag specific for hME method:acgttggatg (SEQ ID NO:916)

Extension:
Terminator Bases Mix: CGT

```
Extend Primer (HFE S65C_E5):        (SEQ ID NO: 57)
5' TTCGTGTTCTATGATCATGAG 3'         (6442.2 Da)

Analyte A:                          (SEQ ID NO: 917)
5' TTCGTGTTCTATGATCATGAGAG 3'       (7068.6 Da)

Analyte T:                          (SEQ ID NO: 918)
5'-TTCGTGTTCTATGATCATGAGT-3'        (6730.4 Da)
```

Genotype Calls: A negative (wild type)
  T homozygous (mutant)
  AT heterozygous

TABLE 44

Sequence, length and mass of extension
primer, extended primers and pause
product for HFE S65C-E5 assay, mutation A193T

| Allele | Sequence | Length | Mass |
|---|---|---|---|
| HFE S65C_E5 | TTCGTGTTCTATGATCATGAG | 21 bp | 6442.2 Da |
| A NEGATIVE | TTCGTGTTCTATGATCATGAGAG | 23 bp | 7068.6 Da |
| T HOMOZYGOUS | TTCGTGTTCTATGATCATGAGT | 22 bp | 6730.4 Da |
| Pause | TTCGTGTTCTATGATCATGAGA | 22 bp | Da |

(SEQ ID NOS: 919, 920, and 512-513, respectively)

Testing Procedure

Blood specimens and quality control procedures were performed according to protocols described in Example 1. Table 45, below, provides a list of controls used in the presently described assay.

TABLE 45

Controls Used in the Assays

| | | | |
|---|---|---|---|
| HFE H63D | | | |
| NA13591 | G | HFE H63D | homozygous mutant |
| 393547 | C | HFE H63D | negative- wild type |
| GM7798 | C | HFE H63D | negative- wild type |
| GM8810 | C | HFE H63D | negative- wild type |
| GM9729 | C | HFE H63D | negative- wild type |
| NA14646 | C | HFE H63D | negative- wild type |
| NA14702 | C | HFE H63D | negative- wild type |
| NA16028 | C | HFE H63D | negative- wild type |
| GM12783 | CG | HFE H63D | heterozygous |
| NA14641 | CG | HFE H63D | heterozygous |
| NA14650 | CG | HFE H63D | heterozygous |
| NA16000 | CG | HFE H63D | heterozygous |
| HFE C282Y | | | |
| 393547 | A | HFE C282Y | homozygous mutant |
| NA14646 | A | HFE C282Y | homozygous mutant |
| GM5896 | G | HFE C282Y | negative- wild type |
| GM6023 | G | HFE C282Y | negative- wild type |
| GM7798 | G | HFE C282Y | negative- wild type |
| GM8810 | G | HFE C282Y | negative- wild type |
| NA13591 | G | HFE C282Y | negative- wild type |
| NA14702 | G | HFE C282Y | negative- wild type |
| NA16000 | G | HFE C282Y | negative- wild type |
| NA16028 | G | HFE C282Y | negative- wild type |
| NA14641 | AG | HFE C282Y | heterozygous |
| NA14650 | AG | HFE C282Y | heterozygous |
| HFE S65C | | | |
| 393547 | A | HFE S65C | negative- wild type |
| GM12783 | A | HFE S65C | negative- wild type |
| GM5896 | A | HFE S65C | negative- wild type |
| GM6023 | A | HFE S65C | negative- wild type |
| GM7798 | A | HFE S65C | negative- wild type |
| GM8810 | A | HFE S65C | negative- wild type |
| GM9729 | A | HFE S65C | negative- wild type |

TABLE 45-continued

Controls Used in the Assays

| | | | |
|---|---|---|---|
| NA13591 | A | HFE S65C | negative- wild type |
| NA14641 | A | HFE S65C | negative- wild type |
| NA14646 | A | HFE S65C | negative- wild type |
| NA14650 | A | HFE S65C | negative- wild type |
| NA14702 | A | HFE S65C | negative- wild type |
| NA16000 | A | HFE S65C | negative- wild type |
| NA16028 | AT | HFE S65C | heterozygous |

PCR, dephosphorylation, homogenous MASSEXTEND (HME), and spectroclean resin clean up procedures were carried out as described in Example 1, above.

Results Analysis

Figure 7:
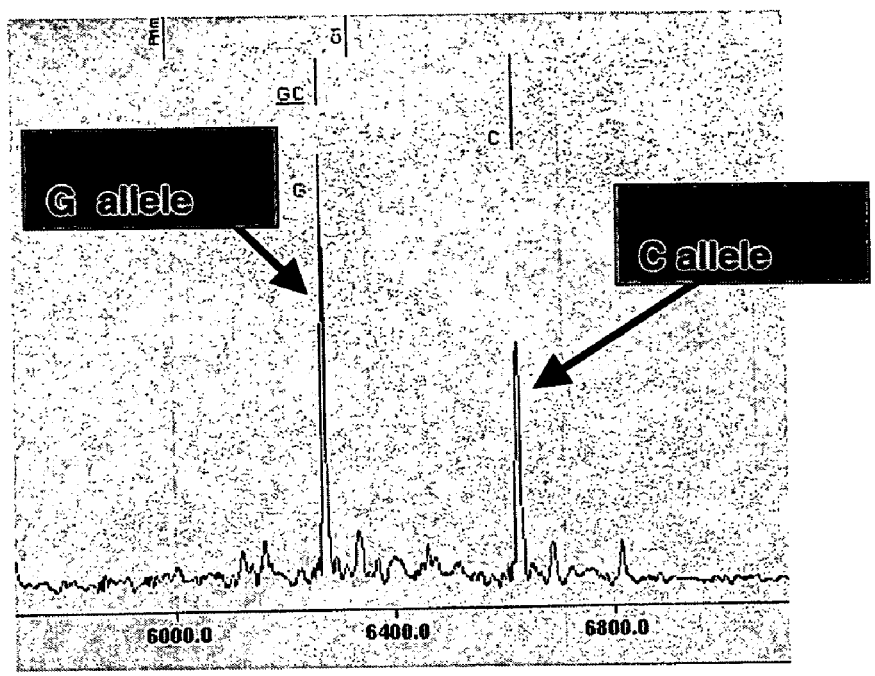
FIG. 7 is a mass spectrum of heterozygous "GC" alleles (heterozygous positive) for H63D Histidine to Aspartic acid (C187G) mutation in the FM3-E assay.
Figure 8:
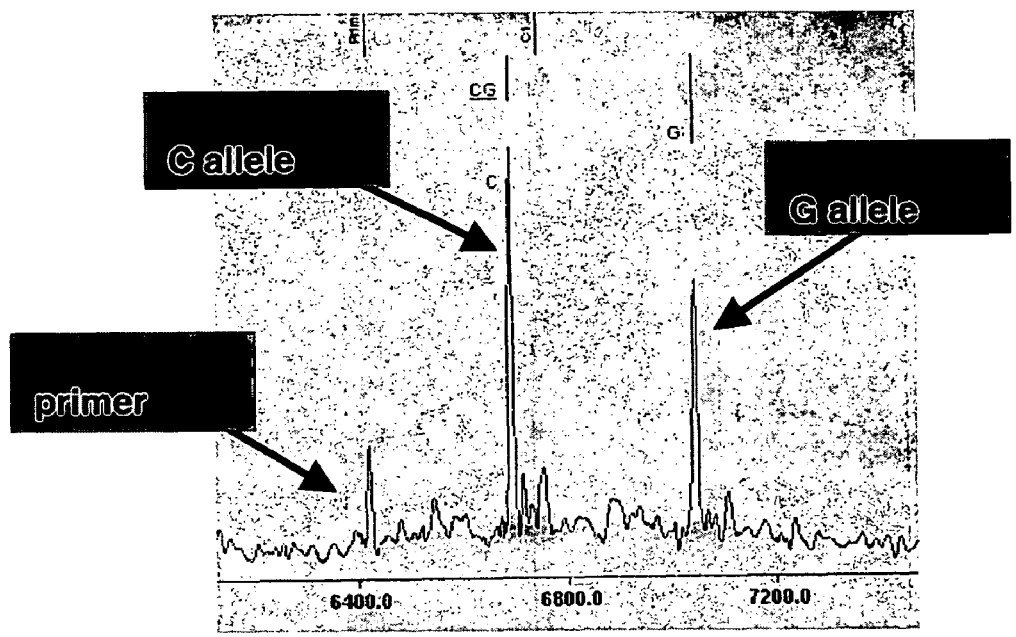
FIG. 8 is a mass spectrum of heterozygous "GC" alleles (heterozygous positive) for H63D Histidine to Aspartic acid (C187G) mutation in the HFE-E3 assay.
Figure 9:
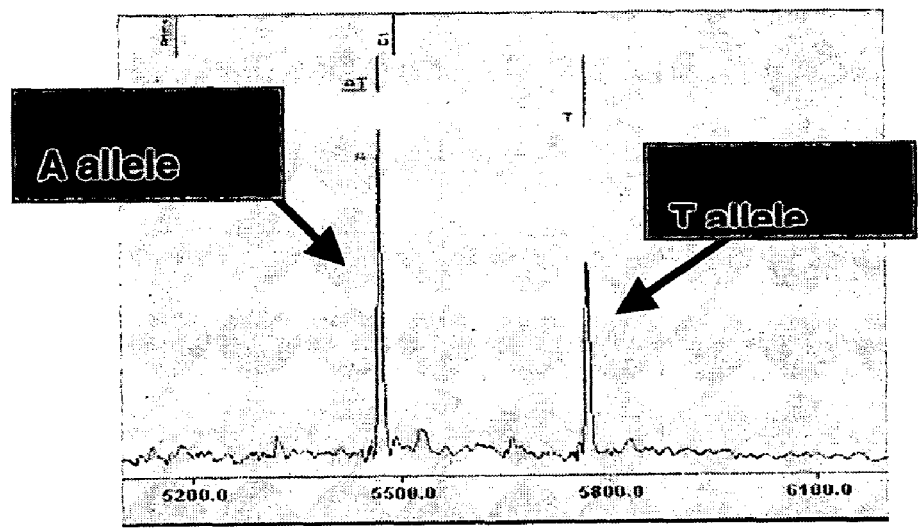
FIG. 9 is a mass spectrum of heterozygous "GA" alleles (heterozygous positive) for S65C Serine to Cysteine (A193T) mutation in the HFE S65C E1 assay.
Figure 10:
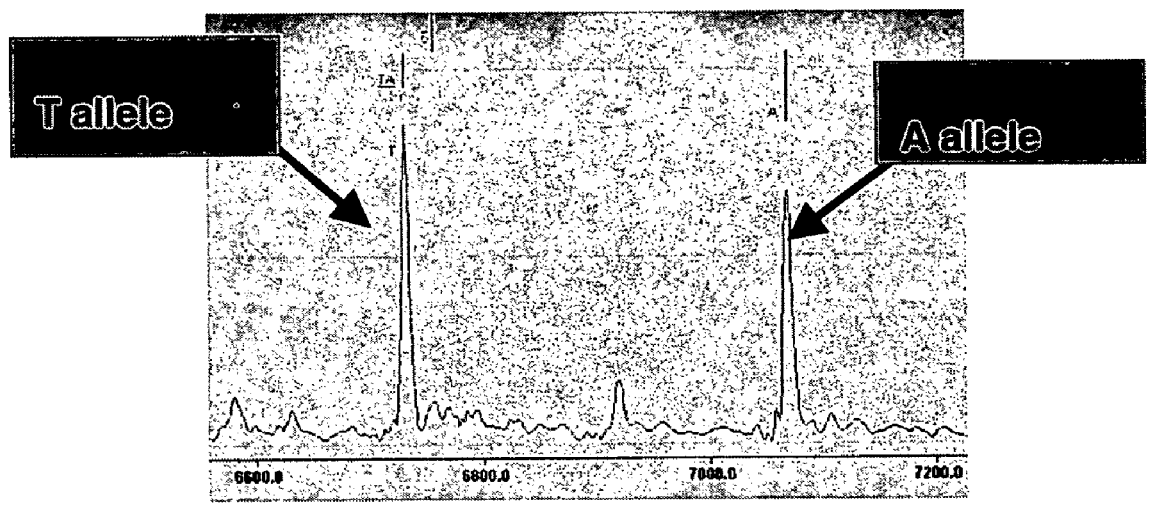
FIG. 10 is a mass spectrum of heterozygous "GA" alleles (heterozygous positive) for S65C Serine to Cysteine (A193T) mutation in the HFE S65C E5 assay.
Figure 11:
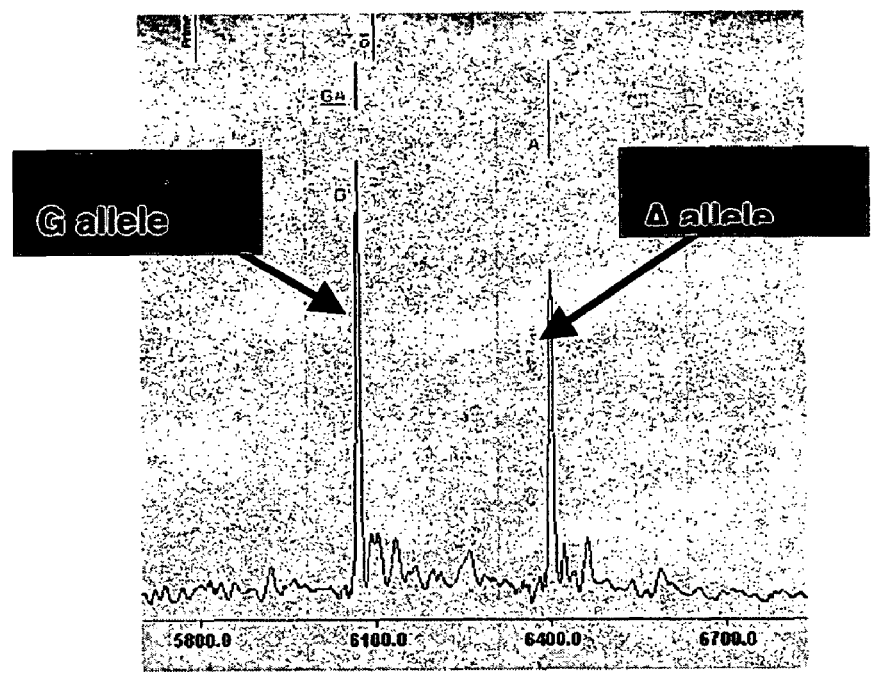
FIG. 11 is a mass spectrum of heterozygous "GA" alleles (heterozygous positive) for C282Y cysteine to tyrosine (G845A) mutation in the FM6-E assay.
Figure 12:
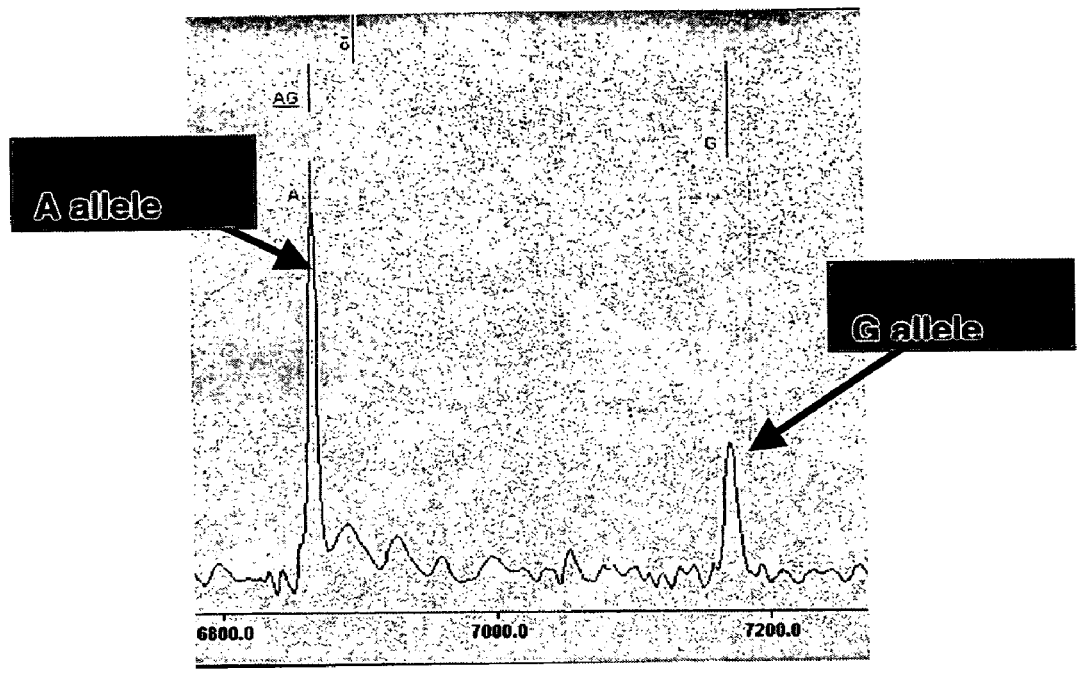
FIG. 12 is a mass spectrum of heterozygous "GA" alleles (heterozygous positive) for C282Y cysteine to tyrosine (G845A) mutation in the HFE-E6 assay.

Results were analyzed as described in Example 1, above. FIG. 7 is a mass spectrum of heterozygous "GA" alleles (heterozygous positive) for H63D Histidine to Aspartic acid (C187G) mutation in the FM3-E assay. FIG. 8 is a mass spectrum of heterozygous "GC" alleles (heterozygous positive) for H63D Histidine to Aspartic acid (C187G) mutation in the HFE-E3 assay. FIG. 9 is a mass spectrum of heterozygous "GA" alleles (heterozygous positive) for S65C Serine to Cysteine (A193T) mutation in the HFE S65C E1 assay. FIG. 10 is a mass spectrum of heterozygous "GA" alleles (heterozygous positive) for S65C Serine to Cysteine (A193T) mutation in the FIFE S65C E5 assay. FIG. 11 is a mass spectrum of heterozygous "GA" alleles (heterozygous positive) for C282Y cysteine to tyrosine (G845A) mutation in the FM6-E assay. FIG. 12 is a mass spectrum of heterozygous "GA" alleles (heterozygous positive) for C282Y cysteine to tyrosine (G845A) mutation in the HFE-E6 assay.

Exemplary test results are provided in Tables 46 to 48, below.

Validation Tests Results

TABLE 46

H63D mutation tested by HFE-E3_FM3-E assays

| Source of DNA/Assay | Conservative | Moderate | Aggressive | Low Probability |
|---|---|---|---|---|
| ARUP 131 specimens | | | | |
| FM3-E | 130 | 1 | 0 | 0 |
| HFE-E3 | 123 | 7 | 1 | 0 |

Distribution of Genotypes:

| | |
|---|---|
| GG HOMOZYGOUS | N = 5 |
| CC NEGATIVE | N = 68 |
| GC HETEROZYGOUS | N = 58 |

Summary:
a) FIFE assays, FM3-E and HFE-E3, were validated in two runs "DD33" and "Validation HFE-E3_FM3-E" for a total of 131 samples.
b) The samples were obtained from ARUP and our results are compared to the results from ARUP.
c) The results from 129 samples were in accordance with ARUP results for both assays.
d) For two samples, 01hFE_021220 & 101hFE_021220, our results differ from those from ARUP. The sample: 101hFE_021220 is a duplicate (re-extracted and PCRed a second time) of the sample 01hFE_021220. All 4 of our results agreed. We suggest that our results are correct.

e) Thirteen samples which did not give any result in one of the assays were re-run in subsequent runs and results were obtained for all the samples.

TABLE 47

C282Y mutation tested by FM6-E and HFE-E6 Assays

| Source of DNA/Assay | Conservative | Moderate | Aggressive | Low Probability |
|---|---|---|---|---|
| ARUP 124 specimens | | | | |
| FM6-E | 124 | 0 | 0 | 0 |
| HFE-E6 | 122 | 2 | 0 | 0 |

Distribution of Genotypes:

| | |
|---|---|
| GG HOMOZYGOUS | N = 32 |
| CC NEGATIVE | N = 47 |
| GC HETEROZYGOUS | N = 45 |

Summary:
a) HFE assays, FM6-E and HFE-E6, were validated in the run "VALIDATION HFE-FM6 HFE-E 041603" a total of 124 samples.
b) The samples were obtained from ARUP and our results are compared to the results from ARUP.
c) The results from 122 samples agreed with ARUP results for both assays.
d) For two samples (04hFE_021220 & 104hFE_021220) our results differ from those from ARUP. Sample 104hFE_021220 is a re-extracted second time sample 04hFE_021220, and all 4 of our results agree. Therefore, we suggest that our results are correct.

TABLE 48

S65C mutation tested by HFE S65C_E1 and HFE S65C_E5 assays

| Source of DNA/Assay | Conservative | Moderate | Aggressive | Low Probability |
|---|---|---|---|---|
| ARUP 102 specimens | | | | |
| HFE S65C_E1 | 102 | 0 | 0 | 0 |
| HFE S65C_E5 | 99 | 3 | 0 | 0 |

Distribution of Genotypes:

| | |
|---|---|
| TT HOMOZYGOUS | N = 0 |
| AA NEGATIVE | N = 98 |
| AT HETEROZYGOUS | N = 4 |

Summary:
a) HFE assays, HFE S65C_E1 and HFE S65C_E5, were at total of 103 samples.
b) The samples were obtained from ARUP and our results are compared to the results from ARUP.
c) The results from 98 samples agree with ARUP results for both assays.
d) For six samples (01hFE_021220 & 101hFE_021220, 04hFE_021220 & 104hFE_021220, 41hFE_021126 & 141hFE_021126) our results differ from those from ARUP. The samples: 101hFE_021220, 104hFE__021220, and 141hFE__021126 are duplicates (re-extracted and PCRed second time) of the samples 01hFE__021220, 04hFE__021220, and 41hFE__021126. All 4 of our results agree for each sample.
e) In addition, since samples 01hFE__021220 and 04hFE__021220 had different calls for two mutations suggesting a mixup in the ARUP samples.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A fully automated system for performing an assay on a biological sample, comprising:
   (a) a sample transfer module for transferring a portion of the sample to a well of a first multi-well plate and programmed to exchange with at least one other module of the system information about the location of the portion in the first multi-well plate;
   (b) a nucleic acid extraction module for extracting nucleic acids from cells within the portion and for transferring the portion from the first multi-well plate to a well of a second multi-well plate;
   (c) a nucleic acid measurement module for measuring the concentration of nucleic acids in the portion;
   (d) a PCR preparation module for adding polymerase chain reaction (PCR) reaction materials to the portion and programmed to receive information from (a) about the location of the portion in the first or second multi-well plate, and wherein the PCR preparation module comprises the primer set SEQ ID NO: 13, SEQ ID NO: 14, and SEQ ID NO: 15;
   (e) a thermocyling module for amplifying a target sequence and extending a primer in the portion;
   (f) a primer extension preparation module for adding primer extension reaction materials to the portion;
   (g) a mass spectrometry preparation module for moving a sample of the portion to a support for analysis by mass spectrometry;
   (h) a mass spectrometry module for analyzing the sample;
   (i) a central controller:
   (1) in communication with, and programmed to exchange information about the biological sample with, an outside system or database; and
   (2) in communication with, and programmed to exchange information about the biological sample with, at least (a)-(h) of the system; and
   (j) plate editor software programmed to a multi-well plate where the portion will be located prior to dispensing of the portion into a well of the multi-well plate, exchange information with at least (a), (d) and (i) of the system and an outside system or database, exchange information with (a) and (d) about which well in a multi-well plate will receive or contains the portion, and exchange information with (d) about which assay to perform on the portion.

* * * * *

UNITED STATES PATENT AND TRADEMARK OFFICE
CERTIFICATE OF CORRECTION

| | | |
|---|---|---|
| PATENT NO. | : 7,939,310 B2 | Page 1 of 1 |
| APPLICATION NO. | : 10/913280 | |
| DATED | : May 10, 2011 | |
| INVENTOR(S) | : Ginns et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 266 days.

Signed and Sealed this
Twenty-seventh Day of September, 2011

David J. Kappos
*Director of the United States Patent and Trademark Office*

SEQUENCE LISTING

<160> NUMBER OF SEQ ID NOS: 920

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
acgttggatg atgccttcac aaagcggaag         30

<210> SEQ ID NO 2
<211> LENGTH: 30
<212> TYPE: DNA
<213> ORGANISM: Artificial Sequence
<220> FEATURE:
<223> OTHER INFORMATION: Primer

<400> SEQUENCE: 2
acgttggatg cttgaaggag aaggtgtctg         30

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
tgcgtgatga tgaaatcg         18

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4
acgttggatg agtgatgccc atgtcggtg         29

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
acgttggatg ctgacctgaa gcacttgaag         30

<210> SEQ ID NO 6

```
<211> LENGTH: 20
<212> TYPE: DNA
<213> ORGANISM: Artificial Sequence
<220> FEATURE:
<223> OTHER INFORMATION: Primer

<400> SEQUENCE: 6
ggagaaggtg tctgcgggag                                              20

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
acgttggatg tctacctgaa gagcaagtcc                                   30

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
acgttggatg tctcccgaga ggtaaagaac                                   30

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
aacaaagact tcaaagacac tt                                           22

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
acgttggatg actactacct cttctacctg                                   30

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
acgttggatg ctccagcatc actcactttg                                   30

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
```
gaggagctga ccagtgaaag                                                        19

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
acgttggatg actcatattc tgggctcctg                                             30

<210> SEQ ID NO 14
<211> LENGTH: 30
<212> TYPE: DNA
<213> ORGANISM: Artificial Sequence
<220> FEATURE:
<223> OTHER INFORMATION: Primer

<400> SEQUENCE: 14
acgttggatg agagagctgc ccatgaatag                                             30

<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15
cactgggagc attgaggct                                                         19

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
acgttggatg tggaaccaat cccgtgaaag                                             30

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
acgttggatg agagagctgc ccatgaatag                                             30

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
caataaaagt gactctcagc                                                        20

<210> SEQ ID NO 19
<211> LENGTH: 30
<212> TYPE: DNA
<213> ORGANISM: Artificial Sequence
<220> FEATURE:

```
<223> OTHER INFORMATION: Primer

<400> SEQUENCE: 19
acgttggatg aagaccatac tacagtgacg                              30

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20
acgttggatg cattatttag ccaggagacc                              30

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gacaaaatac ctgtattcct                                         20

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
acgttggatg ctctgggcta ataggactac                              30

<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
acgttggatg ctgaaaggtt acttcaagga c                            31

<210> SEQ ID NO 24
<211> LENGTH: 18
<212> TYPE: DNA
<213> ORGANISM: Artificial Sequence
<220> FEATURE:
<223> OTHER INFORMATION: Primer

<400> SEQUENCE: 24
gcagatccct ggacaggc                                           18

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
acgttggatg gtcgtgtatg ccactttgac                              30

<210> SEQ ID NO 26
```

```
<211> LENGTH: 30
<212> TYPE: DNA
<213> ORGANISM: Artificial Sequence
<220> FEATURE:
<223> OTHER INFORMATION: Primer

<400> SEQUENCE: 26
acgttggatg tgaggctgta atcgcacagc                                              30

<210> SEQ ID NO 27
<211> LENGTH: 19
<212> TYPE: DNA
<213> ORGANISM: Artificial Sequence
<220> FEATURE:
<223> OTHER INFORMATION: Primer

<400> SEQUENCE: 27
ccactttgac attacaccc                                                          19

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
acgttggatg tctttcagga gacgggtacg                                              30

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
acgttggatg agatgagcag cttctgcagc                                              30

<210> SEQ ID NO 30
<211> LENGTH: 18
<212> TYPE: DNA
<213> ORGANISM: Artificial Sequence
<220> FEATURE:
<223> OTHER INFORMATION: Primer

<400> SEQUENCE: 30
tctgcgcgaa tgttacca                                                           18

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
acgttggatg aggcgttgct ctttaagcac                                              30

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
```

```
acgttggatg agtgcgtgag cttaccgttc                              30
```

<210> SEQ ID NO 33
<211> LENGTH: 18
<212> TYPE: DNA
<213> ORGANISM: Artificial Sequence
<220> FEATURE:
<223> OTHER INFORMATION: Primer

<400> SEQUENCE: 33

```
ttaagcacgc cggcgcgg                                           18
```

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34

```
acgttggatg tcatttgcgc cgccagaatg                              30
```

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35

```
acgttggatg ttgctcttta agcacgccgg                              30
```

<210> SEQ ID NO 36
<211> LENGTH: 18
<212> TYPE: DNA
<213> ORGANISM: Artificial Sequence
<220> FEATURE:
<223> OTHER INFORMATION: Primer

<400> SEQUENCE: 36

```
gccgccagaa tgagcaga                                           18
```

<210> SEQ ID NO 37
<211> LENGTH: 29
<212> TYPE: DNA
<213> ORGANISM: Artificial Sequence
<220> FEATURE:
<223> OTHER INFORMATION: Primer

<400> SEQUENCE: 37

```
acgttggatg gagacgacgt ggacggcac                               29
```

<210> SEQ ID NO 38
<211> LENGTH: 30
<212> TYPE: DNA
<213> ORGANISM: Artificial Sequence
<220> FEATURE:
<223> OTHER INFORMATION: Primer

<400> SEQUENCE: 38

```
acgttggatg cgtgcttgga cacgcgactt                              30
```

<210> SEQ ID NO 39
<211> LENGTH: 18
<212> TYPE: DNA
<213> ORGANISM: Artificial Sequence
<220> FEATURE:

<223> OTHER INFORMATION: Primer

<400> SEQUENCE: 39
ctccttgtcc gaagccgc                                                18

<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40
acgttggatg atgaccagct gttcgtgttc                                   30

<210> SEQ ID NO 41
<211> LENGTH: 30
<212> TYPE: DNA
<213> ORGANISM: Artificial Sequence
<220> FEATURE:
<223> OTHER INFORMATION: Primer

<400> SEQUENCE: 41
acgttggatg tctactggaa acccatggag                                   30

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
ctccacacgg cgactctcat                                              20

<210> SEQ ID NO 43
<211> LENGTH: 29
<212> TYPE: DNA
<213> ORGANISM: Artificial Sequence
<220> FEATURE:
<223> OTHER INFORMATION: Primer

<400> SEQUENCE: 43
acgttggatg ttcatgggtg cctcagagc                                    29

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44
acgttggatg ccacatctgg cttgaaattc                                   30

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
cagctgttcg tgttctatga t                                            21

<210> SEQ ID NO 46

```
<211> LENGTH: 30
<212> TYPE: DNA
<213> ORGANISM: Artificial Sequence
<220> FEATURE:
<223> OTHER INFORMATION: Primer

<400> SEQUENCE: 46
acgttggatg tggataacct tggctgtacc                                          30

<210> SEQ ID NO 47
<211> LENGTH: 31
<212> TYPE: DNA
<213> ORGANISM: Artificial Sequence
<220> FEATURE:
<223> OTHER INFORMATION: Primer

<400> SEQUENCE: 47
acgttggatg tatcacaatg aggggctgat c                                        31

<210> SEQ ID NO 48
<211> LENGTH: 19
<212> TYPE: DNA
<213> ORGANISM: Artificial Sequence
<220> FEATURE:
<223> OTHER INFORMATION: Primer

<400> SEQUENCE: 48
gcctgggtgc tccacctgg                                                      19

<210> SEQ ID NO 49
<211> LENGTH: 30
<212> TYPE: DNA
<213> ORGANISM: Artificial Sequence
<220> FEATURE:
<223> OTHER INFORMATION: Primer

<400> SEQUENCE: 49
acgttggatg taatggggat gggacctacc                                          30

<210> SEQ ID NO 50
<211> LENGTH: 31
<212> TYPE: DNA
<213> ORGANISM: Artificial Sequence
<220> FEATURE:
<223> OTHER INFORMATION: Primer

<400> SEQUENCE: 50
acgttggatg tgctctcatc agtcacatac c                                        31

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
gggaagagca gagatatacg t                                                   21

<210> SEQ ID NO 52
<211> LENGTH: 30
<212> TYPE: DNA
<213> ORGANISM: Artificial Sequence
<220> FEATURE:
<223> OTHER INFORMATION: Primer

<400> SEQUENCE: 52
```

```
acgttggatg atgaccagct gttcgtgttc                                              30

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
acgttggatg tctactggaa acccatggag                                              30

<210> SEQ ID NO 54
<211> LENGTH: 17
<212> TYPE: DNA
<213> ORGANISM: Artificial Sequence
<220> FEATURE:
<223> OTHER INFORMATION: Primer

<400> SEQUENCE: 54
gggctccaca cggcgac                                                            17

<210> SEQ ID NO 55
<211> LENGTH: 29
<212> TYPE: DNA
<213> ORGANISM: Artificial Sequence
<220> FEATURE:
<223> OTHER INFORMATION: Primer

<400> SEQUENCE: 55
acgttggatg ttcatgggtg cctcagagc                                               29

<210> SEQ ID NO 56
<211> LENGTH: 30
<212> TYPE: DNA
<213> ORGANISM: Artificial Sequence
<220> FEATURE:
<223> OTHER INFORMATION: Primer

<400> SEQUENCE: 56
acgttggatg ccacatctgg cttgaaattc                                              30

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
ttcgtgttct atgatcatga g                                                       21

<210> SEQ ID NO 58
<211> LENGTH: 30
<212> TYPE: DNA
<213> ORGANISM: Artificial Sequence
<220> FEATURE:
<223> OTHER INFORMATION: Primer

<400> SEQUENCE: 58
acgttggatg cgcttctacc acgaatgctc                                              30

<210> SEQ ID NO 59
<211> LENGTH: 30
<212> TYPE: DNA
<213> ORGANISM: Artificial Sequence
<220> FEATURE:
```

```
<223> OTHER INFORMATION: Primer

<400> SEQUENCE: 59
acgttggatg ataaatacag cccgtcgctc                                       30

<210> SEQ ID NO 60
<211> LENGTH: 24
<212> TYPE: DNA
<213> ORGANISM: Artificial Sequence
<220> FEATURE:
<223> OTHER INFORMATION: Primer

<400> SEQUENCE: 60
ctttctgacg tattcgtgca gcat                                             24

<210> SEQ ID NO 61
<211> LENGTH: 30
<212> TYPE: DNA
<213> ORGANISM: Artificial Sequence
<220> FEATURE:
<223> OTHER INFORMATION: Primer

<400> SEQUENCE: 61
acgttggatg ccaggatgaa caggaagaag                                       30

<210> SEQ ID NO 62
<211> LENGTH: 30
<212> TYPE: DNA
<213> ORGANISM: Artificial Sequence
<220> FEATURE:
<223> OTHER INFORMATION: Primer

<400> SEQUENCE: 62
acgttggatg acgaggcggg cagtgtgtat                                       30

<210> SEQ ID NO 63
<211> LENGTH: 17
<212> TYPE: DNA
<213> ORGANISM: Artificial Sequence
<220> FEATURE:
<223> OTHER INFORMATION: Primer

<400> SEQUENCE: 63
caggaagaag cccaccc                                                     17

<210> SEQ ID NO 64
<211> LENGTH: 30
<212> TYPE: DNA
<213> ORGANISM: Artificial Sequence
<220> FEATURE:
<223> OTHER INFORMATION: Primer

<400> SEQUENCE: 64
acgttggatg taaacgtagc agggtagtgg                                       30

<210> SEQ ID NO 65
<211> LENGTH: 31
<212> TYPE: DNA
<213> ORGANISM: Artificial Sequence
<220> FEATURE:
<223> OTHER INFORMATION: Primer

<400> SEQUENCE: 65
acgttggatg ctctgttgaa gcaaagagaa c                                     31

<210> SEQ ID NO 66
```

```
<211> LENGTH: 17
<212> TYPE: DNA
<213> ORGANISM: Artificial Sequence
<220> FEATURE:
<223> OTHER INFORMATION: Primer

<400> SEQUENCE: 66
gtggagccag agaagtc                                                    17

<210> SEQ ID NO 67
<211> LENGTH: 30
<212> TYPE: DNA
<213> ORGANISM: Artificial Sequence
<220> FEATURE:
<223> OTHER INFORMATION: Primer

<400> SEQUENCE: 67
acgttggatg taccgtgtac cccgtgtttg                                      30

<210> SEQ ID NO 68
<211> LENGTH: 30
<212> TYPE: DNA
<213> ORGANISM: Artificial Sequence
<220> FEATURE:
<223> OTHER INFORMATION: Primer

<400> SEQUENCE: 68
acgttggatg tgagcgttag tttagttgtc                                      30

<210> SEQ ID NO 69
<211> LENGTH: 17
<212> TYPE: DNA
<213> ORGANISM: Artificial Sequence
<220> FEATURE:
<223> OTHER INFORMATION: Primer

<400> SEQUENCE: 69
ccccgtgttt gtgaatg                                                    17

<210> SEQ ID NO 70
<211> LENGTH: 30
<212> TYPE: DNA
<213> ORGANISM: Artificial Sequence
<220> FEATURE:
<223> OTHER INFORMATION: Primer

<400> SEQUENCE: 70
acgttggatg ccgtgtaaga tgtaagctgg                                      30

<210> SEQ ID NO 71
<211> LENGTH: 30
<212> TYPE: DNA
<213> ORGANISM: Artificial Sequence
<220> FEATURE:
<223> OTHER INFORMATION: Primer

<400> SEQUENCE: 71
acgttggatg gaagcttttg caaagacaac                                      30

<210> SEQ ID NO 72
<211> LENGTH: 18
<212> TYPE: DNA
<213> ORGANISM: Artificial Sequence
<220> FEATURE:
<223> OTHER INFORMATION: Primer

<400> SEQUENCE: 72
```

```
cagcagcgaa tactttt                                                    18

<210> SEQ ID NO 73
<211> LENGTH: 30
<212> TYPE: DNA
<213> ORGANISM: Artificial Sequence
<220> FEATURE:
<223> OTHER INFORMATION: Primer

<400> SEQUENCE: 73
acgttggatg atttcctccc tgcgccattg                                      30

<210> SEQ ID NO 74
<211> LENGTH: 30
<212> TYPE: DNA
<213> ORGANISM: Artificial Sequence
<220> FEATURE:
<223> OTHER INFORMATION: Primer

<400> SEQUENCE: 74
acgttggatg ttaggatgga tgatagcagc                                      30

<210> SEQ ID NO 75
<211> LENGTH: 23
<212> TYPE: DNA
<213> ORGANISM: Artificial Sequence
<220> FEATURE:
<223> OTHER INFORMATION: Primer

<400> SEQUENCE: 75
aaaattatag agaaagttga tta                                             23

<210> SEQ ID NO 76
<211> LENGTH: 30
<212> TYPE: DNA
<213> ORGANISM: Artificial Sequence
<220> FEATURE:
<223> OTHER INFORMATION: Primer

<400> SEQUENCE: 76
acgttggatg agcctttgag tagggtaagc                                      30

<210> SEQ ID NO 77
<211> LENGTH: 30
<212> TYPE: DNA
<213> ORGANISM: Artificial Sequence
<220> FEATURE:
<223> OTHER INFORMATION: Primer

<400> SEQUENCE: 77
acgttggatg cccaggcaac agagtaagac                                      30

<210> SEQ ID NO 78
<211> LENGTH: 18
<212> TYPE: DNA
<213> ORGANISM: Artificial Sequence
<220> FEATURE:
<223> OTHER INFORMATION: Primer

<400> SEQUENCE: 78
ggcagcctca caggattg                                                   18

<210> SEQ ID NO 79
<211> LENGTH: 30
<212> TYPE: DNA
<213> ORGANISM: Artificial Sequence
<220> FEATURE:
```

<223> OTHER INFORMATION: Primer

<400> SEQUENCE: 79
acgttggatg agtgcctcct tgagtatctg                                              30

<210> SEQ ID NO 80
<211> LENGTH: 30
<212> TYPE: DNA
<213> ORGANISM: Artificial Sequence
<220> FEATURE:
<223> OTHER INFORMATION: Primer

<400> SEQUENCE: 80
acgttggatg ttgggtgcgt aactttgtcg                                              30

<210> SEQ ID NO 81
<211> LENGTH: 17
<212> TYPE: DNA
<213> ORGANISM: Artificial Sequence
<220> FEATURE:
<223> OTHER INFORMATION: Primer

<400> SEQUENCE: 81
cacctacctg tggcgtc                                                            17

<210> SEQ ID NO 82
<211> LENGTH: 30
<212> TYPE: DNA
<213> ORGANISM: Artificial Sequence
<220> FEATURE:
<223> OTHER INFORMATION: Primer

<400> SEQUENCE: 82
acgttggatg aacgctgtct tcagcccact                                              30

<210> SEQ ID NO 83
<211> LENGTH: 30
<212> TYPE: DNA
<213> ORGANISM: Artificial Sequence
<220> FEATURE:
<223> OTHER INFORMATION: Primer

<400> SEQUENCE: 83
acgttggatg ttgggtgcgt aactttgtcg                                              30

<210> SEQ ID NO 84
<211> LENGTH: 18
<212> TYPE: DNA
<213> ORGANISM: Artificial Sequence
<220> FEATURE:
<223> OTHER INFORMATION: Primer

<400> SEQUENCE: 84
gttgtggtcg tgctaaac                                                           18

<210> SEQ ID NO 85
<211> LENGTH: 30
<212> TYPE: DNA
<213> ORGANISM: Artificial Sequence
<220> FEATURE:
<223> OTHER INFORMATION: Primer

<400> SEQUENCE: 85
acgttggatg ttctacttca ggcagtgtcg                                              30

<210> SEQ ID NO 86

-continued

```
<211> LENGTH: 30
<212> TYPE: DNA
<213> ORGANISM: Artificial Sequence
<220> FEATURE:
<223> OTHER INFORMATION: Primer

<400> SEQUENCE: 86
acgttggatg cccaggcaac agagtaagac                                       30

<210> SEQ ID NO 87
<211> LENGTH: 19
<212> TYPE: DNA
<213> ORGANISM: Artificial Sequence
<220> FEATURE:
<223> OTHER INFORMATION: Primer

<400> SEQUENCE: 87
cactgccttg actcactca                                                   19

<210> SEQ ID NO 88
<211> LENGTH: 30
<212> TYPE: DNA
<213> ORGANISM: Artificial Sequence
<220> FEATURE:
<223> OTHER INFORMATION: Primer

<400> SEQUENCE: 88
acgttggatg gctggttgcc agtcagaaga                                       30

<210> SEQ ID NO 89
<211> LENGTH: 30
<212> TYPE: DNA
<213> ORGANISM: Artificial Sequence
<220> FEATURE:
<223> OTHER INFORMATION: Primer

<400> SEQUENCE: 89
acgttggatg tttagcacga ccacaacagc                                       30

<210> SEQ ID NO 90
<211> LENGTH: 18
<212> TYPE: DNA
<213> ORGANISM: Artificial Sequence
<220> FEATURE:
<223> OTHER INFORMATION: Primer

<400> SEQUENCE: 90
ccagtcagaa gaacgacc                                                    18

<210> SEQ ID NO 91
<211> LENGTH: 30
<212> TYPE: DNA
<213> ORGANISM: Artificial Sequence
<220> FEATURE:
<223> OTHER INFORMATION: Primer

<400> SEQUENCE: 91
acgttggatg ctacaatgat gggactgtcg                                       30

<210> SEQ ID NO 92
<211> LENGTH: 30
<212> TYPE: DNA
<213> ORGANISM: Artificial Sequence
<220> FEATURE:
<223> OTHER INFORMATION: Primer

<400> SEQUENCE: 92
```
acgttggatg actggaacct tgccctgaac         30

<210> SEQ ID NO 93
<211> LENGTH: 19
<212> TYPE: DNA
<213> ORGANISM: Artificial Sequence
<220> FEATURE:
<223> OTHER INFORMATION: Primer

<400> SEQUENCE: 93
ctgtcgacaa agttacgca         19

<210> SEQ ID NO 94
<211> LENGTH: 28
<212> TYPE: DNA
<213> ORGANISM: Artificial Sequence
<220> FEATURE:
<223> OTHER INFORMATION: Primer

<400> SEQUENCE: 94
acgttggatg tcggggttca gggcaagg         28

<210> SEQ ID NO 95
<211> LENGTH: 30
<212> TYPE: DNA
<213> ORGANISM: Artificial Sequence
<220> FEATURE:
<223> OTHER INFORMATION: Primer

<400> SEQUENCE: 95
acgttggatg gttgagcctt tgtctctttg         30

<210> SEQ ID NO 96
<211> LENGTH: 17
<212> TYPE: DNA
<213> ORGANISM: Artificial Sequence
<220> FEATURE:
<223> OTHER INFORMATION: Primer

<400> SEQUENCE: 96
ccacatggta caggagg         17

<210> SEQ ID NO 97
<211> LENGTH: 30
<212> TYPE: DNA
<213> ORGANISM: Artificial Sequence
<220> FEATURE:
<223> OTHER INFORMATION: Primer

<400> SEQUENCE: 97
acgttggatg cgtaactttg tcgacagtcc         30

<210> SEQ ID NO 98
<211> LENGTH: 29
<212> TYPE: DNA
<213> ORGANISM: Artificial Sequence
<220> FEATURE:
<223> OTHER INFORMATION: Primer

<400> SEQUENCE: 98
acgttggatg gccctccact cacctgaag         29

<210> SEQ ID NO 99
<211> LENGTH: 22
<212> TYPE: DNA
<213> ORGANISM: Artificial Sequence
<220> FEATURE:

<223> OTHER INFORMATION: Primer

<400> SEQUENCE: 99
catcattgta gacatcacca ag                                         22

<210> SEQ ID NO 100
<211> LENGTH: 31
<212> TYPE: DNA
<213> ORGANISM: Artificial Sequence
<220> FEATURE:
<223> OTHER INFORMATION: Primer

<400> SEQUENCE: 100
acgttggatg ctgaaaggtt acttcaagga c                               31

<210> SEQ ID NO 101
<211> LENGTH: 30
<212> TYPE: DNA
<213> ORGANISM: Artificial Sequence
<220> FEATURE:
<223> OTHER INFORMATION: Primer

<400> SEQUENCE: 101
acgttggatg ctctgggcta ataggactac                                 30

<210> SEQ ID NO 102
<211> LENGTH: 22
<212> TYPE: DNA
<213> ORGANISM: Artificial Sequence
<220> FEATURE:
<223> OTHER INFORMATION: Primer

<400> SEQUENCE: 102
ggacaaaata cctgtattcc tc                                         22

<210> SEQ ID NO 103
<211> LENGTH: 30
<212> TYPE: DNA
<213> ORGANISM: Artificial Sequence
<220> FEATURE:
<223> OTHER INFORMATION: Primer

<400> SEQUENCE: 103
acgttggatg ctctgggcta ataggactac                                 30

<210> SEQ ID NO 104
<211> LENGTH: 31
<212> TYPE: DNA
<213> ORGANISM: Artificial Sequence
<220> FEATURE:
<223> OTHER INFORMATION: Primer

<400> SEQUENCE: 104
acgttggatg ctgaaaggtt acttcaagga c                               31

<210> SEQ ID NO 105
<211> LENGTH: 17
<212> TYPE: DNA
<213> ORGANISM: Artificial Sequence
<220> FEATURE:
<223> OTHER INFORMATION: Primer

<400> SEQUENCE: 105
cagatccctg gacaggc                                               17

<210> SEQ ID NO 106

```
<211> LENGTH: 30
<212> TYPE: DNA
<213> ORGANISM: Artificial Sequence
<220> FEATURE:
<223> OTHER INFORMATION: Primer

<400> SEQUENCE: 106
acgttggatg aaagttctct gcctccaagg                                      30

<210> SEQ ID NO 107
<211> LENGTH: 29
<212> TYPE: DNA
<213> ORGANISM: Artificial Sequence
<220> FEATURE:
<223> OTHER INFORMATION: Primer

<400> SEQUENCE: 107
acgttggatg ggccaggtgc agctctcag                                       29

<210> SEQ ID NO 108
<211> LENGTH: 17
<212> TYPE: DNA
<213> ORGANISM: Artificial Sequence
<220> FEATURE:
<223> OTHER INFORMATION: Primer

<400> SEQUENCE: 108
acacaggcgt cctctga                                                    17

<210> SEQ ID NO 109
<211> LENGTH: 30
<212> TYPE: DNA
<213> ORGANISM: Artificial Sequence
<220> FEATURE:
<223> OTHER INFORMATION: Primer

<400> SEQUENCE: 109
acgttggatg gcaccaacac ttcaaatacg                                      30

<210> SEQ ID NO 110
<211> LENGTH: 30
<212> TYPE: DNA
<213> ORGANISM: Artificial Sequence
<220> FEATURE:
<223> OTHER INFORMATION: Primer

<400> SEQUENCE: 110
acgttggatg tgggacaagt tttcatctgc                                      30

<210> SEQ ID NO 111
<211> LENGTH: 22
<212> TYPE: DNA
<213> ORGANISM: Artificial Sequence
<220> FEATURE:
<223> OTHER INFORMATION: Primer

<400> SEQUENCE: 111
gatctagaat tccaaacccc ta                                              22

<210> SEQ ID NO 112
<211> LENGTH: 30
<212> TYPE: DNA
<213> ORGANISM: Artificial Sequence
<220> FEATURE:
<223> OTHER INFORMATION: Primer

<400> SEQUENCE: 112
```
acgttggatg tgacgatgcc cgtcaggtac                30

<210> SEQ ID NO 113
<211> LENGTH: 30
<212> TYPE: DNA
<213> ORGANISM: Artificial Sequence
<220> FEATURE:
<223> OTHER INFORMATION: Primer

<400> SEQUENCE: 113
acgttggatg tactcggatg gcagcaagga                30

<210> SEQ ID NO 114
<211> LENGTH: 17
<212> TYPE: DNA
<213> ORGANISM: Artificial Sequence
<220> FEATURE:
<223> OTHER INFORMATION: Primer

<400> SEQUENCE: 114
tcaggtacca cgtgccc                17

<210> SEQ ID NO 115
<211> LENGTH: 30
<212> TYPE: DNA
<213> ORGANISM: Artificial Sequence
<220> FEATURE:
<223> OTHER INFORMATION: Primer

<400> SEQUENCE: 115
acgttggatg tcaaagaagt gcagagcaag                30

<210> SEQ ID NO 116
<211> LENGTH: 30
<212> TYPE: DNA
<213> ORGANISM: Artificial Sequence
<220> FEATURE:
<223> OTHER INFORMATION: Primer

<400> SEQUENCE: 116
acgttggatg agaaccacag aattctggac                30

<210> SEQ ID NO 117
<211> LENGTH: 21
<212> TYPE: DNA
<213> ORGANISM: Artificial Sequence
<220> FEATURE:
<223> OTHER INFORMATION: Primer

<400> SEQUENCE: 117
tgcagagcaa gatttactct c                21

<210> SEQ ID NO 118
<211> LENGTH: 30
<212> TYPE: DNA
<213> ORGANISM: Artificial Sequence
<220> FEATURE:
<223> OTHER INFORMATION: Primer

<400> SEQUENCE: 118
acgttggatg ccacagaatt ctggacaatc                30

<210> SEQ ID NO 119
<211> LENGTH: 30
<212> TYPE: DNA
<213> ORGANISM: Artificial Sequence
<220> FEATURE:

```
<223> OTHER INFORMATION: Primer

<400> SEQUENCE: 119
acgttggatg aattcaaaga agtgcagagc                                    30

<210> SEQ ID NO 120
<211> LENGTH: 21
<212> TYPE: DNA
<213> ORGANISM: Artificial Sequence
<220> FEATURE:
<223> OTHER INFORMATION: Primer

<400> SEQUENCE: 120
cttaactcct ggatacaggt a                                             21

<210> SEQ ID NO 121
<211> LENGTH: 30
<212> TYPE: DNA
<213> ORGANISM: Artificial Sequence
<220> FEATURE:
<223> OTHER INFORMATION: Primer

<400> SEQUENCE: 121
acgttggatg tacaagcttt gtgtcctggg                                    30

<210> SEQ ID NO 122
<211> LENGTH: 30
<212> TYPE: DNA
<213> ORGANISM: Artificial Sequence
<220> FEATURE:
<223> OTHER INFORMATION: Primer

<400> SEQUENCE: 122
acgttggatg tgagcagcaa tcatgtgtcc                                    30

<210> SEQ ID NO 123
<211> LENGTH: 18
<212> TYPE: DNA
<213> ORGANISM: Artificial Sequence
<220> FEATURE:
<223> OTHER INFORMATION: Primer

<400> SEQUENCE: 123
ggcacaacag tgacaatc                                                 18

<210> SEQ ID NO 124
<211> LENGTH: 30
<212> TYPE: DNA
<213> ORGANISM: Artificial Sequence
<220> FEATURE:
<223> OTHER INFORMATION: Primer

<400> SEQUENCE: 124
acgttggatg tcaagggtca tacccacatg                                    30

<210> SEQ ID NO 125
<211> LENGTH: 30
<212> TYPE: DNA
<213> ORGANISM: Artificial Sequence
<220> FEATURE:
<223> OTHER INFORMATION: Primer

<400> SEQUENCE: 125
acgttggatg cctgatagaa gtagaccctg                                    30

<210> SEQ ID NO 126
```

```
<211> LENGTH: 21
<212> TYPE: DNA
<213> ORGANISM: Artificial Sequence
<220> FEATURE:
<223> OTHER INFORMATION: Primer

<400> SEQUENCE: 126
tgctggcatt ctacatcagt a                                            21

<210> SEQ ID NO 127
<211> LENGTH: 30
<212> TYPE: DNA
<213> ORGANISM: Artificial Sequence
<220> FEATURE:
<223> OTHER INFORMATION: Primer

<400> SEQUENCE: 127
acgttggatg tgagcagcaa tcatgtgtcc                                   30

<210> SEQ ID NO 128
<211> LENGTH: 30
<212> TYPE: DNA
<213> ORGANISM: Artificial Sequence
<220> FEATURE:
<223> OTHER INFORMATION: Primer

<400> SEQUENCE: 128
acgttggatg tacaagcttt gtgtcctggg                                   30

<210> SEQ ID NO 129
<211> LENGTH: 17
<212> TYPE: DNA
<213> ORGANISM: Artificial Sequence
<220> FEATURE:
<223> OTHER INFORMATION: Primer

<400> SEQUENCE: 129
agtggagagg ggttcac                                                 17

<210> SEQ ID NO 130
<211> LENGTH: 30
<212> TYPE: DNA
<213> ORGANISM: Artificial Sequence
<220> FEATURE:
<223> OTHER INFORMATION: Primer

<400> SEQUENCE: 130
acgttggatg ttacccacag cagggtacac                                   30

<210> SEQ ID NO 131
<211> LENGTH: 30
<212> TYPE: DNA
<213> ORGANISM: Artificial Sequence
<220> FEATURE:
<223> OTHER INFORMATION: Primer

<400> SEQUENCE: 131
acgttggatg agactcgtca ggaccaactg                                   30

<210> SEQ ID NO 132
<211> LENGTH: 18
<212> TYPE: DNA
<213> ORGANISM: Artificial Sequence
<220> FEATURE:
<223> OTHER INFORMATION: Primer

<400> SEQUENCE: 132
```
cccaggaact tcctcaca                                                      18

<210> SEQ ID NO 133
<211> LENGTH: 30
<212> TYPE: DNA
<213> ORGANISM: Artificial Sequence
<220> FEATURE:
<223> OTHER INFORMATION: Primer

<400> SEQUENCE: 133
acgttggatg agttaccctt gctccttgcc                                         30

<210> SEQ ID NO 134
<211> LENGTH: 30
<212> TYPE: DNA
<213> ORGANISM: Artificial Sequence
<220> FEATURE:
<223> OTHER INFORMATION: Primer

<400> SEQUENCE: 134
acgttggatg ctcccggagt agtttccatc                                         30

<210> SEQ ID NO 135
<211> LENGTH: 22
<212> TYPE: DNA
<213> ORGANISM: Artificial Sequence
<220> FEATURE:
<223> OTHER INFORMATION: Primer

<400> SEQUENCE: 135
ccccacatcc ttgcaggtta cc                                                 22

<210> SEQ ID NO 136
<211> LENGTH: 30
<212> TYPE: DNA
<213> ORGANISM: Artificial Sequence
<220> FEATURE:
<223> OTHER INFORMATION: Primer

<400> SEQUENCE: 136
acgttggatg agactcgtca ggaccaactg                                         30

<210> SEQ ID NO 137
<211> LENGTH: 30
<212> TYPE: DNA
<213> ORGANISM: Artificial Sequence
<220> FEATURE:
<223> OTHER INFORMATION: Primer

<400> SEQUENCE: 137
acgttggatg ttacccacag cagggtacac                                         30

<210> SEQ ID NO 138
<211> LENGTH: 17
<212> TYPE: DNA
<213> ORGANISM: Artificial Sequence
<220> FEATURE:
<223> OTHER INFORMATION: Primer

<400> SEQUENCE: 138
gaccaccgtc acagcac                                                       17

<210> SEQ ID NO 139
<211> LENGTH: 30
<212> TYPE: DNA
<213> ORGANISM: Artificial Sequence
<220> FEATURE:

<223> OTHER INFORMATION: Primer

<400> SEQUENCE: 139
acgttggatg ctgtgggtaa ccatgaaagc                              30

<210> SEQ ID NO 140
<211> LENGTH: 30
<212> TYPE: DNA
<213> ORGANISM: Artificial Sequence
<220> FEATURE:
<223> OTHER INFORMATION: Primer

<400> SEQUENCE: 140
acgttggatg ttggccatcg cttcatagag                              30

<210> SEQ ID NO 141
<211> LENGTH: 18
<212> TYPE: DNA
<213> ORGANISM: Artificial Sequence
<220> FEATURE:
<223> OTHER INFORMATION: Primer

<400> SEQUENCE: 141
caatagcttc cctccccc                                           18

<210> SEQ ID NO 142
<211> LENGTH: 30
<212> TYPE: DNA
<213> ORGANISM: Artificial Sequence
<220> FEATURE:
<223> OTHER INFORMATION: Primer

<400> SEQUENCE: 142
acgttggatg ctcccggagt agtttccatc                              30

<210> SEQ ID NO 143
<211> LENGTH: 30
<212> TYPE: DNA
<213> ORGANISM: Artificial Sequence
<220> FEATURE:
<223> OTHER INFORMATION: Primer

<400> SEQUENCE: 143
acgttggatg agttaccctt gctccttgcc                              30

<210> SEQ ID NO 144
<211> LENGTH: 22
<212> TYPE: DNA
<213> ORGANISM: Artificial Sequence
<220> FEATURE:
<223> OTHER INFORMATION: Primer

<400> SEQUENCE: 144
gtttccatct atttggtaca ca                                      22

<210> SEQ ID NO 145
<211> LENGTH: 30
<212> TYPE: DNA
<213> ORGANISM: Artificial Sequence
<220> FEATURE:
<223> OTHER INFORMATION: Primer

<400> SEQUENCE: 145
acgttggatg atgaggaaga aaggcttcgg                              30

<210> SEQ ID NO 146

```
<211> LENGTH: 29
<212> TYPE: DNA
<213> ORGANISM: Artificial Sequence
<220> FEATURE:
<223> OTHER INFORMATION: Primer

<400> SEQUENCE: 146
acgttggatg ccacccaccc tccttcctt                                              29

<210> SEQ ID NO 147
<211> LENGTH: 21
<212> TYPE: DNA
<213> ORGANISM: Artificial Sequence
<220> FEATURE:
<223> OTHER INFORMATION: Primer

<400> SEQUENCE: 147
ggagtccttc tacatccaga c                                                      21

<210> SEQ ID NO 148
<211> LENGTH: 30
<212> TYPE: DNA
<213> ORGANISM: Artificial Sequence
<220> FEATURE:
<223> OTHER INFORMATION: Primer

<400> SEQUENCE: 148
acgttggatg acaggaggac ccccaaggga                                             30

<210> SEQ ID NO 149
<211> LENGTH: 30
<212> TYPE: DNA
<213> ORGANISM: Artificial Sequence
<220> FEATURE:
<223> OTHER INFORMATION: Primer

<400> SEQUENCE: 149
acgttggatg tcaagcagct ggagtccttc                                             30

<210> SEQ ID NO 150
<211> LENGTH: 18
<212> TYPE: DNA
<213> ORGANISM: Artificial Sequence
<220> FEATURE:
<223> OTHER INFORMATION: Primer

<400> SEQUENCE: 150
accctccttc cttcctca                                                          18

<210> SEQ ID NO 151
<211> LENGTH: 30
<212> TYPE: DNA
<213> ORGANISM: Artificial Sequence
<220> FEATURE:
<223> OTHER INFORMATION: Primer

<400> SEQUENCE: 151
acgttggatg tgtggacaac acaaacctgg                                             30

<210> SEQ ID NO 152
<211> LENGTH: 30
<212> TYPE: DNA
<213> ORGANISM: Artificial Sequence
<220> FEATURE:
<223> OTHER INFORMATION: Primer

<400> SEQUENCE: 152
```
acgttggatg tctctaagggg agaactcctg              30

<210> SEQ ID NO 153
<211> LENGTH: 17
<212> TYPE: DNA
<213> ORGANISM: Artificial Sequence
<220> FEATURE:
<223> OTHER INFORMATION: Primer

<400> SEQUENCE: 153
ctggtcccca ggctctg                             17

<210> SEQ ID NO 154
<211> LENGTH: 30
<212> TYPE: DNA
<213> ORGANISM: Artificial Sequence
<220> FEATURE:
<223> OTHER INFORMATION: Primer

<400> SEQUENCE: 154
acgttggatg tctctaagggg agaactcctg              30

<210> SEQ ID NO 155
<211> LENGTH: 30
<212> TYPE: DNA
<213> ORGANISM: Artificial Sequence
<220> FEATURE:
<223> OTHER INFORMATION: Primer

<400> SEQUENCE: 155
acgttggatg tgtggacaac acaaacctgg               30

<210> SEQ ID NO 156
<211> LENGTH: 17
<212> TYPE: DNA
<213> ORGANISM: Artificial Sequence
<220> FEATURE:
<223> OTHER INFORMATION: Primer

<400> SEQUENCE: 156 cccccccgaaa accctta                            17

<210> SEQ ID NO 157
<211> LENGTH: 30
<212> TYPE: DNA
<213> ORGANISM: Artificial Sequence
<220> FEATURE:
<223> OTHER INFORMATION: Primer

<400> SEQUENCE: 157
acgttggatg cttgcagagt ttgacactcc               30

<210> SEQ ID NO 158
<211> LENGTH: 30
<212> TYPE: DNA
<213> ORGANISM: Artificial Sequence
<220> FEATURE:
<223> OTHER INFORMATION: Primer

<400> SEQUENCE: 158
acgttggatg cataacaagc agagtccctc               30

<210> SEQ ID NO 159
<211> LENGTH: 17
<212> TYPE: DNA
<213> ORGANISM: Artificial Sequence
<220> FEATURE:

<223> OTHER INFORMATION: Primer

<400> SEQUENCE: 159
ctttgtcctg gggacca                                                        17

<210> SEQ ID NO 160
<211> LENGTH: 30
<212> TYPE: DNA
<213> ORGANISM: Artificial Sequence
<220> FEATURE:
<223> OTHER INFORMATION: Primer

<400> SEQUENCE: 160
acgttggatg cataacaagc agagtccctc                                          30

<210> SEQ ID NO 161
<211> LENGTH: 30
<212> TYPE: DNA
<213> ORGANISM: Artificial Sequence
<220> FEATURE:
<223> OTHER INFORMATION: Primer

<400> SEQUENCE: 161
acgttggatg cttgcagagt ttgacactcc                                          30

<210> SEQ ID NO 162
<211> LENGTH: 23
<212> TYPE: DNA
<213> ORGANISM: Artificial Sequence
<220> FEATURE:
<223> OTHER INFORMATION: Primer

<400> SEQUENCE: 162
ctggtcccag acatcattct tac                                                 23

<210> SEQ ID NO 163
<211> LENGTH: 30
<212> TYPE: DNA
<213> ORGANISM: Artificial Sequence
<220> FEATURE:
<223> OTHER INFORMATION: Primer

<400> SEQUENCE: 163
acgttggatg acacagcaca ggatgtgaag                                          30

<210> SEQ ID NO 164
<211> LENGTH: 30
<212> TYPE: DNA
<213> ORGANISM: Artificial Sequence
<220> FEATURE:
<223> OTHER INFORMATION: Primer

<400> SEQUENCE: 164
acgttggatg ggagtgtcaa actctgcaag                                          30

<210> SEQ ID NO 165
<211> LENGTH: 21
<212> TYPE: DNA
<213> ORGANISM: Artificial Sequence
<220> FEATURE:
<223> OTHER INFORMATION: Primer

<400> SEQUENCE: 165
gtcattgaat acgcacggct c                                                   21

<210> SEQ ID NO 166

```
<211> LENGTH: 30
<212> TYPE: DNA
<213> ORGANISM: Artificial Sequence
<220> FEATURE:
<223> OTHER INFORMATION: Primer

<400> SEQUENCE: 166
acgttggatg ggagtgtcaa actctgcaag                                   30

<210> SEQ ID NO 167
<211> LENGTH: 30
<212> TYPE: DNA
<213> ORGANISM: Artificial Sequence
<220> FEATURE:
<223> OTHER INFORMATION: Primer

<400> SEQUENCE: 167
acgttggatg acacagcaca ggatgtgaag                                   30

<210> SEQ ID NO 168
<211> LENGTH: 18
<212> TYPE: DNA
<213> ORGANISM: Artificial Sequence
<220> FEATURE:
<223> OTHER INFORMATION: Primer

<400> SEQUENCE: 168
caagcacacg gatacccc                                                18

<210> SEQ ID NO 169
<211> LENGTH: 30
<212> TYPE: DNA
<213> ORGANISM: Artificial Sequence
<220> FEATURE:
<223> OTHER INFORMATION: Primer

<400> SEQUENCE: 169
acgttggatg acacagcaca ggatgtgaag                                   30

<210> SEQ ID NO 170
<211> LENGTH: 30
<212> TYPE: DNA
<213> ORGANISM: Artificial Sequence
<220> FEATURE:
<223> OTHER INFORMATION: Primer

<400> SEQUENCE: 170
acgttggatg ggagtgtcaa actctgcaag                                   30

<210> SEQ ID NO 171
<211> LENGTH: 22
<212> TYPE: DNA
<213> ORGANISM: Artificial Sequence
<220> FEATURE:
<223> OTHER INFORMATION: Primer

<400> SEQUENCE: 171
gaaggaggtc attgaatacg ca                                           22

<210> SEQ ID NO 172
<211> LENGTH: 30
<212> TYPE: DNA
<213> ORGANISM: Artificial Sequence
<220> FEATURE:
<223> OTHER INFORMATION: Primer

<400> SEQUENCE: 172
```

```
acgttggatg ggagtgtcaa actctgcaag                                    30

<210> SEQ ID NO 173
<211> LENGTH: 30
<212> TYPE: DNA
<213> ORGANISM: Artificial Sequence
<220> FEATURE:
<223> OTHER INFORMATION: Primer

<400> SEQUENCE: 173
acgttggatg acacagcaca ggatgtgaag                                    30

<210> SEQ ID NO 174
<211> LENGTH: 17
<212> TYPE: DNA
<213> ORGANISM: Artificial Sequence
<220> FEATURE:
<223> OTHER INFORMATION: Primer

<400> SEQUENCE: 174
acggataccc cggagcc                                                  17

<210> SEQ ID NO 175
<211> LENGTH: 30
<212> TYPE: DNA
<213> ORGANISM: Artificial Sequence
<220> FEATURE:
<223> OTHER INFORMATION: Primer

<400> SEQUENCE: 175
acgttggatg tatgaaggag ctggaactgg                                    30

<210> SEQ ID NO 176
<211> LENGTH: 30
<212> TYPE: DNA
<213> ORGANISM: Artificial Sequence
<220> FEATURE:
<223> OTHER INFORMATION: Primer

<400> SEQUENCE: 176
acgttggatg ggccatagga tatacggttc                                    30

<210> SEQ ID NO 177
<211> LENGTH: 17
<212> TYPE: DNA
<213> ORGANISM: Artificial Sequence
<220> FEATURE:
<223> OTHER INFORMATION: Primer

<400> SEQUENCE: 177
ccgggccctt ctctctg                                                  17

<210> SEQ ID NO 178
<211> LENGTH: 30
<212> TYPE: DNA
<213> ORGANISM: Artificial Sequence
<220> FEATURE:
<223> OTHER INFORMATION: Primer

<400> SEQUENCE: 178
acgttggatg ggccatagga tatacggttc                                    30

<210> SEQ ID NO 179
<211> LENGTH: 30
<212> TYPE: DNA
<213> ORGANISM: Artificial Sequence
<220> FEATURE:
```

```
<223> OTHER INFORMATION: Primer

<400> SEQUENCE: 179
acgttggatg tatgaaggag ctggaactgg                                30

<210> SEQ ID NO 180
<211> LENGTH: 17
<212> TYPE: DNA
<213> ORGANISM: Artificial Sequence
<220> FEATURE:
<223> OTHER INFORMATION: Primer

<400> SEQUENCE: 180
gttcaggtac caggggg                                              17

<210> SEQ ID NO 181
<211> LENGTH: 30
<212> TYPE: DNA
<213> ORGANISM: Artificial Sequence
<220> FEATURE:
<223> OTHER INFORMATION: Primer

<400> SEQUENCE: 181
acgttggatg attcgtcaga tctggtaggg                                30

<210> SEQ ID NO 182
<211> LENGTH: 30
<212> TYPE: DNA
<213> ORGANISM: Artificial Sequence
<220> FEATURE:
<223> OTHER INFORMATION: Primer

<400> SEQUENCE: 182
acgttggatg attctctgag ctcccccttac                               30

<210> SEQ ID NO 183
<211> LENGTH: 17
<212> TYPE: DNA
<213> ORGANISM: Artificial Sequence
<220> FEATURE:
<223> OTHER INFORMATION: Primer

<400> SEQUENCE: 183
tggtaggggt ttgaatg                                              17

<210> SEQ ID NO 184
<211> LENGTH: 30
<212> TYPE: DNA
<213> ORGANISM: Artificial Sequence
<220> FEATURE:
<223> OTHER INFORMATION: Primer

<400> SEQUENCE: 184
acgttggatg atagatgtga cctcccttcc                                30

<210> SEQ ID NO 185
<211> LENGTH: 30
<212> TYPE: DNA
<213> ORGANISM: Artificial Sequence
<220> FEATURE:
<223> OTHER INFORMATION: Primer

<400> SEQUENCE: 185
acgttggatg tggcgacgca atgaaaacag                                30

<210> SEQ ID NO 186
```

```
<211> LENGTH: 20
<212> TYPE: DNA
<213> ORGANISM: Artificial Sequence
<220> FEATURE:
<223> OTHER INFORMATION: Primer

<400> SEQUENCE: 186
cacttgattt tttttctcct                                              20

<210> SEQ ID NO 187
<211> LENGTH: 30
<212> TYPE: DNA
<213> ORGANISM: Artificial Sequence
<220> FEATURE:
<223> OTHER INFORMATION: Primer

<400> SEQUENCE: 187
acgttggatg tttttctcc cacaatgtag                                    30

<210> SEQ ID NO 188
<211> LENGTH: 30
<212> TYPE: DNA
<213> ORGANISM: Artificial Sequence
<220> FEATURE:
<223> OTHER INFORMATION: Primer

<400> SEQUENCE: 188
acgttggatg aactgggaat ttcatgaatc                                   30

<210> SEQ ID NO 189
<211> LENGTH: 24
<212> TYPE: DNA
<213> ORGANISM: Artificial Sequence
<220> FEATURE:
<223> OTHER INFORMATION: Primer

<400> SEQUENCE: 189
atgtagtaaa aatacatatg ccat                                         24

<210> SEQ ID NO 190
<211> LENGTH: 31
<212> TYPE: DNA
<213> ORGANISM: Artificial Sequence
<220> FEATURE:
<223> OTHER INFORMATION: Primer

<400> SEQUENCE: 190
acgttggatg ctgaaatcag gtaagacata g                                 31

<210> SEQ ID NO 191
<211> LENGTH: 30
<212> TYPE: DNA
<213> ORGANISM: Artificial Sequence
<220> FEATURE:
<223> OTHER INFORMATION: Primer

<400> SEQUENCE: 191
acgttggatg gcacataaag ccatggcata                                   30

<210> SEQ ID NO 192
<211> LENGTH: 23
<212> TYPE: DNA
<213> ORGANISM: Artificial Sequence
<220> FEATURE:
<223> OTHER INFORMATION: Primer

<400> SEQUENCE: 192
```
attataagaa ttattttttc tcc 23

<210> SEQ ID NO 193
<211> LENGTH: 30
<212> TYPE: DNA
<213> ORGANISM: Artificial Sequence
<220> FEATURE:
<223> OTHER INFORMATION: Primer

<400> SEQUENCE: 193
acgttggatg aggaagtcca aggagctgca 30

<210> SEQ ID NO 194
<211> LENGTH: 29
<212> TYPE: DNA
<213> ORGANISM: Artificial Sequence
<220> FEATURE:
<223> OTHER INFORMATION: Primer

<400> SEQUENCE: 194
acgttggatg tcgccgcggt actgcacca 29

<210> SEQ ID NO 195
<211> LENGTH: 17
<212> TYPE: DNA
<213> ORGANISM: Artificial Sequence
<220> FEATURE:
<223> OTHER INFORMATION: Primer

<400> SEQUENCE: 195
cggacatgga ggacgtg 17

<210> SEQ ID NO 196
<211> LENGTH: 30
<212> TYPE: DNA
<213> ORGANISM: Artificial Sequence
<220> FEATURE:
<223> OTHER INFORMATION: Primer

<400> SEQUENCE: 196
acgttggatg gagagctgag agaaactgtg 30

<210> SEQ ID NO 197
<211> LENGTH: 30
<212> TYPE: DNA
<213> ORGANISM: Artificial Sequence
<220> FEATURE:
<223> OTHER INFORMATION: Primer

<400> SEQUENCE: 197
acgttggatg cccaggaaag tatttcaagc 30

<210> SEQ ID NO 198
<211> LENGTH: 22
<212> TYPE: DNA
<213> ORGANISM: Artificial Sequence
<220> FEATURE:
<223> OTHER INFORMATION: Primer

<400> SEQUENCE: 198
tcatgacttc aagagttctt tt 22

<210> SEQ ID NO 199
<211> LENGTH: 30
<212> TYPE: DNA
<213> ORGANISM: Artificial Sequence
<220> FEATURE:

<223> OTHER INFORMATION: Primer

<400> SEQUENCE: 199
acgttggatg tccgtaagca tttccgaagc                                30

<210> SEQ ID NO 200
<211> LENGTH: 30
<212> TYPE: DNA
<213> ORGANISM: Artificial Sequence
<220> FEATURE:
<223> OTHER INFORMATION: Primer

<400> SEQUENCE: 200
acgttggatg cttggtagct ggactttctg                                30

<210> SEQ ID NO 201
<211> LENGTH: 17
<212> TYPE: DNA
<213> ORGANISM: Artificial Sequence
<220> FEATURE:
<223> OTHER INFORMATION: Primer

<400> SEQUENCE: 201
tttccgaagc cagagga                                              17

<210> SEQ ID NO 202
<211> LENGTH: 30
<212> TYPE: DNA
<213> ORGANISM: Artificial Sequence
<220> FEATURE:
<223> OTHER INFORMATION: Primer

<400> SEQUENCE: 202
acgttggatg gtcctcctca tcatgctttg                                30

<210> SEQ ID NO 203
<211> LENGTH: 30
<212> TYPE: DNA
<213> ORGANISM: Artificial Sequence
<220> FEATURE:
<223> OTHER INFORMATION: Primer

<400> SEQUENCE: 203
acgttggatg gatggtctct acacattcac                                30

<210> SEQ ID NO 204
<211> LENGTH: 20
<212> TYPE: DNA
<213> ORGANISM: Artificial Sequence
<220> FEATURE:
<223> OTHER INFORMATION: Primer

<400> SEQUENCE: 204
cctgtaccaa tacatcctgc                                           20

<210> SEQ ID NO 205
<211> LENGTH: 30
<212> TYPE: DNA
<213> ORGANISM: Artificial Sequence
<220> FEATURE:
<223> OTHER INFORMATION: Primer

<400> SEQUENCE: 205
acgttggatg tgtggtttgc ttgtgggatg                                30

<210> SEQ ID NO 206

```
<211> LENGTH: 30
<212> TYPE: DNA
<213> ORGANISM: Artificial Sequence
<220> FEATURE:
<223> OTHER INFORMATION: Primer

<400> SEQUENCE: 206
acgttggatg ggtcaaggtc acattcttcc                              30

<210> SEQ ID NO 207
<211> LENGTH: 18
<212> TYPE: DNA
<213> ORGANISM: Artificial Sequence
<220> FEATURE:
<223> OTHER INFORMATION: Primer

<400> SEQUENCE: 207
gagaaggtgg gatccaaa                                           18

<210> SEQ ID NO 208
<211> LENGTH: 30
<212> TYPE: DNA
<213> ORGANISM: Artificial Sequence
<220> FEATURE:
<223> OTHER INFORMATION: Primer

<400> SEQUENCE: 208
acgttggatg cacttgttgg ctgaaccatt                              30

<210> SEQ ID NO 209
<211> LENGTH: 30
<212> TYPE: DNA
<213> ORGANISM: Artificial Sequence
<220> FEATURE:
<223> OTHER INFORMATION: Primer

<400> SEQUENCE: 209
acgttggatg tctaaactag accaacaaag                              30

<210> SEQ ID NO 210
<211> LENGTH: 17
<212> TYPE: DNA
<213> ORGANISM: Artificial Sequence
<220> FEATURE:
<223> OTHER INFORMATION: Primer

<400> SEQUENCE: 210
aacatcttcc cagcaaa                                            17

<210> SEQ ID NO 211
<211> LENGTH: 30
<212> TYPE: DNA
<213> ORGANISM: Artificial Sequence
<220> FEATURE:
<223> OTHER INFORMATION: Primer

<400> SEQUENCE: 211
acgttggatg cacttgttgg ctgaaccatt                              30

<210> SEQ ID NO 212
<211> LENGTH: 30
<212> TYPE: DNA
<213> ORGANISM: Artificial Sequence
<220> FEATURE:
<223> OTHER INFORMATION: Primer

<400> SEQUENCE: 212
```
acgttggatg tctaaactag accaacaaag                                    30

<210> SEQ ID NO 213
<211> LENGTH: 19
<212> TYPE: DNA
<213> ORGANISM: Artificial Sequence
<220> FEATURE:
<223> OTHER INFORMATION: Primer

<400> SEQUENCE: 213
gcaacatctt cccagcaaa                                                19

<210> SEQ ID NO 214
<211> LENGTH: 30
<212> TYPE: DNA
<213> ORGANISM: Artificial Sequence
<220> FEATURE:
<223> OTHER INFORMATION: Primer

<400> SEQUENCE: 214
acgttggatg gcttatgttt tctgacaatg                                    30

<210> SEQ ID NO 215
<211> LENGTH: 32
<212> TYPE: DNA
<213> ORGANISM: Artificial Sequence
<220> FEATURE:
<223> OTHER INFORMATION: Primer

<400> SEQUENCE: 215
acgttggatg gtctaaaaca aagataaac ac                                  32

<210> SEQ ID NO 216
<211> LENGTH: 19
<212> TYPE: DNA
<213> ORGANISM: Artificial Sequence
<220> FEATURE:
<223> OTHER INFORMATION: Primer

<400> SEQUENCE: 216
attctatttc aaaaggggc                                                19

<210> SEQ ID NO 217
<211> LENGTH: 30
<212> TYPE: DNA
<213> ORGANISM: Artificial Sequence
<220> FEATURE:
<223> OTHER INFORMATION: Primer

<400> SEQUENCE: 217
acgttggatg gcttatgttt tctgacaatg                                    30

<210> SEQ ID NO 218
<211> LENGTH: 32
<212> TYPE: DNA
<213> ORGANISM: Artificial Sequence
<220> FEATURE:
<223> OTHER INFORMATION: Primer

<400> SEQUENCE: 218
acgttggatg gtctaaaaca aagataaac ac                                  32

<210> SEQ ID NO 219
<211> LENGTH: 20
<212> TYPE: DNA
<213> ORGANISM: Artificial Sequence
<220> FEATURE:

<223> OTHER INFORMATION: Primer

<400> SEQUENCE: 219
aattctattt caaaaggggc                                               20

<210> SEQ ID NO 220
<211> LENGTH: 30
<212> TYPE: DNA
<213> ORGANISM: Artificial Sequence
<220> FEATURE:
<223> OTHER INFORMATION: Primer

<400> SEQUENCE: 220
acgttggatg gctttatcct aaggcctctc                                    30

<210> SEQ ID NO 221
<211> LENGTH: 30
<212> TYPE: DNA
<213> ORGANISM: Artificial Sequence
<220> FEATURE:
<223> OTHER INFORMATION: Primer

<400> SEQUENCE: 221
acgttggatg ctgtaggttg cttactgttc                                    30

<210> SEQ ID NO 222
<211> LENGTH: 18
<212> TYPE: DNA
<213> ORGANISM: Artificial Sequence
<220> FEATURE:
<223> OTHER INFORMATION: Primer

<400> SEQUENCE: 222
tgtgcagttg gtctttct                                                 18

<210> SEQ ID NO 223
<211> LENGTH: 30
<212> TYPE: DNA
<213> ORGANISM: Artificial Sequence
<220> FEATURE:
<223> OTHER INFORMATION: Primer

<400> SEQUENCE: 223
acgttggatg ttaaaggttg attctacttg                                    30

<210> SEQ ID NO 224
<211> LENGTH: 30
<212> TYPE: DNA
<213> ORGANISM: Artificial Sequence
<220> FEATURE:
<223> OTHER INFORMATION: Primer

<400> SEQUENCE: 224
acgttggatg aagacctaca agtagccgag                                    30

<210> SEQ ID NO 225
<211> LENGTH: 21
<212> TYPE: DNA
<213> ORGANISM: Artificial Sequence
<220> FEATURE:
<223> OTHER INFORMATION: Primer

<400> SEQUENCE: 225
ggttgattct acttggaatt t                                             21

<210> SEQ ID NO 226

```
<211> LENGTH: 30
<212> TYPE: DNA
<213> ORGANISM: Artificial Sequence
<220> FEATURE:
<223> OTHER INFORMATION: Primer

<400> SEQUENCE: 226
acgttggatg tggaaccaat cccgtgaaag                                       30

<210> SEQ ID NO 227
<211> LENGTH: 30
<212> TYPE: DNA
<213> ORGANISM: Artificial Sequence
<220> FEATURE:
<223> OTHER INFORMATION: Primer

<400> SEQUENCE: 227
acgttggatg tgaatagcac tgggagcatt                                       30

<210> SEQ ID NO 228
<211> LENGTH: 22
<212> TYPE: DNA
<213> ORGANISM: Artificial Sequence
<220> FEATURE:
<223> OTHER INFORMATION: Primer

<400> SEQUENCE: 228
cccaataaaa gtgactctca gc                                               22

<210> SEQ ID NO 229
<211> LENGTH: 30
<212> TYPE: DNA
<213> ORGANISM: Artificial Sequence
<220> FEATURE:
<223> OTHER INFORMATION: Primer

<400> SEQUENCE: 229
acgttggatg tggaaccaat cccgtgaaag                                       30

<210> SEQ ID NO 230
<211> LENGTH: 30
<212> TYPE: DNA
<213> ORGANISM: Artificial Sequence
<220> FEATURE:
<223> OTHER INFORMATION: Primer

<400> SEQUENCE: 230
acgttggatg tgaatagcac tgggagcatt                                       30

<210> SEQ ID NO 231
<211> LENGTH: 23
<212> TYPE: DNA
<213> ORGANISM: Artificial Sequence
<220> FEATURE:
<223> OTHER INFORMATION: Primer

<400> SEQUENCE: 231
tcccaataaa agtgactctc agc                                              23

<210> SEQ ID NO 232
<211> LENGTH: 30
<212> TYPE: DNA
<213> ORGANISM: Artificial Sequence
<220> FEATURE:
<223> OTHER INFORMATION: Primer

<400> SEQUENCE: 232
```
acgttggatg ctctgggcta ataggactac                                    30

<210> SEQ ID NO 233
<211> LENGTH: 31
<212> TYPE: DNA
<213> ORGANISM: Artificial Sequence
<220> FEATURE:
<223> OTHER INFORMATION: Primer

<400> SEQUENCE: 233
acgttggatg ctgaaaggtt acttcaagga c                                  31

<210> SEQ ID NO 234
<211> LENGTH: 17
<212> TYPE: DNA
<213> ORGANISM: Artificial Sequence
<220> FEATURE:
<223> OTHER INFORMATION: Primer

<400> SEQUENCE: 234
cagatccctg gacaggc                                                  17

<210> SEQ ID NO 235
<211> LENGTH: 31
<212> TYPE: DNA
<213> ORGANISM: Artificial Sequence
<220> FEATURE:
<223> OTHER INFORMATION: Primer

<400> SEQUENCE: 235
acgttggatg ctgaaaggtt acttcaagga c                                  31

<210> SEQ ID NO 236
<211> LENGTH: 30
<212> TYPE: DNA
<213> ORGANISM: Artificial Sequence
<220> FEATURE:
<223> OTHER INFORMATION: Primer

<400> SEQUENCE: 236
acgttggatg ctctgggcta ataggactac                                    30

<210> SEQ ID NO 237
<211> LENGTH: 22
<212> TYPE: DNA
<213> ORGANISM: Artificial Sequence
<220> FEATURE:
<223> OTHER INFORMATION: Primer

<400> SEQUENCE: 237
aggacaaaat acctgtattc ct                                            22

<210> SEQ ID NO 238
<211> LENGTH: 30
<212> TYPE: DNA
<213> ORGANISM: Artificial Sequence
<220> FEATURE:
<223> OTHER INFORMATION: Primer

<400> SEQUENCE: 238
acgttggatg gtccagggat ctgctcttac                                    30

<210> SEQ ID NO 239
<211> LENGTH: 30
<212> TYPE: DNA
<213> ORGANISM: Artificial Sequence
<220> FEATURE:

```
<223> OTHER INFORMATION: Primer

<400> SEQUENCE: 239
acgttggatg catactacag tgacgtggac                                30

<210> SEQ ID NO 240
<211> LENGTH: 17
<212> TYPE: DNA
<213> ORGANISM: Artificial Sequence
<220> FEATURE:
<223> OTHER INFORMATION: Primer

<400> SEQUENCE: 240
gcccagaggc gatgtct                                              17

<210> SEQ ID NO 241
<211> LENGTH: 30
<212> TYPE: DNA
<213> ORGANISM: Artificial Sequence
<220> FEATURE:
<223> OTHER INFORMATION: Primer

<400> SEQUENCE: 241
acgttggatg tgacgatgcc cgtcaggtac                                30

<210> SEQ ID NO 242
<211> LENGTH: 30
<212> TYPE: DNA
<213> ORGANISM: Artificial Sequence
<220> FEATURE:
<223> OTHER INFORMATION: Primer

<400> SEQUENCE: 242
acgttggatg tactcggatg gcagcaagga                                30

<210> SEQ ID NO 243
<211> LENGTH: 17
<212> TYPE: DNA
<213> ORGANISM: Artificial Sequence
<220> FEATURE:
<223> OTHER INFORMATION: Primer

<400> SEQUENCE: 243
tcaggtacca cgtgccc                                              17

<210> SEQ ID NO 244
<211> LENGTH: 30
<212> TYPE: DNA
<213> ORGANISM: Artificial Sequence
<220> FEATURE:
<223> OTHER INFORMATION: Primer

<400> SEQUENCE: 244
acgttggatg ctaatgcagc ggaagatgac                                30

<210> SEQ ID NO 245
<211> LENGTH: 30
<212> TYPE: DNA
<213> ORGANISM: Artificial Sequence
<220> FEATURE:
<223> OTHER INFORMATION: Primer

<400> SEQUENCE: 245
acgttggatg tcataccttg caggttgacg                                30

<210> SEQ ID NO 246
```

```
<211> LENGTH: 20
<212> TYPE: DNA
<213> ORGANISM: Artificial Sequence
<220> FEATURE:
<223> OTHER INFORMATION: Primer

<400> SEQUENCE: 246
ccacagtgga gcttcagggc                                                   20

<210> SEQ ID NO 247
<211> LENGTH: 30
<212> TYPE: DNA
<213> ORGANISM: Artificial Sequence
<220> FEATURE:
<223> OTHER INFORMATION: Primer

<400> SEQUENCE: 247
acgttggatg tcgtagccag cgaatagtag                                        30

<210> SEQ ID NO 248
<211> LENGTH: 30
<212> TYPE: DNA
<213> ORGANISM: Artificial Sequence
<220> FEATURE:
<223> OTHER INFORMATION: Primer

<400> SEQUENCE: 248
acgttggatg tctcccacga gagcatcatc                                        30

<210> SEQ ID NO 249
<211> LENGTH: 20
<212> TYPE: DNA
<213> ORGANISM: Artificial Sequence
<220> FEATURE:
<223> OTHER INFORMATION: Primer

<400> SEQUENCE: 249
ccactgaggg agaaggccac                                                   20

<210> SEQ ID NO 250
<211> LENGTH: 30
<212> TYPE: DNA
<213> ORGANISM: Artificial Sequence
<220> FEATURE:
<223> OTHER INFORMATION: Primer

<400> SEQUENCE: 250
acgttggatg acaggttcct gggacagctt                                        30

<210> SEQ ID NO 251
<211> LENGTH: 30
<212> TYPE: DNA
<213> ORGANISM: Artificial Sequence
<220> FEATURE:
<223> OTHER INFORMATION: Primer

<400> SEQUENCE: 251
acgttggatg tgttcactgc cttccacttc                                        30

<210> SEQ ID NO 252
<211> LENGTH: 21
<212> TYPE: DNA
<213> ORGANISM: Artificial Sequence
<220> FEATURE:
<223> OTHER INFORMATION: Primer

<400> SEQUENCE: 252
```
gggacagctt cctcaaaatc t                                                    21

<210> SEQ ID NO 253
<211> LENGTH: 30
<212> TYPE: DNA
<213> ORGANISM: Artificial Sequence
<220> FEATURE:
<223> OTHER INFORMATION: Primer

<400> SEQUENCE: 253
acgttggatg tattcagcag cttctggtgg                                           30

<210> SEQ ID NO 254
<211> LENGTH: 30
<212> TYPE: DNA
<213> ORGANISM: Artificial Sequence
<220> FEATURE:
<223> OTHER INFORMATION: Primer

<400> SEQUENCE: 254
acgttggatg ccatcatgtg attcaccgtc                                           30

<210> SEQ ID NO 255
<211> LENGTH: 17
<212> TYPE: DNA
<213> ORGANISM: Artificial Sequence
<220> FEATURE:
<223> OTHER INFORMATION: Primer

<400> SEQUENCE: 255
gggcgacgaa gtgctac                                                         17

<210> SEQ ID NO 256
<211> LENGTH: 31
<212> TYPE: DNA
<213> ORGANISM: Artificial Sequence
<220> FEATURE:
<223> OTHER INFORMATION: Primer

<400> SEQUENCE: 256
acgttggatg atccactcaa ggctcccttg c                                         31

<210> SEQ ID NO 257
<211> LENGTH: 30
<212> TYPE: DNA
<213> ORGANISM: Artificial Sequence
<220> FEATURE:
<223> OTHER INFORMATION: Primer

<400> SEQUENCE: 257
acgttggatg ttggcagcag gagcagcaag                                           30

<210> SEQ ID NO 258
<211> LENGTH: 17
<212> TYPE: DNA
<213> ORGANISM: Artificial Sequence
<220> FEATURE:
<223> OTHER INFORMATION: Primer

<400> SEQUENCE: 258
gctcccttgc ccacagg                                                         17

<210> SEQ ID NO 259
<211> LENGTH: 30
<212> TYPE: DNA
<213> ORGANISM: Artificial Sequence
<220> FEATURE:

```
<223> OTHER INFORMATION: Primer

<400> SEQUENCE: 259
acgttggatg tgttagccag actgagcttc                                              30

<210> SEQ ID NO 260
<211> LENGTH: 30
<212> TYPE: DNA
<213> ORGANISM: Artificial Sequence
<220> FEATURE:
<223> OTHER INFORMATION: Primer

<400> SEQUENCE: 260
acgttggatg acctgaaagg caatgagctg                                              30

<210> SEQ ID NO 261
<211> LENGTH: 20
<212> TYPE: DNA
<213> ORGANISM: Artificial Sequence
<220> FEATURE:
<223> OTHER INFORMATION: Primer

<400> SEQUENCE: 261
tctccagctt gggtgtgggc                                                         20

<210> SEQ ID NO 262
<211> LENGTH: 30
<212> TYPE: DNA
<213> ORGANISM: Artificial Sequence
<220> FEATURE:
<223> OTHER INFORMATION: Primer

<400> SEQUENCE: 262
acgttggatg actgtggggt tcaacctctg                                              30

<210> SEQ ID NO 263
<211> LENGTH: 29
<212> TYPE: DNA
<213> ORGANISM: Artificial Sequence
<220> FEATURE:
<223> OTHER INFORMATION: Primer

<400> SEQUENCE: 263
acgttggatg agggaccgt ggtctgttc                                                29

<210> SEQ ID NO 264
<211> LENGTH: 17
<212> TYPE: DNA
<213> ORGANISM: Artificial Sequence
<220> FEATURE:
<223> OTHER INFORMATION: Primer

<400> SEQUENCE: 264
cgagactggg aacagcc                                                            17

<210> SEQ ID NO 265
<211> LENGTH: 30
<212> TYPE: DNA
<213> ORGANISM: Artificial Sequence
<220> FEATURE:
<223> OTHER INFORMATION: Primer

<400> SEQUENCE: 265
acgttggatg tggcctatta gcaccaaaac                                              30

<210> SEQ ID NO 266
```

```
<211> LENGTH: 30
<212> TYPE: DNA
<213> ORGANISM: Artificial Sequence
<220> FEATURE:
<223> OTHER INFORMATION: Primer

<400> SEQUENCE: 266
acgttggatg tcccagacat cccaatatgg                                              30

<210> SEQ ID NO 267
<211> LENGTH: 19
<212> TYPE: DNA
<213> ORGANISM: Artificial Sequence
<220> FEATURE:
<223> OTHER INFORMATION: Primer

<400> SEQUENCE: 267
ttgcatattg aattgctcc                                                          19

<210> SEQ ID NO 268
<211> LENGTH: 30
<212> TYPE: DNA
<213> ORGANISM: Artificial Sequence
<220> FEATURE:
<223> OTHER INFORMATION: Primer

<400> SEQUENCE: 268
acgttggatg tcccagacat cccaatatgg                                              30

<210> SEQ ID NO 269
<211> LENGTH: 30
<212> TYPE: DNA
<213> ORGANISM: Artificial Sequence
<220> FEATURE:
<223> OTHER INFORMATION: Primer

<400> SEQUENCE: 269
acgttggatg tggcctatta gcaccaaaac                                              30

<210> SEQ ID NO 270
<211> LENGTH: 19
<212> TYPE: DNA
<213> ORGANISM: Artificial Sequence
<220> FEATURE:
<223> OTHER INFORMATION: Primer

<400> SEQUENCE: 270
gggacctcac aaacacatt                                                          19

<210> SEQ ID NO 271
<211> LENGTH: 30
<212> TYPE: DNA
<213> ORGANISM: Artificial Sequence
<220> FEATURE:
<223> OTHER INFORMATION: Primer

<400> SEQUENCE: 271
acgttggatg tcccctctt catcatcttc                                               30

<210> SEQ ID NO 272
<211> LENGTH: 30
<212> TYPE: DNA
<213> ORGANISM: Artificial Sequence
<220> FEATURE:
<223> OTHER INFORMATION: Primer

<400> SEQUENCE: 272
```

-continued

```
acgttggatg tctgtatacc ctgaccttgg                                     30

<210> SEQ ID NO 273
<211> LENGTH: 17
<212> TYPE: DNA
<213> ORGANISM: Artificial Sequence
<220> FEATURE:
<223> OTHER INFORMATION: Primer

<400> SEQUENCE: 273
ttccgcttga agaagcc                                                   17

<210> SEQ ID NO 274
<211> LENGTH: 30
<212> TYPE: DNA
<213> ORGANISM: Artificial Sequence
<220> FEATURE:
<223> OTHER INFORMATION: Primer

<400> SEQUENCE: 274
acgttggatg atccaaactg gctgccattg                                     30

<210> SEQ ID NO 275
<211> LENGTH: 30
<212> TYPE: DNA
<213> ORGANISM: Artificial Sequence
<220> FEATURE:
<223> OTHER INFORMATION: Primer

<400> SEQUENCE: 275
acgttggatg tgctcttggg accttgtgct                                     30

<210> SEQ ID NO 276
<211> LENGTH: 17
<212> TYPE: DNA
<213> ORGANISM: Artificial Sequence
<220> FEATURE:
<223> OTHER INFORMATION: Primer

<400> SEQUENCE: 276
tggggcctgc atagaag                                                   17

<210> SEQ ID NO 277
<211> LENGTH: 30
<212> TYPE: DNA
<213> ORGANISM: Artificial Sequence
<220> FEATURE:
<223> OTHER INFORMATION: Primer

<400> SEQUENCE: 277
acgttggatg ttgtgctcag cctcaatgtg                                     30

<210> SEQ ID NO 278
<211> LENGTH: 30
<212> TYPE: DNA
<213> ORGANISM: Artificial Sequence
<220> FEATURE:
<223> OTHER INFORMATION: Primer

<400> SEQUENCE: 278
acgttggatg acatgggtgt ctccatgcag                                     30

<210> SEQ ID NO 279
<211> LENGTH: 18
<212> TYPE: DNA
<213> ORGANISM: Artificial Sequence
<220> FEATURE:
```

```
<223> OTHER INFORMATION: Primer

<400> SEQUENCE: 279
cctcaatgtg tccctacc                                                 18

<210> SEQ ID NO 280
<211> LENGTH: 30
<212> TYPE: DNA
<213> ORGANISM: Artificial Sequence
<220> FEATURE:
<223> OTHER INFORMATION: Primer

<400> SEQUENCE: 280
acgttggatg ctcttacctt gagagggttg                                    30

<210> SEQ ID NO 281
<211> LENGTH: 30
<212> TYPE: DNA
<213> ORGANISM: Artificial Sequence
<220> FEATURE:
<223> OTHER INFORMATION: Primer

<400> SEQUENCE: 281
acgttggatg acatcctgga tatacagccc                                    30

<210> SEQ ID NO 282
<211> LENGTH: 17
<212> TYPE: DNA
<213> ORGANISM: Artificial Sequence
<220> FEATURE:
<223> OTHER INFORMATION: Primer

<400> SEQUENCE: 282
ggctgtggga agcactg                                                  17

<210> SEQ ID NO 283
<211> LENGTH: 30
<212> TYPE: DNA
<213> ORGANISM: Artificial Sequence
<220> FEATURE:
<223> OTHER INFORMATION: Primer

<400> SEQUENCE: 283
acgttggatg cacgcatggt tcaacgtgtc                                    30

<210> SEQ ID NO 284
<211> LENGTH: 30
<212> TYPE: DNA
<213> ORGANISM: Artificial Sequence
<220> FEATURE:
<223> OTHER INFORMATION: Primer

<400> SEQUENCE: 284
acgttggatg acactcacct gagcttcccc                                    30

<210> SEQ ID NO 285
<211> LENGTH: 19
<212> TYPE: DNA
<213> ORGANISM: Artificial Sequence
<220> FEATURE:
<223> OTHER INFORMATION: Primer

<400> SEQUENCE: 285
tcccctatgc ggtgccccc                                                19

<210> SEQ ID NO 286
```

```
<211> LENGTH: 30
<212> TYPE: DNA
<213> ORGANISM: Artificial Sequence
<220> FEATURE:
<223> OTHER INFORMATION: Primer

<400> SEQUENCE: 286
acgttggatg cacgcatggt tcaacgtgtc                                          30

<210> SEQ ID NO 287
<211> LENGTH: 30
<212> TYPE: DNA
<213> ORGANISM: Artificial Sequence
<220> FEATURE:
<223> OTHER INFORMATION: Primer

<400> SEQUENCE: 287
acgttggatg acactcacct gagcttcccc                                          30

<210> SEQ ID NO 288
<211> LENGTH: 21
<212> TYPE: DNA
<213> ORGANISM: Artificial Sequence
<220> FEATURE:
<223> OTHER INFORMATION: Primer

<400> SEQUENCE: 288
ttcaacgtgt cctccctccc c                                                   21

<210> SEQ ID NO 289
<211> LENGTH: 30
<212> TYPE: DNA
<213> ORGANISM: Artificial Sequence
<220> FEATURE:
<223> OTHER INFORMATION: Primer

<400> SEQUENCE: 289
acgttggatg cagattctcc ttcaggtcac                                          30

<210> SEQ ID NO 290
<211> LENGTH: 30
<212> TYPE: DNA
<213> ORGANISM: Artificial Sequence
<220> FEATURE:
<223> OTHER INFORMATION: Primer

<400> SEQUENCE: 290
acgttggatg ttgctggact tctctttggg                                          30

<210> SEQ ID NO 291
<211> LENGTH: 20
<212> TYPE: DNA
<213> ORGANISM: Artificial Sequence
<220> FEATURE:
<223> OTHER INFORMATION: Primer

<400> SEQUENCE: 291
ggtcacagcg aggtgagccc                                                     20

<210> SEQ ID NO 292
<211> LENGTH: 30
<212> TYPE: DNA
<213> ORGANISM: Artificial Sequence
<220> FEATURE:
<223> OTHER INFORMATION: Primer

<400> SEQUENCE: 292
```
acgttggatg ttgctggact tctctttggg                                    30

<210> SEQ ID NO 293
<211> LENGTH: 30
<212> TYPE: DNA
<213> ORGANISM: Artificial Sequence
<220> FEATURE:
<223> OTHER INFORMATION: Primer

<400> SEQUENCE: 293
acgttggatg agcagattct ccttcaggtc                                    30

<210> SEQ ID NO 294
<211> LENGTH: 20
<212> TYPE: DNA
<213> ORGANISM: Artificial Sequence
<220> FEATURE:
<223> OTHER INFORMATION: Primer

<400> SEQUENCE: 294
gccctgcctc tgggctcacc                                               20

<210> SEQ ID NO 295
<211> LENGTH: 30
<212> TYPE: DNA
<213> ORGANISM: Artificial Sequence
<220> FEATURE:
<223> OTHER INFORMATION: Primer

<400> SEQUENCE: 295
acgttggatg tgctcagagg aggactatcg                                    30

<210> SEQ ID NO 296
<211> LENGTH: 30
<212> TYPE: DNA
<213> ORGANISM: Artificial Sequence
<220> FEATURE:
<223> OTHER INFORMATION: Primer

<400> SEQUENCE: 296
acgttggatg attgaccaca gaggcactcg                                    30

<210> SEQ ID NO 297
<211> LENGTH: 17
<212> TYPE: DNA
<213> ORGANISM: Artificial Sequence
<220> FEATURE:
<223> OTHER INFORMATION: Primer

<400> SEQUENCE: 297
ccttcccagc aggacga                                                  17

<210> SEQ ID NO 298
<211> LENGTH: 30
<212> TYPE: DNA
<213> ORGANISM: Artificial Sequence
<220> FEATURE:
<223> OTHER INFORMATION: Primer

<400> SEQUENCE: 298
acgttggatg actaccaaca tgacactgcc                                    30

<210> SEQ ID NO 299
<211> LENGTH: 30
<212> TYPE: DNA
<213> ORGANISM: Artificial Sequence
<220> FEATURE:

```
<223> OTHER INFORMATION: Primer

<400> SEQUENCE: 299
acgttggatg taccactgat gccaagactc                              30

<210> SEQ ID NO 300
<211> LENGTH: 20
<212> TYPE: DNA
<213> ORGANISM: Artificial Sequence
<220> FEATURE:
<223> OTHER INFORMATION: Primer

<400> SEQUENCE: 300
acatgacact gcccgtcatt                                         20

<210> SEQ ID NO 301
<211> LENGTH: 30
<212> TYPE: DNA
<213> ORGANISM: Artificial Sequence
<220> FEATURE:
<223> OTHER INFORMATION: Primer

<400> SEQUENCE: 301
acgttggatg gaagccaatc cgcaggttac                              30

<210> SEQ ID NO 302
<211> LENGTH: 30
<212> TYPE: DNA
<213> ORGANISM: Artificial Sequence
<220> FEATURE:
<223> OTHER INFORMATION: Primer

<400> SEQUENCE: 302
acgttggatg atctgtggag catccagaac                              30

<210> SEQ ID NO 303
<211> LENGTH: 17
<212> TYPE: DNA
<213> ORGANISM: Artificial Sequence
<220> FEATURE:
<223> OTHER INFORMATION: Primer

<400> SEQUENCE: 303
ggttactggt gagcttt                                            17

<210> SEQ ID NO 304
<211> LENGTH: 30
<212> TYPE: DNA
<213> ORGANISM: Artificial Sequence
<220> FEATURE:
<223> OTHER INFORMATION: Primer

<400> SEQUENCE: 304
acgttggatg gagactatgt atcactcacc                              30

<210> SEQ ID NO 305
<211> LENGTH: 30
<212> TYPE: DNA
<213> ORGANISM: Artificial Sequence
<220> FEATURE:
<223> OTHER INFORMATION: Primer

<400> SEQUENCE: 305
acgttggatg ggacacaatg gattaggctg                              30

<210> SEQ ID NO 306
```

```
<211> LENGTH: 19
<212> TYPE: DNA
<213> ORGANISM: Artificial Sequence
<220> FEATURE:
<223> OTHER INFORMATION: Primer

<400> SEQUENCE: 306
ggtcttttcc aaactcttt                                                   19

<210> SEQ ID NO 307
<211> LENGTH: 30
<212> TYPE: DNA
<213> ORGANISM: Artificial Sequence
<220> FEATURE:
<223> OTHER INFORMATION: Primer

<400> SEQUENCE: 307
acgttggatg gaagcaaaga aaggaaagag                                       30

<210> SEQ ID NO 308
<211> LENGTH: 30
<212> TYPE: DNA
<213> ORGANISM: Artificial Sequence
<220> FEATURE:
<223> OTHER INFORMATION: Primer

<400> SEQUENCE: 308
acgttggatg ttacacctgc aactgtgatg                                       30

<210> SEQ ID NO 309
<211> LENGTH: 21
<212> TYPE: DNA
<213> ORGANISM: Artificial Sequence
<220> FEATURE:
<223> OTHER INFORMATION: Primer

<400> SEQUENCE: 309
gaaaggaaag agacttacca a                                                21

<210> SEQ ID NO 310
<211> LENGTH: 30
<212> TYPE: DNA
<213> ORGANISM: Artificial Sequence
<220> FEATURE:
<223> OTHER INFORMATION: Primer

<400> SEQUENCE: 310
acgttggatg ttctagccct ttgccagttc                                       30

<210> SEQ ID NO 311
<211> LENGTH: 30
<212> TYPE: DNA
<213> ORGANISM: Artificial Sequence
<220> FEATURE:
<223> OTHER INFORMATION: Primer

<400> SEQUENCE: 311
acgttggatg tgcagatttc ctggcacatc                                       30

<210> SEQ ID NO 312
<211> LENGTH: 17
<212> TYPE: DNA
<213> ORGANISM: Artificial Sequence
<220> FEATURE:
<223> OTHER INFORMATION: Primer

<400> SEQUENCE: 312
```

```
ggtaagtcca gcagtcg                                                          17

<210> SEQ ID NO 313
<211> LENGTH: 30
<212> TYPE: DNA
<213> ORGANISM: Artificial Sequence
<220> FEATURE:
<223> OTHER INFORMATION: Primer

<400> SEQUENCE: 313
acgttggatg tctcccgaga ggtaaagaac                                             30

<210> SEQ ID NO 314
<211> LENGTH: 30
<212> TYPE: DNA
<213> ORGANISM: Artificial Sequence
<220> FEATURE:
<223> OTHER INFORMATION: Primer

<400> SEQUENCE: 314
acgttggatg aggagctgct gaagatgtgg                                             30

<210> SEQ ID NO 315
<211> LENGTH: 23
<212> TYPE: DNA
<213> ORGANISM: Artificial Sequence
<220> FEATURE:
<223> OTHER INFORMATION: Primer

<400> SEQUENCE: 315
gaacaaagac ttcaaagaca ctt                                                    23

<210> SEQ ID NO 316
<211> LENGTH: 30
<212> TYPE: DNA
<213> ORGANISM: Artificial Sequence
<220> FEATURE:
<223> OTHER INFORMATION: Primer

<400> SEQUENCE: 316
acgttggatg cttcacaaag cggaagaatg                                             30

<210> SEQ ID NO 317
<211> LENGTH: 30
<212> TYPE: DNA
<213> ORGANISM: Artificial Sequence
<220> FEATURE:
<223> OTHER INFORMATION: Primer

<400> SEQUENCE: 317
acgttggatg cttgaaggag aaggtgtctg                                             30

<210> SEQ ID NO 318
<211> LENGTH: 17
<212> TYPE: DNA
<213> ORGANISM: Artificial Sequence
<220> FEATURE:
<223> OTHER INFORMATION: Primer

<400> SEQUENCE: 318
gcgtgatgat gaaatcg                                                           17

<210> SEQ ID NO 319
<211> LENGTH: 30
<212> TYPE: DNA
<213> ORGANISM: Artificial Sequence
<220> FEATURE:
```

```
<223> OTHER INFORMATION: Primer

<400> SEQUENCE: 319
acgttggatg cttgaaggag aaggtgtctg                                30

<210> SEQ ID NO 320
<211> LENGTH: 30
<212> TYPE: DNA
<213> ORGANISM: Artificial Sequence
<220> FEATURE:
<223> OTHER INFORMATION: Primer

<400> SEQUENCE: 320
acgttggatg cttcacaaag cggaagaatg                                30

<210> SEQ ID NO 321
<211> LENGTH: 17
<212> TYPE: DNA
<213> ORGANISM: Artificial Sequence
<220> FEATURE:
<223> OTHER INFORMATION: Primer

<400> SEQUENCE: 321
gaaggtgtct gcgggag                                              17

<210> SEQ ID NO 322
<211> LENGTH: 30
<212> TYPE: DNA
<213> ORGANISM: Artificial Sequence
<220> FEATURE:
<223> OTHER INFORMATION: Primer

<400> SEQUENCE: 322
acgttggatg cacagagaga gtctggacac                                30

<210> SEQ ID NO 323
<211> LENGTH: 30
<212> TYPE: DNA
<213> ORGANISM: Artificial Sequence
<220> FEATURE:
<223> OTHER INFORMATION: Primer

<400> SEQUENCE: 323
acgttggatg ctcttggtct ttccctcatc                                30

<210> SEQ ID NO 324
<211> LENGTH: 18
<212> TYPE: DNA
<213> ORGANISM: Artificial Sequence
<220> FEATURE:
<223> OTHER INFORMATION: Primer

<400> SEQUENCE: 324
gagtctggac acgtgggg                                             18

<210> SEQ ID NO 325
<211> LENGTH: 30
<212> TYPE: DNA
<213> ORGANISM: Artificial Sequence
<220> FEATURE:
<223> OTHER INFORMATION: Primer

<400> SEQUENCE: 325
acgttggatg ctccgatgat acacggctga                                30

<210> SEQ ID NO 326
```

```
<211> LENGTH: 30
<212> TYPE: DNA
<213> ORGANISM: Artificial Sequence
<220> FEATURE:
<223> OTHER INFORMATION: Primer

<400> SEQUENCE: 326
acgttggatg gttgttgaca caagagagcc                                    30

<210> SEQ ID NO 327
<211> LENGTH: 17
<212> TYPE: DNA
<213> ORGANISM: Artificial Sequence
<220> FEATURE:
<223> OTHER INFORMATION: Primer

<400> SEQUENCE: 327
tacacggctg actcccc                                                  17

<210> SEQ ID NO 328
<211> LENGTH: 30
<212> TYPE: DNA
<213> ORGANISM: Artificial Sequence
<220> FEATURE:
<223> OTHER INFORMATION: Primer

<400> SEQUENCE: 328
acgttggatg attgtacctt ggcaggttgg                                    30

<210> SEQ ID NO 329
<211> LENGTH: 30
<212> TYPE: DNA
<213> ORGANISM: Artificial Sequence
<220> FEATURE:
<223> OTHER INFORMATION: Primer

<400> SEQUENCE: 329
acgttggatg aatggctctg cacaaacagc                                    30

<210> SEQ ID NO 330
<211> LENGTH: 19
<212> TYPE: DNA
<213> ORGANISM: Artificial Sequence
<220> FEATURE:
<223> OTHER INFORMATION: Primer

<400> SEQUENCE: 330
tggcaggttg gcacggtag                                                19

<210> SEQ ID NO 331
<211> LENGTH: 30
<212> TYPE: DNA
<213> ORGANISM: Artificial Sequence
<220> FEATURE:
<223> OTHER INFORMATION: Primer

<400> SEQUENCE: 331
acgttggatg agttacagaa cccccacatc                                    30

<210> SEQ ID NO 332
<211> LENGTH: 30
<212> TYPE: DNA
<213> ORGANISM: Artificial Sequence
<220> FEATURE:
<223> OTHER INFORMATION: Primer

<400> SEQUENCE: 332
```
acgttggatg cagcaaatgc atctgttccc                                    30

<210> SEQ ID NO 333
<211> LENGTH: 17
<212> TYPE: DNA
<213> ORGANISM: Artificial Sequence
<220> FEATURE:
<223> OTHER INFORMATION: Primer

<400> SEQUENCE: 333
tccaaaactc gacagaa                                                  17

<210> SEQ ID NO 334
<211> LENGTH: 30
<212> TYPE: DNA
<213> ORGANISM: Artificial Sequence
<220> FEATURE:
<223> OTHER INFORMATION: Primer

<400> SEQUENCE: 334
acgttggatg agtcacagtc ggtgccaatg                                    30

<210> SEQ ID NO 335
<211> LENGTH: 30
<212> TYPE: DNA
<213> ORGANISM: Artificial Sequence
<220> FEATURE:
<223> OTHER INFORMATION: Primer

<400> SEQUENCE: 335
acgttggatg taccttcgag tgcatctgcg                                    30

<210> SEQ ID NO 336
<211> LENGTH: 17
<212> TYPE: DNA
<213> ORGANISM: Artificial Sequence
<220> FEATURE:
<223> OTHER INFORMATION: Primer

<400> SEQUENCE: 336
cggtgccaat gtggcgg                                                  17

<210> SEQ ID NO 337
<211> LENGTH: 30
<212> TYPE: DNA
<213> ORGANISM: Artificial Sequence
<220> FEATURE:
<223> OTHER INFORMATION: Primer

<400> SEQUENCE: 337
acgttggatg acgactgctt cgcgctctac                                    30

<210> SEQ ID NO 338
<211> LENGTH: 30
<212> TYPE: DNA
<213> ORGANISM: Artificial Sequence
<220> FEATURE:
<223> OTHER INFORMATION: Primer

<400> SEQUENCE: 338
acgttggatg agcgcactgt cattaggtgg                                    30

<210> SEQ ID NO 339
<211> LENGTH: 17
<212> TYPE: DNA
<213> ORGANISM: Artificial Sequence
<220> FEATURE:

-continued

<223> OTHER INFORMATION: Primer

<400> SEQUENCE: 339
cgctctaccc gggcccc                                                17

<210> SEQ ID NO 340
<211> LENGTH: 30
<212> TYPE: DNA
<213> ORGANISM: Artificial Sequence
<220> FEATURE:
<223> OTHER INFORMATION: Primer

<400> SEQUENCE: 340
acgttggatg gatttgtgtg taggaccctg                                  30

<210> SEQ ID NO 341
<211> LENGTH: 30
<212> TYPE: DNA
<213> ORGANISM: Artificial Sequence
<220> FEATURE:
<223> OTHER INFORMATION: Primer

<400> SEQUENCE: 341
acgttggatg gtccccaaaa gaaatggagg                                  30

<210> SEQ ID NO 342
<211> LENGTH: 17
<212> TYPE: DNA
<213> ORGANISM: Artificial Sequence
<220> FEATURE:
<223> OTHER INFORMATION: Primer

<400> SEQUENCE: 342
gaggctgaac cccgtcc                                                17

<210> SEQ ID NO 343
<211> LENGTH: 30
<212> TYPE: DNA
<213> ORGANISM: Artificial Sequence
<220> FEATURE:
<223> OTHER INFORMATION: Primer

<400> SEQUENCE: 343
acgttggatg ctaggaacct tgcagcttac                                  30

<210> SEQ ID NO 344
<211> LENGTH: 30
<212> TYPE: DNA
<213> ORGANISM: Artificial Sequence
<220> FEATURE:
<223> OTHER INFORMATION: Primer

<400> SEQUENCE: 344
acgttggatg ccctagagat ccagaaatcg                                  30

<210> SEQ ID NO 345
<211> LENGTH: 18
<212> TYPE: DNA
<213> ORGANISM: Artificial Sequence
<220> FEATURE:
<223> OTHER INFORMATION: Primer

<400> SEQUENCE: 345
ctcccattca cgaggcca                                               18

<210> SEQ ID NO 346

```
<211> LENGTH: 30
<212> TYPE: DNA
<213> ORGANISM: Artificial Sequence
<220> FEATURE:
<223> OTHER INFORMATION: Primer

<400> SEQUENCE: 346
acgttggatg caattcagac ccaaactgcc                                    30

<210> SEQ ID NO 347
<211> LENGTH: 30
<212> TYPE: DNA
<213> ORGANISM: Artificial Sequence
<220> FEATURE:
<223> OTHER INFORMATION: Primer

<400> SEQUENCE: 347
acgttggatg tgctgtttgt gtctgtgctc                                    30

<210> SEQ ID NO 348
<211> LENGTH: 17
<212> TYPE: DNA
<213> ORGANISM: Artificial Sequence
<220> FEATURE:
<223> OTHER INFORMATION: Primer

<400> SEQUENCE: 348
cccaaactgc caatcac                                                  17

<210> SEQ ID NO 349
<211> LENGTH: 30
<212> TYPE: DNA
<213> ORGANISM: Artificial Sequence
<220> FEATURE:
<223> OTHER INFORMATION: Primer

<400> SEQUENCE: 349
acgttggatg gaaaccggtc aatgcttatg                                    30

<210> SEQ ID NO 350
<211> LENGTH: 30
<212> TYPE: DNA
<213> ORGANISM: Artificial Sequence
<220> FEATURE:
<223> OTHER INFORMATION: Primer

<400> SEQUENCE: 350
acgttggatg attgtgtcgc ttcgtcactg                                    30

<210> SEQ ID NO 351
<211> LENGTH: 17
<212> TYPE: DNA
<213> ORGANISM: Artificial Sequence
<220> FEATURE:
<223> OTHER INFORMATION: Primer

<400> SEQUENCE: 351
gagcaagata gaggcgt                                                  17

<210> SEQ ID NO 352
<211> LENGTH: 30
<212> TYPE: DNA
<213> ORGANISM: Artificial Sequence
<220> FEATURE:
<223> OTHER INFORMATION: Primer

<400> SEQUENCE: 352
```

```
acgttggatg tctgatttcc caggaacctc                                    30

<210> SEQ ID NO 353
<211> LENGTH: 30
<212> TYPE: DNA
<213> ORGANISM: Artificial Sequence
<220> FEATURE:
<223> OTHER INFORMATION: Primer

<400> SEQUENCE: 353
acgttggatg atggaccctg cagaacctac                                    30

<210> SEQ ID NO 354
<211> LENGTH: 20
<212> TYPE: DNA
<213> ORGANISM: Artificial Sequence
<220> FEATURE:
<223> OTHER INFORMATION: Primer

<400> SEQUENCE: 354
taccaacaga accaccttcc                                               20

<210> SEQ ID NO 355
<211> LENGTH: 29
<212> TYPE: DNA
<213> ORGANISM: Artificial Sequence
<220> FEATURE:
<223> OTHER INFORMATION: Primer

<400> SEQUENCE: 355
acgttggatg tgttccccca ggacgaacc                                     29

<210> SEQ ID NO 356
<211> LENGTH: 30
<212> TYPE: DNA
<213> ORGANISM: Artificial Sequence
<220> FEATURE:
<223> OTHER INFORMATION: Primer

<400> SEQUENCE: 356
acgttggatg aagtcgagga ggagagaatg                                    30

<210> SEQ ID NO 357
<211> LENGTH: 19
<212> TYPE: DNA
<213> ORGANISM: Artificial Sequence
<220> FEATURE:
<223> OTHER INFORMATION: Primer

<400> SEQUENCE: 357
cccaggacga acccggacc                                                19

<210> SEQ ID NO 358
<211> LENGTH: 30
<212> TYPE: DNA
<213> ORGANISM: Artificial Sequence
<220> FEATURE:
<223> OTHER INFORMATION: Primer

<400> SEQUENCE: 358
acgttggatg aaatgcaagc cgtcgacaac                                    30

<210> SEQ ID NO 359
<211> LENGTH: 30
<212> TYPE: DNA
<213> ORGANISM: Artificial Sequence
<220> FEATURE:
```

<223> OTHER INFORMATION: Primer

<400> SEQUENCE: 359
acgttggatg agaggacctg ggtgattttg                               30

<210> SEQ ID NO 360
<211> LENGTH: 20
<212> TYPE: DNA
<213> ORGANISM: Artificial Sequence
<220> FEATURE:
<223> OTHER INFORMATION: Primer

<400> SEQUENCE: 360
aacctcacct ctgcgcctgg                                          20

<210> SEQ ID NO 361
<211> LENGTH: 30
<212> TYPE: DNA
<213> ORGANISM: Artificial Sequence
<220> FEATURE:
<223> OTHER INFORMATION: Primer

<400> SEQUENCE: 361
acgttggatg tcaatttcac ttatctctgg                               30

<210> SEQ ID NO 362
<211> LENGTH: 30
<212> TYPE: DNA
<213> ORGANISM: Artificial Sequence
<220> FEATURE:
<223> OTHER INFORMATION: Primer

<400> SEQUENCE: 362
acgttggatg tatggcatct acatcttggg                               30

<210> SEQ ID NO 363
<211> LENGTH: 23
<212> TYPE: DNA
<213> ORGANISM: Artificial Sequence
<220> FEATURE:
<223> OTHER INFORMATION: Primer

<400> SEQUENCE: 363
tggtgaaata aaaagattac aaa                                      23

<210> SEQ ID NO 364
<211> LENGTH: 30
<212> TYPE: DNA
<213> ORGANISM: Artificial Sequence
<220> FEATURE:
<223> OTHER INFORMATION: Primer

<400> SEQUENCE: 364
acgttggatg ccaacaagaa atgcaagccg                               30

<210> SEQ ID NO 365
<211> LENGTH: 30
<212> TYPE: DNA
<213> ORGANISM: Artificial Sequence
<220> FEATURE:
<223> OTHER INFORMATION: Primer

<400> SEQUENCE: 365
acgttggatg agaggacctg ggtgattttg                               30

<210> SEQ ID NO 366

```
<211> LENGTH: 17
<212> TYPE: DNA
<213> ORGANISM: Artificial Sequence
<220> FEATURE:
<223> OTHER INFORMATION: Primer

<400> SEQUENCE: 366
atgcaagccg tcgacaa                                                    17

<210> SEQ ID NO 367
<211> LENGTH: 30
<212> TYPE: DNA
<213> ORGANISM: Artificial Sequence
<220> FEATURE:
<223> OTHER INFORMATION: Primer

<400> SEQUENCE: 367
acgttggatg cagcagagtt ggaggaattg                                      30

<210> SEQ ID NO 368
<211> LENGTH: 30
<212> TYPE: DNA
<213> ORGANISM: Artificial Sequence
<220> FEATURE:
<223> OTHER INFORMATION: Primer

<400> SEQUENCE: 368
acgttggatg ggatggcact tttcaagaag                                      30

<210> SEQ ID NO 369
<211> LENGTH: 19
<212> TYPE: DNA
<213> ORGANISM: Artificial Sequence
<220> FEATURE:
<223> OTHER INFORMATION: Primer

<400> SEQUENCE: 369
tgtatggaga cattgatgc                                                  19

<210> SEQ ID NO 370
<211> LENGTH: 30
<212> TYPE: DNA
<213> ORGANISM: Artificial Sequence
<220> FEATURE:
<223> OTHER INFORMATION: Primer

<400> SEQUENCE: 370
acgttggatg gaaggagtga gggctgaagg                                      30

<210> SEQ ID NO 371
<211> LENGTH: 30
<212> TYPE: DNA
<213> ORGANISM: Artificial Sequence
<220> FEATURE:
<223> OTHER INFORMATION: Primer

<400> SEQUENCE: 371
acgttggatg taccagtgtg actgcacccg                                      30

<210> SEQ ID NO 372
<211> LENGTH: 20
<212> TYPE: DNA
<213> ORGANISM: Artificial Sequence
<220> FEATURE:
<223> OTHER INFORMATION: Primer

<400> SEQUENCE: 372
```

-continued aggcccagct cacggatggt          20

<210> SEQ ID NO 373
<211> LENGTH: 30
<212> TYPE: DNA
<213> ORGANISM: Artificial Sequence
<220> FEATURE:
<223> OTHER INFORMATION: Primer

<400> SEQUENCE: 373
acgttggatg tccttaaaga gccgcagttg          30

<210> SEQ ID NO 374
<211> LENGTH: 30
<212> TYPE: DNA
<213> ORGANISM: Artificial Sequence
<220> FEATURE:
<223> OTHER INFORMATION: Primer

<400> SEQUENCE: 374
acgttggatg aaccctctc tgtccacagg          30

<210> SEQ ID NO 375
<211> LENGTH: 17
<212> TYPE: DNA
<213> ORGANISM: Artificial Sequence
<220> FEATURE:
<223> OTHER INFORMATION: Primer

<400> SEQUENCE: 375
gtctccataa atgtggc          17

<210> SEQ ID NO 376
<211> LENGTH: 30
<212> TYPE: DNA
<213> ORGANISM: Artificial Sequence
<220> FEATURE:
<223> OTHER INFORMATION: Primer

<400> SEQUENCE: 376
acgttggatg tcctaggtac tcaccccatg          30

<210> SEQ ID NO 377
<211> LENGTH: 30
<212> TYPE: DNA
<213> ORGANISM: Artificial Sequence
<220> FEATURE:
<223> OTHER INFORMATION: Primer

<400> SEQUENCE: 377
acgttggatg acttcaccca ccagttcttc          30

<210> SEQ ID NO 378
<211> LENGTH: 17
<212> TYPE: DNA
<213> ORGANISM: Artificial Sequence
<220> FEATURE:
<223> OTHER INFORMATION: Primer

<400> SEQUENCE: 378
aagccaggac ccatctt          17

<210> SEQ ID NO 379
<211> LENGTH: 30
<212> TYPE: DNA
<213> ORGANISM: Artificial Sequence
<220> FEATURE:

```
<223> OTHER INFORMATION: Primer

<400> SEQUENCE: 379
acgttggatg gaaaaaggtg gacctggaag                                30

<210> SEQ ID NO 380
<211> LENGTH: 30
<212> TYPE: DNA
<213> ORGANISM: Artificial Sequence
<220> FEATURE:
<223> OTHER INFORMATION: Primer

<400> SEQUENCE: 380
acgttggatg ctcctacaag gagataaggg                                30

<210> SEQ ID NO 381
<211> LENGTH: 19
<212> TYPE: DNA
<213> ORGANISM: Artificial Sequence
<220> FEATURE:
<223> OTHER INFORMATION: Primer

<400> SEQUENCE: 381
aatggcatca tggatctga                                            19

<210> SEQ ID NO 382
<211> LENGTH: 30
<212> TYPE: DNA
<213> ORGANISM: Artificial Sequence
<220> FEATURE:
<223> OTHER INFORMATION: Primer

<400> SEQUENCE: 382
acgttggatg gatctgaact caggtctgtc                                30

<210> SEQ ID NO 383
<211> LENGTH: 30
<212> TYPE: DNA
<213> ORGANISM: Artificial Sequence
<220> FEATURE:
<223> OTHER INFORMATION: Primer

<400> SEQUENCE: 383
acgttggatg tccattgtgg gtagaagcag                                30

<210> SEQ ID NO 384
<211> LENGTH: 17
<212> TYPE: DNA
<213> ORGANISM: Artificial Sequence
<220> FEATURE:
<223> OTHER INFORMATION: Primer

<400> SEQUENCE: 384
cgtccacaca cttcgca                                              17

<210> SEQ ID NO 385
<211> LENGTH: 30
<212> TYPE: DNA
<213> ORGANISM: Artificial Sequence
<220> FEATURE:
<223> OTHER INFORMATION: Primer

<400> SEQUENCE: 385
acgttggatg accctcactc cctgcttctg                                30

<210> SEQ ID NO 386
```

```
<211> LENGTH: 30
<212> TYPE: DNA
<213> ORGANISM: Artificial Sequence
<220> FEATURE:
<223> OTHER INFORMATION: Primer

<400> SEQUENCE: 386
acgttggatg acatgacaga gacagaaccg                                    30

<210> SEQ ID NO 387
<211> LENGTH: 19
<212> TYPE: DNA
<213> ORGANISM: Artificial Sequence
<220> FEATURE:
<223> OTHER INFORMATION: Primer

<400> SEQUENCE: 387
ccctgcttct gagttccat                                                19

<210> SEQ ID NO 388
<211> LENGTH: 30
<212> TYPE: DNA
<213> ORGANISM: Artificial Sequence
<220> FEATURE:
<223> OTHER INFORMATION: Primer

<400> SEQUENCE: 388
acgttggatg atccgtgagc tgggccttca                                    30

<210> SEQ ID NO 389
<211> LENGTH: 30
<212> TYPE: DNA
<213> ORGANISM: Artificial Sequence
<220> FEATURE:
<223> OTHER INFORMATION: Primer

<400> SEQUENCE: 389
acgttggatg ttagggtcta ggagaaaggg                                    30

<210> SEQ ID NO 390
<211> LENGTH: 17
<212> TYPE: DNA
<213> ORGANISM: Artificial Sequence
<220> FEATURE:
<223> OTHER INFORMATION: Primer

<400> SEQUENCE: 390
cagccctcac tccttcc                                                  17

<210> SEQ ID NO 391
<211> LENGTH: 30
<212> TYPE: DNA
<213> ORGANISM: Artificial Sequence
<220> FEATURE:
<223> OTHER INFORMATION: Primer

<400> SEQUENCE: 391
acgttggatg actgctctgg acctaatttg                                    30

<210> SEQ ID NO 392
<211> LENGTH: 30
<212> TYPE: DNA
<213> ORGANISM: Artificial Sequence
<220> FEATURE:
<223> OTHER INFORMATION: Primer

<400> SEQUENCE: 392
```

```
acgttggatg tctacctgtg gacagagagg                                30
```

<210> SEQ ID NO 393
<211> LENGTH: 18
<212> TYPE: DNA
<213> ORGANISM: Artificial Sequence
<220> FEATURE:
<223> OTHER INFORMATION: Primer

<400> SEQUENCE: 393

```
ggacctaatt tggcacgc                                             18
```

<210> SEQ ID NO 394
<211> LENGTH: 30
<212> TYPE: DNA
<213> ORGANISM: Artificial Sequence
<220> FEATURE:
<223> OTHER INFORMATION: Primer

<400> SEQUENCE: 394

```
acgttggatg agtctttgcc agggaagacc                                30
```

<210> SEQ ID NO 395
<211> LENGTH: 30
<212> TYPE: DNA
<213> ORGANISM: Artificial Sequence
<220> FEATURE:
<223> OTHER INFORMATION: Primer

<400> SEQUENCE: 395

```
acgttggatg tgggaaactc aagtaccagg                                30
```

<210> SEQ ID NO 396
<211> LENGTH: 17
<212> TYPE: DNA
<213> ORGANISM: Artificial Sequence
<220> FEATURE:
<223> OTHER INFORMATION: Primer

<400> SEQUENCE: 396

```
ccctctgccc tacccccc                                             17
```

<210> SEQ ID NO 397
<211> LENGTH: 30
<212> TYPE: DNA
<213> ORGANISM: Artificial Sequence
<220> FEATURE:
<223> OTHER INFORMATION: Primer

<400> SEQUENCE: 397

```
acgttggatg aacatgaggt tggtgccttg                                30
```

<210> SEQ ID NO 398
<211> LENGTH: 30
<212> TYPE: DNA
<213> ORGANISM: Artificial Sequence
<220> FEATURE:
<223> OTHER INFORMATION: Primer

<400> SEQUENCE: 398

```
acgttggatg agttgccaga tgcccagctc                                30
```

<210> SEQ ID NO 399
<211> LENGTH: 17
<212> TYPE: DNA
<213> ORGANISM: Artificial Sequence
<220> FEATURE:

<223> OTHER INFORMATION: Primer

<400> SEQUENCE: 399
gggggtcagg tatgaac                                                    17

<210> SEQ ID NO 400
<211> LENGTH: 30
<212> TYPE: DNA
<213> ORGANISM: Artificial Sequence
<220> FEATURE:
<223> OTHER INFORMATION: Primer

<400> SEQUENCE: 400
acgttggatg tgcaggaaat agccactcag                                      30

<210> SEQ ID NO 401
<211> LENGTH: 30
<212> TYPE: DNA
<213> ORGANISM: Artificial Sequence
<220> FEATURE:
<223> OTHER INFORMATION: Primer

<400> SEQUENCE: 401
acgttggatg ctatttccaa tcctgccctg                                      30

<210> SEQ ID NO 402
<211> LENGTH: 20
<212> TYPE: DNA
<213> ORGANISM: Artificial Sequence
<220> FEATURE:
<223> OTHER INFORMATION: Primer

<400> SEQUENCE: 402
cgtactcctc gatgacaatc                                                 20

<210> SEQ ID NO 403
<211> LENGTH: 30
<212> TYPE: DNA
<213> ORGANISM: Artificial Sequence
<220> FEATURE:
<223> OTHER INFORMATION: Primer

<400> SEQUENCE: 403
acgttggatg ttcccatcct taaagagccg                                      30

<210> SEQ ID NO 404
<211> LENGTH: 30
<212> TYPE: DNA
<213> ORGANISM: Artificial Sequence
<220> FEATURE:
<223> OTHER INFORMATION: Primer

<400> SEQUENCE: 404
acgttggatg tctgtccaca ggtagacctc                                      30

<210> SEQ ID NO 405
<211> LENGTH: 17
<212> TYPE: DNA
<213> ORGANISM: Artificial Sequence
<220> FEATURE:
<223> OTHER INFORMATION: Primer

<400> SEQUENCE: 405
ttgatactga cgctcca                                                    17

<210> SEQ ID NO 406

```
<211> LENGTH: 30
<212> TYPE: DNA
<213> ORGANISM: Artificial Sequence
<220> FEATURE:
<223> OTHER INFORMATION: Primer

<400> SEQUENCE: 406
acgttggatg tcatctctct cctctgcagg                                    30

<210> SEQ ID NO 407
<211> LENGTH: 28
<212> TYPE: DNA
<213> ORGANISM: Artificial Sequence
<220> FEATURE:
<223> OTHER INFORMATION: Primer

<400> SEQUENCE: 407
acgttggatg ctgggtccgc gagcagga                                      28

<210> SEQ ID NO 408
<211> LENGTH: 17
<212> TYPE: DNA
<213> ORGANISM: Artificial Sequence
<220> FEATURE:
<223> OTHER INFORMATION: Primer

<400> SEQUENCE: 408
gttcctgctc ctgctcc                                                  17

<210> SEQ ID NO 409
<211> LENGTH: 30
<212> TYPE: DNA
<213> ORGANISM: Artificial Sequence
<220> FEATURE:
<223> OTHER INFORMATION: Primer

<400> SEQUENCE: 409
acgttggatg ggatggcact tttcaagaag                                    30

<210> SEQ ID NO 410
<211> LENGTH: 30
<212> TYPE: DNA
<213> ORGANISM: Artificial Sequence
<220> FEATURE:
<223> OTHER INFORMATION: Primer

<400> SEQUENCE: 410
acgttggatg cagcagagtt ggaggaattg                                    30

<210> SEQ ID NO 411
<211> LENGTH: 20
<212> TYPE: DNA
<213> ORGANISM: Artificial Sequence
<220> FEATURE:
<223> OTHER INFORMATION: Primer

<400> SEQUENCE: 411
cacttttcaa gaagcagtcc                                               20

<210> SEQ ID NO 412
<211> LENGTH: 30
<212> TYPE: DNA
<213> ORGANISM: Artificial Sequence
<220> FEATURE:
<223> OTHER INFORMATION: Primer

<400> SEQUENCE: 412
```

-continued acgttggatg ttctcaccca cagtgaatcc                            30

<210> SEQ ID NO 413
<211> LENGTH: 30
<212> TYPE: DNA
<213> ORGANISM: Artificial Sequence
<220> FEATURE:
<223> OTHER INFORMATION: Primer

<400> SEQUENCE: 413
acgttggatg gggtgcagtc acactggtag                            30

<210> SEQ ID NO 414
<211> LENGTH: 18
<212> TYPE: DNA
<213> ORGANISM: Artificial Sequence
<220> FEATURE:
<223> OTHER INFORMATION: Primer

<400> SEQUENCE: 414
ttgttactat ccatgcca                                         18

<210> SEQ ID NO 415
<211> LENGTH: 30
<212> TYPE: DNA
<213> ORGANISM: Artificial Sequence
<220> FEATURE:
<223> OTHER INFORMATION: Primer

<400> SEQUENCE: 415
acgttggatg ctgttgttac tatccatgcc                            30

<210> SEQ ID NO 416
<211> LENGTH: 30
<212> TYPE: DNA
<213> ORGANISM: Artificial Sequence
<220> FEATURE:
<223> OTHER INFORMATION: Primer

<400> SEQUENCE: 416
acgttggatg aatagcccgt gcgggtgcag                            30

<210> SEQ ID NO 417
<211> LENGTH: 17
<212> TYPE: DNA
<213> ORGANISM: Artificial Sequence
<220> FEATURE:
<223> OTHER INFORMATION: Primer

<400> SEQUENCE: 417
ccgcttcggc cttgacc                                          17

<210> SEQ ID NO 418
<211> LENGTH: 30
<212> TYPE: DNA
<213> ORGANISM: Artificial Sequence
<220> FEATURE:
<223> OTHER INFORMATION: Primer

<400> SEQUENCE: 418
acgttggatg gagcaggagc aggaacagca                            30

<210> SEQ ID NO 419
<211> LENGTH: 30
<212> TYPE: DNA
<213> ORGANISM: Artificial Sequence
<220> FEATURE:

```
<223> OTHER INFORMATION: Primer

<400> SEQUENCE: 419
acgttggatg tcatctctct cctctgcagg                              30

<210> SEQ ID NO 420
<211> LENGTH: 17
<212> TYPE: DNA
<213> ORGANISM: Artificial Sequence
<220> FEATURE:
<223> OTHER INFORMATION: Primer

<400> SEQUENCE: 420
caggaacagc aagaacc                                            17

<210> SEQ ID NO 421
<211> LENGTH: 30
<212> TYPE: DNA
<213> ORGANISM: Artificial Sequence
<220> FEATURE:
<223> OTHER INFORMATION: Primer

<400> SEQUENCE: 421
acgttggatg cacccatctg cactcaaaac                              30

<210> SEQ ID NO 422
<211> LENGTH: 30
<212> TYPE: DNA
<213> ORGANISM: Artificial Sequence
<220> FEATURE:
<223> OTHER INFORMATION: Primer

<400> SEQUENCE: 422
acgttggatg tctgattctg aggtgaaggc                              30

<210> SEQ ID NO 423
<211> LENGTH: 17
<212> TYPE: DNA
<213> ORGANISM: Artificial Sequence
<220> FEATURE:
<223> OTHER INFORMATION: Primer

<400> SEQUENCE: 423
tgtgtggccc tggcact                                            17

<210> SEQ ID NO 424
<211> LENGTH: 30
<212> TYPE: DNA
<213> ORGANISM: Artificial Sequence
<220> FEATURE:
<223> OTHER INFORMATION: Primer

<400> SEQUENCE: 424
acgttggatg ccttcaatga gtaccgcaag                              30

<210> SEQ ID NO 425
<211> LENGTH: 30
<212> TYPE: DNA
<213> ORGANISM: Artificial Sequence
<220> FEATURE:
<223> OTHER INFORMATION: Primer

<400> SEQUENCE: 425
acgttggatg ggaaacagct gctcacctac                              30

<210> SEQ ID NO 426
```

```
<211> LENGTH: 20
<212> TYPE: DNA
<213> ORGANISM: Artificial Sequence
<220> FEATURE:
<223> OTHER INFORMATION: Primer

<400> SEQUENCE: 426
ggcatgaaac cctacacctc                                                    20

<210> SEQ ID NO 427
<211> LENGTH: 30
<212> TYPE: DNA
<213> ORGANISM: Artificial Sequence
<220> FEATURE:
<223> OTHER INFORMATION: Primer

<400> SEQUENCE: 427
acgttggatg tgcactgata cctgttttg                                          30

<210> SEQ ID NO 428
<211> LENGTH: 31
<212> TYPE: DNA
<213> ORGANISM: Artificial Sequence
<220> FEATURE:
<223> OTHER INFORMATION: Primer

<400> SEQUENCE: 428
acgttggatg gcatcttcca tgatgcatta g                                       31

<210> SEQ ID NO 429
<211> LENGTH: 22
<212> TYPE: DNA
<213> ORGANISM: Artificial Sequence
<220> FEATURE:
<223> OTHER INFORMATION: Primer

<400> SEQUENCE: 429
ttttgtttga tgacagaaaa at                                                 22

<210> SEQ ID NO 430
<211> LENGTH: 30
<212> TYPE: DNA
<213> ORGANISM: Artificial Sequence
<220> FEATURE:
<223> OTHER INFORMATION: Primer

<400> SEQUENCE: 430
acgttggatg gagactgaat tgaggcagtg                                         30

<210> SEQ ID NO 431
<211> LENGTH: 30
<212> TYPE: DNA
<213> ORGANISM: Artificial Sequence
<220> FEATURE:
<223> OTHER INFORMATION: Primer

<400> SEQUENCE: 431
acgttggatg atatgttctc ctgcctactg                                         30

<210> SEQ ID NO 432
<211> LENGTH: 17
<212> TYPE: DNA
<213> ORGANISM: Artificial Sequence
<220> FEATURE:
<223> OTHER INFORMATION: Primer

<400> SEQUENCE: 432
```
tgaaaaccca cttctcc                                                          17

<210> SEQ ID NO 433
<211> LENGTH: 30
<212> TYPE: DNA
<213> ORGANISM: Artificial Sequence
<220> FEATURE:
<223> OTHER INFORMATION: Primer

<400> SEQUENCE: 433
acgttggatg taaggaacac atttttaggg                                            30

<210> SEQ ID NO 434
<211> LENGTH: 30
<212> TYPE: DNA
<213> ORGANISM: Artificial Sequence
<220> FEATURE:
<223> OTHER INFORMATION: Primer

<400> SEQUENCE: 434
acgttggatg tcaggtatgc ttcctttgac                                            30

<210> SEQ ID NO 435
<211> LENGTH: 24
<212> TYPE: DNA
<213> ORGANISM: Artificial Sequence
<220> FEATURE:
<223> OTHER INFORMATION: Primer

<400> SEQUENCE: 435
gggattttaa aatatgggta taag                                                  24

<210> SEQ ID NO 436
<211> LENGTH: 30
<212> TYPE: DNA
<213> ORGANISM: Artificial Sequence
<220> FEATURE:
<223> OTHER INFORMATION: Primer

<400> SEQUENCE: 436
acgttggatg agcactaccc atgatagatg                                            30

<210> SEQ ID NO 437
<211> LENGTH: 30
<212> TYPE: DNA
<213> ORGANISM: Artificial Sequence
<220> FEATURE:
<223> OTHER INFORMATION: Primer

<400> SEQUENCE: 437
acgttggatg tggaacatag ttggatgagg                                            30

<210> SEQ ID NO 438
<211> LENGTH: 22
<212> TYPE: DNA
<213> ORGANISM: Artificial Sequence
<220> FEATURE:
<223> OTHER INFORMATION: Primer

<400> SEQUENCE: 438
caaaagcaaa gatgaaattc ca                                                    22

<210> SEQ ID NO 439
<211> LENGTH: 30
<212> TYPE: DNA
<213> ORGANISM: Artificial Sequence
<220> FEATURE:

<223> OTHER INFORMATION: Primer

<400> SEQUENCE: 439
acgttggatg ttcctgggtt tccgattttc        30

<210> SEQ ID NO 440
<211> LENGTH: 30
<212> TYPE: DNA
<213> ORGANISM: Artificial Sequence
<220> FEATURE:
<223> OTHER INFORMATION: Primer

<400> SEQUENCE: 440
acgttggatg aaaattgcgt aagcccggtg        30

<210> SEQ ID NO 441
<211> LENGTH: 22
<212> TYPE: DNA
<213> ORGANISM: Artificial Sequence
<220> FEATURE:
<223> OTHER INFORMATION: Primer

<400> SEQUENCE: 441
tgggtttccg attttctcat tt        22

<210> SEQ ID NO 442
<211> LENGTH: 30
<212> TYPE: DNA
<213> ORGANISM: Artificial Sequence
<220> FEATURE:
<223> OTHER INFORMATION: Primer

<400> SEQUENCE: 442
acgttggatg agggatcaga caggagagtg        30

<210> SEQ ID NO 443
<211> LENGTH: 30
<212> TYPE: DNA
<213> ORGANISM: Artificial Sequence
<220> FEATURE:
<223> OTHER INFORMATION: Primer

<400> SEQUENCE: 443
acgttggatg gagaaaatcg gaaacccagg        30

<210> SEQ ID NO 444
<211> LENGTH: 17
<212> TYPE: DNA
<213> ORGANISM: Artificial Sequence
<220> FEATURE:
<223> OTHER INFORMATION: Primer

<400> SEQUENCE: 444 cccctctgc tcccaaa        17

<210> SEQ ID NO 445
<211> LENGTH: 30
<212> TYPE: DNA
<213> ORGANISM: Artificial Sequence
<220> FEATURE:
<223> OTHER INFORMATION: Primer

<400> SEQUENCE: 445
acgttggatg taaccttact cgccccagtc        30

<210> SEQ ID NO 446

```
<211> LENGTH: 30
<212> TYPE: DNA
<213> ORGANISM: Artificial Sequence
<220> FEATURE:
<223> OTHER INFORMATION: Primer

<400> SEQUENCE: 446
acgttggatg ccgtgtctgg tctgtacgtc                                              30

<210> SEQ ID NO 447
<211> LENGTH: 20
<212> TYPE: DNA
<213> ORGANISM: Artificial Sequence
<220> FEATURE:
<223> OTHER INFORMATION: Primer

<400> SEQUENCE: 447
ccgacgtgac ttcctcgacc                                                         20

<210> SEQ ID NO 448
<211> LENGTH: 30
<212> TYPE: DNA
<213> ORGANISM: Artificial Sequence
<220> FEATURE:
<223> OTHER INFORMATION: Primer

<400> SEQUENCE: 448
acgttggatg acagggtaac tgcttaggac                                              30

<210> SEQ ID NO 449
<211> LENGTH: 30
<212> TYPE: DNA
<213> ORGANISM: Artificial Sequence
<220> FEATURE:
<223> OTHER INFORMATION: Primer

<400> SEQUENCE: 449
acgttggatg actgttctcc gtaccttcac                                              30

<210> SEQ ID NO 450
<211> LENGTH: 21
<212> TYPE: DNA
<213> ORGANISM: Artificial Sequence
<220> FEATURE:
<223> OTHER INFORMATION: Primer

<400> SEQUENCE: 450
tgaggagaat ttacctttcc c                                                       21

<210> SEQ ID NO 451
<211> LENGTH: 30
<212> TYPE: DNA
<213> ORGANISM: Artificial Sequence
<220> FEATURE:
<223> OTHER INFORMATION: Primer

<400> SEQUENCE: 451
acgttggatg atttacggtg aaactctggc                                              30

<210> SEQ ID NO 452
<211> LENGTH: 30
<212> TYPE: DNA
<213> ORGANISM: Artificial Sequence
<220> FEATURE:
<223> OTHER INFORMATION: Primer

<400> SEQUENCE: 452
```
acgttggatg agtcaaagga agcatacctg                            30

<210> SEQ ID NO 453
<211> LENGTH: 20
<212> TYPE: DNA
<213> ORGANISM: Artificial Sequence
<220> FEATURE:
<223> OTHER INFORMATION: Primer

<400> SEQUENCE: 453
tgaaactctg gctagacagc                                       20

<210> SEQ ID NO 454
<211> LENGTH: 30
<212> TYPE: DNA
<213> ORGANISM: Artificial Sequence
<220> FEATURE:
<223> OTHER INFORMATION: Primer

<400> SEQUENCE: 454
acgttggatg aggaaggttc tctcggttag                            30

<210> SEQ ID NO 455
<211> LENGTH: 30
<212> TYPE: DNA
<213> ORGANISM: Artificial Sequence
<220> FEATURE:
<223> OTHER INFORMATION: Primer

<400> SEQUENCE: 455
acgttggatg tgctgaggag ttcctggacg                            30

<210> SEQ ID NO 456
<211> LENGTH: 19
<212> TYPE: DNA
<213> ORGANISM: Artificial Sequence
<220> FEATURE:
<223> OTHER INFORMATION: Primer

<400> SEQUENCE: 456
ggttagcgac caattgtca                                        19

<210> SEQ ID NO 457
<211> LENGTH: 30
<212> TYPE: DNA
<213> ORGANISM: Artificial Sequence
<220> FEATURE:
<223> OTHER INFORMATION: Primer

<400> SEQUENCE: 457
acgttggatg attcccttcc ttcgaaatgc                            30

<210> SEQ ID NO 458
<211> LENGTH: 30
<212> TYPE: DNA
<213> ORGANISM: Artificial Sequence
<220> FEATURE:
<223> OTHER INFORMATION: Primer

<400> SEQUENCE: 458
acgttggatg ctttgagaag gctaaaaacc                            30

<210> SEQ ID NO 459
<211> LENGTH: 22
<212> TYPE: DNA
<213> ORGANISM: Artificial Sequence
<220> FEATURE:

```
<223> OTHER INFORMATION: Primer

<400> SEQUENCE: 459
gaaatgcaat tatgagttat gt                                        22

<210> SEQ ID NO 460
<211> LENGTH: 30
<212> TYPE: DNA
<213> ORGANISM: Artificial Sequence
<220> FEATURE:
<223> OTHER INFORMATION: Primer

<400> SEQUENCE: 460
acgttggatg cttctggtag aaaagcctcg                                30

<210> SEQ ID NO 461
<211> LENGTH: 30
<212> TYPE: DNA
<213> ORGANISM: Artificial Sequence
<220> FEATURE:
<223> OTHER INFORMATION: Primer

<400> SEQUENCE: 461
acgttggatg ccataagtcc tttcaaggag                                30

<210> SEQ ID NO 462
<211> LENGTH: 21
<212> TYPE: DNA
<213> ORGANISM: Artificial Sequence
<220> FEATURE:
<223> OTHER INFORMATION: Primer

<400> SEQUENCE: 462
ttggtgaaac catggtagaa g                                         21

<210> SEQ ID NO 463
<211> LENGTH: 30
<212> TYPE: DNA
<213> ORGANISM: Artificial Sequence
<220> FEATURE:
<223> OTHER INFORMATION: Primer

<400> SEQUENCE: 463
acgttggatg tgctgaggcg aggctggaga                                30

<210> SEQ ID NO 464
<211> LENGTH: 31
<212> TYPE: DNA
<213> ORGANISM: Artificial Sequence
<220> FEATURE:
<223> OTHER INFORMATION: Primer

<400> SEQUENCE: 464
acgttggatg acctggaacc agatcctgga c                              31

<210> SEQ ID NO 465
<211> LENGTH: 17
<212> TYPE: DNA
<213> ORGANISM: Artificial Sequence
<220> FEATURE:
<223> OTHER INFORMATION: Primer

<400> SEQUENCE: 465
gcgcggcgga acaggat                                              17

<210> SEQ ID NO 466
```

```
<211> LENGTH: 30
<212> TYPE: DNA
<213> ORGANISM: Artificial Sequence
<220> FEATURE:
<223> OTHER INFORMATION: Primer

<400> SEQUENCE: 466
acgttggatg ggtggtgcat acctgtaatc                                            30

<210> SEQ ID NO 467
<211> LENGTH: 30
<212> TYPE: DNA
<213> ORGANISM: Artificial Sequence
<220> FEATURE:
<223> OTHER INFORMATION: Primer

<400> SEQUENCE: 467
acgttggatg aaacatcact tcccctgtcg                                            30

<210> SEQ ID NO 468
<211> LENGTH: 17
<212> TYPE: DNA
<213> ORGANISM: Artificial Sequence
<220> FEATURE:
<223> OTHER INFORMATION: Primer

<400> SEQUENCE: 468
tacctgtaat cccagct                                                          17

<210> SEQ ID NO 469
<211> LENGTH: 30
<212> TYPE: DNA
<213> ORGANISM: Artificial Sequence
<220> FEATURE:
<223> OTHER INFORMATION: Primer

<400> SEQUENCE: 469
acgttggatg ctgggacacc acgatggtac                                            30

<210> SEQ ID NO 470
<211> LENGTH: 30
<212> TYPE: DNA
<213> ORGANISM: Artificial Sequence
<220> FEATURE:
<223> OTHER INFORMATION: Primer

<400> SEQUENCE: 470
acgttggatg acgcgctcct ccttcctcac                                            30

<210> SEQ ID NO 471
<211> LENGTH: 18
<212> TYPE: DNA
<213> ORGANISM: Artificial Sequence
<220> FEATURE:
<223> OTHER INFORMATION: Primer

<400> SEQUENCE: 471
cggtgaggac gaggccgc                                                         18

<210> SEQ ID NO 472
<211> LENGTH: 30
<212> TYPE: DNA
<213> ORGANISM: Artificial Sequence
<220> FEATURE:
<223> OTHER INFORMATION: Primer

<400> SEQUENCE: 472
```

-continued

```
acgttggatg taccatcgtg gtgtcccagc                                              30

<210> SEQ ID NO 473
<211> LENGTH: 30
<212> TYPE: DNA
<213> ORGANISM: Artificial Sequence
<220> FEATURE:
<223> OTHER INFORMATION: Primer

<400> SEQUENCE: 473
acgttggatg aagaagatca tgacgacgcc                                              30

<210> SEQ ID NO 474
<211> LENGTH: 19
<212> TYPE: DNA
<213> ORGANISM: Artificial Sequence
<220> FEATURE:
<223> OTHER INFORMATION: Primer

<400> SEQUENCE: 474
cagcacgccg cgctcttcg                                                          19

<210> SEQ ID NO 475
<211> LENGTH: 30
<212> TYPE: DNA
<213> ORGANISM: Artificial Sequence
<220> FEATURE:
<223> OTHER INFORMATION: Primer

<400> SEQUENCE: 475
acgttggatg aagaagatca tgacgacgcc                                              30

<210> SEQ ID NO 476
<211> LENGTH: 30
<212> TYPE: DNA
<213> ORGANISM: Artificial Sequence
<220> FEATURE:
<223> OTHER INFORMATION: Primer

<400> SEQUENCE: 476
acgttggatg taccatcgtg gtgtcccagc                                              30

<210> SEQ ID NO 477
<211> LENGTH: 17
<212> TYPE: DNA
<213> ORGANISM: Artificial Sequence
<220> FEATURE:
<223> OTHER INFORMATION: Primer

<400> SEQUENCE: 477
cgacagagac ggcagcc                                                            17

<210> SEQ ID NO 478
<211> LENGTH: 30
<212> TYPE: DNA
<213> ORGANISM: Artificial Sequence
<220> FEATURE:
<223> OTHER INFORMATION: Primer

<400> SEQUENCE: 478
acgttggatg agagcgctac ctgggtatca                                              30

<210> SEQ ID NO 479
<211> LENGTH: 29
<212> TYPE: DNA
<213> ORGANISM: Artificial Sequence
<220> FEATURE:
```

<223> OTHER INFORMATION: Primer

<400> SEQUENCE: 479
acgttggatg acaccagccc cacggtggc                                29

<210> SEQ ID NO 480
<211> LENGTH: 17
<212> TYPE: DNA
<213> ORGANISM: Artificial Sequence
<220> FEATURE:
<223> OTHER INFORMATION: Primer

<400> SEQUENCE: 480
cgcccggcgg tcgcctc                                             17

<210> SEQ ID NO 481
<211> LENGTH: 30
<212> TYPE: DNA
<213> ORGANISM: Artificial Sequence
<220> FEATURE:
<223> OTHER INFORMATION: Primer

<400> SEQUENCE: 481
acgttggatg accaggaccc cgggtattgc                               30

<210> SEQ ID NO 482
<211> LENGTH: 29
<212> TYPE: DNA
<213> ORGANISM: Artificial Sequence
<220> FEATURE:
<223> OTHER INFORMATION: Primer

<400> SEQUENCE: 482
acgttggatg caccgtgggg ctggtgtgg                                29

<210> SEQ ID NO 483
<211> LENGTH: 17
<212> TYPE: DNA
<213> ORGANISM: Artificial Sequence
<220> FEATURE:
<223> OTHER INFORMATION: Primer

<400> SEQUENCE: 483
caggcccagc gccagcg                                             17

<210> SEQ ID NO 484
<211> LENGTH: 30
<212> TYPE: DNA
<213> ORGANISM: Artificial Sequence
<220> FEATURE:
<223> OTHER INFORMATION: Primer

<400> SEQUENCE: 484
acgttggatg agcgtcagga agcaccagga                               30

<210> SEQ ID NO 485
<211> LENGTH: 29
<212> TYPE: DNA
<213> ORGANISM: Artificial Sequence
<220> FEATURE:
<223> OTHER INFORMATION: Primer

<400> SEQUENCE: 485
acgttggatg tgggcctgct gccctgct                                 29

<210> SEQ ID NO 486

```
<211> LENGTH: 17
<212> TYPE: DNA
<213> ORGANISM: Artificial Sequence
<220> FEATURE:
<223> OTHER INFORMATION: Primer

<400> SEQUENCE: 486
aggaccccgg gtattgc                                                    17

<210> SEQ ID NO 487
<211> LENGTH: 30
<212> TYPE: DNA
<213> ORGANISM: Artificial Sequence
<220> FEATURE:
<223> OTHER INFORMATION: Primer

<400> SEQUENCE: 487
acgttggatg ttcgggctgc tcttctccat                                      30

<210> SEQ ID NO 488
<211> LENGTH: 30
<212> TYPE: DNA
<213> ORGANISM: Artificial Sequence
<220> FEATURE:
<223> OTHER INFORMATION: Primer

<400> SEQUENCE: 488
acgttggatg tggtagacgt ggcacagggt                                      30

<210> SEQ ID NO 489
<211> LENGTH: 21
<212> TYPE: DNA
<213> ORGANISM: Artificial Sequence
<220> FEATURE:
<223> OTHER INFORMATION: Primer

<400> SEQUENCE: 489
ctgtccttcc tgctgaacac g                                               21

<210> SEQ ID NO 490
<211> LENGTH: 30
<212> TYPE: DNA
<213> ORGANISM: Artificial Sequence
<220> FEATURE:
<223> OTHER INFORMATION: Primer

<400> SEQUENCE: 490
acgttggatg agagccccta ctcaccagaa                                      30

<210> SEQ ID NO 491
<211> LENGTH: 30
<212> TYPE: DNA
<213> ORGANISM: Artificial Sequence
<220> FEATURE:
<223> OTHER INFORMATION: Primer

<400> SEQUENCE: 491
acgttggatg aggtggagat gatggctcag                                      30

<210> SEQ ID NO 492
<211> LENGTH: 18
<212> TYPE: DNA
<213> ORGANISM: Artificial Sequence
<220> FEATURE:
<223> OTHER INFORMATION: Primer

<400> SEQUENCE: 492
```
gggcagccaa cacacgct                                                    18

<210> SEQ ID NO 493
<211> LENGTH: 30
<212> TYPE: DNA
<213> ORGANISM: Artificial Sequence
<220> FEATURE:
<223> OTHER INFORMATION: Primer

<400> SEQUENCE: 493
acgttggatg gtcaacccaa aaccctgctg                                       30

<210> SEQ ID NO 494
<211> LENGTH: 30
<212> TYPE: DNA
<213> ORGANISM: Artificial Sequence
<220> FEATURE:
<223> OTHER INFORMATION: Primer

<400> SEQUENCE: 494
acgttggatg tctgcctgtt ctgaggattc                                       30

<210> SEQ ID NO 495
<211> LENGTH: 17
<212> TYPE: DNA
<213> ORGANISM: Artificial Sequence
<220> FEATURE:
<223> OTHER INFORMATION: Primer

<400> SEQUENCE: 495
gctgctgatg cccactg                                                     17

<210> SEQ ID NO 496
<211> LENGTH: 30
<212> TYPE: DNA
<213> ORGANISM: Artificial Sequence
<220> FEATURE:
<223> OTHER INFORMATION: Primer

<400> SEQUENCE: 496
acgttggatg gcagtggtaa gtcgcattgg                                       30

<210> SEQ ID NO 497
<211> LENGTH: 30
<212> TYPE: DNA
<213> ORGANISM: Artificial Sequence
<220> FEATURE:
<223> OTHER INFORMATION: Primer

<400> SEQUENCE: 497
acgttggatg tggcaatggc atcatctgcg                                       30

<210> SEQ ID NO 498
<211> LENGTH: 21
<212> TYPE: DNA
<213> ORGANISM: Artificial Sequence
<220> FEATURE:
<223> OTHER INFORMATION: Primer

<400> SEQUENCE: 498
gccacgcaca ccaggttctc a                                                21

<210> SEQ ID NO 499
<211> LENGTH: 30
<212> TYPE: DNA
<213> ORGANISM: Artificial Sequence
<220> FEATURE:

<223> OTHER INFORMATION: Primer

<400> SEQUENCE: 499
acgttggatg aactggtttc ctctagtggg                    30

<210> SEQ ID NO 500
<211> LENGTH: 30
<212> TYPE: DNA
<213> ORGANISM: Artificial Sequence
<220> FEATURE:
<223> OTHER INFORMATION: Primer

<400> SEQUENCE: 500
acgttggatg aaacccaagt gccttcagag                    30

<210> SEQ ID NO 501
<211> LENGTH: 20
<212> TYPE: DNA
<213> ORGANISM: Artificial Sequence
<220> FEATURE:
<223> OTHER INFORMATION: Primer

<400> SEQUENCE: 501
gggttagatg ttcatctctg                               20

<210> SEQ ID NO 502
<211> LENGTH: 30
<212> TYPE: DNA
<213> ORGANISM: Artificial Sequence
<220> FEATURE:
<223> OTHER INFORMATION: Primer

<400> SEQUENCE: 502
acgttggatg tttctgcact aggtctgcac                    30

<210> SEQ ID NO 503
<211> LENGTH: 30
<212> TYPE: DNA
<213> ORGANISM: Artificial Sequence
<220> FEATURE:
<223> OTHER INFORMATION: Primer

<400> SEQUENCE: 503
acgttggatg ttaacgcaga tcgagttggg                    30

<210> SEQ ID NO 504
<211> LENGTH: 17
<212> TYPE: DNA
<213> ORGANISM: Artificial Sequence
<220> FEATURE:
<223> OTHER INFORMATION: Primer

<400> SEQUENCE: 504
atgagtgtcg aaatgga                                  17

<210> SEQ ID NO 505
<211> LENGTH: 18
<212> TYPE: DNA
<213> ORGANISM: Artificial Sequence
<220> FEATURE:
<223> OTHER INFORMATION: Primer

<400> SEQUENCE: 505
caggaagaag cccacccc                                 18

<210> SEQ ID NO 506

```
<211> LENGTH: 18
<212> TYPE: DNA
<213> ORGANISM: Artificial Sequence
<220> FEATURE:
<223> OTHER INFORMATION: Primer

<400> SEQUENCE: 506
caggaagaag cccaccct                                                   18

<210> SEQ ID NO 507
<211> LENGTH: 20
<212> TYPE: DNA
<213> ORGANISM: Artificial Sequence
<220> FEATURE:
<223> OTHER INFORMATION: Primer

<400> SEQUENCE: 507
caggaagaag cccacccggt                                                 20

<210> SEQ ID NO 508
<211> LENGTH: 18
<212> TYPE: DNA
<213> ORGANISM: Artificial Sequence
<220> FEATURE:
<223> OTHER INFORMATION: Primer

<400> SEQUENCE: 508
gtggagccag agaagtcc                                                   18

<210> SEQ ID NO 509
<211> LENGTH: 19
<212> TYPE: DNA
<213> ORGANISM: Artificial Sequence
<220> FEATURE:
<223> OTHER INFORMATION: Primer

<400> SEQUENCE: 509
gtggagccag agaagtctg                                                  19

<210> SEQ ID NO 510
<211> LENGTH: 18
<212> TYPE: DNA
<213> ORGANISM: Artificial Sequence
<220> FEATURE:
<223> OTHER INFORMATION: Primer

<400> SEQUENCE: 510
ccccgtgttt gtgaatgc                                                   18

<210> SEQ ID NO 511
<211> LENGTH: 19
<212> TYPE: DNA
<213> ORGANISM: Artificial Sequence
<220> FEATURE:
<223> OTHER INFORMATION: Primer

<400> SEQUENCE: 511
ccccgtgttt gtgaatgag                                                  19

<210> SEQ ID NO 512
<211> LENGTH: 22
<212> TYPE: DNA
<213> ORGANISM: Artificial Sequence
<220> FEATURE:
<223> OTHER INFORMATION: Primer

<400> SEQUENCE: 512
```

```
ttcgtgttct atgatcatga gt                                    22

<210> SEQ ID NO 513
<211> LENGTH: 22
<212> TYPE: DNA
<213> ORGANISM: Artificial Sequence
<220> FEATURE:
<223> OTHER INFORMATION: Primer

<400> SEQUENCE: 513
ttcgtgttct atgatcatga ga                                    22

<210> SEQ ID NO 514
<211> LENGTH: 19
<212> TYPE: DNA
<213> ORGANISM: Artificial Sequence
<220> FEATURE:
<223> OTHER INFORMATION: Primer

<400> SEQUENCE: 514
cagcagcgaa tactttttt                                        19

<210> SEQ ID NO 515
<211> LENGTH: 20
<212> TYPE: DNA
<213> ORGANISM: Artificial Sequence
<220> FEATURE:
<223> OTHER INFORMATION: Primer

<400> SEQUENCE: 515
cagcagcgaa tactttttgc                                       20

<210> SEQ ID NO 516
<211> LENGTH: 24
<212> TYPE: DNA
<213> ORGANISM: Artificial Sequence
<220> FEATURE:
<223> OTHER INFORMATION: Primer

<400> SEQUENCE: 516
aaaattatag agaaagttga ttac                                  24

<210> SEQ ID NO 517
<211> LENGTH: 25
<212> TYPE: DNA
<213> ORGANISM: Artificial Sequence
<220> FEATURE:
<223> OTHER INFORMATION: Primer

<400> SEQUENCE: 517
aaaattatag agaaagttga ttaac                                 25

<210> SEQ ID NO 518
<211> LENGTH: 19
<212> TYPE: DNA
<213> ORGANISM: Artificial Sequence
<220> FEATURE:
<223> OTHER INFORMATION: Primer

<400> SEQUENCE: 518
ggcagcctca caggattgc                                        19

<210> SEQ ID NO 519
<211> LENGTH: 20
<212> TYPE: DNA
<213> ORGANISM: Artificial Sequence
<220> FEATURE:
```

```
<223> OTHER INFORMATION: Primer

<400> SEQUENCE: 519
ggcagcctca caggattggc                                              20

<210> SEQ ID NO 520
<211> LENGTH: 18
<212> TYPE: DNA
<213> ORGANISM: Artificial Sequence
<220> FEATURE:
<223> OTHER INFORMATION: Primer

<400> SEQUENCE: 520
cacctacctg tggcgtca                                                18

<210> SEQ ID NO 521
<211> LENGTH: 19
<212> TYPE: DNA
<213> ORGANISM: Artificial Sequence
<220> FEATURE:
<223> OTHER INFORMATION: Primer

<400> SEQUENCE: 521
cacctacctg tggcgtcgc                                               19

<210> SEQ ID NO 522
<211> LENGTH: 19
<212> TYPE: DNA
<213> ORGANISM: Artificial Sequence
<220> FEATURE:
<223> OTHER INFORMATION: Primer

<400> SEQUENCE: 522
gttgtggtcg tgctaaacc                                               19

<210> SEQ ID NO 523
<211> LENGTH: 20
<212> TYPE: DNA
<213> ORGANISM: Artificial Sequence
<220> FEATURE:
<223> OTHER INFORMATION: Primer

<400> SEQUENCE: 523
gttgtggtcg tgctaaactg                                              20

<210> SEQ ID NO 524
<211> LENGTH: 20
<212> TYPE: DNA
<213> ORGANISM: Artificial Sequence
<220> FEATURE:
<223> OTHER INFORMATION: Primer

<400> SEQUENCE: 524
cactgccttg actcactcac                                              20

<210> SEQ ID NO 525
<211> LENGTH: 21
<212> TYPE: DNA
<213> ORGANISM: Artificial Sequence
<220> FEATURE:
<223> OTHER INFORMATION: Primer

<400> SEQUENCE: 525
cactgccttg actcactcat c                                            21

<210> SEQ ID NO 526
```

```
<211> LENGTH: 19
<212> TYPE: DNA
<213> ORGANISM: Artificial Sequence
<220> FEATURE:
<223> OTHER INFORMATION: Primer

<400> SEQUENCE: 526
ccagtcagaa gaacgaccc                                                      19

<210> SEQ ID NO 527
<211> LENGTH: 20
<212> TYPE: DNA
<213> ORGANISM: Artificial Sequence
<220> FEATURE:
<223> OTHER INFORMATION: Primer

<400> SEQUENCE: 527
ccagtcagaa gaacgacctg                                                     20

<210> SEQ ID NO 528
<211> LENGTH: 20
<212> TYPE: DNA
<213> ORGANISM: Artificial Sequence
<220> FEATURE:
<223> OTHER INFORMATION: Primer

<400> SEQUENCE: 528
ctgtcgacaa agttacgcac                                                     20

<210> SEQ ID NO 529
<211> LENGTH: 21
<212> TYPE: DNA
<213> ORGANISM: Artificial Sequence
<220> FEATURE:
<223> OTHER INFORMATION: Primer

<400> SEQUENCE: 529
ctgtcgacaa agttacgcaa c                                                   21

<210> SEQ ID NO 530
<211> LENGTH: 18
<212> TYPE: DNA
<213> ORGANISM: Artificial Sequence
<220> FEATURE:
<223> OTHER INFORMATION: Primer

<400> SEQUENCE: 530
ccacatggta caggaggc                                                       18

<210> SEQ ID NO 531
<211> LENGTH: 20
<212> TYPE: DNA
<213> ORGANISM: Artificial Sequence
<220> FEATURE:
<223> OTHER INFORMATION: Primer

<400> SEQUENCE: 531
ccacatggta caggaggttc                                                     20

<210> SEQ ID NO 532
<211> LENGTH: 23
<212> TYPE: DNA
<213> ORGANISM: Artificial Sequence
<220> FEATURE:
<223> OTHER INFORMATION: Primer

<400> SEQUENCE: 532
```

```
catcattgta gacatcacca agc                                          23

<210> SEQ ID NO 533
<211> LENGTH: 24
<212> TYPE: DNA
<213> ORGANISM: Artificial Sequence
<220> FEATURE:
<223> OTHER INFORMATION: Primer

<400> SEQUENCE: 533
catcattgta gacatcacca agga                                         24

<210> SEQ ID NO 534
<211> LENGTH: 23
<212> TYPE: DNA
<213> ORGANISM: Artificial Sequence
<220> FEATURE:
<223> OTHER INFORMATION: Primer

<400> SEQUENCE: 534
ggacaaaata cctgtattcc tca                                          23

<210> SEQ ID NO 535
<211> LENGTH: 24
<212> TYPE: DNA
<213> ORGANISM: Artificial Sequence
<220> FEATURE:
<223> OTHER INFORMATION: Primer

<400> SEQUENCE: 535
ggacaaaata cctgtattcc tcgc                                         24

<210> SEQ ID NO 536
<211> LENGTH: 18
<212> TYPE: DNA
<213> ORGANISM: Artificial Sequence
<220> FEATURE:
<223> OTHER INFORMATION: Primer

<400> SEQUENCE: 536
cagatccctg gacaggca                                                18

<210> SEQ ID NO 537
<211> LENGTH: 19
<212> TYPE: DNA
<213> ORGANISM: Artificial Sequence
<220> FEATURE:
<223> OTHER INFORMATION: Primer

<400> SEQUENCE: 537
cagatccctg gacaggcga                                               19

<210> SEQ ID NO 538
<211> LENGTH: 18
<212> TYPE: DNA
<213> ORGANISM: Artificial Sequence
<220> FEATURE:
<223> OTHER INFORMATION: Primer

<400> SEQUENCE: 538
acacaggcgt cctctgaa                                                18

<210> SEQ ID NO 539
<211> LENGTH: 19
<212> TYPE: DNA
<213> ORGANISM: Artificial Sequence
<220> FEATURE:
```

<223> OTHER INFORMATION: Primer

<400> SEQUENCE: 539
acacaggcgt cctctgagc                                              19

<210> SEQ ID NO 540
<211> LENGTH: 23
<212> TYPE: DNA
<213> ORGANISM: Artificial Sequence
<220> FEATURE:
<223> OTHER INFORMATION: Primer

<400> SEQUENCE: 540
gatctagaat tccaaacccc taa                                         23

<210> SEQ ID NO 541
<211> LENGTH: 24
<212> TYPE: DNA
<213> ORGANISM: Artificial Sequence
<220> FEATURE:
<223> OTHER INFORMATION: Primer

<400> SEQUENCE: 541
gatctagaat tccaaacccc tagt                                        24

<210> SEQ ID NO 542
<211> LENGTH: 18
<212> TYPE: DNA
<213> ORGANISM: Artificial Sequence
<220> FEATURE:
<223> OTHER INFORMATION: Primer

<400> SEQUENCE: 542
tcaggtacca cgtgcccc                                               18

<210> SEQ ID NO 543
<211> LENGTH: 19
<212> TYPE: DNA
<213> ORGANISM: Artificial Sequence
<220> FEATURE:
<223> OTHER INFORMATION: Primer

<400> SEQUENCE: 543
tcaggtacca cgtgccctg                                              19

<210> SEQ ID NO 544
<211> LENGTH: 22
<212> TYPE: DNA
<213> ORGANISM: Artificial Sequence
<220> FEATURE:
<223> OTHER INFORMATION: Primer

<400> SEQUENCE: 544
tgcagagcaa gatttactct ct                                          22

<210> SEQ ID NO 545
<211> LENGTH: 23
<212> TYPE: DNA
<213> ORGANISM: Artificial Sequence
<220> FEATURE:
<223> OTHER INFORMATION: Primer

<400> SEQUENCE: 545
tgcagagcaa gatttactct cat                                         23

<210> SEQ ID NO 546

```
<211> LENGTH: 22
<212> TYPE: DNA
<213> ORGANISM: Artificial Sequence
<220> FEATURE:
<223> OTHER INFORMATION: Primer

<400> SEQUENCE: 546
cttaactcct ggatacaggt at                                          22

<210> SEQ ID NO 547
<211> LENGTH: 23
<212> TYPE: DNA
<213> ORGANISM: Artificial Sequence
<220> FEATURE:
<223> OTHER INFORMATION: Primer

<400> SEQUENCE: 547
cttaactcct ggatacaggt aag                                         23

<210> SEQ ID NO 548
<211> LENGTH: 19
<212> TYPE: DNA
<213> ORGANISM: Artificial Sequence
<220> FEATURE:
<223> OTHER INFORMATION: Primer

<400> SEQUENCE: 548
ggcacaacag tgacaatcc                                              19

<210> SEQ ID NO 549
<211> LENGTH: 21
<212> TYPE: DNA
<213> ORGANISM: Artificial Sequence
<220> FEATURE:
<223> OTHER INFORMATION: Primer

<400> SEQUENCE: 549
ggcacaacag tgacaatcgg t                                           21

<210> SEQ ID NO 550
<211> LENGTH: 22
<212> TYPE: DNA
<213> ORGANISM: Artificial Sequence
<220> FEATURE:
<223> OTHER INFORMATION: Primer

<400> SEQUENCE: 550
tgctggcatt ctacatcagt aa                                          22

<210> SEQ ID NO 551
<211> LENGTH: 23
<212> TYPE: DNA
<213> ORGANISM: Artificial Sequence
<220> FEATURE:
<223> OTHER INFORMATION: Primer

<400> SEQUENCE: 551
tgctggcatt ctacatcagt agc                                         23

<210> SEQ ID NO 552
<211> LENGTH: 18
<212> TYPE: DNA
<213> ORGANISM: Artificial Sequence
<220> FEATURE:
<223> OTHER INFORMATION: Primer

<400> SEQUENCE: 552
```
agtggagagg ggttcacc                                          18

<210> SEQ ID NO 553
<211> LENGTH: 20
<212> TYPE: DNA
<213> ORGANISM: Artificial Sequence
<220> FEATURE:
<223> OTHER INFORMATION: Primer

<400> SEQUENCE: 553
agtggagagg ggttcacgga                                        20

<210> SEQ ID NO 554
<211> LENGTH: 19
<212> TYPE: DNA
<213> ORGANISM: Artificial Sequence
<220> FEATURE:
<223> OTHER INFORMATION: Primer

<400> SEQUENCE: 554
cccaggaact tcctcacaa                                         19

<210> SEQ ID NO 555
<211> LENGTH: 21
<212> TYPE: DNA
<213> ORGANISM: Artificial Sequence
<220> FEATURE:
<223> OTHER INFORMATION: Primer

<400> SEQUENCE: 555
cccaggaact tcctcacagg t                                      21

<210> SEQ ID NO 556
<211> LENGTH: 23
<212> TYPE: DNA
<213> ORGANISM: Artificial Sequence
<220> FEATURE:
<223> OTHER INFORMATION: Primer

<400> SEQUENCE: 556
ccccacatcc ttgcaggtta cct                                    23

<210> SEQ ID NO 557
<211> LENGTH: 24
<212> TYPE: DNA
<213> ORGANISM: Artificial Sequence
<220> FEATURE:
<223> OTHER INFORMATION: Primer

<400> SEQUENCE: 557
ccccacatcc ttgcaggtta ccgt                                   24

<210> SEQ ID NO 558
<211> LENGTH: 18
<212> TYPE: DNA
<213> ORGANISM: Artificial Sequence
<220> FEATURE:
<223> OTHER INFORMATION: Primer

<400> SEQUENCE: 558
gaccaccgtc acagcacc                                          18

<210> SEQ ID NO 559
<211> LENGTH: 20
<212> TYPE: DNA
<213> ORGANISM: Artificial Sequence
<220> FEATURE:

```
<223> OTHER INFORMATION: Primer

<400> SEQUENCE: 559
gaccaccgtc acagcacttg                                              20

<210> SEQ ID NO 560
<211> LENGTH: 19
<212> TYPE: DNA
<213> ORGANISM: Artificial Sequence
<220> FEATURE:
<223> OTHER INFORMATION: Primer

<400> SEQUENCE: 560
caatagcttc cctcccccc                                               19

<210> SEQ ID NO 561
<211> LENGTH: 21
<212> TYPE: DNA
<213> ORGANISM: Artificial Sequence
<220> FEATURE:
<223> OTHER INFORMATION: Primer

<400> SEQUENCE: 561
caatagcttc cctcccccctt c                                           21

<210> SEQ ID NO 562
<211> LENGTH: 23
<212> TYPE: DNA
<213> ORGANISM: Artificial Sequence
<220> FEATURE:
<223> OTHER INFORMATION: Primer

<400> SEQUENCE: 562
gtttccatct atttggtaca cac                                          23

<210> SEQ ID NO 563
<211> LENGTH: 24
<212> TYPE: DNA
<213> ORGANISM: Artificial Sequence
<220> FEATURE:
<223> OTHER INFORMATION: Primer

<400> SEQUENCE: 563
gtttccatct atttggtaca caag                                         24

<210> SEQ ID NO 564
<211> LENGTH: 22
<212> TYPE: DNA
<213> ORGANISM: Artificial Sequence
<220> FEATURE:
<223> OTHER INFORMATION: Primer

<400> SEQUENCE: 564
ggagtccttc tacatccaga ca                                           22

<210> SEQ ID NO 565
<211> LENGTH: 23
<212> TYPE: DNA
<213> ORGANISM: Artificial Sequence
<220> FEATURE:
<223> OTHER INFORMATION: Primer

<400> SEQUENCE: 565
ggagtccttc tacatccaga cgt                                          23

<210> SEQ ID NO 566
```

```
<211> LENGTH: 19
<212> TYPE: DNA
<213> ORGANISM: Artificial Sequence
<220> FEATURE:
<223> OTHER INFORMATION: Primer

<400> SEQUENCE: 566
accctccttc cttcctcac                                                19

<210> SEQ ID NO 567
<211> LENGTH: 20
<212> TYPE: DNA
<213> ORGANISM: Artificial Sequence
<220> FEATURE:
<223> OTHER INFORMATION: Primer

<400> SEQUENCE: 567
accctccttc cttcctcatg                                               20

<210> SEQ ID NO 568
<211> LENGTH: 18
<212> TYPE: DNA
<213> ORGANISM: Artificial Sequence
<220> FEATURE:
<223> OTHER INFORMATION: Primer

<400> SEQUENCE: 568
ctggtcccca ggctctgc                                                 18

<210> SEQ ID NO 569
<211> LENGTH: 19
<212> TYPE: DNA
<213> ORGANISM: Artificial Sequence
<220> FEATURE:
<223> OTHER INFORMATION: Primer

<400> SEQUENCE: 569
ctggtcccca ggctctggt                                                19

<210> SEQ ID NO 570
<211> LENGTH: 18
<212> TYPE: DNA
<213> ORGANISM: Artificial Sequence
<220> FEATURE:
<223> OTHER INFORMATION: Primer

<400> SEQUENCE: 570 cccccgaaa acccttac                                                  18

<210> SEQ ID NO 571
<211> LENGTH: 19
<212> TYPE: DNA
<213> ORGANISM: Artificial Sequence
<220> FEATURE:
<223> OTHER INFORMATION: Primer

<400> SEQUENCE: 571 cccccgaaa acccttagc                                                 19

<210> SEQ ID NO 572
<211> LENGTH: 18
<212> TYPE: DNA
<213> ORGANISM: Artificial Sequence
<220> FEATURE:
<223> OTHER INFORMATION: Primer

<400> SEQUENCE: 572
```

-continued

| | |
|---|---|
| ctttgtcctg gggaccaa | 18 |

<210> SEQ ID NO 573
<211> LENGTH: 20
<212> TYPE: DNA
<213> ORGANISM: Artificial Sequence
<220> FEATURE:
<223> OTHER INFORMATION: Primer

<400> SEQUENCE: 573

| | |
|---|---|
| ctttgtcctg gggaccaggt | 20 |

<210> SEQ ID NO 574
<211> LENGTH: 24
<212> TYPE: DNA
<213> ORGANISM: Artificial Sequence
<220> FEATURE:
<223> OTHER INFORMATION: Primer

<400> SEQUENCE: 574

| | |
|---|---|
| ctggtcccag acatcattct tacc | 24 |

<210> SEQ ID NO 575
<211> LENGTH: 26
<212> TYPE: DNA
<213> ORGANISM: Artificial Sequence
<220> FEATURE:
<223> OTHER INFORMATION: Primer

<400> SEQUENCE: 575

| | |
|---|---|
| ctggtcccag acatcattct tacttg | 26 |

<210> SEQ ID NO 576
<211> LENGTH: 22
<212> TYPE: DNA
<213> ORGANISM: Artificial Sequence
<220> FEATURE:
<223> OTHER INFORMATION: Primer

<400> SEQUENCE: 576

| | |
|---|---|
| gtcattgaat acgcacggct cc | 22 |

<210> SEQ ID NO 577
<211> LENGTH: 23
<212> TYPE: DNA
<213> ORGANISM: Artificial Sequence
<220> FEATURE:
<223> OTHER INFORMATION: Primer

<400> SEQUENCE: 577

| | |
|---|---|
| gtcattgaat acgcacggct ctg | 23 |

<210> SEQ ID NO 578
<211> LENGTH: 19
<212> TYPE: DNA
<213> ORGANISM: Artificial Sequence
<220> FEATURE:
<223> OTHER INFORMATION: Primer

<400> SEQUENCE: 578

| | |
|---|---|
| caagcacacg gataccca | 19 |

<210> SEQ ID NO 579
<211> LENGTH: 21
<212> TYPE: DNA
<213> ORGANISM: Artificial Sequence
<220> FEATURE:

-continued

```
<223> OTHER INFORMATION: Primer

<400> SEQUENCE: 579
caagcacacg gatacccgg a                                          21

<210> SEQ ID NO 580
<211> LENGTH: 23
<212> TYPE: DNA
<213> ORGANISM: Artificial Sequence
<220> FEATURE:
<223> OTHER INFORMATION: Primer

<400> SEQUENCE: 580
gaaggaggtc attgaatacg cac                                       23

<210> SEQ ID NO 581
<211> LENGTH: 24
<212> TYPE: DNA
<213> ORGANISM: Artificial Sequence
<220> FEATURE:
<223> OTHER INFORMATION: Primer

<400> SEQUENCE: 581
gaaggaggtc attgaatacg catg                                      24

<210> SEQ ID NO 582
<211> LENGTH: 18
<212> TYPE: DNA
<213> ORGANISM: Artificial Sequence
<220> FEATURE:
<223> OTHER INFORMATION: Primer

<400> SEQUENCE: 582 acggatacccc cggagcca                                            18

<210> SEQ ID NO 583
<211> LENGTH: 19
<212> TYPE: DNA
<213> ORGANISM: Artificial Sequence
<220> FEATURE:
<223> OTHER INFORMATION: Primer

<400> SEQUENCE: 583 acggatacccc cggagccgt                                           19

<210> SEQ ID NO 584
<211> LENGTH: 19
<212> TYPE: DNA
<213> ORGANISM: Artificial Sequence
<220> FEATURE:
<223> OTHER INFORMATION: Primer

<400> SEQUENCE: 584
ccgggccctt ctctctgct                                            19

<210> SEQ ID NO 585
<211> LENGTH: 19
<212> TYPE: DNA
<213> ORGANISM: Artificial Sequence
<220> FEATURE:
<223> OTHER INFORMATION: Primer

<400> SEQUENCE: 585
ccgggccctt ctctctgta                                            19

<210> SEQ ID NO 586
```

```
<211> LENGTH: 18
<212> TYPE: DNA
<213> ORGANISM: Artificial Sequence
<220> FEATURE:
<223> OTHER INFORMATION: Primer

<400> SEQUENCE: 586
gttcaggtac caggggggc                                              18

<210> SEQ ID NO 587
<211> LENGTH: 19
<212> TYPE: DNA
<213> ORGANISM: Artificial Sequence
<220> FEATURE:
<223> OTHER INFORMATION: Primer

<400> SEQUENCE: 587
gttcaggtac caggggga                                               19

<210> SEQ ID NO 588
<211> LENGTH: 18
<212> TYPE: DNA
<213> ORGANISM: Artificial Sequence
<220> FEATURE:
<223> OTHER INFORMATION: Primer

<400> SEQUENCE: 588
tggtaggggt ttgaatgc                                               18

<210> SEQ ID NO 589
<211> LENGTH: 19
<212> TYPE: DNA
<213> ORGANISM: Artificial Sequence
<220> FEATURE:
<223> OTHER INFORMATION: Primer

<400> SEQUENCE: 589
tggtaggggt ttgaatgtc                                              19

<210> SEQ ID NO 590
<211> LENGTH: 21
<212> TYPE: DNA
<213> ORGANISM: Artificial Sequence
<220> FEATURE:
<223> OTHER INFORMATION: Primer

<400> SEQUENCE: 590
cacttgattt tttttctcct c                                           21

<210> SEQ ID NO 591
<211> LENGTH: 22
<212> TYPE: DNA
<213> ORGANISM: Artificial Sequence
<220> FEATURE:
<223> OTHER INFORMATION: Primer

<400> SEQUENCE: 591
cacttgattt tttttctcct tg                                          22

<210> SEQ ID NO 592
<211> LENGTH: 25
<212> TYPE: DNA
<213> ORGANISM: Artificial Sequence
<220> FEATURE:
<223> OTHER INFORMATION: Primer

<400> SEQUENCE: 592
```

```
atgtagtaaa aatacatatg ccata                                          25
```

<210> SEQ ID NO 593
<211> LENGTH: 27
<212> TYPE: DNA
<213> ORGANISM: Artificial Sequence
<220> FEATURE:
<223> OTHER INFORMATION: Primer

<400> SEQUENCE: 593

```
atgtagtaaa aatacatatg ccatggc                                        27
```

<210> SEQ ID NO 594
<211> LENGTH: 24
<212> TYPE: DNA
<213> ORGANISM: Artificial Sequence
<220> FEATURE:
<223> OTHER INFORMATION: Primer

<400> SEQUENCE: 594

```
attataagaa ttatttttc tccc                                            24
```

<210> SEQ ID NO 595
<211> LENGTH: 25
<212> TYPE: DNA
<213> ORGANISM: Artificial Sequence
<220> FEATURE:
<223> OTHER INFORMATION: Primer

<400> SEQUENCE: 595

```
attataagaa ttatttttc tccta                                           25
```

<210> SEQ ID NO 596
<211> LENGTH: 18
<212> TYPE: DNA
<213> ORGANISM: Artificial Sequence
<220> FEATURE:
<223> OTHER INFORMATION: Primer

<400> SEQUENCE: 596

```
cggacatgga ggacgtgc                                                  18
```

<210> SEQ ID NO 597
<211> LENGTH: 19
<212> TYPE: DNA
<213> ORGANISM: Artificial Sequence
<220> FEATURE:
<223> OTHER INFORMATION: Primer

<400> SEQUENCE: 597

```
cggacatgga ggacgtgtg                                                 19
```

<210> SEQ ID NO 598
<211> LENGTH: 23
<212> TYPE: DNA
<213> ORGANISM: Artificial Sequence
<220> FEATURE:
<223> OTHER INFORMATION: Primer

<400> SEQUENCE: 598

```
tcatgacttc aagagttctt ttc                                            23
```

<210> SEQ ID NO 599
<211> LENGTH: 24
<212> TYPE: DNA
<213> ORGANISM: Artificial Sequence
<220> FEATURE:

-continued

```
<223> OTHER INFORMATION: Primer

<400> SEQUENCE: 599
tcatgacttc aagagttctt ttta                                    24

<210> SEQ ID NO 600
<211> LENGTH: 18
<212> TYPE: DNA
<213> ORGANISM: Artificial Sequence
<220> FEATURE:
<223> OTHER INFORMATION: Primer

<400> SEQUENCE: 600
tttccgaagc cagaggaa                                           18

<210> SEQ ID NO 601
<211> LENGTH: 19
<212> TYPE: DNA
<213> ORGANISM: Artificial Sequence
<220> FEATURE:
<223> OTHER INFORMATION: Primer

<400> SEQUENCE: 601
tttccgaagc cagaggaga                                          19

<210> SEQ ID NO 602
<211> LENGTH: 21
<212> TYPE: DNA
<213> ORGANISM: Artificial Sequence
<220> FEATURE:
<223> OTHER INFORMATION: Primer

<400> SEQUENCE: 602
cctgtaccaa tacatcctgc c                                       21

<210> SEQ ID NO 603
<211> LENGTH: 22
<212> TYPE: DNA
<213> ORGANISM: Artificial Sequence
<220> FEATURE:
<223> OTHER INFORMATION: Primer

<400> SEQUENCE: 603
cctgtaccaa tacatcctgc ag                                      22

<210> SEQ ID NO 604
<211> LENGTH: 19
<212> TYPE: DNA
<213> ORGANISM: Artificial Sequence
<220> FEATURE:
<223> OTHER INFORMATION: Primer

<400> SEQUENCE: 604
gagaaggtgg gatccaaac                                          19

<210> SEQ ID NO 605
<211> LENGTH: 20
<212> TYPE: DNA
<213> ORGANISM: Artificial Sequence
<220> FEATURE:
<223> OTHER INFORMATION: Primer

<400> SEQUENCE: 605
gagaaggtgg gatccaaatg                                         20

<210> SEQ ID NO 606
```

```
<211> LENGTH: 18
<212> TYPE: DNA
<213> ORGANISM: Artificial Sequence
<220> FEATURE:
<223> OTHER INFORMATION: Primer

<400> SEQUENCE: 606
aacatcttcc cagcaaaa                                                    18

<210> SEQ ID NO 607
<211> LENGTH: 19
<212> TYPE: DNA
<213> ORGANISM: Artificial Sequence
<220> FEATURE:
<223> OTHER INFORMATION: Primer

<400> SEQUENCE: 607
aacatcttcc cagcaaagc                                                   19

<210> SEQ ID NO 608
<211> LENGTH: 20
<212> TYPE: DNA
<213> ORGANISM: Artificial Sequence
<220> FEATURE:
<223> OTHER INFORMATION: Primer

<400> SEQUENCE: 608
gcaacatctt cccagcaaaa                                                  20

<210> SEQ ID NO 609
<211> LENGTH: 21
<212> TYPE: DNA
<213> ORGANISM: Artificial Sequence
<220> FEATURE:
<223> OTHER INFORMATION: Primer

<400> SEQUENCE: 609
gcaacatctt cccagcaaag c                                                21

<210> SEQ ID NO 610
<211> LENGTH: 20
<212> TYPE: DNA
<213> ORGANISM: Artificial Sequence
<220> FEATURE:
<223> OTHER INFORMATION: Primer

<400> SEQUENCE: 610
attctatttc aaaaggggcc                                                  20

<210> SEQ ID NO 611
<211> LENGTH: 21
<212> TYPE: DNA
<213> ORGANISM: Artificial Sequence
<220> FEATURE:
<223> OTHER INFORMATION: Primer

<400> SEQUENCE: 611
attctatttc aaaaggggct a                                                21

<210> SEQ ID NO 612
<211> LENGTH: 21
<212> TYPE: DNA
<213> ORGANISM: Artificial Sequence
<220> FEATURE:
<223> OTHER INFORMATION: Primer

<400> SEQUENCE: 612
```

```
aattctattt caaaaggggc c                                            21

<210> SEQ ID NO 613
<211> LENGTH: 22
<212> TYPE: DNA
<213> ORGANISM: Artificial Sequence
<220> FEATURE:
<223> OTHER INFORMATION: Primer

<400> SEQUENCE: 613
aattctattt caaaaggggc ta                                           22

<210> SEQ ID NO 614
<211> LENGTH: 19
<212> TYPE: DNA
<213> ORGANISM: Artificial Sequence
<220> FEATURE:
<223> OTHER INFORMATION: Primer

<400> SEQUENCE: 614
tgtgcagttg gtctttcta                                               19

<210> SEQ ID NO 615
<211> LENGTH: 20
<212> TYPE: DNA
<213> ORGANISM: Artificial Sequence
<220> FEATURE:
<223> OTHER INFORMATION: Primer

<400> SEQUENCE: 615
tgtgcagttg gtctttctgc                                              20

<210> SEQ ID NO 616
<211> LENGTH: 22
<212> TYPE: DNA
<213> ORGANISM: Artificial Sequence
<220> FEATURE:
<223> OTHER INFORMATION: Primer

<400> SEQUENCE: 616
ggttgattct acttggaatt tt                                           22

<210> SEQ ID NO 617
<211> LENGTH: 23
<212> TYPE: DNA
<213> ORGANISM: Artificial Sequence
<220> FEATURE:
<223> OTHER INFORMATION: Primer

<400> SEQUENCE: 617
ggttgattct acttggaatt tat                                          23

<210> SEQ ID NO 618
<211> LENGTH: 23
<212> TYPE: DNA
<213> ORGANISM: Artificial Sequence
<220> FEATURE:
<223> OTHER INFORMATION: Primer

<400> SEQUENCE: 618
cccaataaaa gtgactctca gca                                          23

<210> SEQ ID NO 619
<211> LENGTH: 24
<212> TYPE: DNA
<213> ORGANISM: Artificial Sequence
<220> FEATURE:
```

```
<223> OTHER INFORMATION: Primer

<400> SEQUENCE: 619
cccaataaaa gtgactctca gcga                                          24

<210> SEQ ID NO 620
<211> LENGTH: 24
<212> TYPE: DNA
<213> ORGANISM: Artificial Sequence
<220> FEATURE:
<223> OTHER INFORMATION: Primer

<400> SEQUENCE: 620
tcccaataaa agtgactctc agca                                          24

<210> SEQ ID NO 621
<211> LENGTH: 25
<212> TYPE: DNA
<213> ORGANISM: Artificial Sequence
<220> FEATURE:
<223> OTHER INFORMATION: Primer

<400> SEQUENCE: 621
tcccaataaa agtgactctc agcga                                         25

<210> SEQ ID NO 622
<211> LENGTH: 18
<212> TYPE: DNA
<213> ORGANISM: Artificial Sequence
<220> FEATURE:
<223> OTHER INFORMATION: Primer

<400> SEQUENCE: 622
cagatccctg gacaggca                                                 18

<210> SEQ ID NO 623
<211> LENGTH: 19
<212> TYPE: DNA
<213> ORGANISM: Artificial Sequence
<220> FEATURE:
<223> OTHER INFORMATION: Primer

<400> SEQUENCE: 623
cagatccctg gacaggcga                                                19

<210> SEQ ID NO 624
<211> LENGTH: 23
<212> TYPE: DNA
<213> ORGANISM: Artificial Sequence
<220> FEATURE:
<223> OTHER INFORMATION: Primer

<400> SEQUENCE: 624
aggacaaaat acctgtattc ctc                                           23

<210> SEQ ID NO 625
<211> LENGTH: 24
<212> TYPE: DNA
<213> ORGANISM: Artificial Sequence
<220> FEATURE:
<223> OTHER INFORMATION: Primer

<400> SEQUENCE: 625
aggacaaaat acctgtattc cttg                                          24

<210> SEQ ID NO 626
```

```
<211> LENGTH: 18
<212> TYPE: DNA
<213> ORGANISM: Artificial Sequence
<220> FEATURE:
<223> OTHER INFORMATION: Primer

<400> SEQUENCE: 626
gcccagaggc gatgtctc                                                       18

<210> SEQ ID NO 627
<211> LENGTH: 20
<212> TYPE: DNA
<213> ORGANISM: Artificial Sequence
<220> FEATURE:
<223> OTHER INFORMATION: Primer

<400> SEQUENCE: 627
gcccagaggc gatgtctttc                                                     20

<210> SEQ ID NO 628
<211> LENGTH: 18
<212> TYPE: DNA
<213> ORGANISM: Artificial Sequence
<220> FEATURE:
<223> OTHER INFORMATION: Primer

<400> SEQUENCE: 628
tcaggtacca cgtgcccc                                                       18

<210> SEQ ID NO 629
<211> LENGTH: 19
<212> TYPE: DNA
<213> ORGANISM: Artificial Sequence
<220> FEATURE:
<223> OTHER INFORMATION: Primer

<400> SEQUENCE: 629
tcaggtacca cgtgccctg                                                      19

<210> SEQ ID NO 630
<211> LENGTH: 21
<212> TYPE: DNA
<213> ORGANISM: Artificial Sequence
<220> FEATURE:
<223> OTHER INFORMATION: Primer

<400> SEQUENCE: 630
ccacagtgga gcttcagggc t                                                   21

<210> SEQ ID NO 631
<211> LENGTH: 22
<212> TYPE: DNA
<213> ORGANISM: Artificial Sequence
<220> FEATURE:
<223> OTHER INFORMATION: Primer

<400> SEQUENCE: 631
ccacagtgga gcttcagggc gt                                                  22

<210> SEQ ID NO 632
<211> LENGTH: 21
<212> TYPE: DNA
<213> ORGANISM: Artificial Sequence
<220> FEATURE:
<223> OTHER INFORMATION: Primer

<400> SEQUENCE: 632
```
ccactgaggg agaaggccac a                                                 21

<210> SEQ ID NO 633
<211> LENGTH: 23
<212> TYPE: DNA
<213> ORGANISM: Artificial Sequence
<220> FEATURE:
<223> OTHER INFORMATION: Primer

<400> SEQUENCE: 633
ccactgaggg agaaggccac gga                                               23

<210> SEQ ID NO 634
<211> LENGTH: 22
<212> TYPE: DNA
<213> ORGANISM: Artificial Sequence
<220> FEATURE:
<223> OTHER INFORMATION: Primer

<400> SEQUENCE: 634
gggacagctt cctcaaaatc tt                                                22

<210> SEQ ID NO 635
<211> LENGTH: 24
<212> TYPE: DNA
<213> ORGANISM: Artificial Sequence
<220> FEATURE:
<223> OTHER INFORMATION: Primer

<400> SEQUENCE: 635
gggacagctt cctcaaaatc tgga                                              24

<210> SEQ ID NO 636
<211> LENGTH: 18
<212> TYPE: DNA
<213> ORGANISM: Artificial Sequence
<220> FEATURE:
<223> OTHER INFORMATION: Primer

<400> SEQUENCE: 636
gggcgacgaa gtgctaca                                                     18

<210> SEQ ID NO 637
<211> LENGTH: 19
<212> TYPE: DNA
<213> ORGANISM: Artificial Sequence
<220> FEATURE:
<223> OTHER INFORMATION: Primer

<400> SEQUENCE: 637
gggcgacgaa gtgctacga                                                    19

<210> SEQ ID NO 638
<211> LENGTH: 18
<212> TYPE: DNA
<213> ORGANISM: Artificial Sequence
<220> FEATURE:
<223> OTHER INFORMATION: Primer

<400> SEQUENCE: 638
gctcccttgc ccacaggc                                                     18

<210> SEQ ID NO 639
<211> LENGTH: 19
<212> TYPE: DNA
<213> ORGANISM: Artificial Sequence
<220> FEATURE:

<223> OTHER INFORMATION: Primer

<400> SEQUENCE: 639
gctcccttgc ccacaggtc                                              19

<210> SEQ ID NO 640
<211> LENGTH: 21
<212> TYPE: DNA
<213> ORGANISM: Artificial Sequence
<220> FEATURE:
<223> OTHER INFORMATION: Primer

<400> SEQUENCE: 640
tctccagctt gggtgtgggc a                                           21

<210> SEQ ID NO 641
<211> LENGTH: 22
<212> TYPE: DNA
<213> ORGANISM: Artificial Sequence
<220> FEATURE:
<223> OTHER INFORMATION: Primer

<400> SEQUENCE: 641
tctccagctt gggtgtgggc gt                                          22

<210> SEQ ID NO 642
<211> LENGTH: 18
<212> TYPE: DNA
<213> ORGANISM: Artificial Sequence
<220> FEATURE:
<223> OTHER INFORMATION: Primer

<400> SEQUENCE: 642
cgagactggg aacagccc                                               18

<210> SEQ ID NO 643
<211> LENGTH: 20
<212> TYPE: DNA
<213> ORGANISM: Artificial Sequence
<220> FEATURE:
<223> OTHER INFORMATION: Primer

<400> SEQUENCE: 643
cgagactggg aacagccggt                                             20

<210> SEQ ID NO 644
<211> LENGTH: 20
<212> TYPE: DNA
<213> ORGANISM: Artificial Sequence
<220> FEATURE:
<223> OTHER INFORMATION: Primer

<400> SEQUENCE: 644
ttgcatattg aattgctcca                                             20

<210> SEQ ID NO 645
<211> LENGTH: 21
<212> TYPE: DNA
<213> ORGANISM: Artificial Sequence
<220> FEATURE:
<223> OTHER INFORMATION: Primer

<400> SEQUENCE: 645
ttgcatattg aattgctccg a                                           21

<210> SEQ ID NO 646

```
<211> LENGTH: 20
<212> TYPE: DNA
<213> ORGANISM: Artificial Sequence
<220> FEATURE:
<223> OTHER INFORMATION: Primer

<400> SEQUENCE: 646
gggacctcac aaacacattc                                                    20

<210> SEQ ID NO 647
<211> LENGTH: 21
<212> TYPE: DNA
<213> ORGANISM: Artificial Sequence
<220> FEATURE:
<223> OTHER INFORMATION: Primer

<400> SEQUENCE: 647
gggacctcac aaacacattt g                                                  21

<210> SEQ ID NO 648
<211> LENGTH: 18
<212> TYPE: DNA
<213> ORGANISM: Artificial Sequence
<220> FEATURE:
<223> OTHER INFORMATION: Primer

<400> SEQUENCE: 648
ttccgcttga agaagcca                                                      18

<210> SEQ ID NO 649
<211> LENGTH: 19
<212> TYPE: DNA
<213> ORGANISM: Artificial Sequence
<220> FEATURE:
<223> OTHER INFORMATION: Primer

<400> SEQUENCE: 649
ttccgcttga agaagccga                                                     19

<210> SEQ ID NO 650
<211> LENGTH: 18
<212> TYPE: DNA
<213> ORGANISM: Artificial Sequence
<220> FEATURE:
<223> OTHER INFORMATION: Primer

<400> SEQUENCE: 650
tggggcctgc atagaaga                                                      18

<210> SEQ ID NO 651
<211> LENGTH: 19
<212> TYPE: DNA
<213> ORGANISM: Artificial Sequence
<220> FEATURE:
<223> OTHER INFORMATION: Primer

<400> SEQUENCE: 651
tggggcctgc atagaaggt                                                     19

<210> SEQ ID NO 652
<211> LENGTH: 19
<212> TYPE: DNA
<213> ORGANISM: Artificial Sequence
<220> FEATURE:
<223> OTHER INFORMATION: Primer

<400> SEQUENCE: 652
```
cctcaatgtg tccctacca                                                    19

<210> SEQ ID NO 653
<211> LENGTH: 20
<212> TYPE: DNA
<213> ORGANISM: Artificial Sequence
<220> FEATURE:
<223> OTHER INFORMATION: Primer

<400> SEQUENCE: 653
cctcaatgtg tccctaccgc                                                   20

<210> SEQ ID NO 654
<211> LENGTH: 18
<212> TYPE: DNA
<213> ORGANISM: Artificial Sequence
<220> FEATURE:
<223> OTHER INFORMATION: Primer

<400> SEQUENCE: 654
ggctgtggga agcactga                                                     18

<210> SEQ ID NO 655
<211> LENGTH: 19
<212> TYPE: DNA
<213> ORGANISM: Artificial Sequence
<220> FEATURE:
<223> OTHER INFORMATION: Primer

<400> SEQUENCE: 655
ggctgtggga agcactgga                                                    19

<210> SEQ ID NO 656
<211> LENGTH: 20
<212> TYPE: DNA
<213> ORGANISM: Artificial Sequence
<220> FEATURE:
<223> OTHER INFORMATION: Primer

<400> SEQUENCE: 656
tcccctatgc ggtgcccccca                                                  20

<210> SEQ ID NO 657
<211> LENGTH: 21
<212> TYPE: DNA
<213> ORGANISM: Artificial Sequence
<220> FEATURE:
<223> OTHER INFORMATION: Primer

<400> SEQUENCE: 657
tcccctatgc ggtgcccccg c                                                 21

<210> SEQ ID NO 658
<211> LENGTH: 22
<212> TYPE: DNA
<213> ORGANISM: Artificial Sequence
<220> FEATURE:
<223> OTHER INFORMATION: Primer

<400> SEQUENCE: 658
ttcaacgtgt cctccctccc ct                                                22

<210> SEQ ID NO 659
<211> LENGTH: 24
<212> TYPE: DNA
<213> ORGANISM: Artificial Sequence
<220> FEATURE:

<223> OTHER INFORMATION: Primer

<400> SEQUENCE: 659
ttcaacgtgt cctccctccc caat    24

<210> SEQ ID NO 660
<211> LENGTH: 21
<212> TYPE: DNA
<213> ORGANISM: Artificial Sequence
<220> FEATURE:
<223> OTHER INFORMATION: Primer

<400> SEQUENCE: 660
ggtcacagcg aggtgagccc a    21

<210> SEQ ID NO 661
<211> LENGTH: 23
<212> TYPE: DNA
<213> ORGANISM: Artificial Sequence
<220> FEATURE:
<223> OTHER INFORMATION: Primer

<400> SEQUENCE: 661
ggtcacagcg aggtgagccc gga    23

<210> SEQ ID NO 662
<211> LENGTH: 21
<212> TYPE: DNA
<213> ORGANISM: Artificial Sequence
<220> FEATURE:
<223> OTHER INFORMATION: Primer

<400> SEQUENCE: 662
gccctgcctc tgggctcacc c    21

<210> SEQ ID NO 663
<211> LENGTH: 22
<212> TYPE: DNA
<213> ORGANISM: Artificial Sequence
<220> FEATURE:
<223> OTHER INFORMATION: Primer

<400> SEQUENCE: 663
gccctgcctc tgggctcacc tc    22

<210> SEQ ID NO 664
<211> LENGTH: 18
<212> TYPE: DNA
<213> ORGANISM: Artificial Sequence
<220> FEATURE:
<223> OTHER INFORMATION: Primer

<400> SEQUENCE: 664
ccttcccagc aggacgaa    18

<210> SEQ ID NO 665
<211> LENGTH: 19
<212> TYPE: DNA
<213> ORGANISM: Artificial Sequence
<220> FEATURE:
<223> OTHER INFORMATION: Primer

<400> SEQUENCE: 665
ccttcccagc aggacgagt    19

<210> SEQ ID NO 666

```
<211> LENGTH: 21
<212> TYPE: DNA
<213> ORGANISM: Artificial Sequence
<220> FEATURE:
<223> OTHER INFORMATION: Primer

<400> SEQUENCE: 666
acatgacact gcccgtcatt a                                              21

<210> SEQ ID NO 667
<211> LENGTH: 24
<212> TYPE: DNA
<213> ORGANISM: Artificial Sequence
<220> FEATURE:
<223> OTHER INFORMATION: Primer

<400> SEQUENCE: 667
acatgacact gcccgtcatt gggc                                           24

<210> SEQ ID NO 668
<211> LENGTH: 18
<212> TYPE: DNA
<213> ORGANISM: Artificial Sequence
<220> FEATURE:
<223> OTHER INFORMATION: Primer

<400> SEQUENCE: 668
ggttactggt gagctttc                                                  18

<210> SEQ ID NO 669
<211> LENGTH: 19
<212> TYPE: DNA
<213> ORGANISM: Artificial Sequence
<220> FEATURE:
<223> OTHER INFORMATION: Primer

<400> SEQUENCE: 669
ggttactggt gagcttttg                                                 19

<210> SEQ ID NO 670
<211> LENGTH: 20
<212> TYPE: DNA
<213> ORGANISM: Artificial Sequence
<220> FEATURE:
<223> OTHER INFORMATION: Primer

<400> SEQUENCE: 670
ggtcttttcc aaactctttt                                                20

<210> SEQ ID NO 671
<211> LENGTH: 22
<212> TYPE: DNA
<213> ORGANISM: Artificial Sequence
<220> FEATURE:
<223> OTHER INFORMATION: Primer

<400> SEQUENCE: 671
ggtcttttcc aaactctttg gt                                             22

<210> SEQ ID NO 672
<211> LENGTH: 22
<212> TYPE: DNA
<213> ORGANISM: Artificial Sequence
<220> FEATURE:
<223> OTHER INFORMATION: Primer

<400> SEQUENCE: 672
```

-continued

```
gaaaggaaag agacttacca aa                                           22

<210> SEQ ID NO 673
<211> LENGTH: 23
<212> TYPE: DNA
<213> ORGANISM: Artificial Sequence
<220> FEATURE:
<223> OTHER INFORMATION: Primer

<400> SEQUENCE: 673
gaaaggaaag agacttacca agc                                          23

<210> SEQ ID NO 674
<211> LENGTH: 18
<212> TYPE: DNA
<213> ORGANISM: Artificial Sequence
<220> FEATURE:
<223> OTHER INFORMATION: Primer

<400> SEQUENCE: 674
ggtaagtcca gcagtcgc                                                18

<210> SEQ ID NO 675
<211> LENGTH: 19
<212> TYPE: DNA
<213> ORGANISM: Artificial Sequence
<220> FEATURE:
<223> OTHER INFORMATION: Primer

<400> SEQUENCE: 675
ggtaagtcca gcagtcggt                                               19

<210> SEQ ID NO 676
<211> LENGTH: 24
<212> TYPE: DNA
<213> ORGANISM: Artificial Sequence
<220> FEATURE:
<223> OTHER INFORMATION: Primer

<400> SEQUENCE: 676
gaacaaagac ttcaaagaca cttt                                         24

<210> SEQ ID NO 677
<211> LENGTH: 25
<212> TYPE: DNA
<213> ORGANISM: Artificial Sequence
<220> FEATURE:
<223> OTHER INFORMATION: Primer

<400> SEQUENCE: 677
gaacaaagac ttcaaagaca cttgc                                        25

<210> SEQ ID NO 678
<211> LENGTH: 18
<212> TYPE: DNA
<213> ORGANISM: Artificial Sequence
<220> FEATURE:
<223> OTHER INFORMATION: Primer

<400> SEQUENCE: 678
gcgtgatgat gaaatcga                                                18

<210> SEQ ID NO 679
<211> LENGTH: 19
<212> TYPE: DNA
<213> ORGANISM: Artificial Sequence
<220> FEATURE:
```

```
<223> OTHER INFORMATION: Primer

<400> SEQUENCE: 679
gcgtgatgat gaaatcggc                                                    19

<210> SEQ ID NO 680
<211> LENGTH: 18
<212> TYPE: DNA
<213> ORGANISM: Artificial Sequence
<220> FEATURE:
<223> OTHER INFORMATION: Primer

<400> SEQUENCE: 680
gaaggtgtct gcgggagc                                                     18

<210> SEQ ID NO 681
<211> LENGTH: 19
<212> TYPE: DNA
<213> ORGANISM: Artificial Sequence
<220> FEATURE:
<223> OTHER INFORMATION: Primer

<400> SEQUENCE: 681
gaaggtgtct gcgggagtc                                                    19

<210> SEQ ID NO 682
<211> LENGTH: 19
<212> TYPE: DNA
<213> ORGANISM: Artificial Sequence
<220> FEATURE:
<223> OTHER INFORMATION: Primer

<400> SEQUENCE: 682
gagtctggac acgtgggga                                                    19

<210> SEQ ID NO 683
<211> LENGTH: 20
<212> TYPE: DNA
<213> ORGANISM: Artificial Sequence
<220> FEATURE:
<223> OTHER INFORMATION: Primer

<400> SEQUENCE: 683
gagtctggac acgtggggga                                                   20

<210> SEQ ID NO 684
<211> LENGTH: 18
<212> TYPE: DNA
<213> ORGANISM: Artificial Sequence
<220> FEATURE:
<223> OTHER INFORMATION: Primer

<400> SEQUENCE: 684
tacacggctg actccccc                                                     18

<210> SEQ ID NO 685
<211> LENGTH: 19
<212> TYPE: DNA
<213> ORGANISM: Artificial Sequence
<220> FEATURE:
<223> OTHER INFORMATION: Primer

<400> SEQUENCE: 685
tacacggctg actccccac                                                    19

<210> SEQ ID NO 686
```

```
<211> LENGTH: 20
<212> TYPE: DNA
<213> ORGANISM: Artificial Sequence
<220> FEATURE:
<223> OTHER INFORMATION: Primer

<400> SEQUENCE: 686
tggcaggttg gcacggtagt                                              20

<210> SEQ ID NO 687
<211> LENGTH: 21
<212> TYPE: DNA
<213> ORGANISM: Artificial Sequence
<220> FEATURE:
<223> OTHER INFORMATION: Primer

<400> SEQUENCE: 687
tggcaggttg gcacggtagg t                                            21

<210> SEQ ID NO 688
<211> LENGTH: 18
<212> TYPE: DNA
<213> ORGANISM: Artificial Sequence
<220> FEATURE:
<223> OTHER INFORMATION: Primer

<400> SEQUENCE: 688
tccaaaactc gacagaac                                                18

<210> SEQ ID NO 689
<211> LENGTH: 19
<212> TYPE: DNA
<213> ORGANISM: Artificial Sequence
<220> FEATURE:
<223> OTHER INFORMATION: Primer

<400> SEQUENCE: 689
tccaaaactc gacagaatg                                               19

<210> SEQ ID NO 690
<211> LENGTH: 18
<212> TYPE: DNA
<213> ORGANISM: Artificial Sequence
<220> FEATURE:
<223> OTHER INFORMATION: Primer

<400> SEQUENCE: 690
cggtgccaat gtggcgga                                                18

<210> SEQ ID NO 691
<211> LENGTH: 19
<212> TYPE: DNA
<213> ORGANISM: Artificial Sequence
<220> FEATURE:
<223> OTHER INFORMATION: Primer

<400> SEQUENCE: 691
cggtgccaat gtggcgggc                                               19

<210> SEQ ID NO 692
<211> LENGTH: 18
<212> TYPE: DNA
<213> ORGANISM: Artificial Sequence
<220> FEATURE:
<223> OTHER INFORMATION: Primer

<400> SEQUENCE: 692
```

```
cgctctaccc gggcccca                                          18

<210> SEQ ID NO 693
<211> LENGTH: 19
<212> TYPE: DNA
<213> ORGANISM: Artificial Sequence
<220> FEATURE:
<223> OTHER INFORMATION: Primer

<400> SEQUENCE: 693
cgctctaccc gggcccgc                                          19

<210> SEQ ID NO 694
<211> LENGTH: 18
<212> TYPE: DNA
<213> ORGANISM: Artificial Sequence
<220> FEATURE:
<223> OTHER INFORMATION: Primer

<400> SEQUENCE: 694
gaggctgaac cccgtccc                                          18

<210> SEQ ID NO 695
<211> LENGTH: 19
<212> TYPE: DNA
<213> ORGANISM: Artificial Sequence
<220> FEATURE:
<223> OTHER INFORMATION: Primer

<400> SEQUENCE: 695
gaggctgaac cccgtcctc                                         19

<210> SEQ ID NO 696
<211> LENGTH: 19
<212> TYPE: DNA
<213> ORGANISM: Artificial Sequence
<220> FEATURE:
<223> OTHER INFORMATION: Primer

<400> SEQUENCE: 696
ctcccattca cgaggccac                                         19

<210> SEQ ID NO 697
<211> LENGTH: 20
<212> TYPE: DNA
<213> ORGANISM: Artificial Sequence
<220> FEATURE:
<223> OTHER INFORMATION: Primer

<400> SEQUENCE: 697
ctcccattca cgaggccagc                                        20

<210> SEQ ID NO 698
<211> LENGTH: 18
<212> TYPE: DNA
<213> ORGANISM: Artificial Sequence
<220> FEATURE:
<223> OTHER INFORMATION: Primer

<400> SEQUENCE: 698
cccaaactgc caatcacc                                          18

<210> SEQ ID NO 699
<211> LENGTH: 19
<212> TYPE: DNA
<213> ORGANISM: Artificial Sequence
<220> FEATURE:
```

```
<223> OTHER INFORMATION: Primer

<400> SEQUENCE: 699
cccaaactgc caatcactg                                                    19

<210> SEQ ID NO 700
<211> LENGTH: 18
<212> TYPE: DNA
<213> ORGANISM: Artificial Sequence
<220> FEATURE:
<223> OTHER INFORMATION: Primer

<400> SEQUENCE: 700
gagcaagata gaggcgtt                                                     18

<210> SEQ ID NO 701
<211> LENGTH: 19
<212> TYPE: DNA
<213> ORGANISM: Artificial Sequence
<220> FEATURE:
<223> OTHER INFORMATION: Primer

<400> SEQUENCE: 701
gagcaagata gaggcgtac                                                    19

<210> SEQ ID NO 702
<211> LENGTH: 21
<212> TYPE: DNA
<213> ORGANISM: Artificial Sequence
<220> FEATURE:
<223> OTHER INFORMATION: Primer

<400> SEQUENCE: 702
taccaacaga accaccttcc c                                                 21

<210> SEQ ID NO 703
<211> LENGTH: 22
<212> TYPE: DNA
<213> ORGANISM: Artificial Sequence
<220> FEATURE:
<223> OTHER INFORMATION: Primer

<400> SEQUENCE: 703
taccaacaga accaccttcc tc                                                22

<210> SEQ ID NO 704
<211> LENGTH: 20
<212> TYPE: DNA
<213> ORGANISM: Artificial Sequence
<220> FEATURE:
<223> OTHER INFORMATION: Primer

<400> SEQUENCE: 704
cccaggacga acccggacca                                                   20

<210> SEQ ID NO 705
<211> LENGTH: 22
<212> TYPE: DNA
<213> ORGANISM: Artificial Sequence
<220> FEATURE:
<223> OTHER INFORMATION: Primer

<400> SEQUENCE: 705
cccaggacga acccggaccg gc                                                22

<210> SEQ ID NO 706
```

```
<211> LENGTH: 21
<212> TYPE: DNA
<213> ORGANISM: Artificial Sequence
<220> FEATURE:
<223> OTHER INFORMATION: Primer

<400> SEQUENCE: 706
aacctcacct ctgcgcctgg t                                              21

<210> SEQ ID NO 707
<211> LENGTH: 22
<212> TYPE: DNA
<213> ORGANISM: Artificial Sequence
<220> FEATURE:
<223> OTHER INFORMATION: Primer

<400> SEQUENCE: 707
aacctcacct ctgcgcctgg ga                                             22

<210> SEQ ID NO 708
<211> LENGTH: 24
<212> TYPE: DNA
<213> ORGANISM: Artificial Sequence
<220> FEATURE:
<223> OTHER INFORMATION: Primer

<400> SEQUENCE: 708
tggtgaaata aaaagattac aaac                                           24

<210> SEQ ID NO 709
<211> LENGTH: 25
<212> TYPE: DNA
<213> ORGANISM: Artificial Sequence
<220> FEATURE:
<223> OTHER INFORMATION: Primer

<400> SEQUENCE: 709
tggtgaaata aaaagattac aaatg                                          25

<210> SEQ ID NO 710
<211> LENGTH: 18
<212> TYPE: DNA
<213> ORGANISM: Artificial Sequence
<220> FEATURE:
<223> OTHER INFORMATION: Primer

<400> SEQUENCE: 710
atgcaagccg tcgacaac                                                  18

<210> SEQ ID NO 711
<211> LENGTH: 19
<212> TYPE: DNA
<213> ORGANISM: Artificial Sequence
<220> FEATURE:
<223> OTHER INFORMATION: Primer

<400> SEQUENCE: 711
atgcaagccg tcgacaatc                                                 19

<210> SEQ ID NO 712
<211> LENGTH: 20
<212> TYPE: DNA
<213> ORGANISM: Artificial Sequence
<220> FEATURE:
<223> OTHER INFORMATION: Primer

<400> SEQUENCE: 712
```

```
tgtatggaga cattgatgca                                          20

<210> SEQ ID NO 713
<211> LENGTH: 21
<212> TYPE: DNA
<213> ORGANISM: Artificial Sequence
<220> FEATURE:
<223> OTHER INFORMATION: Primer

<400> SEQUENCE: 713
tgtatggaga cattgatgcg t                                        21

<210> SEQ ID NO 714
<211> LENGTH: 21
<212> TYPE: DNA
<213> ORGANISM: Artificial Sequence
<220> FEATURE:
<223> OTHER INFORMATION: Primer

<400> SEQUENCE: 714
aggcccagct cacggatggt a                                        21

<210> SEQ ID NO 715
<211> LENGTH: 22
<212> TYPE: DNA
<213> ORGANISM: Artificial Sequence
<220> FEATURE:
<223> OTHER INFORMATION: Primer

<400> SEQUENCE: 715
aggcccagct cacggatggt gc                                       22

<210> SEQ ID NO 716
<211> LENGTH: 18
<212> TYPE: DNA
<213> ORGANISM: Artificial Sequence
<220> FEATURE:
<223> OTHER INFORMATION: Primer

<400> SEQUENCE: 716
gtctccataa atgtggcc                                            18

<210> SEQ ID NO 717
<211> LENGTH: 19
<212> TYPE: DNA
<213> ORGANISM: Artificial Sequence
<220> FEATURE:
<223> OTHER INFORMATION: Primer

<400> SEQUENCE: 717
gtctccataa atgtggctg                                           19

<210> SEQ ID NO 718
<211> LENGTH: 18
<212> TYPE: DNA
<213> ORGANISM: Artificial Sequence
<220> FEATURE:
<223> OTHER INFORMATION: Primer

<400> SEQUENCE: 718
aagccaggac ccatcttt                                            18

<210> SEQ ID NO 719
<211> LENGTH: 19
<212> TYPE: DNA
<213> ORGANISM: Artificial Sequence
<220> FEATURE:
```

```
-continued

<223> OTHER INFORMATION: Primer

<400> SEQUENCE: 719
aagccaggac ccatcttgc                                                  19

<210> SEQ ID NO 720
<211> LENGTH: 20
<212> TYPE: DNA
<213> ORGANISM: Artificial Sequence
<220> FEATURE:
<223> OTHER INFORMATION: Primer

<400> SEQUENCE: 720
aatggcatca tggatctgac                                                 20

<210> SEQ ID NO 721
<211> LENGTH: 21
<212> TYPE: DNA
<213> ORGANISM: Artificial Sequence
<220> FEATURE:
<223> OTHER INFORMATION: Primer

<400> SEQUENCE: 721
aatggcatca tggatctgat g                                               21

<210> SEQ ID NO 722
<211> LENGTH: 18
<212> TYPE: DNA
<213> ORGANISM: Artificial Sequence
<220> FEATURE:
<223> OTHER INFORMATION: Primer

<400> SEQUENCE: 722
cgtccacaca cttcgcaa                                                   18

<210> SEQ ID NO 723
<211> LENGTH: 21
<212> TYPE: DNA
<213> ORGANISM: Artificial Sequence
<220> FEATURE:
<223> OTHER INFORMATION: Primer

<400> SEQUENCE: 723
cgtccacaca cttcgcaggg t                                               21

<210> SEQ ID NO 724
<211> LENGTH: 21
<212> TYPE: DNA
<213> ORGANISM: Artificial Sequence
<220> FEATURE:
<223> OTHER INFORMATION: Primer

<400> SEQUENCE: 724
ccctgcttct gagttccatg a                                               21

<210> SEQ ID NO 725
<211> LENGTH: 22
<212> TYPE: DNA
<213> ORGANISM: Artificial Sequence
<220> FEATURE:
<223> OTHER INFORMATION: Primer

<400> SEQUENCE: 725
ccctgcttct gagttccatg gt                                              22

<210> SEQ ID NO 726
```

```
<211> LENGTH: 18
<212> TYPE: DNA
<213> ORGANISM: Artificial Sequence
<220> FEATURE:
<223> OTHER INFORMATION: Primer

<400> SEQUENCE: 726
cagccctcac tccttcca                                                     18

<210> SEQ ID NO 727
<211> LENGTH: 19
<212> TYPE: DNA
<213> ORGANISM: Artificial Sequence
<220> FEATURE:
<223> OTHER INFORMATION: Primer

<400> SEQUENCE: 727
cagccctcac tccttccgt                                                    19

<210> SEQ ID NO 728
<211> LENGTH: 19
<212> TYPE: DNA
<213> ORGANISM: Artificial Sequence
<220> FEATURE:
<223> OTHER INFORMATION: Primer

<400> SEQUENCE: 728
ggacctaatt tggcacgca                                                    19

<210> SEQ ID NO 729
<211> LENGTH: 20
<212> TYPE: DNA
<213> ORGANISM: Artificial Sequence
<220> FEATURE:
<223> OTHER INFORMATION: Primer

<400> SEQUENCE: 729
ggacctaatt tggcacgcgt                                                   20

<210> SEQ ID NO 730
<211> LENGTH: 18
<212> TYPE: DNA
<213> ORGANISM: Artificial Sequence
<220> FEATURE:
<223> OTHER INFORMATION: Primer

<400> SEQUENCE: 730
ccctctgccc taccccct                                                     18

<210> SEQ ID NO 731
<211> LENGTH: 20
<212> TYPE: DNA
<213> ORGANISM: Artificial Sequence
<220> FEATURE:
<223> OTHER INFORMATION: Primer

<400> SEQUENCE: 731
ccctctgccc taccccggc                                                    20

<210> SEQ ID NO 732
<211> LENGTH: 18
<212> TYPE: DNA
<213> ORGANISM: Artificial Sequence
<220> FEATURE:
<223> OTHER INFORMATION: Primer

<400> SEQUENCE: 732
```
gggggtcagg tatgaact                                                                 18

<210> SEQ ID NO 733
<211> LENGTH: 19
<212> TYPE: DNA
<213> ORGANISM: Artificial Sequence
<220> FEATURE:
<223> OTHER INFORMATION: Primer

<400> SEQUENCE: 733
gggggtcagg tatgaacgt                                                                19

<210> SEQ ID NO 734
<211> LENGTH: 21
<212> TYPE: DNA
<213> ORGANISM: Artificial Sequence
<220> FEATURE:
<223> OTHER INFORMATION: Primer

<400> SEQUENCE: 734
cgtactcctc gatgacaatc c                                                             21

<210> SEQ ID NO 735
<211> LENGTH: 23
<212> TYPE: DNA
<213> ORGANISM: Artificial Sequence
<220> FEATURE:
<223> OTHER INFORMATION: Primer

<400> SEQUENCE: 735
cgtactcctc gatgacaatc ttg                                                           23

<210> SEQ ID NO 736
<211> LENGTH: 18
<212> TYPE: DNA
<213> ORGANISM: Artificial Sequence
<220> FEATURE:
<223> OTHER INFORMATION: Primer

<400> SEQUENCE: 736
ttgatactga cgctccat                                                                 18

<210> SEQ ID NO 737
<211> LENGTH: 19
<212> TYPE: DNA
<213> ORGANISM: Artificial Sequence
<220> FEATURE:
<223> OTHER INFORMATION: Primer

<400> SEQUENCE: 737
ttgatactga cgctccaga                                                                19

<210> SEQ ID NO 738
<211> LENGTH: 18
<212> TYPE: DNA
<213> ORGANISM: Artificial Sequence
<220> FEATURE:
<223> OTHER INFORMATION: Primer

<400> SEQUENCE: 738
gttcctgctc ctgctccc                                                                 18

<210> SEQ ID NO 739
<211> LENGTH: 19
<212> TYPE: DNA
<213> ORGANISM: Artificial Sequence
<220> FEATURE:

```
<223> OTHER INFORMATION: Primer

<400> SEQUENCE: 739
gttcctgctc ctgctcctg                                              19

<210> SEQ ID NO 740
<211> LENGTH: 21
<212> TYPE: DNA
<213> ORGANISM: Artificial Sequence
<220> FEATURE:
<223> OTHER INFORMATION: Primer

<400> SEQUENCE: 740
cacttttcaa gaagcagtcc a                                           21

<210> SEQ ID NO 741
<211> LENGTH: 25
<212> TYPE: DNA
<213> ORGANISM: Artificial Sequence
<220> FEATURE:
<223> OTHER INFORMATION: Primer

<400> SEQUENCE: 741
cacttttcaa gaagcagtcc ggggt                                       25

<210> SEQ ID NO 742
<211> LENGTH: 19
<212> TYPE: DNA
<213> ORGANISM: Artificial Sequence
<220> FEATURE:
<223> OTHER INFORMATION: Primer

<400> SEQUENCE: 742
ttgttactat ccatgccaa                                              19

<210> SEQ ID NO 743
<211> LENGTH: 20
<212> TYPE: DNA
<213> ORGANISM: Artificial Sequence
<220> FEATURE:
<223> OTHER INFORMATION: Primer

<400> SEQUENCE: 743
ttgttactat ccatgccagc                                             20

<210> SEQ ID NO 744
<211> LENGTH: 18
<212> TYPE: DNA
<213> ORGANISM: Artificial Sequence
<220> FEATURE:
<223> OTHER INFORMATION: Primer

<400> SEQUENCE: 744
ccgcttcggc cttgacca                                               18

<210> SEQ ID NO 745
<211> LENGTH: 19
<212> TYPE: DNA
<213> ORGANISM: Artificial Sequence
<220> FEATURE:
<223> OTHER INFORMATION: Primer

<400> SEQUENCE: 745
ccgcttcggc cttgaccgc                                              19

<210> SEQ ID NO 746
```

```
<211> LENGTH: 18
<212> TYPE: DNA
<213> ORGANISM: Artificial Sequence
<220> FEATURE:
<223> OTHER INFORMATION: Primer

<400> SEQUENCE: 746
caggaacagc aagaacca                                                    18

<210> SEQ ID NO 747
<211> LENGTH: 20
<212> TYPE: DNA
<213> ORGANISM: Artificial Sequence
<220> FEATURE:
<223> OTHER INFORMATION: Primer

<400> SEQUENCE: 747
caggaacagc aagaaccgga                                                  20

<210> SEQ ID NO 748
<211> LENGTH: 18
<212> TYPE: DNA
<213> ORGANISM: Artificial Sequence
<220> FEATURE:
<223> OTHER INFORMATION: Primer

<400> SEQUENCE: 748
tgtgtggccc tggcacta                                                    18

<210> SEQ ID NO 749
<211> LENGTH: 19
<212> TYPE: DNA
<213> ORGANISM: Artificial Sequence
<220> FEATURE:
<223> OTHER INFORMATION: Primer

<400> SEQUENCE: 749
tgtgtggccc tggcactga                                                   19

<210> SEQ ID NO 750
<211> LENGTH: 21
<212> TYPE: DNA
<213> ORGANISM: Artificial Sequence
<220> FEATURE:
<223> OTHER INFORMATION: Primer

<400> SEQUENCE: 750
ggcatgaaac cctacacctc c                                                21

<210> SEQ ID NO 751
<211> LENGTH: 24
<212> TYPE: DNA
<213> ORGANISM: Artificial Sequence
<220> FEATURE:
<223> OTHER INFORMATION: Primer

<400> SEQUENCE: 751
ggcatgaaac cctacacctc tttc                                             24

<210> SEQ ID NO 752
<211> LENGTH: 23
<212> TYPE: DNA
<213> ORGANISM: Artificial Sequence
<220> FEATURE:
<223> OTHER INFORMATION: Primer

<400> SEQUENCE: 752
```
ttttgtttga tgacagaaaa ata                                           23

<210> SEQ ID NO 753
<211> LENGTH: 24
<212> TYPE: DNA
<213> ORGANISM: Artificial Sequence
<220> FEATURE:
<223> OTHER INFORMATION: Primer

<400> SEQUENCE: 753
ttttgtttga tgacagaaaa atga                                          24

<210> SEQ ID NO 754
<211> LENGTH: 18
<212> TYPE: DNA
<213> ORGANISM: Artificial Sequence
<220> FEATURE:
<223> OTHER INFORMATION: Primer

<400> SEQUENCE: 754
tgaaaaccca cttctccc                                                 18

<210> SEQ ID NO 755
<211> LENGTH: 19
<212> TYPE: DNA
<213> ORGANISM: Artificial Sequence
<220> FEATURE:
<223> OTHER INFORMATION: Primer

<400> SEQUENCE: 755
tgaaaaccca cttctccac                                                19

<210> SEQ ID NO 756
<211> LENGTH: 25
<212> TYPE: DNA
<213> ORGANISM: Artificial Sequence
<220> FEATURE:
<223> OTHER INFORMATION: Primer

<400> SEQUENCE: 756
gggattttaa aatatgggta taagc                                         25

<210> SEQ ID NO 757
<211> LENGTH: 26
<212> TYPE: DNA
<213> ORGANISM: Artificial Sequence
<220> FEATURE:
<223> OTHER INFORMATION: Primer

<400> SEQUENCE: 757
gggattttaa aatatgggta taagtg                                        26

<210> SEQ ID NO 758
<211> LENGTH: 23
<212> TYPE: DNA
<213> ORGANISM: Artificial Sequence
<220> FEATURE:
<223> OTHER INFORMATION: Primer

<400> SEQUENCE: 758
caaaagcaaa gatgaaattc caa                                           23

<210> SEQ ID NO 759
<211> LENGTH: 24
<212> TYPE: DNA
<213> ORGANISM: Artificial Sequence
<220> FEATURE:

<223> OTHER INFORMATION: Primer

<400> SEQUENCE: 759
caaaagcaaa gatgaaattc cagc                                            24

<210> SEQ ID NO 760
<211> LENGTH: 24
<212> TYPE: DNA
<213> ORGANISM: Artificial Sequence
<220> FEATURE:
<223> OTHER INFORMATION: Primer

<400> SEQUENCE: 760
tgggtttccg attttctcat ttcg                                            24

<210> SEQ ID NO 761
<211> LENGTH: 24
<212> TYPE: DNA
<213> ORGANISM: Artificial Sequence
<220> FEATURE:
<223> OTHER INFORMATION: Primer

<400> SEQUENCE: 761
tgggtttccg attttctcat ttgc                                            24

<210> SEQ ID NO 762
<211> LENGTH: 18
<212> TYPE: DNA
<213> ORGANISM: Artificial Sequence
<220> FEATURE:
<223> OTHER INFORMATION: Primer

<400> SEQUENCE: 762
ccccctctgc tcccaaac                                                   18

<210> SEQ ID NO 763
<211> LENGTH: 20
<212> TYPE: DNA
<213> ORGANISM: Artificial Sequence
<220> FEATURE:
<223> OTHER INFORMATION: Primer

<400> SEQUENCE: 763
ccccctctgc tcccaaattg                                                 20

<210> SEQ ID NO 764
<211> LENGTH: 21
<212> TYPE: DNA
<213> ORGANISM: Artificial Sequence
<220> FEATURE:
<223> OTHER INFORMATION: Primer

<400> SEQUENCE: 764
ccgacgtgac ttcctcgacc c                                               21

<210> SEQ ID NO 765
<211> LENGTH: 22
<212> TYPE: DNA
<213> ORGANISM: Artificial Sequence
<220> FEATURE:
<223> OTHER INFORMATION: Primer

<400> SEQUENCE: 765
ccgacgtgac ttcctcgacc gt                                              22

<210> SEQ ID NO 766

```
<211> LENGTH: 22
<212> TYPE: DNA
<213> ORGANISM: Artificial Sequence
<220> FEATURE:
<223> OTHER INFORMATION: Primer

<400> SEQUENCE: 766
tgaggagaat ttacctttcc cc                                               22

<210> SEQ ID NO 767
<211> LENGTH: 23
<212> TYPE: DNA
<213> ORGANISM: Artificial Sequence
<220> FEATURE:
<223> OTHER INFORMATION: Primer

<400> SEQUENCE: 767
tgaggagaat ttacctttcc cgc                                              23

<210> SEQ ID NO 768
<211> LENGTH: 21
<212> TYPE: DNA
<213> ORGANISM: Artificial Sequence
<220> FEATURE:
<223> OTHER INFORMATION: Primer

<400> SEQUENCE: 768
tgaaactctg gctagacagc a                                                21

<210> SEQ ID NO 769
<211> LENGTH: 22
<212> TYPE: DNA
<213> ORGANISM: Artificial Sequence
<220> FEATURE:
<223> OTHER INFORMATION: Primer

<400> SEQUENCE: 769
tgaaactctg gctagacagc gt                                               22

<210> SEQ ID NO 770
<211> LENGTH: 20
<212> TYPE: DNA
<213> ORGANISM: Artificial Sequence
<220> FEATURE:
<223> OTHER INFORMATION: Primer

<400> SEQUENCE: 770
ggttagcgac caattgtcat                                                  20

<210> SEQ ID NO 771
<211> LENGTH: 21
<212> TYPE: DNA
<213> ORGANISM: Artificial Sequence
<220> FEATURE:
<223> OTHER INFORMATION: Primer

<400> SEQUENCE: 771
ggttagcgac caattgtcag a                                                21

<210> SEQ ID NO 772
<211> LENGTH: 23
<212> TYPE: DNA
<213> ORGANISM: Artificial Sequence
<220> FEATURE:
<223> OTHER INFORMATION: Primer

<400> SEQUENCE: 772
```
gaaatgcaat tatgagttat gtc                                                    23

<210> SEQ ID NO 773
<211> LENGTH: 24
<212> TYPE: DNA
<213> ORGANISM: Artificial Sequence
<220> FEATURE:
<223> OTHER INFORMATION: Primer

<400> SEQUENCE: 773
gaaatgcaat tatgagttat gtgt                                                   24

<210> SEQ ID NO 774
<211> LENGTH: 22
<212> TYPE: DNA
<213> ORGANISM: Artificial Sequence
<220> FEATURE:
<223> OTHER INFORMATION: Primer

<400> SEQUENCE: 774
ttggtgaaac catggtagaa gc                                                     22

<210> SEQ ID NO 775
<211> LENGTH: 24
<212> TYPE: DNA
<213> ORGANISM: Artificial Sequence
<220> FEATURE:
<223> OTHER INFORMATION: Primer

<400> SEQUENCE: 775
ttggtgaaac catggtagaa gttg                                                   24

<210> SEQ ID NO 776
<211> LENGTH: 18
<212> TYPE: DNA
<213> ORGANISM: Artificial Sequence
<220> FEATURE:
<223> OTHER INFORMATION: Primer

<400> SEQUENCE: 776
gcgcggcgga acaggata                                                          18

<210> SEQ ID NO 777
<211> LENGTH: 19
<212> TYPE: DNA
<213> ORGANISM: Artificial Sequence
<220> FEATURE:
<223> OTHER INFORMATION: Primer

<400> SEQUENCE: 777
gcgcggcgga acaggatgt                                                         19

<210> SEQ ID NO 778
<211> LENGTH: 18
<212> TYPE: DNA
<213> ORGANISM: Artificial Sequence
<220> FEATURE:
<223> OTHER INFORMATION: Primer

<400> SEQUENCE: 778
tacctgtaat cccagcta                                                          18

<210> SEQ ID NO 779
<211> LENGTH: 19
<212> TYPE: DNA
<213> ORGANISM: Artificial Sequence
<220> FEATURE:

```
<223> OTHER INFORMATION: Primer

<400> SEQUENCE: 779
tacctgtaat cccagctgc                                                    19

<210> SEQ ID NO 780
<211> LENGTH: 19
<212> TYPE: DNA
<213> ORGANISM: Artificial Sequence
<220> FEATURE:
<223> OTHER INFORMATION: Primer

<400> SEQUENCE: 780
cggtgaggac gaggccgct                                                    19

<210> SEQ ID NO 781
<211> LENGTH: 20
<212> TYPE: DNA
<213> ORGANISM: Artificial Sequence
<220> FEATURE:
<223> OTHER INFORMATION: Primer

<400> SEQUENCE: 781
cggtgaggac gaggccgcag                                                   20

<210> SEQ ID NO 782
<211> LENGTH: 20
<212> TYPE: DNA
<213> ORGANISM: Artificial Sequence
<220> FEATURE:
<223> OTHER INFORMATION: Primer

<400> SEQUENCE: 782
cagcacgccg cgctcttcgt                                                   20

<210> SEQ ID NO 783
<211> LENGTH: 21
<212> TYPE: DNA
<213> ORGANISM: Artificial Sequence
<220> FEATURE:
<223> OTHER INFORMATION: Primer

<400> SEQUENCE: 783
cagcacgccg cgctcttcga g                                                 21

<210> SEQ ID NO 784
<211> LENGTH: 18
<212> TYPE: DNA
<213> ORGANISM: Artificial Sequence
<220> FEATURE:
<223> OTHER INFORMATION: Primer

<400> SEQUENCE: 784
cgacagagac ggcagcct                                                     18

<210> SEQ ID NO 785
<211> LENGTH: 19
<212> TYPE: DNA
<213> ORGANISM: Artificial Sequence
<220> FEATURE:
<223> OTHER INFORMATION: Primer

<400> SEQUENCE: 785
cgacagagac ggcagccag                                                    19

<210> SEQ ID NO 786
```

```
<211> LENGTH: 18
<212> TYPE: DNA
<213> ORGANISM: Artificial Sequence
<220> FEATURE:
<223> OTHER INFORMATION: Primer

<400> SEQUENCE: 786
cgcccggcgg tcgcctca                                               18

<210> SEQ ID NO 787
<211> LENGTH: 19
<212> TYPE: DNA
<213> ORGANISM: Artificial Sequence
<220> FEATURE:
<223> OTHER INFORMATION: Primer

<400> SEQUENCE: 787
cgcccggcgg tcgcctcgc                                              19

<210> SEQ ID NO 788
<211> LENGTH: 18
<212> TYPE: DNA
<213> ORGANISM: Artificial Sequence
<220> FEATURE:
<223> OTHER INFORMATION: Primer

<400> SEQUENCE: 788
caggcccagc gccagcgc                                               18

<210> SEQ ID NO 789
<211> LENGTH: 19
<212> TYPE: DNA
<213> ORGANISM: Artificial Sequence
<220> FEATURE:
<223> OTHER INFORMATION: Primer

<400> SEQUENCE: 789
caggcccagc gccagcgtg                                              19

<210> SEQ ID NO 790
<211> LENGTH: 18
<212> TYPE: DNA
<213> ORGANISM: Artificial Sequence
<220> FEATURE:
<223> OTHER INFORMATION: Primer

<400> SEQUENCE: 790
aggaccccgg gtattgct                                               18

<210> SEQ ID NO 791
<211> LENGTH: 19
<212> TYPE: DNA
<213> ORGANISM: Artificial Sequence
<220> FEATURE:
<223> OTHER INFORMATION: Primer

<400> SEQUENCE: 791
aggaccccgg gtattgcac                                              19

<210> SEQ ID NO 792
<211> LENGTH: 22
<212> TYPE: DNA
<213> ORGANISM: Artificial Sequence
<220> FEATURE:
<223> OTHER INFORMATION: Primer

<400> SEQUENCE: 792
```

-continued ctgtccttcc tgctgaacac ga                                          22

<210> SEQ ID NO 793
<211> LENGTH: 23
<212> TYPE: DNA
<213> ORGANISM: Artificial Sequence
<220> FEATURE:
<223> OTHER INFORMATION: Primer

<400> SEQUENCE: 793
ctgtccttcc tgctgaacac ggt                                         23

<210> SEQ ID NO 794
<211> LENGTH: 19
<212> TYPE: DNA
<213> ORGANISM: Artificial Sequence
<220> FEATURE:
<223> OTHER INFORMATION: Primer

<400> SEQUENCE: 794
gggcagccaa cacacgctt                                              19

<210> SEQ ID NO 795
<211> LENGTH: 21
<212> TYPE: DNA
<213> ORGANISM: Artificial Sequence
<220> FEATURE:
<223> OTHER INFORMATION: Primer

<400> SEQUENCE: 795
gggcagccaa cacacgctgg c                                           21

<210> SEQ ID NO 796
<211> LENGTH: 18
<212> TYPE: DNA
<213> ORGANISM: Artificial Sequence
<220> FEATURE:
<223> OTHER INFORMATION: Primer

<400> SEQUENCE: 796
gctgctgatg cccactgc                                               18

<210> SEQ ID NO 797
<211> LENGTH: 19
<212> TYPE: DNA
<213> ORGANISM: Artificial Sequence
<220> FEATURE:
<223> OTHER INFORMATION: Primer

<400> SEQUENCE: 797
gctgctgatg cccactgtc                                              19

<210> SEQ ID NO 798
<211> LENGTH: 22
<212> TYPE: DNA
<213> ORGANISM: Artificial Sequence
<220> FEATURE:
<223> OTHER INFORMATION: Primer

<400> SEQUENCE: 798
gccacgcaca ccaggttctc ac                                          22

<210> SEQ ID NO 799
<211> LENGTH: 24
<212> TYPE: DNA
<213> ORGANISM: Artificial Sequence
<220> FEATURE:

<223> OTHER INFORMATION: Primer

<400> SEQUENCE: 799
gccacgcaca ccaggttctc attg                                          24

<210> SEQ ID NO 800
<211> LENGTH: 21
<212> TYPE: DNA
<213> ORGANISM: Artificial Sequence
<220> FEATURE:
<223> OTHER INFORMATION: Primer

<400> SEQUENCE: 800
gggttagatg ttcatctctg c                                             21

<210> SEQ ID NO 801
<211> LENGTH: 22
<212> TYPE: DNA
<213> ORGANISM: Artificial Sequence
<220> FEATURE:
<223> OTHER INFORMATION: Primer

<400> SEQUENCE: 801
gggttagatg ttcatctctg ag                                            22

<210> SEQ ID NO 802
<211> LENGTH: 18
<212> TYPE: DNA
<213> ORGANISM: Artificial Sequence
<220> FEATURE:
<223> OTHER INFORMATION: Primer

<400> SEQUENCE: 802
atgagtgtcg aaatggac                                                 18

<210> SEQ ID NO 803
<211> LENGTH: 19
<212> TYPE: DNA
<213> ORGANISM: Artificial Sequence
<220> FEATURE:
<223> OTHER INFORMATION: Primer

<400> SEQUENCE: 803
atgagtgtcg aaatggagc                                                19

<210> SEQ ID NO 804
<211> LENGTH: 48
<212> TYPE: DNA
<213> ORGANISM: Homo sapiens

<400> SEQUENCE: 804
aaagctgcgt gatgatgaaa tcggctcccg cagacacctt ctccttca                48

<210> SEQ ID NO 805
<211> LENGTH: 48
<212> TYPE: DNA
<213> ORGANISM: Homo sapiens

<400> SEQUENCE: 805
aaagctgcgt gatgatgaaa tcgactcccg cagacacctt ctccttca                48

<210> SEQ ID NO 806
<211> LENGTH: 18
<212> TYPE: DNA
<213> ORGANISM: Artificial Sequence
<220> FEATURE:

<223> OTHER INFORMATION: Primer

<400> SEQUENCE: 806
tgcgtgatga tgaaatcg                                            18

<210> SEQ ID NO 807
<211> LENGTH: 19
<212> TYPE: DNA
<213> ORGANISM: Artificial Sequence
<220> FEATURE:
<223> OTHER INFORMATION: Primer

<400> SEQUENCE: 807
tgcgtgatga tgaaatcga                                           19

<210> SEQ ID NO 808
<211> LENGTH: 20
<212> TYPE: DNA
<213> ORGANISM: Artificial Sequence
<220> FEATURE:
<223> OTHER INFORMATION: Primer

<400> SEQUENCE: 808
tgcgtgatga tgaaatcggc                                          20

<210> SEQ ID NO 809
<211> LENGTH: 48
<212> TYPE: DNA
<213> ORGANISM: Homo sapiens

<400> SEQUENCE: 809
aaagctgcgt gatgatgaaa tcggctcccg cagacacctt ctccttca           48

<210> SEQ ID NO 810
<211> LENGTH: 48
<212> TYPE: DNA
<213> ORGANISM: Homo sapiens

<400> SEQUENCE: 810
aaagctgcgt gatgatgaaa tcgactcccg cagacacctt ctccttca           48

<210> SEQ ID NO 811
<211> LENGTH: 20
<212> TYPE: DNA
<213> ORGANISM: Artificial Sequence
<220> FEATURE:
<223> OTHER INFORMATION: Primer

<400> SEQUENCE: 811
ggagaaggtg tctgcgggag                                          20

<210> SEQ ID NO 812
<211> LENGTH: 22
<212> TYPE: DNA
<213> ORGANISM: Artificial Sequence
<220> FEATURE:
<223> OTHER INFORMATION: Primer

<400> SEQUENCE: 812
ggagaaggtg tctgcgggag tc                                       22

<210> SEQ ID NO 813
<211> LENGTH: 21
<212> TYPE: DNA
<213> ORGANISM: Artificial Sequence
<220> FEATURE:

```
<223> OTHER INFORMATION: Primer

<400> SEQUENCE: 813
ggagaaggtg tctgcgggag c                                              21

<210> SEQ ID NO 814
<211> LENGTH: 48
<212> TYPE: DNA
<213> ORGANISM: Homo sapiens

<400> SEQUENCE: 814
gggaggagct gaccagtgaa gaaagtgtct ttgaagtctt tgttctttt                48

<210> SEQ ID NO 815
<211> LENGTH: 48
<212> TYPE: DNA
<213> ORGANISM: Homo sapiens

<400> SEQUENCE: 815
gggaggagct gaccagtgaa gcaagtgtct ttgaagtctt tgttctttt                48

<210> SEQ ID NO 816
<211> LENGTH: 10
<212> TYPE: DNA
<213> ORGANISM: Artificial Sequence
<220> FEATURE:
<223> OTHER INFORMATION: Primer

<400> SEQUENCE: 816
acgttggatg                                                          10

<210> SEQ ID NO 817
<211> LENGTH: 22
<212> TYPE: DNA
<213> ORGANISM: Artificial Sequence
<220> FEATURE:
<223> OTHER INFORMATION: Primer

<400> SEQUENCE: 817
aacaaagact tcaaagacac tt                                            22

<210> SEQ ID NO 818
<211> LENGTH: 23
<212> TYPE: DNA
<213> ORGANISM: Artificial Sequence
<220> FEATURE:
<223> OTHER INFORMATION: Primer

<400> SEQUENCE: 818
aacaaagact tcaaagacac ttt                                           23

<210> SEQ ID NO 819
<211> LENGTH: 24
<212> TYPE: DNA
<213> ORGANISM: Artificial Sequence
<220> FEATURE:
<223> OTHER INFORMATION: Primer

<400> SEQUENCE: 819
aacaaagact tcaaagacac ttgc                                          24

<210> SEQ ID NO 820
<211> LENGTH: 48
<212> TYPE: DNA
<213> ORGANISM: Homo sapiens
```

-continued

```
<400> SEQUENCE: 820
gggaggagct gaccagtgaa gaaagtgtct ttgaagtctt tgttcttt          48

<210> SEQ ID NO 821
<211> LENGTH: 48
<212> TYPE: DNA
<213> ORGANISM: Homo sapiens

<400> SEQUENCE: 821
gggaggagct gaccagtgaa gaacgtgtct ttgaagtctt tgttcttt          48

<210> SEQ ID NO 822
<211> LENGTH: 19
<212> TYPE: DNA
<213> ORGANISM: Artificial Sequence
<220> FEATURE:
<223> OTHER INFORMATION: Primer

<400> SEQUENCE: 822
gaggagctga ccagtgaag                                         19

<210> SEQ ID NO 823
<211> LENGTH: 23
<212> TYPE: DNA
<213> ORGANISM: Artificial Sequence
<220> FEATURE:
<223> OTHER INFORMATION: Primer

<400> SEQUENCE: 823
gaggagctga ccagtgaaga aag                                    23

<210> SEQ ID NO 824
<211> LENGTH: 20
<212> TYPE: DNA
<213> ORGANISM: Artificial Sequence
<220> FEATURE:
<223> OTHER INFORMATION: Primer

<400> SEQUENCE: 824
gaggagctga ccagtgaagc                                        20

<210> SEQ ID NO 825
<211> LENGTH: 19
<212> TYPE: DNA
<213> ORGANISM: Artificial Sequence
<220> FEATURE:
<223> OTHER INFORMATION: Primer

<400> SEQUENCE: 825
cactgggagc attgaggct                                         19

<210> SEQ ID NO 826
<211> LENGTH: 20
<212> TYPE: DNA
<213> ORGANISM: Artificial Sequence
<220> FEATURE:
<223> OTHER INFORMATION: Primer

<400> SEQUENCE: 826
cactgggagc attgaggctc                                        20

<210> SEQ ID NO 827
<211> LENGTH: 21
<212> TYPE: DNA
<213> ORGANISM: Artificial Sequence
<220> FEATURE:
```

<223> OTHER INFORMATION: Primer

<400> SEQUENCE: 827
cactgggagc attgaggctt g                                          21

<210> SEQ ID NO 828
<211> LENGTH: 38
<212> TYPE: DNA
<213> ORGANISM: Homo sapiens

<400> SEQUENCE: 828
ccaataaaag tgactctcag cgagcctcaa tgctccca                        38

<210> SEQ ID NO 829
<211> LENGTH: 38
<212> TYPE: DNA
<213> ORGANISM: Homo sapiens

<400> SEQUENCE: 829
ccaataaaag tgactctcag caagcctcaa tgctccca                        38

<210> SEQ ID NO 830
<211> LENGTH: 20
<212> TYPE: DNA
<213> ORGANISM: Artificial Sequence
<220> FEATURE:
<223> OTHER INFORMATION: Primer

<400> SEQUENCE: 830
caataaaagt gactctcagc                                            20

<210> SEQ ID NO 831
<211> LENGTH: 22
<212> TYPE: DNA
<213> ORGANISM: Artificial Sequence
<220> FEATURE:
<223> OTHER INFORMATION: Primer

<400> SEQUENCE: 831
caataaaagt gactctcagc ga                                         22

<210> SEQ ID NO 832
<211> LENGTH: 21
<212> TYPE: DNA
<213> ORGANISM: Artificial Sequence
<220> FEATURE:
<223> OTHER INFORMATION: Primer

<400> SEQUENCE: 832
caataaaagt gactctcagc a                                          21

<210> SEQ ID NO 833
<211> LENGTH: 47
<212> TYPE: DNA
<213> ORGANISM: Homo sapiens

<400> SEQUENCE: 833
cttcaaggac aaaatacctg tattcctcgc ctgtccaggg atctgct               47

<210> SEQ ID NO 834
<211> LENGTH: 47
<212> TYPE: DNA
<213> ORGANISM: Homo sapiens

<400> SEQUENCE: 834
cttcaaggac aaaatacctg tattccttgc ctgtccaggg atctgct                    47

<210> SEQ ID NO 835
<211> LENGTH: 20
<212> TYPE: DNA
<213> ORGANISM: Artificial Sequence
<220> FEATURE:
<223> OTHER INFORMATION: Primer

<400> SEQUENCE: 835
gacaaaatac ctgtattcct                                                  20

<210> SEQ ID NO 836
<211> LENGTH: 21
<212> TYPE: DNA
<213> ORGANISM: Artificial Sequence
<220> FEATURE:
<223> OTHER INFORMATION: Primer

<400> SEQUENCE: 836
gacaaaatac ctgtattcct c                                                21

<210> SEQ ID NO 837
<211> LENGTH: 22
<212> TYPE: DNA
<213> ORGANISM: Artificial Sequence
<220> FEATURE:
<223> OTHER INFORMATION: Primer

<400> SEQUENCE: 837
gacaaaatac ctgtattcct tg                                               22

<210> SEQ ID NO 838
<211> LENGTH: 47
<212> TYPE: DNA
<213> ORGANISM: Homo sapiens

<400> SEQUENCE: 838
cttcaaggac aaaatacctg tattcctcgc ctgtccaggg atctgct                    47

<210> SEQ ID NO 839
<211> LENGTH: 47
<212> TYPE: DNA
<213> ORGANISM: Homo sapiens

<400> SEQUENCE: 839
cttcaaggac aaaatacctg tattccttgc ctgtccaggg atctgct                    47

<210> SEQ ID NO 840
<211> LENGTH: 18
<212> TYPE: DNA
<213> ORGANISM: Artificial Sequence
<220> FEATURE:
<223> OTHER INFORMATION: Primer

<400> SEQUENCE: 840
gcagatccct ggacaggc                                                    18

<210> SEQ ID NO 841
<211> LENGTH: 20
<212> TYPE: DNA
<213> ORGANISM: Artificial Sequence
<220> FEATURE:
<223> OTHER INFORMATION: Primer

<400> SEQUENCE: 841
gcagatccct ggacaggcga                                          20

<210> SEQ ID NO 842
<211> LENGTH: 19
<212> TYPE: DNA
<213> ORGANISM: Artificial Sequence
<220> FEATURE:
<223> OTHER INFORMATION: Primer

<400> SEQUENCE: 842
gcagatccct ggacaggca                                           19

<210> SEQ ID NO 843
<211> LENGTH: 52
<212> TYPE: DNA
<213> ORGANISM: Homo sapiens

<400> SEQUENCE: 843
tgtatgccac tttgacatta cacccatgaa cgtgctcatc gacgtgaacc cg       52

<210> SEQ ID NO 844
<211> LENGTH: 52
<212> TYPE: DNA
<213> ORGANISM: Homo sapiens

<400> SEQUENCE: 844
tgtatgccac tttgacatta cacccgtgaa cgtgctcatc gacgtgaacc cg       52

<210> SEQ ID NO 845
<211> LENGTH: 19
<212> TYPE: DNA
<213> ORGANISM: Artificial Sequence
<220> FEATURE:
<223> OTHER INFORMATION: Primer

<400> SEQUENCE: 845
ccactttgac attacaccc                                           19

<210> SEQ ID NO 846
<211> LENGTH: 20
<212> TYPE: DNA
<213> ORGANISM: Artificial Sequence
<220> FEATURE:
<223> OTHER INFORMATION: Primer

<400> SEQUENCE: 846
ccactttgac attacaccca                                          20

<210> SEQ ID NO 847
<211> LENGTH: 21
<212> TYPE: DNA
<213> ORGANISM: Artificial Sequence
<220> FEATURE:
<223> OTHER INFORMATION: Primer

<400> SEQUENCE: 847
ccactttgac attacacccg t                                        21

<210> SEQ ID NO 848
<211> LENGTH: 44
<212> TYPE: DNA
<213> ORGANISM: Homo sapiens

<400> SEQUENCE: 848
ctcgcaccgt ctgcgcgaat gttaccaccc tgctttccga ccca               44

```
<210> SEQ ID NO 849
<211> LENGTH: 44
<212> TYPE: DNA
<213> ORGANISM: Homo sapiens

<400> SEQUENCE: 849
ctcgcaccgt ctgcgcgaat gttaccagcc tgctttccga ccca            44

<210> SEQ ID NO 850
<211> LENGTH: 18
<212> TYPE: DNA
<213> ORGANISM: Artificial Sequence
<220> FEATURE:
<223> OTHER INFORMATION: Primer

<400> SEQUENCE: 850
tctgcgcgaa tgttacca                                          18

<210> SEQ ID NO 851
<211> LENGTH: 19
<212> TYPE: DNA
<213> ORGANISM: Artificial Sequence
<220> FEATURE:
<223> OTHER INFORMATION: Primer

<400> SEQUENCE: 851
tctgcgcgaa tgttaccac                                         19

<210> SEQ ID NO 852
<211> LENGTH: 20
<212> TYPE: DNA
<213> ORGANISM: Artificial Sequence
<220> FEATURE:
<223> OTHER INFORMATION: Primer

<400> SEQUENCE: 852
tctgcgcgaa tgttaccagc                                        20

<210> SEQ ID NO 853
<211> LENGTH: 52
<212> TYPE: DNA
<213> ORGANISM: Homo sapiens

<400> SEQUENCE: 853
cgttgctctt taagcacgcc ggcgcggcct gccgcgcgtt ggagaacggt aa     52

<210> SEQ ID NO 854
<211> LENGTH: 52
<212> TYPE: DNA
<213> ORGANISM: Homo sapiens

<400> SEQUENCE: 854
cgttgctctt taagcacgcc ggcgcggtct gccgcgcgtt ggagaacggt aa     52

<210> SEQ ID NO 855
<211> LENGTH: 18
<212> TYPE: DNA
<213> ORGANISM: Artificial Sequence
<220> FEATURE:
<223> OTHER INFORMATION: Primer

<400> SEQUENCE: 855
ttaagcacgc cggcgcgg                                          18

<210> SEQ ID NO 856
```

```
<211> LENGTH: 19
<212> TYPE: DNA
<213> ORGANISM: Artificial Sequence
<220> FEATURE:
<223> OTHER INFORMATION: Primer

<400> SEQUENCE: 856
ttaagcacgc cggcgcggc                                                    19

<210> SEQ ID NO 857
<211> LENGTH: 20
<212> TYPE: DNA
<213> ORGANISM: Artificial Sequence
<220> FEATURE:
<223> OTHER INFORMATION: Primer

<400> SEQUENCE: 857
ttaagcacgc cggcgcggtc                                                   20

<210> SEQ ID NO 858
<211> LENGTH: 52
<212> TYPE: DNA
<213> ORGANISM: Homo sapiens

<400> SEQUENCE: 858
aagctcacgc actgctccga cgcctatctg ctcattctgg cggcgcaaat ga              52

<210> SEQ ID NO 859
<211> LENGTH: 52
<212> TYPE: DNA
<213> ORGANISM: Homo sapiens

<400> SEQUENCE: 859
aagctcacgc actgctccga cgcctatttg ctcattctgg cggcgcaaat ga              52

<210> SEQ ID NO 860
<211> LENGTH: 18
<212> TYPE: DNA
<213> ORGANISM: Artificial Sequence
<220> FEATURE:
<223> OTHER INFORMATION: Primer

<400> SEQUENCE: 860
gccgccagaa tgagcaga                                                     18

<210> SEQ ID NO 861
<211> LENGTH: 20
<212> TYPE: DNA
<213> ORGANISM: Artificial Sequence
<220> FEATURE:
<223> OTHER INFORMATION: Primer

<400> SEQUENCE: 861
gccgccagaa tgagcagata                                                   20

<210> SEQ ID NO 862
<211> LENGTH: 19
<212> TYPE: DNA
<213> ORGANISM: Artificial Sequence
<220> FEATURE:
<223> OTHER INFORMATION: Primer

<400> SEQUENCE: 862
gccgccagaa tgagcagac                                                    19

<210> SEQ ID NO 863
```

```
<211> LENGTH: 51
<212> TYPE: DNA
<213> ORGANISM: Homo sapiens

<400> SEQUENCE: 863
cgtgatgcgt gacggagaaa aagaggacgc ggcttcggac aaggagaacc t          51

<210> SEQ ID NO 864
<211> LENGTH: 51
<212> TYPE: DNA
<213> ORGANISM: Homo sapiens

<400> SEQUENCE: 864
cgtgatgcgt gacggagaaa aagaggatgc ggcttcggac aaggagaacc t          51

<210> SEQ ID NO 865
<211> LENGTH: 18
<212> TYPE: DNA
<213> ORGANISM: Artificial Sequence
<220> FEATURE:
<223> OTHER INFORMATION: Primer

<400> SEQUENCE: 865
ctccttgtcc gaagccgc                                               18

<210> SEQ ID NO 866
<211> LENGTH: 20
<212> TYPE: DNA
<213> ORGANISM: Artificial Sequence
<220> FEATURE:
<223> OTHER INFORMATION: Primer

<400> SEQUENCE: 866
ctccttgtcc gaagccgcgt                                             20

<210> SEQ ID NO 867
<211> LENGTH: 19
<212> TYPE: DNA
<213> ORGANISM: Artificial Sequence
<220> FEATURE:
<223> OTHER INFORMATION: Primer

<400> SEQUENCE: 867
ctccttgtcc gaagccgca                                              19

<210> SEQ ID NO 868
<211> LENGTH: 41
<212> TYPE: DNA
<213> ORGANISM: Homo sapiens

<400> SEQUENCE: 868
ccacgaatgc tcgcagacca tgctgcacga atacgtcaga a                     41

<210> SEQ ID NO 869
<211> LENGTH: 41
<212> TYPE: DNA
<213> ORGANISM: Homo sapiens

<400> SEQUENCE: 869
ccacgaatgc tcgcagacta tgctgcacga atacgtcaga a                     41

<210> SEQ ID NO 870
<211> LENGTH: 24
<212> TYPE: DNA
<213> ORGANISM: Artificial Sequence
<220> FEATURE:
```

<223> OTHER INFORMATION: Primer

<400> SEQUENCE: 870
ctttctgacg tattcgtgca gcat                                       24

<210> SEQ ID NO 871
<211> LENGTH: 27
<212> TYPE: DNA
<213> ORGANISM: Artificial Sequence
<220> FEATURE:
<223> OTHER INFORMATION: Primer

<400> SEQUENCE: 871
ctttctgacg tattcgtgca gcatggt                                    27

<210> SEQ ID NO 872
<211> LENGTH: 25
<212> TYPE: DNA
<213> ORGANISM: Artificial Sequence
<220> FEATURE:
<223> OTHER INFORMATION: Primer

<400> SEQUENCE: 872
ctttctgacg tattcgtgca gcata                                      25

<210> SEQ ID NO 873
<211> LENGTH: 42
<212> TYPE: DNA
<213> ORGANISM: Homo sapiens

<400> SEQUENCE: 873
ttcgtgttct atgatcatga gagtcgccgt gtggagcccc ga                   42

<210> SEQ ID NO 874
<211> LENGTH: 42
<212> TYPE: DNA
<213> ORGANISM: Homo sapiens

<400> SEQUENCE: 874
ttcgtgttct atgatgatga gagtcgccgt gtggagcccc ga                   42

<210> SEQ ID NO 875
<211> LENGTH: 20
<212> TYPE: DNA
<213> ORGANISM: Artificial Sequence
<220> FEATURE:
<223> OTHER INFORMATION: Primer

<400> SEQUENCE: 875
atgagagtcg ccgtgtggag                                            20

<210> SEQ ID NO 876
<211> LENGTH: 22
<212> TYPE: DNA
<213> ORGANISM: Homo sapiens

<400> SEQUENCE: 876
ctccacacgg cgactctcat ga                                         22

<210> SEQ ID NO 877
<211> LENGTH: 21
<212> TYPE: DNA
<213> ORGANISM: Homo sapiens

<400> SEQUENCE: 877

```
ctccacacgg cgactctcat c                                        21
```

<210> SEQ ID NO 878
<211> LENGTH: 20
<212> TYPE: DNA
<213> ORGANISM: Artificial Sequence
<220> FEATURE:
<223> OTHER INFORMATION: Primer

<400> SEQUENCE: 878

```
ctccacacgg cgactctcat                                          20
```

<210> SEQ ID NO 879
<211> LENGTH: 22
<212> TYPE: DNA
<213> ORGANISM: Artificial Sequence
<220> FEATURE:
<223> OTHER INFORMATION: Primer

<400> SEQUENCE: 879

```
ctccacacgg cgactctcat ga                                       22
```

<210> SEQ ID NO 880
<211> LENGTH: 21
<212> TYPE: DNA
<213> ORGANISM: Artificial Sequence
<220> FEATURE:
<223> OTHER INFORMATION: Primer

<400> SEQUENCE: 880

```
ctccacacgg cgactctcat c                                        21
```

<210> SEQ ID NO 881
<211> LENGTH: 55
<212> TYPE: DNA
<213> ORGANISM: Homo sapiens

<400> SEQUENCE: 881

```
ggatgaccag ctgttcgtgt tctatgatca tgagagtcgc cgtgtggagc cccga   55
```

<210> SEQ ID NO 882
<211> LENGTH: 54
<212> TYPE: DNA
<213> ORGANISM: Homo sapiens

<400> SEQUENCE: 882

```
ggatgaccag ctgttcgtgt tctatgatga tgagagtcgc cgtgtggagc cccg    54
```

<210> SEQ ID NO 883
<211> LENGTH: 22
<212> TYPE: DNA
<213> ORGANISM: Homo sapiens

<400> SEQUENCE: 883

```
cagctgttcg tgttctatga tc                                       22
```

<210> SEQ ID NO 884
<211> LENGTH: 23
<212> TYPE: DNA
<213> ORGANISM: Homo sapiens

<400> SEQUENCE: 884

```
cagctgttcg tgttctatga tga                                      23
```

<210> SEQ ID NO 885

```
<211> LENGTH: 21
<212> TYPE: DNA
<213> ORGANISM: Artificial Sequence
<220> FEATURE:
<223> OTHER INFORMATION: Primer

<400> SEQUENCE: 885
cagctgttcg tgttctatga t                                              21

<210> SEQ ID NO 886
<211> LENGTH: 22
<212> TYPE: DNA
<213> ORGANISM: Artificial Sequence
<220> FEATURE:
<223> OTHER INFORMATION: Primer

<400> SEQUENCE: 886
cagctgttcg tgttctatga tc                                             22

<210> SEQ ID NO 887
<211> LENGTH: 23
<212> TYPE: DNA
<213> ORGANISM: Artificial Sequence
<220> FEATURE:
<223> OTHER INFORMATION: Primer

<400> SEQUENCE: 887
cagctgttcg tgttctatga tga                                            23

<210> SEQ ID NO 888
<211> LENGTH: 36
<212> TYPE: DNA
<213> ORGANISM: Homo sapiens

<400> SEQUENCE: 888
gagcagagat atacgtgcca ggtggagcac ccaggc                              36

<210> SEQ ID NO 889
<211> LENGTH: 36
<212> TYPE: DNA
<213> ORGANISM: Homo sapiens

<400> SEQUENCE: 889
gagcagagat atacgtacca ggtggagcac ccaggc                              36

<210> SEQ ID NO 890
<211> LENGTH: 19
<212> TYPE: DNA
<213> ORGANISM: Artificial Sequence
<220> FEATURE:
<223> OTHER INFORMATION: Primer

<400> SEQUENCE: 890
ccaggtggag cacccaggc                                                 19

<210> SEQ ID NO 891
<211> LENGTH: 20
<212> TYPE: DNA
<213> ORGANISM: Homo sapiens

<400> SEQUENCE: 891
gcctgggtgc tccacctggc                                                20

<210> SEQ ID NO 892
<211> LENGTH: 21
<212> TYPE: DNA
```

-continued

<213> ORGANISM: Homo sapiens

<400> SEQUENCE: 892
gcctgggtgc tccacctggt a                                              21

<210> SEQ ID NO 893
<211> LENGTH: 19
<212> TYPE: DNA
<213> ORGANISM: Artificial Sequence
<220> FEATURE:
<223> OTHER INFORMATION: Primer

<400> SEQUENCE: 893
gcctgggtgc tccacctgg                                                 19

<210> SEQ ID NO 894
<211> LENGTH: 20
<212> TYPE: DNA
<213> ORGANISM: Artificial Sequence
<220> FEATURE:
<223> OTHER INFORMATION: Primer

<400> SEQUENCE: 894
gcctgggtgc tccacctggc                                                20

<210> SEQ ID NO 895
<211> LENGTH: 21
<212> TYPE: DNA
<213> ORGANISM: Artificial Sequence
<220> FEATURE:
<223> OTHER INFORMATION: Primer

<400> SEQUENCE: 895
gcctgggtgc tccacctggt a                                              21

<210> SEQ ID NO 896
<211> LENGTH: 20
<212> TYPE: DNA
<213> ORGANISM: Artificial Sequence
<220> FEATURE:
<223> OTHER INFORMATION: Primer

<400> SEQUENCE: 896
gcctgggtgc tccacctggt                                                20

<210> SEQ ID NO 897
<211> LENGTH: 43
<212> TYPE: DNA
<213> ORGANISM: Homo sapiens

<400> SEQUENCE: 897
tggggaagag cagagatata cgtgccaggt ggagcaccca ggc                      43

<210> SEQ ID NO 898
<211> LENGTH: 43
<212> TYPE: DNA
<213> ORGANISM: Homo sapiens

<400> SEQUENCE: 898
tggggaagag cagagatata cgtaccaggt ggagcaccca ggc                      43

<210> SEQ ID NO 899
<211> LENGTH: 22
<212> TYPE: DNA
<213> ORGANISM: Homo sapiens

```
<400> SEQUENCE: 899
gggaagagca gagatatacg ta                                22

<210> SEQ ID NO 900
<211> LENGTH: 23
<212> TYPE: DNA
<213> ORGANISM: Homo sapiens

<400> SEQUENCE: 900
gggaagagca gagatatacg tgc                               23

<210> SEQ ID NO 901
<211> LENGTH: 21
<212> TYPE: DNA
<213> ORGANISM: Artificial Sequence
<220> FEATURE:
<223> OTHER INFORMATION: Primer

<400> SEQUENCE: 901
gggaagagca gagatatacg t                                 21

<210> SEQ ID NO 902
<211> LENGTH: 23
<212> TYPE: DNA
<213> ORGANISM: Artificial Sequence
<220> FEATURE:
<223> OTHER INFORMATION: Primer

<400> SEQUENCE: 902
gggaagagca gagatatacg tgc                               23

<210> SEQ ID NO 903
<211> LENGTH: 22
<212> TYPE: DNA
<213> ORGANISM: Artificial Sequence
<220> FEATURE:
<223> OTHER INFORMATION: Primer

<400> SEQUENCE: 903
gggaagagca gagatatacg ta                                22

<210> SEQ ID NO 904
<211> LENGTH: 22
<212> TYPE: DNA
<213> ORGANISM: Artificial Sequence
<220> FEATURE:
<223> OTHER INFORMATION: Primer

<400> SEQUENCE: 904
gggaagagca gagatatacg tg                                22

<210> SEQ ID NO 905
<211> LENGTH: 50
<212> TYPE: DNA
<213> ORGANISM: Homo sapiens

<400> SEQUENCE: 905
cagctgttcg tgttctatga tcatgagagt cgccgtgtgg agccccgaac   50

<210> SEQ ID NO 906
<211> LENGTH: 50
<212> TYPE: DNA
<213> ORGANISM: Homo sapiens

<400> SEQUENCE: 906
```

```
cagctgttcg tgttctatga tcatgagtgt cgccgtgtgg agccccgaac        50
```

<210> SEQ ID NO 907
<211> LENGTH: 17
<212> TYPE: DNA
<213> ORGANISM: Artificial Sequence
<220> FEATURE:
<223> OTHER INFORMATION: Primer

<400> SEQUENCE: 907

```
gtcgccgtgt ggagccc                                           17
```

<210> SEQ ID NO 908
<211> LENGTH: 18
<212> TYPE: DNA
<213> ORGANISM: Artificial Sequence
<220> FEATURE:
<223> OTHER INFORMATION: Primer

<400> SEQUENCE: 908

```
gggctccaca cggcgact                                          18
```

<210> SEQ ID NO 909
<211> LENGTH: 19
<212> TYPE: DNA
<213> ORGANISM: Artificial Sequence
<220> FEATURE:
<223> OTHER INFORMATION: Primer

<400> SEQUENCE: 909

```
gggctccaca cggcgacac                                         19
```

<210> SEQ ID NO 910
<211> LENGTH: 17
<212> TYPE: DNA
<213> ORGANISM: Artificial Sequence
<220> FEATURE:
<223> OTHER INFORMATION: Primer

<400> SEQUENCE: 910

```
gggctccaca cggcgac                                           17
```

<210> SEQ ID NO 911
<211> LENGTH: 18
<212> TYPE: DNA
<213> ORGANISM: Artificial Sequence
<220> FEATURE:
<223> OTHER INFORMATION: Primer

<400> SEQUENCE: 911

```
gggctccaca cggcgact                                          18
```

<210> SEQ ID NO 912
<211> LENGTH: 19
<212> TYPE: DNA
<213> ORGANISM: Artificial Sequence
<220> FEATURE:
<223> OTHER INFORMATION: Primer

<400> SEQUENCE: 912

```
gggctccaca cggcgacac                                         19
```

<210> SEQ ID NO 913
<211> LENGTH: 18
<212> TYPE: DNA
<213> ORGANISM: Artificial Sequence
<220> FEATURE:

<223> OTHER INFORMATION: Primer

<400> SEQUENCE: 913
gggctccaca cggcgaca                                          18

<210> SEQ ID NO 914
<211> LENGTH: 50
<212> TYPE: DNA
<213> ORGANISM: Homo sapiens

<400> SEQUENCE: 914
cagctgttcg tgttctatga tcatgagagt cgccgtgtgg agccccgaac        50

<210> SEQ ID NO 915
<211> LENGTH: 50
<212> TYPE: DNA
<213> ORGANISM: Homo sapiens

<400> SEQUENCE: 915
cagctgttcg tgttctatga tcatgagtgt cgccgtgtgg agccccgaac        50

<210> SEQ ID NO 916
<211> LENGTH: 10
<212> TYPE: DNA
<213> ORGANISM: Artificial Sequence
<220> FEATURE:
<223> OTHER INFORMATION: Primer

<400> SEQUENCE: 916
acgttggatg                                                   10

<210> SEQ ID NO 917
<211> LENGTH: 23
<212> TYPE: DNA
<213> ORGANISM: Homo sapiens

<400> SEQUENCE: 917
ttcgtgttct atgatcatga gag                                    23

<210> SEQ ID NO 918
<211> LENGTH: 22
<212> TYPE: DNA
<213> ORGANISM: Homo sapiens

<400> SEQUENCE: 918
ttcgtgttct atgatcatga gt                                     22

<210> SEQ ID NO 919
<211> LENGTH: 21
<212> TYPE: DNA
<213> ORGANISM: Artificial Sequence
<220> FEATURE:
<223> OTHER INFORMATION: Primer

<400> SEQUENCE: 919
ttcgtgttct atgatcatga g                                      21

<210> SEQ ID NO 920
<211> LENGTH: 23
<212> TYPE: DNA
<213> ORGANISM: Artificial Sequence
<220> FEATURE:
<223> OTHER INFORMATION: Primer

```
<400> SEQUENCE: 920
ttcgtgttct atgatcatga gag                                              23
```